US012655116B2

(12) United States Patent
Waldraff et al.

(10) Patent No.: US 12,655,116 B2
(45) Date of Patent: Jun. 16, 2026

(54) SUBSTITUTED ISOPHTHALIC ACID DIAMIDES

(71) Applicant: Bayer Aktiengesellschaft, Leverkusen (DE)

(72) Inventors: Christian Waldraff, Bad Vilbel (DE); Ralf Braun, Ramberg (DE); Arnim Köhn, Klein-Winternheim (DE); Hartmut Ahrens, Langen (DE); Uwe Döller, Rodgau (DE); Elisabeth Asmus, Hoesbach (DE); Birgit Bollenbach-Wahl, Weiler/Bingen (DE); Christopher Hugh Rosinger, Hofheim (DE); Jan Dittgen, Frankfurt (DE); Anu Bheemaiah Machettira, Frankfurt am Main (DE); Elmar Gatzweiler, Bad Nauheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 695 days.

(21) Appl. No.: 17/916,836

(22) PCT Filed: Apr. 1, 2021

(86) PCT No.: PCT/EP2021/058608

§ 371 (c)(1),
(2) Date: Oct. 4, 2022

(87) PCT Pub. No.: WO2021/204665

PCT Pub. Date: Oct. 14, 2021

(65) Prior Publication Data

US 2023/0159472 A1 May 25, 2023

(30) Foreign Application Priority Data

Apr. 7, 2020 (EP) .................................... 20168349

(51) Int. Cl.

| | |
|---|---|
| ***C07D 257/06*** | (2006.01) |
| ***A01N 43/713*** | (2006.01) |
| ***A01P 13/00*** | (2006.01) |
| ***C07D 271/08*** | (2006.01) |

(52) U.S. Cl.

CPC ......... *C07D 257/06* (2013.01); *A01N 43/713* (2013.01); *A01P 13/00* (2021.08); *C07D 271/08* (2013.01)

(58) Field of Classification Search

CPC .............. C07D 257/06; C07D 271/113; C07D 249/14; C07D 407/10; C07D 409/10; A01N 43/713; A01N 43/653; A01N 43/82

See application file for complete search history.

(56) References Cited

U.S. PATENT DOCUMENTS

| | | | | |
|---|---|---|---|---|
| 8,481,749 B2 | 7/2013 | Braun et al. | | |
| 8,822,378 B2 | 9/2014 | Braun et al. | | |
| 9,101,141 B2 | 8/2015 | Koehn et al. | | |
| 2012/0058892 A1* | 3/2012 | Braun | A01N 43/713 | 504/225 |

FOREIGN PATENT DOCUMENTS

| | | |
|---|---|---|
| WO | 2012028579 A1 | 3/2012 |
| WO | 2012/126932 A1 | 9/2012 |
| WO | 2013/017559 A1 | 2/2013 |
| WO | 2017/144402 A1 | 8/2017 |

OTHER PUBLICATIONS

PCT International Search Report for PCT/EP2021/058608, mailed Jul. 22, 2021.

* cited by examiner

*Primary Examiner* — John Pak

(57) ABSTRACT

Isophthalamides of the general formula (I) are described as herbicides.

(I)

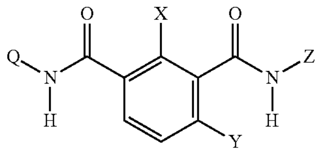

In this formula (I), X, Y and Z represent radicals such as hydrogen, alkyl and halogen. Q represents a heterocyclic ring such as tetrazolyl.

17 Claims, No Drawings

SUBSTITUTED ISOPHTHALIC ACID DIAMIDES

CROSS-REFERENCE TO RELATED APPLICATIONS

This application is the National Stage entry of International Application No. PCT/EP2021/058608, filed 1 Apr. 2021, which claims priority to European Patent Application No. 20168349.7, filed 7 Apr. 2020.

DESCRIPTION

BACKGROUND

Field

The invention relates to the technical field of herbicides, especially that of herbicides for selective control of broad-leaved weeds and weed grasses in useful plants.

Description of Related Art

WO 2012/028579 A1, WO 2012/126932 A1, WO2013/017559 A1 and WO 2017/144402 A1 describe, inter alia, herbicidally active isophthalamides which differ essentially by the nature of the substituents on the two amide functions.

SUMMARY

The isophthalamides specifically disclosed therein always have a tertiary amide group. However, the isophthalamides known from these documents do not always have adequate herbicidal efficacy and/or compatibility with crop plants. It has been found that isophthalamides having a primary or secondary amide group have superior properties compared to the isophthalamides known from the prior art. The present invention thus provides isophthalamides of the formula (I) or salts thereof (I)

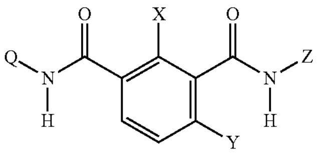

in which the symbols and indices are defined as follows:

Q is $Q^1$, $Q^2$, $Q^3$ or $Q^4$ ($Q^1$)

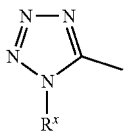

($Q^2$)

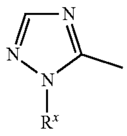

-continued ($Q^3$)

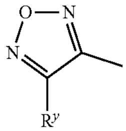

($Q^4$)

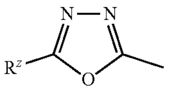

$R^1$ is ($C_1$-$C_6$)-alkyl, halo-($C_1$-$C_6$)-alkyl or ($C_3$-$C_6$)-cycloalkyl, $R^2$ is ($C_1$-$C_6$)-alkyl, $R^x$ is ($C_1$-$C_6$)-alkyl, ($C_1$-$C_6$)-alkyl-O—($C_1$-$C_6$)-alkyl or phenyl, $R^y$ is halogen, ($C_1$-$C_6$)-alkyl or halo-($C_1$-$C_6$)-alkyl, $R^z$ is hydrogen, ($C_1$-$C_6$)-alkyl or halo-($C_1$-$C_6$)-alkyl, X is halogen, ($C_1$-$C_6$)-alkyl, halo-($C_1$-$C_6$)-alkyl, ($C_3$-$C_6$)-cycloalkyl, $R^1$O, $R^2(O)_n$S or $R^1$O—($C_1$-$C_6$)-alkyl or $R^2S(O)_n$—($C_1$-$C_6$)-alkyl, Y is halogen, ($C_1$-$C_6$)-alkyl, halo-($C_1$-$C_6$)-alkyl, $R^1$O or $R^2(O)_n$S Z is hydrogen, one of the following groups, each of which is substituted by s radicals from the group consisting of halogen, cyano, $R^1$C(O), $R^1$OC(O), $R^1$O and $R^2(O)_n$S: ($C_1$-$C_6$)-alkyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, ($C_2$-$C_6$)-alkenyl, ($C_2$-$C_6$)-alkenyl-($C_1$-$C_6$)-alkyl, ($C_2$-$C_6$)-alkynyl, ($C_2$-$C_6$)-alkynyl-($C_1$-$C_6$)-alkyl, ($C_1$-$C_6$)-alkoxy, $R^2$S(O)n-($C_1$-$C_6$)-alkyl, $R^1$C(O), $R^1$OC(O), $R^1$C(O)—($C_1$-$C_6$)-alkyl, $R^1$OC(O)—($C_1$-$C_6$)-alkyl, $R^1$NH—($C_1$-$C_6$)-alkyl, $R^1_2$N—($C_1$-$C_6$)-alkyl, $R^1$NHC(O)—($C_1$-$C_6$)-alkyl or $R^1_2$NC(O)—($C_1$-$C_6$)-alkyl, or one of the following groups, each substituted by s radicals from the group consisting of halogen, ($C_1$-$C_6$)-alkyl, halo-($C_1$-$C_6$)-alkyl, ($C_1$-$C_6$)-alkoxy, halo-($C_1$-$C_6$)-alkoxy, $R^1$C(O) and $R^1$OC(O):

phenyl, benzyl, phenyl, benzyl, heterocyclyl or heterocyclyl-($C_1$-$C_6$)-alkyl, n is 0, 1 or 2, s is 0, 1, 2 or 3.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Halogen-substituted alkyl means straight-chain or branched alkyl groups where some or all of the hydrogen atoms in these groups may be replaced by halogen atoms, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Halogen represents fluorine, chlorine, bromine or iodine.

A heterocyclic radical (heterocyclyl) is a 5- or 6-membered cyclic radical which, as well a carbon atoms, contains at least one heteroatom from the group of N, O, S, and which is saturated, unsaturated, partly saturated or heteroaromatic and may be unsubstituted or substituted, in which case the bonding site is localized on a ring atom. Example of heterocyclic radicals are 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetra-hydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl); 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-thiopyran-2- or 3- or 4-yl; 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyrazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl; 4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl.

Depending on the nature of the substituents and the manner in which they are attached, the compounds of the general formula (I) may be present as stereoisomers. If, for example, one or more asymmetrically substituted carbon atoms are present, there may be enantiomers and diastereomers. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically.

The compounds of formula (I) may form salts. Suitable bases are, for example, organic amines such as trialkylamines, morpholine, piperidine or pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula $[NRR'R''R''']^+$ in which R to R''' are each independently an organic radical, especially alkyl, aryl, aralkyl or alkylaryl. Also useful are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts through adduct formation of a suitable inorganic or organic acid, for example mineral acids such as HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids such as p-toluenesulfonic acid, with a basic group such as amino, alkylamino, dialkylamino, piperidino, morpholino or pyridino. These salts then contain the conjugate base of the acid as anion.

Preference is given to compounds of the general formula (I) where the symbols and indices have the following meanings:

Q is $Q^1$, $Q^2$, $Q^3$ or $Q^4$ ($Q^1$)

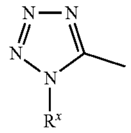

($Q^2$)

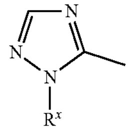

($Q^3$)

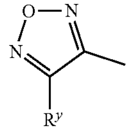

($Q^4$)

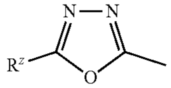

- $R^x$ is Me, Et, Pr, i-Pr, c-Pr, $(CH_2)_2OMe$ or Ph,
- $R^y$ is Cl, Me, Et or $CF_3$,
- $R^z$ is hydrogen, Me, Et or $CF_3$,
- X is halogen, ($C_1$-$C_6$)-alkyl, halo-($C_1$-$C_6$)-alkyl, c-Pr, OMe, OEt, SMe, SEt, $SO_2Me$, $SO_2Et$, $CH_2OMe$, $CH_2SMe$, $CH_2SO_2Me$, $(CH_2)_2SMe$ or $(CH_2)_2SO_2Me$,
- Y is halogen, halo-($C_1$-$C_6$)-alkyl, OMe, SMe, S(O)Me, $SO_2Me$, SEt, S(O)Et or $SO_2Et$,
- Z is hydrogen, ($C_1$-$C_6$)-alkyl, ($C_3$-$C_6$)-cycloalkyl, $CH_2$c-Pr, halo-($C_1$-$C_6$)-alkyl, $(CH_2)_2OMe$, $(CH_2)_2OEt$, allyl, propynyl, $(CH_2)_2SMe$, $(CH_2)_2SO_2Me$, C(O)Me, C(O)cPr, C(O)OMe, C(O)OEt, $CH_2$-(tetrahydrofuran-2-yl), oxetan-3-yl, $CH_2C(O)Me$, $CH_2C(O)$c-Pr, $CH_2C(O)NMe_2$, $CH_2CN$, Ph, $CH_2Ph$ or $CH_2$-(thien-2-yl), OMe, OEt, OPr, Oi-Pr.

Particular preference is given to compounds of the general formula (I) where the symbols and indices have the following meanings:

- Q is $Q^1$ or $Q^4$,
- $R^x$ is Me, Et or Pr,
- $R^z$ is H or Me,
- X is F, Cl, Br, I, Me, Et, c-Pr, OMe, SMe, SEt, $CH_2OMe$ or $CF_3$,

- Y is F, Cl, Br, I, SMe, S(O)Me, $SO_2Me$, $CF_3$, $CHF_2$ or $C_2F_5$,
- Z is hydrogen, Me, Et, c-Pr, Pr, i-Pr, c-Bu, $CH_2$-c-Pr, $CH_2CHF_2$, $CH_2CF_3$, CH(Me)-c-Pr, $(CH_2)_2OMe$, $(CH_2)_2$ SMe, $CH_2CN$, $CH_2$-(tetrahydrofuran-2-yl), $CH_2C(O)NMe_2$, Ph or $CH_2$-(thien-2-yl), oxetan-3-yl, OMe, OEt, OPr, Oi-Pr.

Compounds of the invention can be prepared, for example, by the method specified in Scheme 1 of WO 2012/028579 A1. The corresponding benzoyl chlorides or the parent benzoic acids thereof are known in principle and can be prepared, for example, by the methods described in WO1997/041105, WO1998/029383, WO1999/021852, EP282944, JP11021280, JP11012275 or CN103130730. The working examples described further down further elucidate the mode of preparation of the compounds of the invention.

The workup of the respective reaction mixtures is generally effected by known processes, for example by crystallization, aqueous-extractive workup, by chromatographic methods or by a combination of these methods.

Depending on the nature of the substituents and the manner in which they are attached, the compounds of the general formula (I) may be present as stereoisomers. If, for example, one or more asymmetrically substituted carbon atoms are present, there may be enantiomers and diastereomers. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

The inventive compounds of the formula (I) (and/or salts thereof), referred to collectively as "compounds of the invention" hereinafter, have excellent herbicidal efficacy against a broad spectrum of economically important monocotyledonous and dicotyledonous annual harmful plants.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds of the invention are applied to the soil surface before germination, either the weed seedlings are prevented completely from emerging or the weeds grow until they have reached the cotyledon stage, but then stop growing.

If the active ingredients are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

The compounds of the invention can be selective in crops of useful plants and can also be employed as non-selective herbicides.

By virtue of their herbicidal and plant growth regulatory properties, the active ingredients can also be used to control harmful plants in crops of genetically modified plants which are known or are yet to be developed. In general, the transgenic plants are characterized by particular advantageous properties, for example by resistances to certain active ingredients used in the agrochemical industry, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further particular properties lie in tolerance or resistance to abiotic stress factors, for example heat, cold, drought, salinity and ultraviolet radiation.

Preference is given to using the inventive compounds of the formula (I) or salts thereof in economically important transgenic crops of useful and ornamental plants.

The compounds of the formula (I) can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants.

Alternatively, novel plants with altered properties can be generated with the aid of recombinant methods (see, for example, EP 0221044, EP 0131624). What have been described are, for example, several cases of genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377 A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant).

- transgenic crop plants, for example cotton, capable of producing *Bacillus thuringiensis* toxins (Bt toxins), which make the plants resistant to particular pests (EP 0142924 A, EP 0193259 A),
- transgenic crop plants having a modified fatty acid composition (WO 91/013972 A),
- genetically modified crop plants having novel constituents or secondary metabolites, for example novel phytoalexins, which cause an increase in disease resistance (EP 0309862 A, EP 0464461 A),
- genetically modified plants having reduced photorespiration, which have higher yields and higher stress tolerance (EP 0305398 A),
- transgenic crop plants which produce pharmaceutically or diagnostically important proteins ("molecular pharming"),
- transgenic crop plants which feature higher yields or better quality,
- transgenic crop plants which are distinguished by a combination, for example of the abovementioned novel properties ("gene stacking").

Numerous molecular biology techniques which can be used to produce novel transgenic plants with modified properties are known in principle; see, for example, I. Potrykus and G. Spangenberg (eds), Gene Transfer to Plants, Springer Lab Manual (1995), Springer Verlag Berlin, Heidelberg or Christou, "Trends in Plant Science" 1 (1996) 423-431).

For such genetic manipulations, nucleic acid molecules which allow mutagenesis or sequence alteration by recombination of DNA sequences can be introduced into plasmids. With the aid of standard methods, it is possible, for example, to undertake base exchanges, remove part sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone" [Genes and Clones], VCH Weinheim, 2nd edition, 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants. Obtainable in this way are transgenic plants having properties altered by overexpression, suppression or inhibition of homologous (=natural) genes or gene sequences or expression of heterologous (=foreign) genes or gene sequences.

The compounds (I) of the invention can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The compounds of the invention can be used with particular preference in transgenic crop plants which are resistant to a combination of glyphosates and glufosinates, glyphosates and sulfonylureas or imidazolinones. Most preferably, the compounds of the invention can be used in transgenic crop plants such as corn or soya with the trade name or the designation Optimum™ GAT™ (glyphosate ALS tolerant), for example.

When the active ingredients of the invention are employed in transgenic crops, not only do the effects towards harmful plants observed in other crops occur, but frequently also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the inventive compounds of the formula (I) as herbicides for controlling harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The necessary formulation auxiliaries such as inert materials, surfactants, solvents and further additives are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", volume 7, C. Hanser Verlag Munich, 4th ed. 1986.

On the basis of these formulations, it is also possible to produce combinations with other active ingredients, for example insecticides, acaricides, herbicides, fungicides, and also with safeners, fertilizers and/or growth regulators, for example in the form of a finished formulation or as a tank mix.

Combination partners usable for the compounds of the invention in mixed formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as known, for example, from Weed Research 26 (1986) 441-445 or "The Pesticide Manual", 16th edition, The British Crop Protection Council and the Royal Soc. of Chemistry, 2006, and literature cited therein. Known herbicides or plant growth regulators which can be combined with the compounds of the invention are, for example, the following, where said active ingredients are referred to either by their "common name" in accordance with the International Organization for Standardization (ISO) or by the chemical name or by the code number. They always encompass all the use forms, for example acids, salts, esters and also all isomeric forms such as stereoisomers and optical isomers, even if they are not mentioned explicitly.

Examples of such herbicidal mixing partners are:

acetochlor, acifluorfen, acifluorfen-sodium, aclonifen, alachlor, alidochlore, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalm, chlorotoluron, chlorthal-dimethyl, chlorsulfuron, 3-[5-chloro-4-(trifluoromethyl)pyridin-2-yl]-4-hydroxy-1-methylimidazolidin-2-one, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]-phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, florpyrauxifen, florpyrauxifen-benzyl, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, fluorenol, fluorenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl (2,4-dichlorophenoxy)acetat, 4-hydroxy-1-methoxy-5-methyl-3-[4-(trifluoromethyl)pyridin-2-yl] imidazolidin-2-one, 4-hydroxy-1-methyl-3-[4-(trifluoromethyl)pyridin-2-yl]imidazolidin-2-one, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxotrione (lancotrione), oxyfluorfen, paraquat, paraquat dichloride, pebulate, pendimethalin, penoxsulam, pentachlorophenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, triallate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline, and the following compounds:

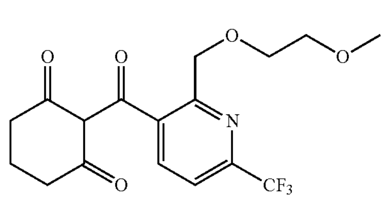

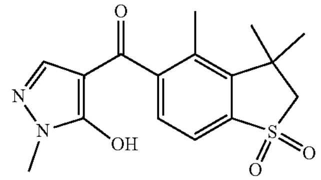

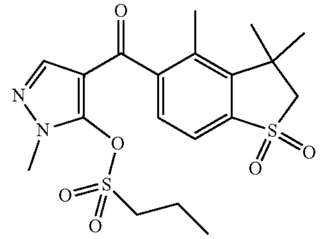

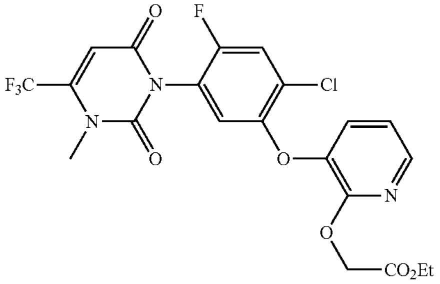

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono (N,N-dimethylalkylammonium), ethephon, flumetralin, fluorenol, fluorenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4[(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Safeners which can be used in combination with the inventive compounds of the formula (I) and optionally in combinations with further active ingredients such as insecticides, acaricides, herbicides, fungicides as listed above are preferably selected from the group consisting of:

S1) Compounds of the formula (S1)

(S1)

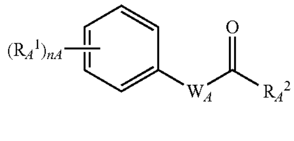

where the symbols and indices have the meanings below:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of the partly unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$, $m_A$ is 0 or 1;

$(W_A^1)$

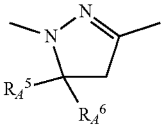

$(W_A^2)$

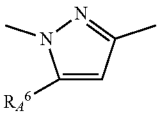

$(W_A^3)$

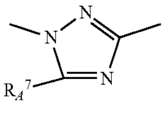

$(W_A^4)$

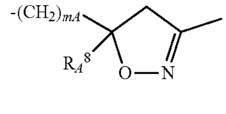

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$ $R_A^3$ is hydrogen or an unsubstituted or substituted aliphatic hydrocarbon radical, preferably having a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type ($S1^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type ($S1^e$), preferably compounds such as ethyl 5-(2,4-dichlorobenzyl)-2-isoxazoline-3-carboxylate (51-8) or ethyl 5-phenyl-2-isoxazoline-3-carboxylate (51-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (51-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

(S2)

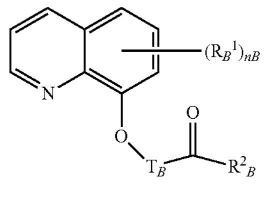

where the symbols and indices have the meanings below:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbon radical, preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type (S2a), preferably 1-methylhexyl(5-chloro-8-quinolinoxy)acetate ("cloquintocet-mexyl") (S2-1), (1,3-dimethylbut-1-yl) (5-chloro-8-quinolinoxy)acetate (S2-2), 4-allyloxybutyl(5-chloro-8-quinolinoxy)acetate (S2-3), 1-allyloxyprop-2-yl(5-chloro-8-quinolinoxy)acetate (S2-4), ethyl(5-chloro-8-quinolinoxy)acetate (S2-5), methyl (5-chloro-8-quinolinoxy)acetate (S2-6), allyl(5-chloro-8-quinolinoxy)acetate (S2-7), 2-(2-propylideneiminoxy)-1-ethyl(5-chloro-8-quinolinoxy)acetate (S2-8), 2-oxoprop-1-yl(5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type ($S2^b$), preferably compounds such as diethyl (5-chloro-8-quinolinoxy)malonate, diallyl(5-chloro-8-quinolinoxy)malonate, methyl ethyl(5-chloro-8-quinolinoxy)malonate and related compounds, as described in EP-A-0 582 198.

S3) Compounds of the formula (S3)

(S3)

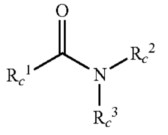

where the symbols and indices are defined as follows:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$alkyl, $(C_2-C_4)$alkenyl, $(C_2-C_4)$alkynyl, $(C_1-C_4)$ haloalkyl, $(C_2-C_4)$haloalkenyl, $(C_1-C_4)$alkylcarbamoyl-$(C_1-C_4)$alkyl, $(C_2-C_4)$alkenylcarbamoyl-$(C_1-C_4)$alkyl, $(C_1-C_4)$alkoxy-$(C_1-C_4)$alkyl, dioxolanyl-$(C_1-C_4)$ alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active ingredients of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9) ((RS)-1-dichloroacetyl-3,3,8a-trimethylperhydropyrrolo [1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-acylsulfonamides of the formula (S4) and salts thereof, (S4)

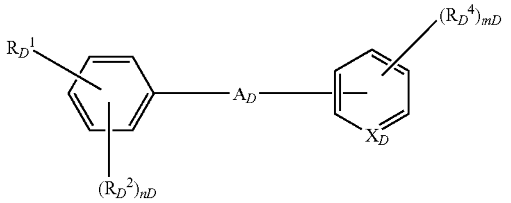

in which the symbols and indices are defined as follows:

$A_D$ is $SO_2—NR_D^3—CO$ or $CO—NR_D^3—SO_2$ $X_D$ is CH or N;

$R_D^1$ is $CO—NR_D^5R_D^6$ or $NHCO—R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group consisting of nitrogen, oxygen and sulfur, where the seven latter radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three latter radicals are substituted by $v_D$ radicals from the group consisting of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

among these, preference is given to compounds of the N-acylsulfonamide type, for example of the formula (S4a) below, which are known, for example, from WO-A-97/45016

($S4^a$)

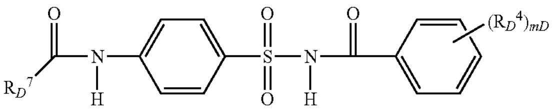

in which $R_D^7$ is $(C_1-C_6)$-alkyl, $(C_3-C_6)$-cycloalkyl, where the 2 latter radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$;

$m_D$ is 1 or 2;

$v_D$ is 0, 1, 2 or 3;

and also acylsulfamoylbenzamides, for example of the formula ($S4^b$) below, which are known, for example, from WO-A-99/16744, ($S4^b$)

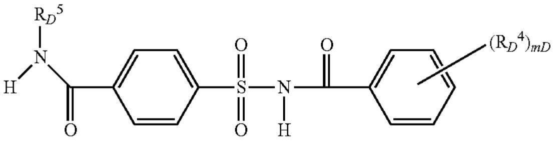

e.g. those in which $R_D^5$=cyclopropyl and $(R_D^4)$=2-OMe ("cyprosulfamide", S4-1), $R_D^5$=cyclopropyl and ($R_D^4$)=5-Cl-2-OMe (S4-2),
$R_D^5$=ethyl and ($R_D^4$)=2-OMe (S4-3),
$R_D^5$=isopropyl and ($R_D^4$)=5-Cl-2-OMe (S4-4) and
$R_D^5$=isopropyl and ($R_D^4$)=2-OMe (S4-5)
and also
compounds of the N-acylsulfamoylphenylurea type of the formula ($S4^c$), which are known, for example, from EP-A-365484, ($S4^c$)

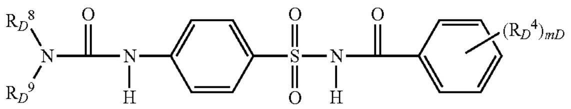

in which
$R_D^8$ and $R_D^9$ are independently hydrogen, ($C_1$-$C_8$)-alkyl, ($C_3$-$C_8$)-cycloalkyl, ($C_3$-$C_6$)-alkenyl, ($C_3$-$C_6$)-alkynyl,
$R_D^4$ is halogen, ($C_1$-$C_4$)-alkyl, ($C_1$-$C_4$)-alkoxy, $CF_3$,
$m_D$ is 1 or 2;
for example
1-[4-(N-2-methoxybenzoylsulfamoyl)phenyl]-3-methylurea ("metcamifen", S4-6),
1-[4-(N-2-methoxybenzoylsulfamoyl)phenyl]-3,3-dimethylurea,
1-[4-(N-4,5-dimethylbenzoylsulfamoyl)phenyl]-3-methylurea,
and also
N-phenylsulfonylterephthalamides of the formula ($S4^d$), which are known, for example, from CN 101838227, ($S4^d$)

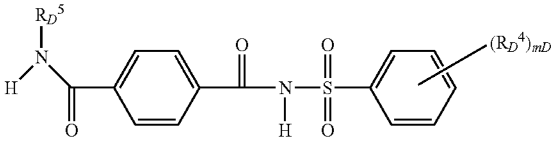

e.g. those in which
$R_D^4$ is halogen, ($C_1$-$C_4$)-alkyl, ($C_1$-$C_4$)-alkoxy, $CF_3$;
$m_D$ is 1 or 2;
$R_D^5$ is hydrogen, ($C_1$-$C_6$)-alkyl, ($C_3$-$C_6$)-cycloalkyl, ($C_2$-$C_6$)-alkenyl, ($C_2$-$C_6$)-alkynyl, ($C_5$-$C_6$)-cycloalkenyl.

S5) Active ingredients from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856, (S7)

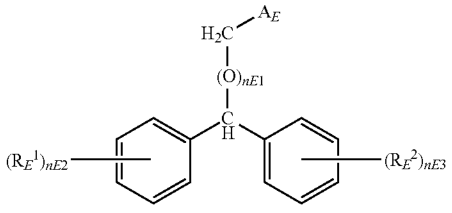

in which the symbols and indices are defined as follows:
$R_E^1$, $R_E^2$ are independently halogen, ($C_1$-$C_4$)-alkyl, ($C_1$-$C_4$)-alkoxy, ($C_1$-$C_4$)-haloalkyl, ($C_1$-$C_4$)-alkylamino, di-($C_1$-$C_4$)-alkylamino, nitro;
$A_E$ is $COOR_E^3$ or $COSR_E^4$
$R_E^3$, $R_E^4$ are independently hydrogen, ($C_1$-$C_4$)-alkyl, ($C_2$-$C_6$)-alkenyl, ($C_2$-$C_4$)-alkynyl, cyanoalkyl, ($C_1$-$C_4$)-haloalkyl, phenyl, nitrophenyl, benzyl, halobenzyl, pyridinylalkyl and alkylammonium,
$n_E^1$ is 0 or 1
$n_E^2$, $n_E^3$ are independently 0, 1 or 2,
preferably:
diphenylmethoxyacetic acid,
ethyl diphenylmethoxyacetate,
methyl diphenylmethoxyacetate (CAS reg. no. 41858-19-9) (57-1).

S8) Compounds of the formula (S8), as described in WO-A-98/27049,
in which (S8)

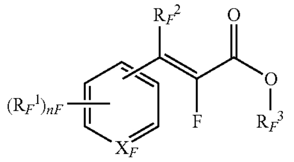

$X_F$ is CH or N,
$n_F$ in the case that $X_F$=N is an integer from 0 to 4 and in the case that $X_F$=CH is an integer from 0 to 5,
$R_F^1$ is halogen, ($C_1$-$C_4$)-alkyl, ($C_1$-$C_4$)-haloalkyl, ($C_1$-$C_4$)-alkoxy, ($C_1$-$C_4$)-haloalkoxy, nitro, ($C_1$-$C_4$)-alkylthio, ($C_1$-$C_4$)-alkylsulfonyl, ($C_1$-$C_4$)-alkoxycarbonyl, optionally substituted phenyl, optionally substituted phenoxy,
$R_F^2$ is hydrogen or ($C_1$-$C_4$)-alkyl,
$R_F^3$ is hydrogen, ($C_1$-$C_8$)-alkyl, ($C_2$-$C_4$)-alkenyl, ($C_2$-$C_4$)-alkynyl or aryl, where each of the abovementioned carbon-containing radicals is unsubstituted or substituted by one or more, preferably up to three identical or different radicals from the group consisting of halogen and alkoxy; or salts thereof,
preferably compounds in which
$X_F$ is CH,
$n_F$ is an integer from 0 to 2,
$R_F^1$ is halogen, ($C_1$-$C_4$)-alkyl, ($C_1$-$C_4$)-haloalkyl, ($C_1$-$C_4$)-alkoxy, ($C_1$-$C_4$)-haloalkoxy,
$R_F^2$ is hydrogen or ($C_1$-$C_4$)-alkyl,
$R_F^3$ is hydrogen, ($C_1$-$C_8$)-alkyl, ($C_2$-$C_4$)-alkenyl, ($C_2$-$C_4$)-alkynyl or aryl, where each of the abovementioned carbon-containing radicals is unsubstituted or substituted by one or more, preferably up to three identical or different radicals from the group consisting of halogen and alkoxy, or salts thereof.

S9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the formulae ($S10^a$) or ($S10^b$) as described in WO-A-2007/023719 and WO-A-2007/023764

($S10^a$)

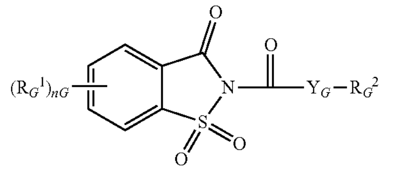

($S10^b$)

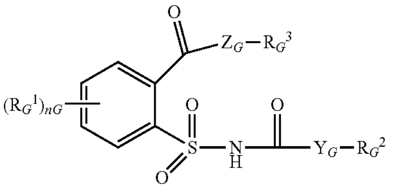

in which $R_G^1$ is halogen, $(C_1\text{-}C_4)$-alkyl, methoxy, nitro, cyano, $CF_3$, $OCF_3$, $Y_G$, $Z_G$ independently of one another represent O or S, $n_G$ is an integer from 0 to 4, $R_G^2$ is $(C_1\text{-}C_{16})$-alkyl, $(C_2\text{-}C_6)$-alkenyl, $(C_3\text{-}C_6)$-cycloalkyl, aryl; benzyl, halobenzyl, $R_G^3$ is hydrogen or $(C_1\text{-}C_6)$-alkyl.

S11) Active ingredients of the oxyimino compounds type (S11), which are known as seed-dressing agents, for example "oxabetrinil" ((Z)-1,3-dioxolan-2-ylmethoxyimino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino (phenyl)acetonitrile) (S11-3), which is known as a seed-dressing safener for millet/sorghum against metolachlor damage.

S12) Active ingredients from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against alachlor and metolachlor damage, "CL 304415" (CAS Reg. No. 31541-57-8)

(4-carboxy-3,4-dihydro-2H-1-benzopyran-4-acetic acid) (S13-4) from American Cyanamid, which is known as a safener for corn against damage by imidazolinones, "MG 191" (CAS Reg. No. 96420-72-3) (2-dichloromethyl-2-methyl-1,3-dioxolane) (S13-5) from Nitrokemia, which is known as a safener for corn, "MG 838" (CAS Reg. No. 133993-74-5)

(2-propenyl 1-oxa-4-azaspiro[4.5]decane-4-carbodithioate) (S13-6) from Nitrokemia, "disulfoton" (0,0-diethyl S-2-ethylthioethyl phosphorodithioate) (S13-7), "dietholate" (0,0-diethyl O-phenyl phosphorothioate) (S13-8), "mephenate" (4-chlorophenyl methylcarbamate) (S13-9).

S14) Active ingredients which, in addition to herbicidal action against harmful plants, also have safener action on crop plants such as rice, for example "dimepiperate" or "MY 93" (S-1-methyl 1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC 940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof (S15)

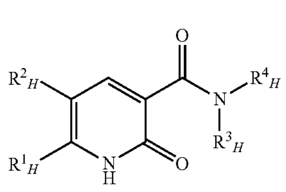

as described in WO-A-2007/131861 and WO-A-2008/131860 in which $R_H^1$ is a $(C_1\text{-}C_6)$-haloalkyl radical and $R_H^2$ is hydrogen or halogen and $R_H^3$, $R_H^4$ are independently hydrogen, $(C_1\text{-}C_{16})$-alkyl, $(C_2\text{-}C_{16})$-alkenyl or $(C_2\text{-}C_{16})$-alkynyl, where each of the 3 latter radicals is unsubstituted or substituted by one or more radicals from the group of halogen, hydroxyl, cyano, $(C_1\text{-}C_4)$-alkoxy, $(C_1\text{-}C_4)$-haloalkoxy, $(C_1\text{-}C_4)$-alkylthio, $(C_1\text{-}C_4)$-alkylamino, di[$(C_1\text{-}C_4)$-alkyl]amino, [$(C_1\text{-}C_4)$-alkoxy]carbonyl, [$(C_1\text{-}C_4)$-haloalkoxy]carbonyl, $(C_3\text{-}C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring, where each of the 4 latter radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly attached nitrogen atom represent a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichloro-ethyl).

Particularly preferred safeners are mefenpyr-diethyl, cyprosulfamide, isoxadifen-ethyl, cloquintocet-mexyl, benoxacor, dichlormid and metcamifen.

Wettable powders are preparations uniformly dispersible in water which, in addition to the active ingredient and apart from a diluent or inert substance, also comprise surfactants of ionic and/or nonionic type (wetting agent, dispersant), e.g. polyethoxylated alkylphenols, polyethoxylated fatty alcohols, polyethoxylated fatty amines, fatty alcohol poly glycolethersulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solids, for example talc, natural clays, such as kaolin, bentonite and pyrophyllite, or diatomaceous earth.

Suspension concentrates may be water- or oil-based. They may be produced, for example, by wet-grinding by means of commercial bead mills and optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto granular inert material capable of adsorption or by applying active ingredient concentrates to the surface of carrier substances, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1% to 99% by weight, especially 0.1% to 95% by weight, of compounds of the invention. In wettable powders, the active ingredient concentration is, for example, about 10% to 90% by weight, the remainder to 100% by weight consisting of customary formulation constituents. In emulsifiable concentrates, the active ingredient concentration may be about 1% to 90% and preferably 5% to 80% by weight. Formulations in the form of dusts comprise 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active ingredient is in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix.

For application, the formulations in the commercial form are diluted if appropriate in a customary manner, for example with water in the case of wettable powders, emulsifiable concentrates, dispersions and water-dispersible granules. Preparations in dust form, granules for soil application or granules for scattering and sprayable solutions are not normally diluted further with other inert substances prior to application.

The required application rate of the compounds of the formula (I) and their salts varies according to the external conditions such as, inter alia, temperature, humidity and the type of herbicide used. It can vary within wide limits, for example between 0.001 and 10.0 kg/ha or more of active substance, but it is preferably between 0.005 and 5 kg/ha, more preferably in the range of from 0.01 to 1.5 kg/ha, more preferably in the range of from 0.05 to 1 kg/ha. This applies both to pre-emergence and to post-emergence application.

A carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture. Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. It is likewise possible to use mixtures of such carriers. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Suitable liquefied gaseous extenders or carriers are liquids which are gaseous at standard temperature and under atmospheric pressure, for example aerosol propellants such as halogenated hydrocarbons, or else butane, propane, nitrogen and carbon dioxide.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins, and synthetic phospholipids. Further additives may be mineral and vegetable oils.

When the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The compositions of the invention may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes. In general, the compositions and formulations of the invention contain between 0.05% and 99% by weight, 0.01% and 98% by weight, preferably between 0.1% and 95% by weight, more preferably between 0.5% and 90% active ingredient, most preferably between 10 and 70 percent by weight. The active ingredients or compositions of the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, sprayable powders, soluble powders, dusts and granules, water-soluble granules or tablets, water-soluble powders for the treatment of seed, wettable powders, natural products and synthetic substances impregnated with active ingredient, and also microencapsulations in polymeric substances and in coating materials for seed, and also ULV cold-fogging and warm-fogging formulations.

The formulations mentioned can be produced in a manner known per se, for example by mixing the active ingredients with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The compositions of the invention include not only formulations which are already ready for use and can be deployed with a suitable apparatus onto the plant or the seed, but also commercial concentrates which have to be diluted with water prior to use.

The active ingredients of the invention may be present as such or in their (commercial standard) formulations, or else in the use forms prepared from these formulations as a mixture with other (known) active ingredients, such as insecticides, attractants, sterilants, bactericides, acaricides, nematicides, fungicides, growth regulators, herbicides, fertilizers, safeners or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

One of the advantages of the present invention is that the particular systemic properties of the inventive active ingredients and compositions mean that treatment of the seed with these active ingredients and compositions protects not only the seed itself but also the resulting plants after emergence from phytopathogenic fungi. In this way, the immediate treatment of the crop at the time of sowing or shortly thereafter can be dispensed with.

It is likewise considered to be advantageous that the inventive active ingredients or compositions can especially also be used for transgenic seed, in which case the plant which grows from this seed is capable of expressing a protein which acts against pests. The treatment of such seed with the inventive active ingredients or compositions, merely through the expression of the protein, for example an insecticidal protein, can result in control of certain pests. Surprisingly, a further synergistic effect can be observed in this case, which additionally increases the effectiveness for protection against attack by pests.

The compositions of the invention are suitable for protection of seed of any plant variety which is used in agriculture, in the greenhouse, in forests or in horticulture and viticulture. In particular, this is the seed of cereals (such as wheat, barley, rye, triticale, sorghum/millet and oats), corn, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), corn and rice is of particular importance.

As also described below, the treatment of transgenic seed with the active ingredients or compositions of the invention is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, when treating the seed, it has to be ensured that the amount of the composition of the invention and/or further additives applied to the seed is chosen such that the germination of the seed is not impaired and the plant which arises therefrom is not damaged. This has to be ensured particularly in the case of active ingredients which can exhibit phytotoxic effects at certain application rates.

The compositions of the invention can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272,417 A, 4,245,432 A, 4,808,430, 5,876,739, U.S. 2003/0176428 A1, WO 2002/080675 A1, WO 2002/028186 A2.

The active ingredients which can be used in accordance with the invention can be converted to the customary seed-dressing formulations, such as solutions, emulsions, suspensions, powders, foams, slurries or other coating compositions for seed, and also ULV formulations.

These formulations are produced in a known manner, by mixing the active ingredients with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active ingredients. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active ingredients. Preference can be given to using nonionic or anionic dispersants or mixtures of nonionic or anionic dispersants. Suitable nonionic dispersants include especially ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances usable for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

The seed-dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For the treatment of seed with the seed-dressing formulations usable in accordance with the invention or with the preparations prepared therefrom by addition of water, useful equipment is all mixing units usable customarily for seed dressing. Specifically, the seed dressing procedure is to place the seed into a mixer, to add the particular desired amount of seed-dressing formulations, either as such or after prior dilution with water, and to mix them until the formulation is distributed homogeneously on the seed. If appropriate, this is followed by a drying operation.

The active ingredients of the invention, given good plant compatibility, favorable homeotherm toxicity and good environmental compatibility, are suitable for protection of plants and plant organs, for increasing harvest yields, and for improving the quality of the harvested crop. They can preferably be used as crop protection agents. They are active against normally sensitive and resistant species and also against all or specific stages of development.

Plants which can be treated in accordance with the invention include the following main crop plants: corn, soybean, cotton, *Brassica* oil seeds such as *Brassica napus* (e.g. Canola), *Brassica rapa*, *B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and chinese cabbage), Leguminosae sp. (for example peanuts, peas, and beans—for example common beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term “parts” or “parts of plants” or “plant parts” has been explained above. Particular preference is given in accordance with the invention to treating plants of the respective commercially customary plant cultivars or those that are in use. Plant cultivars are understood to mean plants having new properties (“traits”) which have been grown by conventional breeding, by mutagenesis or by recombinant DNA techniques. They may be cultivars, varieties, biotypes and genotypes.

The treatment method of the invention can be used for the treatment of genetically modified organisms (GMOs), e.g. plants or seeds. Genetically modified plants (or transgenic plants) are plants in which a heterologous gene has been stably integrated into the genome. The term “heterologous gene” means essentially a gene which is provided or assembled outside the plant and which, upon introduction into the nuclear genome, the chloroplast genome or the mitochondrial genome, imparts to the transformed plant novel or improved agronomical or other traits because it expresses a protein or polypeptide of interest or another gene which is present in the plant, or other genes which are present in the plant are down-regulated or switched off (for example by means of antisense technology, co-suppression technology or RNAi technology [RNA interference]). A heterologous gene that is located in the genome is also called a transgene. A transgene that is defined by its specific presence in the plant genome is called a transformation or transgenic event.

Depending on the plant species or plant cultivars, their location and growth conditions (soils, climate, vegetation period, diet), the inventive treatment may also result in superadditive (“synergistic”) effects. For example, the following effects which exceed the effects actually to be expected are possible: reduced application rates and/or widened spectrum of activity and/or increased efficacy of the active ingredients and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf color, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect on plants. Accordingly, they are suitable for mobilizing the defense system of the plant against attack by unwanted phytopathogenic fungi and/or microorganisms and/or viruses. This may possibly be one of the reasons for the enhanced activity of the inventive combinations for example against fungi. Plant-fortifying (resistance-inducing) substances shall be understood to mean, in the present context, also those substances or combinations of substances which are capable of stimulating the defense system of plants in such a way that, when subsequently inoculated with unwanted phytopathogenic fungi, the plants treated display a substantial degree of resistance to these unwanted phytopathogenic fungi. The inventive substances can therefore be used for protection of plants from attack by the pathogens mentioned within a certain period of time after treatment. The period within which protection is achieved generally extends for from 1 to 10 days, preferably 1 to 7 days, after the treatment of the plants with the active ingredients.

Plants and plant cultivars which are preferably treated in accordance with the invention include all plants which have genetic material which imparts particularly advantageous, useful traits to these plants (whether obtained by breeding and/or biotechnological means).

Plants and plant cultivars which are likewise preferably treated in accordance with the invention are resistant to one or more biotic stress factors, meaning that these plants have a better defense against animal and microbial pests, such as nematodes, insects, mites, phytopathogenic fungi, bacteria, viruses and/or viroids.

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants and plant cultivars which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or lack of shade.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including but not limited to early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and oil composition, nutritional value, reduction in antinutritional compounds, improved processability and better storage stability.

Plants that may be treated according to the invention are hybrid plants that already express the characteristics of heterosis, or hybrid effect, which results generally in higher yield, vigour, better health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science, 221, 370-371), the CP4 gene of the bacterium *Agrobacterium* sp. (Barry et al., 1992, Curr. Topics Plant Physiol. 7, 139-145), the genes encoding a *petunia* EPSPS (Shah et al., 1986, Science 233, 478-481), a tomato EPSPS (Gasser et al., 1988, J. Biol. Chem. 263, 4280-4289) or an *Eleusine* EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally-occurring mutations of the abovementioned genes. Plants which express EPSPS genes which impart glyphosate tolerance have been described. Plants which express other genes which impart glyphosate tolerance, for example decarboxylase genes, have been described.

Other herbicide-resistant plants are for example plants made tolerant to herbicides inhibiting the enzyme glutamine synthase, such as bialaphos, phosphinothricin or glufosinate. Such plants can be obtained by expressing an enzyme detoxifying the herbicide or a mutant of the glutamine synthase enzyme that is resistant to inhibition. One example of such an effective detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite inhibition of the native HPPD enzyme by the HPPD inhibitor. Such plants are described in WO 99/34008 and WO 02/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyloxy (thio)benzoates, and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulfonylurea-tolerant plants and imidazolinone-tolerant plants has been described. Further sulfonylurea- and imidazolinone-tolerant plants have also been described.

Further plants tolerant to imidazolinone and/or sulfonylurea can be obtained by induced mutagenesis, by selection in cell cultures in the presence of the herbicide or by mutation breeding (cf., for example, for soya beans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding the following:

1) an insecticidal crystal protein from *Bacillus thuringiensis* or an insecticidal portion thereof, such as the insecticidal crystal proteins compiled by Crickmore et al. (Microbiology and Molecular Biology Reviews 1998, 62, 807-813), updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, for example proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 2007/107302), or those proteins encoded by synthetic genes as described in U.S. patent application Ser. No. 12/249,016; or
2) a crystal protein from *Bacillus thuringiensis* or a portion thereof which is insecticidal in the presence of a second crystal protein other than *Bacillus thuringiensis* or a portion thereof, such as the binary toxin made up of the Cy34 and Cy35 crystal proteins (Nat. Biotechnol. 2001, 19, 668-72; Applied Environm. Microbiol. 2006, 71, 1765-1774) or the binary toxin made up of the Cry1A or Cry1F proteins and the Cry2Aa or Cry2Ab or Cry2Ae proteins (U.S. patent application Ser. No. 12/214,022 and EP08010791.5); or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 5) to 7) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102; or 9) a secreted protein from *Bacillus thuringiensis* or *Bacillus cereus* which is insecticidal in the presence of a crystal protein from *Bacillus thuringiensis*, such as the binary toxin made up of the proteins VIP3 and Cry1A or Cry1F (U.S. patent applications 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5); or 10) a protein according to point 9) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein).

Of course, insect-resistant transgenic plants, as used herein, also include any plant comprising a combination of genes encoding the proteins of any one of the abovementioned classes 1 to 10. In one embodiment, an insect-resistant plant contains more than one transgene encoding a protein of any one of the above classes 1 to 10, to expand the range of the target insect species affected or to delay insect resistance development to the plants, by using different proteins insecticidal to the same target insect species but having a different mode of action, such as binding to different receptor binding sites in the insect.

In the present context, an "insect-resistant transgenic plant" additionally includes any plant containing at least one transgene comprising a sequence for production of double-stranded RNA which, after consumption of food by an insect pest, prevents the growth of this pest.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific components of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behavior, the gelling strength, the starch granule size and/or the starch granule morphology, is changed in comparison with the synthesized starch in wild-type plant cells or plants, so that this modified starch is better suited to specific applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;

b) plants, such as cotton plants, which contain an altered form of rsw2 or rsw3 homologous nucleic acids, such as cotton plants with an increased expression of sucrose phosphate synthase;

c) plants, such as cotton plants, with increased expression of sucrose synthase;

d) plants, such as cotton plants, wherein the timing of the plasmodesmatal gating at the base of the fiber cell is altered, for example through downregulation of fiber-selective β-1,3-glucanase;

e) plants, such as cotton plants, which have fibres with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which nonregulated status is being requested.

APHIS documents: Various documents which have been published by APHIS with regard to the petition or can be obtained from APHIS on request.

Particularly useful transgenic plants which can be treated in accordance with the invention are plants which comprise one or more genes which code for one or more toxins, for example the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned include maize varieties, cotton varieties and soya bean varieties which are available under the following trade names: Roundup Ready® (tolerance to glyphosates, for example corn, cotton, soya beans), Liberty Link® (tolerance to phosphinothricin, for example oilseed rape), IMI® (tolerance to imidazolinone) and SCS® (tolerance to sulfonylurea), for example corn. Herbicide-resistant plants (plants bred in a conventional manner for herbicide tolerance) which may be mentioned include the varieties sold under the name Clearfield® (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gmc.org/index.php?evidcode=&hstIDXCode=&gType=&AbbrCode=&atCode=&stCode=&coIDCode=&action=gm_crop_database&mode=Submit).

The active ingredients or compositions of the invention can also be used in the protection of materials, for protection of industrial materials against attack and destruction by unwanted microorganisms, for example fungi and insects.

In addition, the compounds of the invention can be used as antifouling compositions, alone or in combinations with other active ingredients.

Industrial materials in the present context are understood to mean non-living materials which have been prepared for use in industry. For example, industrial materials which are to be protected by active ingredients of the invention from microbial alteration or destruction may be adhesives, sizes, paper, wallpaper and cardboard, textiles, carpets, leather, wood, paints and plastic articles, cooling lubricants and other materials which can be infected with or destroyed by microorganisms. The range of materials to be protected also includes parts of production plants and buildings, for example cooling water circuits, cooling and heating systems, and ventilation and air conditioning systems, which may be impaired by the proliferation of microorganisms. Industrial materials within the scope of the present invention preferably include adhesives, sizes, paper and cardboard, leather, wood, paints, cooling lubricants and heat transfer fluids, more preferably wood. The active ingredients or compositions of the invention may prevent adverse effects, such as rotting, decay, discoloration, decoloration or formation of mold. In addition, the compounds of the invention can be used for protection of objects which come into contact with saltwater or brackish water, especially hulls, screens, nets, buildings, moorings and signaling systems, from fouling.

The method of the invention for controlling unwanted fungi can also be employed for protecting storage goods. "Storage goods" are understood to mean natural substances of vegetable or animal origin or processing products thereof of natural origin, for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The active ingredients of the invention may prevent adverse effects, such as rotting, decay, discoloration, decoloration or formation of mold.

Non-limiting examples of pathogens of fungal diseases which can be treated in accordance with the invention include: Diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator*; diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia recondita* or *Puccinia triticina; Uromyces* species, for example *Uromyces appendiculatus*; diseases caused by pathogens from the group of the Oomycetes, for example *Bremia* species, for example *Bremia lactucae; Peronospora* species, for example *Peronospora pisi* or *P. brassicae; Phytophthora* species, for example *Phytophthora infestans*; Plasmopara species, for example Plasmopara viticola; *Pseudoperonospora* species, for example *Pseudoperonospora humuli* or *Pseudoperonospora cubensis; Pythium* species, for example *Pythium ultimum*; leaf blotch diseases and leaf wilt diseases caused, for example, by *Alternaria* species, for example *Alternaria solani; Cercospora* species, for example *Cercospora beticola; Cladosporium* species, for example *Cladosporium cucumerinum; Cochliobolus* species, for example *Cochliobolus sativus* (conidia form: *Drechslera*, syn: *Helminthosporium*); *Colletotrichum* species, for example *Colletotrichum* lindemuthanium; *Cycloconium* species, for example *Cycloconium* oleaginum; *Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola* and *M. fijiensis; Phaeosphaeria* species, for example *Phaeosphaeria nodorum; Pyrenophora* species, for example *Pyrenophora teres; Ramularia* species, for example *Ramularia collo-cygni; Rhynchosporium* species, for example *Rhynchosporium secalis; Septoria* species, for example *Septoria apii; Typhula* species, for example *Typhula incarnata; Venturia* species, for example *Venturia inaequalis*; root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, for example *Rhizoctonia solani; Tapesia* species, for example *Tapesia acuformis; Thielaviopsis* species, for example *Thielaviopsis basicola*; ear and panicle diseases (including corn crops) caused, for example, by *Alternaria* species, for example *Alternaria* spp.; *Aspergillus* species, for example *Aspergillus flavus; Cladosporium* species, for example *Cladosporium* spp.; *Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum*; diseases caused by smut fungi, for example *Sphacelotheca* species, for example *Sphacelotheca reiliana; Tilletia* species, for example *Tilletia caries, T. controversa; Urocystis* species, for example *Urocystis occulta; Ustilago* species, for example *Ustilago nuda, U. nuda tritici*; fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum; Verticillium* species, for example *Verticillium alboatrum*; seed- and soil-borne rot and wilt diseases, and also diseases of seedlings, caused, for example, by *Fusarium* species, for example *Fusarium culmorum; Phytophthora* species, for example *Phytophthora cactorum; Pythium* species, for example *Pythium ultimum; Rhizoctonia* species, for example *Rhizoctonia solani; Sclerotium* species, for example *Sclerotium rolfsii*; cancerous diseases, galls and witches' broom caused, for example, by *Nectria* species, for example *Nectria galligena;* wilt diseases caused, for example, by *Monilinia* species, for example *Monilinia laxa;* deformations of leaves, flowers and fruits caused, for example, by *Taphrina* species, for example *Taphrina deformans*; degenerative diseases of woody plants caused, for example, by Esca species, for example Phaemoniella clamydospora and *Phaeoacremonium aleophilum* and *Fomitiporia mediterranea*; diseases of flowers and seeds caused, for example, by *Botrytis* species, for example *Botrytis cinerea*; diseases of plant tubers caused, for example, by *Rhizoctonia* species, for example *Rhizoctonia solani; Helminthosporium* species, for example *Helminthosporium solani*; diseases caused by bacterial pathogens, for example *Xanthomonas* species, for example *Xanthomonas campestris* pv. *oryzae; Pseudomonas* species, for example *Pseudomonas syringae* pv. lachrymans; *Erwinia* species, for example *Erwinia amylovora.*

The following diseases of soya beans can be controlled with preference:

Fungal diseases on leaves, stems, pods and seeds caused, for example, by *alternaria* leaf spot (*Alternaria* spec. atrans tenuissima), Anthracnose (*Colletotrichum* gloeosporoides *dematium* var. *truncatum*), brown spot (*Septoria glycines*), *Cercospora* leaf spot and blight (*Cercospora kikuchii*), *choanephora* leaf blight (*Choanephora infundibulifera* trispora (Syn.)), *dactuliophora* leaf spot (*Dactuliophora glycines*), downy mildew (*Peronospora manshurica*), *Drechslera* blight (*Drechslera* glycini), frogeye leaf spot (*Cercospora sojina*), *leptosphaerulina* leaf spot (*Leptosphaerulina trifolii*), *Phyllosticta* leaf spot (*Phyllosticta* sojaecola), pod and stem blight (*Phomopsis sojae*), powdery mildew (*Microsphaera diffusa*), *Pyrenochaeta* leaf spot (*Pyrenochaeta* glycines), *Rhizoctonia* aerial, foliage, and web blight (*Rhizoctonia solani*), rust (*Phakopsora pachyrhizi, Phakopsora meibomiae*), scab (*Sphaceloma* glycines), *Stemphylium* leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *Fusarium* blight or wilt, root rot, and pod and collar rot (*Fusarium oxysporum, Fusarium orthoceras, Fusarium semitectum, Fusarium equiseti*), *Mycoleptodiscus* root rot (*Mycoleptodiscus terrestris*), *Neocosmospora* (*Neocosmospora vasinfecta*), pod and stem blight (*Diaporthe phaseolorum*), stem canker (*Diaporthe phaseolorum* var. *caulivora*), *Phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *Rhizoctonia* root rot, stem decay, and damping-off (*Rhizoctonia solani*), *Sclerotinia* stem decay (*Sclerotinia sclerotiorum*), *Sclerotinia* southern blight (*Sclerotinia rolfsii*), *Thielaviopsis* root rot (*Thielaviopsis basicola*).

Microorganisms capable of degrading or altering the industrial materials include, for example, bacteria, fungi, yeasts, algae and slime organisms. The active ingredients of the invention preferably act against fungi, especially molds, wood-discoloring and wood-destroying fungi (Basidiomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora* puetana; *Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Escherichia*, such as *Escherichia coli; Pseudomonas*, such as *Pseudomonas aeruginosa; Staphylococcus*, such as *Staphylococcus aureus.*

In addition, the active ingredients of the invention also have very good antimycotic activity. They have a very broad antimycotic activity spectrum, in particular against dermatophytes and yeasts, molds and diphasic fungi, (for example against *Candida* species, such as *Candida albicans, Can-*

*dida glabrata*), and *Epidermophyton floccosum, Aspergillus* species, such as *Aspergillus niger* and *Aspergillus fumigatus, Trichophyton* species, such as *Trichophyton mentagrophytes*, Microsporon species such as Microsporon canis and audouinii. The enumeration of these fungi in no way constitutes a restriction of the mycotic spectrum that can be controlled, and is merely of illustrative character.

The active ingredients of the invention can therefore be used both in medical and in non-medical applications.

If appropriate, the compounds of the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). They can, as the case may be, also be used as intermediates or precursors for the synthesis of further active ingredients.

The examples which follow illustrate the invention.

A. CHEMICAL EXAMPLES

Synthesis of 4-bromo-2-chloro-$N^3$-ethyl-$N^1$-(1-methyl-1H-tetrazol-5-yl)isophthalamide (Example No. 1-178)

Step 1: Preparation of 6-bromo-2-chloro-3-(methoxycarbonyl)benzoic Acid 1.47 g (5.29 mmol) of methyl 4-bromo-2-chloro-3-formylbenzoate was initially charged 100 ml of acetone. A solution of 636 mg (6.35 mmol) of chromium(VI) oxide in dilute sulfuric acid ($H_2O$:$H_2SO_4$ 3:1) was slowly added dropwise. The mixture was warmed to room temperature and stirred for 12 hours. Thereafter, a little isopropanol was added and the mixture was concentrated under reduced pressure. The residue was taken up in water and extracted with ethyl acetate, and the organic phase was dried and concentrated to dryness. 1.23 g of 6-bromo-2-chloro-3-(methoxycarbonyl)benzoic acid was obtained.

$^1$H-NMR (400 MHz, DMSO-$d_6$): δ=14.30 (br s, 1H); 7.82 (d, 1H); 7.77 (d, 1H); 3.88 (s, 3H).

Step 2: Preparation of methyl 4-bromo-2-chloro-3-(ethylcarbamoyl)benzoate

To an initial charge of 753 mg (2.56 mmol) of 6-bromo-2-chloro-3-(methoxycarbonyl)benzoic acid in 30 ml dichloromethane were added catalytic amounts of dimethylformamide. Thereafter, at room temperature, 490 mg (3.84 mmol) of oxalyl chloride was added and the mixture was stirred for a further 1 hour. The mixture was concentrated to dryness, and the residue was coevaporated with toluene. The resulting residue was taken up in 5 ml of dichloromethane. To an initial charge of 1.9 ml (3.84 mmol) of a 2.5M solution of ethylamine in tetrahydrofuran and 663 mg (5.13 mmol) of Hünig's base in 50 ml dichloromethane was added, at 0° C., the acid chloride solution. The mixture was stirred at room temperature for a further 4 hours. Thereafter, 100 ml of dichloromethane was added and the mixture was washed with aqueous 2M hydrochloric acid. The organic phase was dried and concentrated to dryness. 773 mg of methyl 4-bromo-2-chloro-3-(ethylcarbamoyl)benzoate was obtained.

$^1$H-NMR (400 MHz, DMSO-$d_6$): δ=8.68 (t, 1H); 7.77 (d, 1H); 7.69 (d, 1H); 3.87 (s, 3H); 3.28 (m, 2H); 1.12 (t, 3H).

Step 3: Preparation of 4-bromo-2-chloro-3-(ethylcarbamoyl)benzoic Acid

To 773 mg (2.41 mmol) of methyl 4-bromo-2-chloro-3-(ethylcarbamoyl)benzoate in 80 ml of methanol was added, at room temperature, 192 mg (4.82 mmol) of aqueous 1M sodium hydroxide solution. The mixture was stirred at 50° C. for 12 hours and then concentrated to dryness. The residue was taken up in a little water, and the solution was acidified by means of aqueous 2M hydrochloric acid and extracted with dichloromethane. The organic phase was dried and concentrated. 582 g of 4-bromo-2-chloro-3-(ethylcarbamoyl)benzoic acid was obtained.

$^1$H-NMR (400 MHz, DMSO-$d_6$): δ=13.69 (br s, 1H); 8.65 (t, 1H); 7.72 (d, 1H); 7.66 (d, 1H); 3.26 (m, 2H); 1.12 (t, 3H).

Step 4: Preparation of 4-bromo-2-chloro-$N^3$-ethyl-$N^1$-(1-methyl-1H-tetrazol-5-yl)isophthalamide To an initial charge of 189 mg (0.61 mmol) of 4-bromo-2-chloro-3-(ethylcarbamoyl)benzoic acid and 93.5 mg (0.92 mmol) of 5-amino-1-methyl-1H-tetrazole in 3 ml of pyridine was added, at room temperature, 155 mg (1.22 mmol) of oxalyl chloride. The mixture was stirred for a further 12 hours. Addition of 10 ml of water was followed by extraction with dichloromethane, and drying and concentration of the organic phases. The residue was purified by column chromatography (HPLC, C18, gradient: acetonitrile/water (++0.05% trifluoroacetic acid), 10/90→100/0 in 30 min). 66 mg of 4-bromo-2-chloro-$N^3$-ethyl-$N^1$-(1-methyl-1H-tetrazol-5-yl)isophthalamide was obtained (Example No. 1-178).

The examples listed in the tables below were prepared analogously to the methods mentioned above or can be obtained analogously to the methods mentioned above. These compounds are very particularly preferred.

The abbreviations used here mean:

Me=methyl Bu=butyl Et=ethyl Pr=propyl c=cyclo Ph=phenyl

TABLE 1

Inventive compounds of the general formula (I) in which Q is $Q^1$ and $R^x$ is methyl, and the other substituents have the definitions given below.

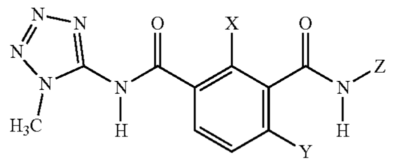

| No. | X | Y | Z |
|---|---|---|---|
| 1-1 | Me | F | Me |
| 1-2 | Me | F | Et |
| 1-3 | Me | F | c-Pr |
| 1-4 | Me | Cl | Me |
| 1-5 | Me | Cl | Et |
| 1-6 | Me | Cl | c-Pr |
| 1-7 | Me | Br | Me |
| 1-8 | Me | Br | Et |
| 1-9 | Me | Br | c-Pr |
| 1-10 | Me | I | Me |
| 1-11 | Me | I | Et |
| 1-12 | Me | I | c-Pr |
| 1-13 | Me | SMe | Me |
| 1-14 | Me | SMe | Et |
| 1-15 | Me | SMe | c-Pr |
| 1-16 | Me | S(O)Me | Me |
| 1-17 | Me | S(O)Me | Et |

TABLE 1-continued

Inventive compounds of the general formula (I) in which Q is $Q^1$ and $R^x$ is methyl, and the other substituents have the definitions given below.

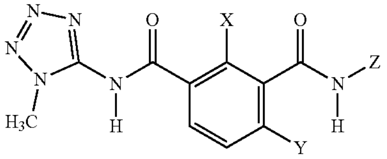

| No. | X | Y | Z |
|---|---|---|---|
| 1-18 | Me | S(O)Me | c-Pr |
| 1-19 | Me | $SO_2Me$ | Me |
| 1-20 | Me | $SO_2Me$ | Et |
| 1-21 | Me | $SO_2Me$ | c-Pr |
| 1-22 | Me | $SO_2Me$ | $CH_2$-c-Pr |
| 1-23 | Me | $SO_2Me$ | $CH_2CF_3$ |
| 1-24 | Me | $SO_2Me$ | $CH_2CHF_2$ |
| 1-25 | Me | $CF_3$ | Me |
| 1-26 | Me | $CF_3$ | Et |
| 1-27 | Me | $CF_3$ | c-Pr |
| 1-28 | Me | $CF_3$ | $CH_2$-c-Pr |
| 1-29 | Me | $CF_3$ | $CH_2CF_3$ |
| 1-30 | Me | $CF_3$ | $CH_2CHF_2$ |
| 1-31 | Me | $CF_3$ | CH(Me)-c-Pr |
| 1-32 | Me | $CF_3$ | Pr |
| 1-33 | Me | $CF_3$ | i-Pr |
| 1-34 | Me | $CF_3$ | $CH_2CH_2OMe$ |
| 1-35 | Me | $CF_3$ | $CH_2CH_2SMe$ |
| 1-36 | Me | $CF_3$ | $CH_2CN$ |
| 1-37 | Me | $CF_3$ | $CH_2$-(tetrahydrofuran-2-yl) |
| 1-38 | Me | $CF_3$ | $CH_2C(O)NMe_2$ |
| 1-39 | Me | $CF_3$ | Ph |
| 1-40 | Me | $CF_3$ | $CH_2$-(thien-2-yl) |
| 1-41 | Me | $CF_3$ | Oxetan-3-yl |
| 1-42 | Me | $CF_3$ | c-Bu |
| 1-43 | Me | $CF_3$ | c-Pentyl |
| 1-44 | Me | $CHF_2$ | Me |
| 1-45 | Me | $CHF_2$ | Et |
| 1-46 | Me | $CHF_2$ | c-Pr |
| 1-47 | Me | $CHF_2$ | $CH_2$-c-Pr |
| 1-48 | Me | $CHF_2$ | $CH_2CF_3$ |
| 1-49 | Me | $CHF_2$ | $CH_2CHF_2$ |
| 1-50 | Me | $C_2F_5$ | Me |
| 1-51 | Me | $C_2F_5$ | Et |
| 1-52 | Me | $C_2F_5$ | c-Pr |
| 1-53 | OMe | Cl | Me |
| 1-54 | OMe | Cl | Et |
| 1-55 | OMe | Cl | c-Pr |
| 1-56 | OMe | $CF_3$ | Me |
| 1-57 | OMe | $CF_3$ | Et |
| 1-58 | OMe | $CF_3$ | c-Pr |
| 1-59 | OMe | $CF_3$ | $CH_2$-c-Pr |
| 1-60 | OMe | $CF_3$ | $CH_2CF_3$ |
| 1-71 | OMe | $CF_3$ | $CH_2CHF_2$ |
| 1-72 | OMe | $CHF_2$ | Me |
| 1-73 | OMe | $CHF_2$ | Et |
| 1-74 | OMe | $CHF_2$ | c-Pr |
| 1-75 | OMe | $CHF_2$ | CH-c-Pr |
| 1-76 | OMe | $CHF_2$ | $CH_2CF_3$ |
| 1-77 | OMe | $CHF_2$ | $CH_2CHF_2$ |
| 1-78 | SMe | $SO_2Me$ | Me |
| 1-79 | SMe | $SO_2Me$ | Et |
| 1-80 | SMe | $SO_2Me$ | c-Pr |
| 1-81 | SMe | $CF_3$ | Me |
| 1-82 | SMe | $CF_3$ | Et |
| 1-83 | SMe | $CF_3$ | c-Pr |
| 1-84 | SMe | $CF_3$ | $CH_2$-c-Pr |
| 1-85 | SMe | $CF_3$ | $CH_2CF_3$ |
| 1-86 | SMe | $CF_3$ | $CH_2CHF_2$ |
| 1-87 | SMe | $CHF_2$ | Me |
| 1-88 | SMe | $CHF_2$ | Et |
| 1-89 | SMe | $CHF_2$ | c-Pr |
| 1-90 | SMe | $CHF_2$ | $CH_2$-c-Pr |
| 1-91 | SMe | $CHF_2$ | $CH_2CF_3$ |
| 1-92 | SMe | $CHF_2$ | $CH_2CHF_2$ |

TABLE 1-continued

Inventive compounds of the general formula (I) in which Q is $Q^1$ and $R^x$ is methyl, and the other substituents have the definitions given below.

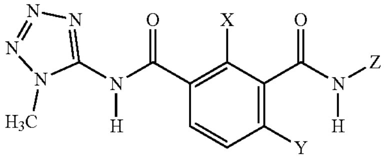

| No. | X | Y | Z |
|---|---|---|---|
| 1-93 | SEt | $CF_3$ | Me |
| 1-94 | SEt | $CF_3$ | Et |
| 1-95 | SEt | $CF_3$ | c-Pr |
| 1-96 | SEt | $CF_3$ | $CH_2$-c-Pr |
| 1-97 | SEt | $CF_3$ | $CH_2CF_3$ |
| 1-98 | SEt | $CF_3$ | $CH_2CHF_2$ |
| 1-99 | SEt | $CHF_2$ | Me |
| 1-100 | SEt | $CHF_2$ | Et |
| 1-101 | SEt | $CHF_2$ | c-Pr |
| 1-102 | SEt | $CHF_2$ | $CH_2$-c-Pr |
| 1-103 | SEt | $CHF_2$ | $CH_2CF_3$ |
| 1-104 | SEt | $CHF_2$ | $CH_2CHF_2$ |
| 1-105 | F | $CF_3$ | Me |
| 1-106 | F | $CF_3$ | Et |
| 1-107 | F | $CF_3$ | c-Pr |
| 1-108 | F | $CF_3$ | $CH_2$-c-Pr |
| 1-109 | F | $CF_3$ | $CH_2CF_3$ |
| 1-110 | F | $CF_3$ | $CH_2CHF_2$ |
| 1-111 | F | $CHF_2$ | Me |
| 1-112 | F | $CHF_2$ | Et |
| 1-113 | F | $CHF_2$ | c-Pr |
| 1-114 | F | $CHF_2$ | $CH_2$-c-Pr |
| 1-115 | F | $CHF_2$ | $CH_2CF_3$ |
| 1-116 | F | $CHF_2$ | $CH_2CHF_2$ |
| 1-117 | Cl | SMe | Me |
| 1-118 | Cl | SMe | Et |
| 1-119 | Cl | SMe | c-Pr |
| 1-120 | Cl | S(O)Me | Me |
| 1-121 | Cl | S(O)Me | Et |
| 1-122 | Cl | S(O)Me | c-Pr |
| 1-123 | Cl | $SO_2Me$ | Me |
| 1-124 | Cl | $SO_2Me$ | Et |
| 1-125 | Cl | $SO_2Me$ | c-Pr |
| 1-126 | Cl | $SO_2Me$ | $CH_2$-c-Pr |
| 1-127 | Cl | $SO_2Me$ | $CH_2CF_3$ |
| 1-128 | Cl | $SO_2Me$ | $CH_2CHF_2$ |
| 1-129 | Cl | $CF_3$ | Me |
| 1-130 | Cl | $CF_3$ | Et |
| 1-131 | Cl | $CF_3$ | c-Pr |
| 1-132 | Cl | $CF_3$ | $CH_2$-c-Pr |
| 1-133 | Cl | $CF_3$ | $CH_2CF_3$ |
| 1-134 | Cl | $CF_3$ | $CH_2CHF_2$ |
| 1-135 | Cl | $CF_3$ | CH(Me)-c-Pr |
| 1-136 | Cl | $CF_3$ | Pr |
| 1-137 | Cl | $CF_3$ | iPr |
| 1-138 | Cl | $CF_3$ | $CH_2CH_2OMe$ |
| 1-139 | Cl | $CF_3$ | $CH_2CH_2SMe$ |
| 1-140 | Cl | $CF_3$ | $CH_2CN$ |
| 1-141 | Cl | $CF_3$ | $CH_2$-(tetrahydrofuran-2-yl) |
| 1-142 | Cl | $CF_3$ | $CH_2C(O)NMe_2$ |
| 1-143 | Cl | $CF_3$ | Ph |
| 1-144 | Cl | $CF_3$ | $CH_2$-(thien-2-yl) |
| 1-145 | Cl | $CF_3$ | Oxetan-3-yl |
| 1-146 | Cl | $CF_3$ | cBu |
| 1-147 | Cl | $CHF_2$ | Me |
| 1-148 | Cl | $CHF_2$ | Et |
| 1-149 | Cl | $CHF_2$ | c-Pr |
| 1-150 | Cl | $CHF_2$ | $CH_2$-c-Pr |
| 1-151 | Cl | $CHF_2$ | $CH_2CF_3$ |
| 1-152 | Cl | $CHF_2$ | $CH_2CHF_2$ |
| 1-153 | Cl | $CHF_2$ | CH(Me)-c-Pr |
| 1-154 | Cl | $CHF_2$ | Pr |
| 1-155 | Cl | $CHF_2$ | iPr |
| 1-156 | Cl | $CHF_2$ | $CH_2CH_2OMe$ |
| 1-157 | Cl | $CHF_2$ | $CH_2CH_2SMe$ |

TABLE 1-continued

Inventive compounds of the general formula (I) in which Q is Q[1] and $R^x$ is methyl, and the other substituents have the definitions given below.

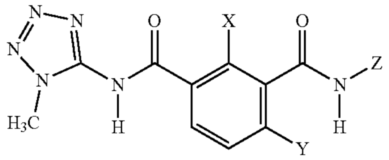

| No. | X | Y | Z |
|---|---|---|---|
| 1-158 | Cl | $CHF_2$ | $CH_2CN$ |
| 1-159 | Cl | $CHF_2$ | $CH_2$-(tetrahydrofuran-2-yl) |
| 1-160 | Cl | $CHF_2$ | $CH_2C(O)NMe_2$ |
| 1-161 | Cl | $CHF_2$ | Ph |
| 1-162 | Cl | $CHF_2$ | $CH_2$-(thien-2-yl) |
| 1-163 | Cl | $CHF_2$ | Oxetan-3-yl |
| 1-164 | Cl | $CHF_2$ | cBu |
| 1-165 | Cl | $C_2F_5$ | Me |
| 1-166 | Cl | $C_2F_5$ | Et |
| 1-167 | Cl | $C_2F_5$ | c-Pr |
| 1-168 | Cl | $C_2F_5$ | $CH_2$-c-Pr |
| 1-169 | Cl | $C_2F_5$ | $CH_2CF_3$ |
| 1-170 | Cl | $C_2F_5$ | $CH_2CHF_2$ |
| 1-171 | Cl | Cl | Me |
| 1-172 | Cl | Cl | Et |
| 1-173 | Cl | Cl | c-Pr |
| 1-174 | Cl | Cl | $CH_2$-c-Pr |
| 1-175 | Cl | Cl | $CH_2CF_3$ |
| 1-176 | Cl | Cl | $CH_2CHF_2$ |
| 1-177 | Cl | Br | Me |
| 1-178 | Cl | Br | Et |
| 1-179 | Cl | Br | c-Pr |
| 1-180 | Cl | Br | $CH_2$-c-Pr |
| 1-181 | Cl | Br | $CH_2CF_3$ |
| 1-182 | Cl | Br | $CH_2CHF_2$ |
| 1-183 | Cl | Br | CH(Me)-c-Pr |
| 1-184 | Cl | Br | Pr |
| 1-185 | Cl | Br | i-Pr |
| 1-186 | Cl | Br | $CH_2CH_2OMe$ |
| 1-187 | Cl | Br | $CH_2CH_2SMe$ |
| 1-188 | Cl | Br | $CH_2CN$ |
| 1-189 | Cl | Br | $CH_2$-(tetrahydrofuran-2-yl) |
| 1-190 | Cl | Br | $CH_2C(O)NMe_2$ |
| 1-191 | Cl | Br | Ph |
| 1-192 | Cl | Br | $CH_2$-(thien-2-yl) |
| 1-193 | Cl | Br | Oxetan-3-yl |
| 1-194 | Cl | Br | cBu |
| 1-195 | Cl | I | Me |
| 1-196 | Cl | I | Et |
| 1-197 | Cl | I | c-Pr |
| 1-198 | Cl | I | $CH_2$-c-Pr |
| 1-199 | Cl | I | $CH_2CF_3$ |
| 1-200 | Cl | I | $CH_2CHF_2$ |
| 1-201 | Br | $SO_2Me$ | Me |
| 1-202 | Br | $SO_2Me$ | Et |
| 1-203 | Br | $SO_2Me$ | c-Pr |
| 1-204 | Br | $SO_2Me$ | $CH_2$-c-Pr |
| 1-205 | Br | $SO_2Me$ | $CH_2CF_3$ |
| 1-206 | Br | $SO_2Me$ | $CH_2CHF_2$ |
| 1-207 | Br | $CF_3$ | Me |
| 1-208 | Br | $CF_3$ | Et |
| 1-209 | Br | $CF_3$ | c-Pr |
| 1-210 | Br | $CF_3$ | $CH_2$-c-Pr |
| 1-211 | Br | $CF_3$ | $CH_2CF_3$ |
| 1-212 | Br | $CF_3$ | $CH_2CHF_2$ |
| 1-213 | Br | $CF_3$ | CH(Me)-c-Pr |
| 1-214 | Br | $CF_3$ | Pr |
| 1-215 | Br | $CF_3$ | i-Pr |
| 1-216 | Br | $CF_3$ | $CH_2CH_2OMe$ |
| 1-217 | Br | $CF_3$ | $CH_2CH_2SMe$ |
| 1-218 | Br | $CF_3$ | $CH_2CN$ |
| 1-219 | Br | $CF_3$ | $CH_2$-(tetrahydrofuran-2-yl) |
| 1-220 | Br | $CF_3$ | $CH_2C(O)NMe_2$ |
| 1-221 | Br | $CF_3$ | Ph |
| 1-222 | Br | $CF_3$ | $CH_2$-(thien-2-yl) |

TABLE 1-continued

Inventive compounds of the general formula (I) in which Q is Q[1] and $R^x$ is methyl, and the other substituents have the definitions given below.

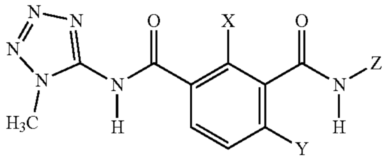

| No. | X | Y | Z |
|---|---|---|---|
| 1-223 | Br | $CF_3$ | Oxetan-3-yl |
| 1-224 | Br | $CF_3$ | c-Bu |
| 1-225 | Br | $CHF_2$ | Me |
| 1-226 | Br | $CHF_2$ | Et |
| 1-227 | Br | $CHF_2$ | c-Pr |
| 1-228 | Br | $CHF_2$ | $CH_2$-c-Pr |
| 1-229 | Br | $CHF_2$ | $CH_2CF_3$ |
| 1-230 | Br | $CHF_2$ | $CH_2CHF_2$ |
| 1-231 | Br | $C_2F_5$ | Me |
| 1-232 | Br | $C_2F_5$ | Et |
| 1-233 | Br | $C_2F_5$ | c-Pr |
| 1-234 | Br | $C_2F_5$ | $CH_2$-c-Pr |
| 1-235 | Br | $C_2F_5$ | $CH_2CF_3$ |
| 1-236 | Br | $C_2F_5$ | $CH_2CHF_2$ |
| 1-237 | I | $SO_2Me$ | Me |
| 1-238 | I | $SO_2Me$ | Et |
| 1-239 | I | $SO_2Me$ | c-Pr |
| 1-240 | I | $CF_3$ | Me |
| 1-241 | I | $CF_3$ | Et |
| 1-242 | I | $CF_3$ | c-Pr |
| 1-243 | I | $CF_3$ | $CH_2$-c-Pr |
| 1-244 | I | $CF_3$ | $CH_2CF_3$ |
| 1-245 | I | $CF_3$ | $CH_2CHF_2$ |
| 1-246 | I | $CHF_2$ | Me |
| 1-247 | I | $CHF_2$ | Et |
| 1-248 | I | $CHF_2$ | c-Pr |
| 1-249 | I | $CHF_2$ | $CH_2$-c-Pr |
| 1-250 | I | $CHF_2$ | $CH_2CF_3$ |
| 1-251 | I | $CHF_2$ | $CH_2CHF_2$ |
| 1-252 | I | $C_2F_5$ | Me |
| 1-253 | I | $C_2F_5$ | Et |
| 1-254 | I | $C_2F_5$ | c-Pr |
| 1-255 | $CH_2OMe$ | $CF_3$ | Me |
| 1-256 | $CH_2OMe$ | $CF_3$ | Et |
| 1-257 | $CH_2OMe$ | $CF_3$ | c-Pr |
| 1-258 | $CH_2OMe$ | $CF_3$ | $CH_2$-c-Pr |
| 1-259 | $CH_2OMe$ | $CF_3$ | $CH_2CF_3$ |
| 1-260 | $CH_2OMe$ | $CF_3$ | $CH_2CHF_2$ |
| 1-261 | $CH_2OMe$ | $CHF_2$ | Me |
| 1-262 | $CH_2OMe$ | $CHF_2$ | Et |
| 1-263 | $CH_2OMe$ | $CHF_2$ | c-Pr |
| 1-264 | $CH_2OMe$ | $CHF_2$ | $CH_2$-c-Pr |
| 1-265 | $CH_2OMe$ | $CHF_2$ | $CH_2CF_3$ |
| 1-266 | $CH_2OMe$ | $CHF_2$ | $CH_2CHF_2$ |
| 1-267 | $CH_2OMe$ | $CHF_2$ | c-Pentyl |
| 1-268 | $CH_2OMe$ | $SO_2Me$ | Me |
| 1-269 | $CH_2OMe$ | $SO_2Me$ | Et |
| 1-270 | $CH_2OMe$ | $SO_2Me$ | c-Pr |
| 1-271 | Et | $CF_3$ | Me |
| 1-272 | Et | $CF_3$ | Et |
| 1-273 | Et | $CF_3$ | c-Pr |
| 1-274 | Et | $CF_3$ | $CH_2$-c-Pr |
| 1-275 | Et | $CF_3$ | $CH_2cF_3$ |
| 1-276 | Et | $CF_3$ | $CH_2CHF_2$ |
| 1-277 | Et | $CHF_2$ | Me |
| 1-278 | Et | $CHF_2$ | Et |
| 1-279 | Et | $CHF_2$ | c-Pr |
| 1-280 | Et | $CHF_2$ | $CH_2$-c-Pr |
| 1-281 | Et | $CHF_2$ | $CH_2cF_3$ |
| 1-282 | Et | $CHF_2$ | $CH_2CHF_2$ |
| 1-283 | Et | $C_2F_5$ | Me |
| 1-284 | Et | $C_2F_5$ | Et |
| 1-285 | Et | $C_2F_5$ | c-Pr |
| 1-286 | c-Pr | $CF_3$ | Me |
| 1-287 | c-Pr | $CF_3$ | Et |

TABLE 1-continued

Inventive compounds of the general formula (I) in which Q is $Q^1$ and $R^x$ is methyl, and the other substituents have the definitions given below.

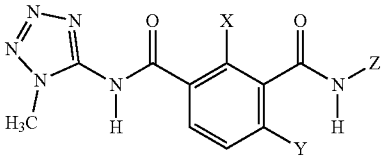

| No. | X | Y | Z |
|---|---|---|---|
| 1-288 | c-Pr | $CF_3$ | c-Pr |
| 1-289 | c-Pr | $CF_3$ | $CH_2$-c-Pr |
| 1-290 | c-Pr | $CF_3$ | $CH_2CF_3$ |
| 1-291 | c-Pr | $CF_3$ | $CH_2CHF_2$ |
| 1-292 | c-Pr | $CF_3$ | CH(Me)-c-Pr |
| 1-293 | c-Pr | $CF_3$ | Pr |
| 1-294 | c-Pr | $CF_3$ | iPr |
| 1-295 | c-Pr | $CF_3$ | $CH_2CH_2OMe$ |
| 1-296 | c-Pr | $CF_3$ | $CH_2CH_2SMe$ |
| 1-297 | c-Pr | $CF_3$ | $CH_2CN$ |
| 1-298 | c-Pr | $CF_3$ | $CH_2$-(tetrahydrofuran-2-yl) |
| 1-299 | c-Pr | $CF_3$ | $CH_2C(O)NMe_2$ |
| 1-300 | c-Pr | $CF_3$ | Ph |
| 1-301 | c-Pr | $CF_3$ | $CH_2$-(thien-2-yl) |
| 1-302 | c-Pr | $CF_3$ | Oxetan-3-yl |
| 1-303 | c-Pr | $CF_3$ | c-Bu |
| 1-304 | c-Pr | $CHF_2$ | Me |
| 1-305 | c-Pr | $CHF_2$ | Et |
| 1-306 | c-Pr | $CHF_2$ | c-Pr |
| 1-307 | c-Pr | $CHF_2$ | $CH_2$-c-Pr |
| 1-308 | c-Pr | $CHF_2$ | $CH_2CF_3$ |
| 1-309 | c-Pr | $CHF_2$ | $CH_2CHF_2$ |
| 1-310 | c-Pr | $CHF_2$ | CH(Me)-c-Pr |
| 1-311 | c-Pr | $CHF_2$ | Pr |
| 1-312 | c-Pr | $CHF_2$ | i-Pr |
| 1-313 | c-Pr | $CHF_2$ | $CH_2CH_2OMe$ |
| 1-314 | c-Pr | $CHF_2$ | $CH_2CH_2SMe$ |
| 1-315 | c-Pr | $CHF_2$ | $CH_2CN$ |
| 1-316 | c-Pr | $CHF_2$ | $CH_2$-(tetrahydrofuran-2-yl) |
| 1-317 | c-Pr | $CHF_2$ | $CH_2C(O)NMe_2$ |
| 1-318 | c-Pr | $CHF_2$ | Ph |
| 1-319 | c-Pr | $CHF_2$ | $CH_2$-(thien-2-yl) |
| 1-320 | c-Pr | $CHF_2$ | Oxetan-3-yl |
| 1-321 | c-Pr | $CHF_2$ | cBu |
| 1-322 | c-Pr | $C_2F_5$ | Me |
| 1-323 | c-Pr | $C_2F_5$ | Et |
| 1-324 | c-Pr | $C_2F_5$ | c-Pr |
| 1-325 | c-Pr | $C_2F_5$ | $CH_2$-c-Pr |
| 1-326 | c-Pr | $C_2F_5$ | $CH_2CF_3$ |
| 1-327 | c-Pr | $C_2F_5$ | $CH_2CHF_2$ |
| 1-328 | c-Pr | $SO_2Me$ | Me |
| 1-329 | c-Pr | $SO_2Me$ | Et |
| 1-330 | c-Pr | $SO_2Me$ | c-Pr |
| 1-331 | $CF_3$ | $CF_3$ | Me |
| 1-332 | $CF_3$ | $CF_3$ | Et |
| 1-333 | $CF_3$ | $CF_3$ | c-Pr |
| 1-334 | $CF_3$ | $CF_3$ | $CH_2$-c-Pr |
| 1-335 | $CF_3$ | $CF_3$ | $CH_2CF_3$ |
| 1-336 | $CF_3$ | $CF_3$ | $CH_2CHF_2$ |
| 1-337 | Cl | $CF_3$ | Acetyl |
| 1-338 | Cl | $CF_3$ | H |
| 1-339 | Me | $CHF_2$ | CH(Me)-c-Pr |
| 1-340 | Br | $CHF_2$ | CH(Me)-c-Pr |
| 1-341 | Et | $CF_3$ | CH(Me)-c-Pr |
| 1-342 | Br | Br | Me |
| 1-343 | Br | Br | Et |
| 1-344 | Br | Br | c-Pr |
| 1-345 | Me | $CHF_2$ | Pr |
| 1-346 | Me | $CHF_2$ | i-Pr |
| 1-347 | Me | $CHF_2$ | $CH_2CH_2OMe$ |
| 1-348 | Me | $CHF_2$ | $CH_2CH_2SMe$ |
| 1-349 | Br | Cl | Me |
| 1-350 | Br | Cl | Et |
| 1-351 | Br | Cl | c-Pr |
| 1-352 | SMe | $CF_3$ | CH(Me)-c-Pr |

TABLE 1-continued

Inventive compounds of the general formula (I) in which Q is $Q^1$ and $R^x$ is methyl, and the other substituents have the definitions given below.

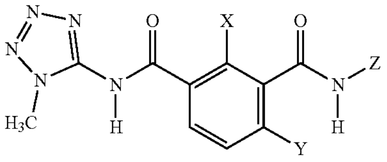

| No. | X | Y | Z |
|---|---|---|---|
| 1-353 | SMe | $CHF_2$ | CH(Me)-c-Pr |
| 1-354 | Cl | OMe | Me |
| 1-355 | Cl | OMe | Et |
| 1-356 | Cl | OMe | c-Pr |
| 1-357 | Cl | $CF_3$ | OMe |
| 1-358 | Cl | $CF_3$ | OEt |
| 1-359 | Cl | $CF_3$ | OPr |
| 1-360 | Cl | $CF_3$ | Oi-Pr |
| 1-361 | Cl | $CHF_2$ | OMe |
| 1-362 | Cl | $CHF_2$ | OEt |
| 1-363 | Cl | $CHF_2$ | OPr |
| 1-364 | Cl | $CHF_2$ | Oi-Pr |

TABLE 2

Inventive compounds of the general formula (I) in which Q is $Q^1$ and $R^x$ is ethyl, and the other substituents have the definitions given below.

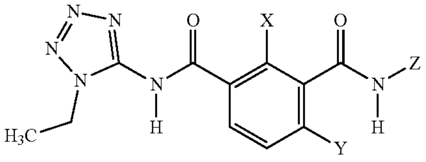

| No. | X | Y | Z |
|---|---|---|---|
| 2-1 | Me | F | Me |
| 2-2 | Me | F | Et |
| 2-3 | Me | F | c-Pr |
| 2-4 | Me | Cl | Me |
| 2-5 | Me | Cl | Et |
| 2-6 | Me | Cl | c-Pr |
| 2-7 | Me | Br | Me |
| 2-8 | Me | Br | Et |
| 2-9 | Me | Br | c-Pr |
| 2-10 | Me | I | Me |
| 2-11 | Me | I | Et |
| 2-12 | Me | I | c-Pr |
| 2-13 | Me | SMe | Me |
| 2-14 | Me | SMe | Et |
| 2-15 | Me | SMe | c-Pr |
| 2-16 | Me | S(O)Me | Me |
| 2-17 | Me | S(O)Me | Et |
| 2-18 | Me | S(O)Me | c-Pr |
| 2-19 | Me | $SO_2Me$ | Me |
| 2-20 | Me | $SO_2Me$ | Et |
| 2-21 | Me | $SO_2Me$ | c-Pr |
| 2-22 | Me | $SO_2Me$ | $CH_2$-c-Pr |
| 2-23 | Me | $SO_2Me$ | $CH_2CF_3$ |
| 2-24 | Me | $SO_2Me$ | $CH_2CHF_2$ |
| 2-25 | Me | $CF_3$ | Me |
| 2-26 | Me | $CF_3$ | Et |
| 2-27 | Me | $CF_3$ | c-Pr |
| 2-28 | Me | $CF_3$ | $CH_2$-c-Pr |
| 2-29 | Me | $CF_3$ | $CH_2CF_3$ |
| 2-30 | Me | $CF_3$ | $CH_2CHF_2$ |
| 2-31 | Me | $CF_3$ | CH(Me)-c-Pr |
| 2-32 | Me | $CF_3$ | Pr |
| 2-33 | Me | $CF_3$ | i-Pr |
| 2-34 | Me | $CF_3$ | $CH_2CH_2OMe$ |

TABLE 2-continued

Inventive compounds of the general formula (I) in which Q is $Q^1$ and $R^x$ is ethyl, and the other substituents have the definitions given below.

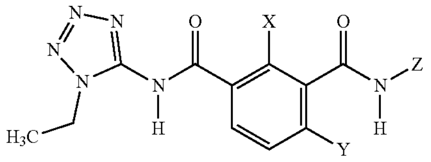

| No. | X | Y | Z |
|---|---|---|---|
| 2-35 | Me | $CF_3$ | $CH_2CH_2SMe$ |
| 2-36 | Me | $CF_3$ | CHCN |
| 2-37 | Me | $CF_3$ | $CH_2$-(tetrahydrofuran-2-yl) |
| 2-38 | Me | $CF_3$ | $CH_2C(O)NMe_2$ |
| 2-39 | Me | $CF_3$ | Ph |
| 2-40 | Me | $CF_3$ | $CH_2$-(thien-2-yl) |
| 2-41 | Me | $CF_3$ | Oxetan-3-yl |
| 2-42 | Me | $CF_3$ | c-Bu |
| 2-43 | Me | $CF_3$ | c-Pentyl |
| 2-44 | Me | $CHF_2$ | Me |
| 2-45 | Me | $CHF_2$ | Et |
| 2-46 | Me | $CHF_2$ | c-Pr |
| 2-47 | Me | $CHF_2$ | $CH_2$-c-Pr |
| 2-48 | Me | $CHF_2$ | $CH_2CF_3$ |
| 2-49 | Me | $CHF_2$ | $CH_2CHF_2$ |
| 2-50 | Me | $C_2F_5$ | Me |
| 2-51 | Me | $C_2F_5$ | Et |
| 2-52 | Me | $C_2F_5$ | c-Pr |
| 2-53 | OMe | Cl | Me |
| 2-54 | OMe | Cl | Et |
| 2-55 | OMe | Cl | c-Pr |
| 2-56 | OMe | $CF_3$ | Me |
| 2-57 | OMe | $CF_3$ | Et |
| 2-58 | OMe | $CF_3$ | c-Pr |
| 2-59 | OMe | $CF_3$ | $CH_2$-c-Pr |
| 2-60 | OMe | $CF_3$ | $CH_2CF_3$ |
| 2-71 | OMe | $CF_3$ | $CH_2CHF_2$ |
| 2-72 | OMe | $CHF_2$ | Me |
| 2-73 | OMe | $CHF_2$ | Et |
| 2-74 | OMe | $CHF_2$ | c-Pr |
| 2-75 | OMe | $CHF_2$ | $CH_2$-c-Pr |
| 2-76 | OMe | $CHF_2$ | $CH_2CF_3$ |
| 2-77 | OMe | $CHF_2$ | $CH_2CHF_2$ |
| 2-78 | SMe | $SO_2Me$ | Me |
| 2-79 | SMe | $SO_2Me$ | Et |
| 2-80 | SMe | $SO_2Me$ | c-Pr |
| 2-81 | SMe | $CF_3$ | Me |
| 2-82 | SMe | $CF_3$ | Et |
| 2-83 | SMe | $CF_3$ | c-Pr |
| 2-84 | SMe | $CF_3$ | $CH_2$-c-Pr |
| 2-85 | SMe | $CF_3$ | $CH_2CF_3$ |
| 2-86 | SMe | $CF_3$ | $CH_2CHF_2$ |
| 2-87 | SMe | $CHF_2$ | Me |
| 2-88 | SMe | $CHF_2$ | Et |
| 2-89 | SMe | $CHF_2$ | c-Pr |
| 2-90 | SMe | $CHF_2$ | $CH_2$-c-Pr |
| 2-91 | SMe | $CHF_2$ | $CH_2CF_3$ |
| 2-92 | SMe | $CHF_2$ | $CH_2CHF_2$ |
| 2-93 | SEt | $CF_3$ | Me |
| 2-94 | SEt | $CF_3$ | Et |
| 2-95 | SEt | $CF_3$ | c-Pr |
| 2-96 | SEt | $CF_3$ | $CH_2$-c-Pr |
| 2-97 | SEt | $CF_3$ | $CH_2CF_3$ |
| 2-98 | SEt | $CF_3$ | $CH_2CHF_2$ |
| 2-99 | SEt | $CHF_2$ | Me |
| 2-100 | SEt | $CHF_2$ | Et |
| 2-101 | SEt | $CHF_2$ | c-Pr |
| 2-102 | SEt | $CHF_2$ | $CH_2$-c-Pr |
| 2-103 | SEt | $CHF_2$ | $CH_2CF_3$ |
| 2-104 | SEt | $CHF_2$ | $CH_2CHF_2$ |
| 2-105 | F | $CF_3$ | Me |
| 2-106 | F | $CF_3$ | Et |
| 2-107 | F | $CF_3$ | c-Pr |
| 2-108 | F | $CF_3$ | $CH_2$-c-Pr |
| 2-109 | F | $CF_3$ | $CH_2CF_3$ |

TABLE 2-continued

Inventive compounds of the general formula (I) in which Q is $Q^1$ and $R^x$ is ethyl, and the other substituents have the definitions given below.

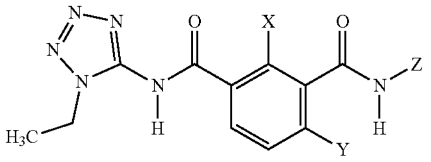

| No. | X | Y | Z |
|---|---|---|---|
| 2-110 | F | $CF_3$ | $CH_2CHF_2$ |
| 2-111 | F | $CHF_2$ | Me |
| 2-112 | F | $CHF_2$ | Et |
| 2-113 | F | $CHF_2$ | c-Pr |
| 2-114 | F | $CHF_2$ | $CH_2$-c-Pr |
| 2-115 | F | $CHF_2$ | $CH_2CF_3$ |
| 2-116 | F | $CHF_2$ | $CH_2CHF_2$ |
| 2-117 | Cl | SMe | Me |
| 2-118 | Cl | SMe | Et |
| 2-119 | Cl | SMe | c-Pr |
| 2-120 | Cl | S(O)Me | Me |
| 2-121 | Cl | S(O)Me | Et |
| 2-122 | Cl | S(O)Me | c-Pr |
| 2-123 | Cl | $SO_2Me$ | Me |
| 2-124 | Cl | $SO_2Me$ | Et |
| 2-125 | Cl | $SO_2Me$ | c-Pr |
| 2-126 | Cl | $SO_2Me$ | $CH_2$-c-Pr |
| 2-127 | Cl | $SO_2Me$ | $CH_2CF_3$ |
| 2-128 | Cl | $SO_2Me$ | $CH_2CHF_2$ |
| 2-129 | Cl | $CF_3$ | Me |
| 2-130 | Cl | $CF_3$ | Et |
| 2-131 | Cl | $CF_3$ | c-Pr |
| 2-132 | Cl | $CF_3$ | $CH_2$-c-Pr |
| 2-133 | Cl | $CF_3$ | $CH_2cF_3$ |
| 2-134 | Cl | $CF_3$ | $CH_2CHF_2$ |
| 2-135 | Cl | $CF_3$ | CH(Me)-c-Pr |
| 2-136 | Cl | $CF_3$ | Pr |
| 2-137 | Cl | $CF_3$ | i-Pr |
| 2-138 | Cl | $CF_3$ | $CH_2CH_2OMe$ |
| 2-139 | Cl | $CF_3$ | $CH_2CH_2SMe$ |
| 2-140 | Cl | $CF_3$ | $CH_2CN$ |
| 2-141 | Cl | $CF_3$ | $CH_2$-(tetrahydrofuran-2-yl) |
| 2-142 | Cl | $CF_3$ | $CH_2C(O)NMe_2$ |
| 2-143 | Cl | $CF_3$ | Ph |
| 2-144 | Cl | $CF_3$ | $CH_2$-(thien-2-yl) |
| 2-145 | Cl | $CF_3$ | Oxetan-3-yl |
| 2-146 | Cl | $CF_3$ | c-Bu |
| 2-147 | Cl | $CHF_2$ | Me |
| 2-148 | Cl | $CHF_2$ | Et |
| 2-149 | Cl | $CHF_2$ | c-Pr |
| 2-150 | Cl | $CHF_2$ | $CH_2$-c-Pr |
| 2-151 | Cl | $CHF_2$ | $CH_2CF_3$ |
| 2-152 | Cl | $CHF_2$ | $CH_2CHF_2$ |
| 2-153 | Cl | $CHF_2$ | CH(Me)-c-Pr |
| 2-154 | Cl | $CHF_2$ | Pr |
| 2-155 | Cl | $CHF_2$ | i-Pr |
| 2-156 | Cl | $CHF_2$ | $CH_2CH_2OMe$ |
| 2-157 | Cl | $CHF_2$ | $CH_2CH_2SMe$ |
| 2-158 | Cl | $CHF_2$ | $CH_2CN$ |
| 2-159 | Cl | $CHF_2$ | $CH_2$-(tetrahydrofuran-2-yl) |
| 2-160 | Cl | $CHF_2$ | $CH_2C(O)NMe_2$ |
| 2-161 | Cl | $CHF_2$ | Ph |
| 2-162 | Cl | $CHF_2$ | $CH_2$-(thien-2-yl) |
| 2-163 | Cl | $CHF_2$ | Oxetan-3-yl |
| 2-164 | Cl | $CHF_2$ | c-Bu |
| 2-165 | Cl | $C_2F_5$ | Me |
| 2-166 | Cl | $C_2F_5$ | Et |
| 2-167 | Cl | $C_2F_5$ | c-Pr |
| 2-168 | Cl | $C_2F_5$ | $CH_2$-c-Pr |
| 2-169 | Cl | $C_2F_5$ | $CH_2CF_3$ |
| 2-170 | Cl | $C_2F_5$ | $CH_2CHF_2$ |
| 2-171 | Cl | Cl | Me |
| 2-172 | Cl | Cl | Et |
| 2-173 | Cl | Cl | c-Pr |
| 2-174 | Cl | Cl | CH-c-Pr |

TABLE 2-continued

Inventive compounds of the general formula (I) in which Q is $Q^1$ and $R^x$ is ethyl, and the other substituents have the definitions given below.

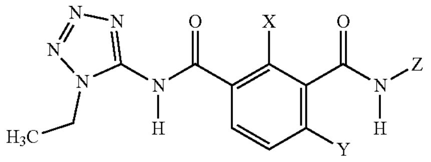

| No. | X | Y | Z |
|---|---|---|---|
| 2-175 | Cl | Cl | $CH_2CF_3$ |
| 2-176 | Cl | Cl | $CH_2CHF_2$ |
| 2-177 | Cl | Br | Me |
| 2-178 | Cl | Br | Et |
| 2-179 | Cl | Br | c-Pr |
| 2-180 | Cl | Br | CH-c-Pr |
| 2-181 | Cl | Br | $CH_2CF_3$ |
| 2-182 | Cl | Br | $CH_2CHF_2$ |
| 2-183 | Cl | Br | CH(Me)-c-Pr |
| 2-184 | Cl | Br | Pr |
| 2-185 | Cl | Br | i-Pr |
| 2-186 | Cl | Br | $CH_2CH_2OMe$ |
| 2-187 | Cl | Br | $CH_2CH_2SMe$ |
| 2-188 | Cl | Br | $CH_2CN$ |
| 2-189 | Cl | Br | $CH_2$-(tetrahydrofuran-2-yl) |
| 2-190 | Cl | Br | $CH_2C(O)NMe_2$ |
| 2-191 | Cl | Br | Ph |
| 2-192 | Cl | Br | $CH_2$-(thien-2-yl) |
| 2-193 | Cl | Br | Oxetan-3-yl |
| 2-194 | Cl | Br | c-Bu |
| 2-195 | Cl | I | Me |
| 2-196 | Cl | I | Et |
| 2-197 | Cl | I | c-Pr |
| 2-198 | Cl | I | $CH_2$-c-Pr |
| 2-199 | Cl | I | $CH_2CF_3$ |
| 2-200 | Cl | I | $CH_2CHF_2$ |
| 2-201 | Br | $SO_2Me$ | Me |
| 2-202 | Br | $SO_2Me$ | Et |
| 2-203 | Br | $SO_2Me$ | c-Pr |
| 2-204 | Br | $SO_2Me$ | $CH_2$-c-Pr |
| 2-205 | Br | $SO_2Me$ | $CH_2CF_3$ |
| 2-206 | Br | $SO_2Me$ | $CH_2CHF_2$ |
| 2-207 | Br | $CF_3$ | Me |
| 2-208 | Br | $CF_3$ | Et |
| 2-209 | Br | $CF_3$ | c-Pr |
| 2-210 | Br | $CF_3$ | $CH_2$-c-Pr |
| 2-211 | Br | $CF_3$ | $CH_2CF_3$ |
| 2-212 | Br | $CF_3$ | $CH_2CHF_2$ |
| 2-213 | Br | $CF_3$ | CH(Me)-c-Pr |
| 2-214 | Br | $CF_3$ | Pr |
| 2-215 | Br | $CF_3$ | i-Pr |
| 2-216 | Br | $CF_3$ | $CH_2CH_2OMe$ |
| 2-217 | Br | $CF_3$ | $CH_2CH_2SMe$ |
| 2-218 | Br | $CF_3$ | $CH_2CN$ |
| 2-219 | Br | $CF_3$ | $CH_2$-(tetrahydrofuran-2-yl) |
| 2-220 | Br | $CF_3$ | $CH_2C(O)NMe_2$ |
| 2-221 | Br | $CF_3$ | Ph |
| 2-222 | Br | $CF_3$ | $CH_2$-(thien-2-yl) |
| 2-223 | Br | $CF_3$ | Oxetan-3-yl |
| 2-224 | Br | $CF_3$ | c-Bu |
| 2-225 | Br | $CHF_2$ | Me |
| 2-226 | Br | $CHF_2$ | Et |
| 2-227 | Br | $CHF_2$ | c-Pr |
| 2-228 | Br | $CHF_2$ | $CH_2$-c-Pr |
| 2-229 | Br | $CHF_2$ | $CH_2CF_3$ |
| 2-230 | Br | $CHF_2$ | $CH_2CHF_2$ |
| 2-231 | Br | $C_2F_5$ | Me |
| 2-232 | Br | $C_2F_5$ | Et |
| 2-233 | Br | $C_2F_5$ | c-Pr |
| 2-234 | Br | $C_2F_5$ | $CH_2$-c-Pr |
| 2-235 | Br | $C_2F_5$ | $CH_2CF_3$ |
| 2-236 | Br | $C_2F_5$ | $CH_2CHF_2$ |
| 2-237 | I | $SO_2Me$ | Me |
| 2-238 | I | $SO_2Me$ | Et |
| 2-239 | I | $SO_2Me$ | c-Pr |

TABLE 2-continued

Inventive compounds of the general formula (I) in which Q is $Q^1$ and $R^x$ is ethyl, and the other substituents have the definitions given below.

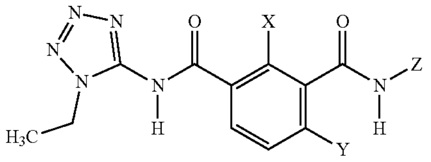

| No. | X | Y | Z |
|---|---|---|---|
| 2-240 | I | $CF_3$ | Me |
| 2-241 | I | $CF_3$ | Et |
| 2-242 | I | $CF_3$ | c-Pr |
| 2-243 | I | $CF_3$ | $CH_2$-c-Pr |
| 2-244 | I | $CF_3$ | $CH_2CF_3$ |
| 2-245 | I | $CF_3$ | $CH_2CHF_2$ |
| 2-246 | I | $CHF_2$ | Me |
| 2-247 | I | $CHF_2$ | Et |
| 2-248 | I | $CHF_2$ | c-Pr |
| 2-249 | I | $CHF_2$ | $CH_2$-c-Pr |
| 2-250 | I | $CHF_2$ | $CH_2CF_3$ |
| 2-251 | I | $CHF_2$ | $CH_2CHF_2$ |
| 2-252 | I | $C_2F_5$ | Me |
| 2-253 | I | $C_2F_5$ | Et |
| 2-254 | I | $C_2F_5$ | c-Pr |
| 2-255 | $CH_2OMe$ | $CF_3$ | Me |
| 2-256 | $CH_2OMe$ | $CF_3$ | Et |
| 2-257 | $CH_2OMe$ | $CF_3$ | c-Pr |
| 2-258 | $CH_2OMe$ | $CF_3$ | $CH_2$-c-Pr |
| 2-259 | $CH_2OMe$ | $CF_3$ | $CH_2CF_3$ |
| 2-260 | $CH_2OMe$ | $CF_3$ | $CH_2CHF_2$ |
| 2-261 | $CH_2OMe$ | $CHF_2$ | Me |
| 2-262 | $CH_2OMe$ | $CHF_2$ | Et |
| 2-263 | $CH_2OMe$ | $CHF_2$ | c-Pr |
| 2-264 | $CH_2OMe$ | $CHF_2$ | $CH_2$-c-Pr |
| 2-265 | $CH_2OMe$ | $CHF_2$ | $CH_2CF_3$ |
| 2-266 | $CH_2OMe$ | $CHF_2$ | $CH_2CHF_2$ |
| 2-267 | $CH_2OMe$ | $CHF_2$ | c-Pentyl |
| 2-268 | $CH_2OMe$ | $SO_2Me$ | Me |
| 2-269 | $CH_2OMe$ | $SO_2Me$ | Et |
| 2-270 | $CH_2OMe$ | $SO_2Me$ | c-Pr |
| 2-271 | Et | $CF_3$ | Me |
| 2-272 | Et | $CF_3$ | Et |
| 2-273 | Et | $CF_3$ | c-Pr |
| 2-274 | Et | $CF_3$ | $CH_2$-c-Pr |
| 2-275 | Et | $CF_3$ | $CH_2CF_3$ |
| 2-276 | Et | $CF_3$ | $CH_2CHF_2$ |
| 2-277 | Et | $CHF_2$ | Me |
| 2-278 | Et | $CHF_2$ | Et |
| 2-279 | Et | $CHF_2$ | c-Pr |
| 2-280 | Et | $CHF_2$ | $CH_2$-c-Pr |
| 2-281 | Et | $CHF_2$ | $CH_2CF_3$ |
| 2-282 | Et | $CHF_2$ | $CH_2CHF_2$ |
| 2-283 | Et | $C_2F_5$ | Me |
| 2-284 | Et | $C_2F_5$ | Et |
| 2-285 | Et | $C_2F_5$ | c-Pr |
| 2-286 | c-Pr | $CF_3$ | Me |
| 2-287 | c-Pr | $CF_3$ | Et |
| 2-288 | c-Pr | $CF_3$ | c-Pr |
| 2-289 | c-Pr | $CF_3$ | $CH_2$-c-Pr |
| 2-290 | c-Pr | $CF_3$ | $CH_2CF_3$ |
| 2-291 | c-Pr | $CF_3$ | $CH_2CHF_2$ |
| 2-292 | c-Pr | $CF_3$ | CH(Me)-c-Pr |
| 2-293 | c-Pr | $CF_3$ | Pr |
| 2-294 | c-Pr | $CF_3$ | i-Pr |
| 2-295 | c-Pr | $CF_3$ | $CH_2CH_2OMe$ |
| 2-296 | c-Pr | $CF_3$ | $CH_2CH_2SMe$ |
| 2-297 | c-Pr | $CF_3$ | $CH_2CN$ |
| 2-298 | c-Pr | $CF_3$ | $CH_2$-(tetrahydrofuran-2-yl) |
| 2-299 | c-Pr | $CF_3$ | $CH_2C(O)NMe_2$ |
| 2-300 | c-Pr | $CF_3$ | Ph |
| 2-301 | c-Pr | $CF_3$ | $CH_2$-(thien-2-yl) |
| 2-302 | c-Pr | $CF_3$ | Oxetan-3-yl |
| 2-303 | c-Pr | $CF_3$ | c-Bu |
| 2-304 | c-Pr | $CHF_2$ | Me |

TABLE 2-continued

Inventive compounds of the general formula (I) in which Q is $Q^1$ and $R^x$ is ethyl, and the other substituents have the definitions given below.

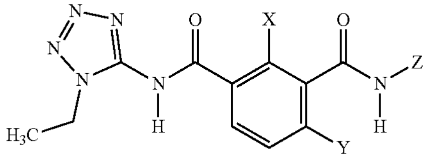

| No. | X | Y | Z |
|---|---|---|---|
| 2-305 | c-Pr | $CHF_2$ | Et |
| 2-306 | c-Pr | $CHF_2$ | c-Pr |
| 2-307 | c-Pr | $CHF_2$ | $CH_2$-c-Pr |
| 2-308 | c-Pr | $CHF_2$ | $CH_2CF_3$ |
| 2-309 | c-Pr | $CHF_2$ | $CH_2CHF_2$ |
| 2-310 | c-Pr | $CHF_2$ | CH(Me)-c-Pr |
| 2-311 | c-Pr | $CHF_2$ | Pr |
| 2-312 | c-Pr | $CHF_2$ | i-Pr |
| 2-313 | c-Pr | $CHF_2$ | $CH_2CH_2OMe$ |
| 2-314 | c-Pr | $CHF_2$ | $CH_2CH_2SMe$ |
| 2-315 | c-Pr | $CHF_2$ | $CH_2CN$ |
| 2-316 | c-Pr | $CHF_2$ | $CH_2$-(tetrahydrofuran-2-yl) |
| 2-317 | c-Pr | $CHF_2$ | $CH_2C(O)NMe_2$ |
| 2-318 | c-Pr | $CHF_2$ | Ph |
| 2-319 | c-Pr | $CHF_2$ | $CH_2$-(thien-2-yl) |
| 2-320 | c-Pr | $CHF_2$ | Oxetan-3-yl |
| 2-321 | c-Pr | $CHF_2$ | c-Bu |
| 2-322 | c-Pr | $C_2F_5$ | Me |
| 2-323 | c-Pr | $C_2F_5$ | Et |
| 2-324 | c-Pr | $C_2F_5$ | c-Pr |
| 2-325 | c-Pr | $C_2F_5$ | $CH_2$-c-Pr |
| 2-326 | c-Pr | $C_2F_5$ | $CH_2CF_3$ |
| 2-327 | c-Pr | $C_2F_5$ | $CH_2CHF_2$ |
| 2-328 | c-Pr | $SO_2Me$ | Me |
| 2-329 | c-Pr | $SO_2Me$ | Et |
| 2-330 | c-Pr | $SO_2Me$ | c-Pr |
| 2-331 | $CF_3$ | $CF_3$ | Me |
| 2-332 | $CF_3$ | $CF_3$ | Et |
| 2-333 | $CF_3$ | $CF_3$ | c-Pr |
| 2-334 | $CF_3$ | $CF_3$ | $CH_2$-c-Pr |
| 2-335 | $CF_3$ | $CF_3$ | $CH_2CF_3$ |
| 2-336 | $CF_3$ | $CF_3$ | $CH_2CHF_2$ |
| 2-337 | Cl | $CF_3$ | Acetyl |
| 2-338 | Cl | $CF_3$ | H |
| 2-339 | Me | $CHF_2$ | CH(Me)-c-Pr |
| 2-340 | Br | $CHF_2$ | CH(Me)-c-Pr |
| 2-341 | Et | $CF_3$ | CH(Me)-c-Pr |
| 2-342 | Br | Br | Et |
| 2-343 | Br | Br | c-Pr |
| 2-344 | Me | $CHF_2$ | Pr |
| 2-345 | Me | $CHF_2$ | i-Pr |
| 2-346 | Me | $CHF_2$ | $CH_2CH_2OMe$ |
| 2-347 | Me | $CHF_2$ | $CH_2CH_2SMe$ |
| 2-348 | Br | Cl | Et |
| 2-349 | Br | Cl | c-Pr |
| 2-350 | SMe | $CF_3$ | CH(Me)-c-Pr |
| 2-351 | SMe | $CHF_2$ | CH(Me)-c-Pr |
| 2-352 | Cl | OMe | Me |
| 2-353 | Cl | OMe | Et |
| 2-354 | Cl | OMe | c-Pr |
| 2-355 | Br | Br | Me |
| 2-356 | Br | Cl | Me |
| 2-357 | Cl | $CF_3$ | OMe |
| 2-358 | Cl | $CF_3$ | OEt |
| 2-359 | Cl | $CF_3$ | OPr |
| 2-360 | Cl | $CF_3$ | Oi-Pr |
| 2-361 | Cl | $CHF_2$ | OMe |
| 2-362 | Cl | $CHF_2$ | OEt |
| 2-363 | Cl | $CHF_2$ | OPr |
| 2-364 | Cl | $CHF_2$ | Oi-Pr |

TABLE 3

Inventive compounds of the general formula (I) in which Q is $Q^1$ and $R^x$ is propyl, and the other substituents have the definitions given below.

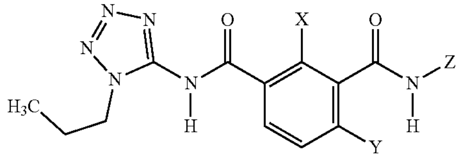

| No. | X | Y | Z |
|---|---|---|---|
| 3-1 | Me | F | Me |
| 3-2 | Me | F | Et |
| 3-3 | Me | F | c-Pr |
| 3-4 | Me | Cl | Me |
| 3-5 | Me | Cl | Et |
| 3-6 | Me | Cl | c-Pr |
| 3-7 | Me | Br | Me |
| 3-8 | Me | Br | Et |
| 3-9 | Me | Br | c-Pr |
| 3-10 | Me | I | Me |
| 3-11 | Me | I | Et |
| 3-12 | Me | I | c-Pr |
| 3-13 | Me | SMe | Me |
| 3-14 | Me | SMe | Et |
| 3-15 | Me | SMe | c-Pr |
| 3-16 | Me | S(O)Me | Me |
| 3-17 | Me | S(O)Me | Et |
| 3-18 | Me | S(O)Me | c-Pr |
| 3-19 | Me | $SO_2Me$ | Me |
| 3-20 | Me | $SO_2Me$ | Et |
| 3-21 | Me | $SO_2Me$ | c-Pr |
| 3-22 | Me | $SO_2Me$ | $CH_2$-c-Pr |
| 3-23 | Me | $SO_2Me$ | $CH_2CF_3$ |
| 3-24 | Me | $SO_2Me$ | $CH_2CHF_2$ |
| 3-25 | Me | $CF_3$ | Me |
| 3-26 | Me | $CF_3$ | Et |
| 3-27 | Me | $CF_3$ | c-Pr |
| 3-28 | Me | $CF_3$ | $CH_2$-c-Pr |
| 3-29 | Me | $CF_3$ | $CH_2CF_3$ |
| 3-30 | Me | $CF_3$ | $CH_2CHF_2$ |
| 3-31 | Me | $CF_3$ | CH(Me)-c-Pr |
| 3-32 | Me | $CF_3$ | Pr |
| 3-33 | Me | $CF_3$ | i-Pr |
| 3-34 | Me | $CF_3$ | $CH_2CH_2OMe$ |
| 3-35 | Me | $CF_3$ | $CH_2CH_2SMe$ |
| 3-36 | Me | $CF_3$ | $CH_2CN$ |
| 3-37 | Me | $CF_3$ | $CH_2$-(tetrahydrofuran-2-yl) |
| 3-38 | Me | $CF_3$ | $CH_2C(O)NMe_2$ |
| 3-39 | Me | $CF_3$ | Ph |
| 3-40 | Me | $CF_3$ | $CH_2$-(thien-2-yl) |
| 3-41 | Me | $CF_3$ | Oxetan-3-yl |
| 3-42 | Me | $CF_3$ | c-Bu |
| 3-43 | Me | $CF_3$ | c-Pentyl |
| 3-44 | Me | $CHF_2$ | Me |
| 3-45 | Me | $CHF_2$ | Et |
| 3-46 | Me | $CHF_2$ | c-Pr |
| 3-47 | Me | $CHF_2$ | $CH_2$-c-Pr |
| 3-48 | Me | $CHF_2$ | $CH_2CF_3$ |
| 3-49 | Me | $CHF_2$ | $CH_2CHF_2$ |
| 3-50 | Me | $C_2F_5$ | Me |
| 3-51 | Me | $C_2F_5$ | Et |
| 3-52 | Me | $C_2F_5$ | c-Pr |
| 3-53 | OMe | Cl | Me |
| 3-54 | OMe | Cl | Et |
| 3-55 | OMe | Cl | c-Pr |
| 3-56 | OMe | $CF_3$ | Me |
| 3-57 | OMe | $CF_3$ | Et |
| 3-58 | OMe | $CF_3$ | c-Pr |
| 3-59 | OMe | $CF_3$ | $CH_2$-c-Pr |
| 3-60 | OMe | $CF_3$ | $CH_2CF_3$ |
| 3-71 | OMe | $CF_3$ | $CH_2CHF_2$ |
| 3-72 | OMe | $CHF_2$ | Me |
| 3-73 | OMe | $CHF_2$ | Et |
| 3-74 | OMe | $CHF_2$ | c-Pr |
| 3-75 | OMe | $CHF_2$ | $CH_2$-c-Pr |

TABLE 3-continued

Inventive compounds of the general formula (I) in which Q is $Q^1$ and $R^x$ is propyl, and the other substituents have the definitions given below.

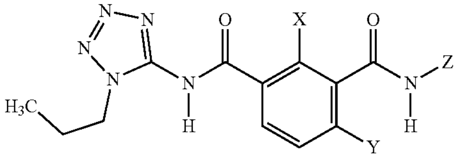

| No. | X | Y | Z |
|---|---|---|---|
| 3-76 | OMe | $CHF_2$ | $CH_2CF_3$ |
| 3-77 | OMe | $CHF_2$ | $CH_2CHF_2$ |
| 3-78 | SMe | $SO_2Me$ | Me |
| 3-79 | SMe | $SO_2Me$ | Et |
| 3-80 | SMe | $SO_2Me$ | c-Pr |
| 3-81 | SMe | $CF_3$ | Me |
| 3-82 | SMe | $CF_3$ | Et |
| 3-83 | SMe | $CF_3$ | c-Pr |
| 3-84 | SMe | $CF_3$ | $CH_2$-c-Pr |
| 3-85 | SMe | $CF_3$ | $CH_2CF_3$ |
| 3-86 | SMe | $CF_3$ | $CH_2CHF_2$ |
| 3-87 | SMe | $CHF_2$ | Me |
| 3-88 | SMe | $CHF_2$ | Et |
| 3-89 | SMe | $CHF_2$ | c-Pr |
| 3-90 | SMe | $CHF_2$ | $CH_2$-c-Pr |
| 3-91 | SMe | $CHF_2$ | $CH_2cF_3$ |
| 3-92 | SMe | $CHF_2$ | $CH_2CHF_2$ |
| 3-93 | SEt | $CF_3$ | Me |
| 3-94 | SEt | $CF_3$ | Et |
| 3-95 | SEt | $CF_3$ | c-Pr |
| 3-96 | SEt | $CF_3$ | $CH_2$-c-Pr |
| 3-97 | SEt | $CF_3$ | $CH_2CF_3$ |
| 3-98 | SEt | $CF_3$ | $CH_2CHF_2$ |
| 3-99 | SEt | $CHF_2$ | Me |
| 3-100 | SEt | $CHF_2$ | Et |
| 3-101 | SEt | $CHF_2$ | c-Pr |
| 3-102 | SEt | $CHF_2$ | $CH_2$-c-Pr |
| 3-103 | SEt | $CHF_2$ | $CH_2CF_3$ |
| 3-104 | SEt | $CHF_2$ | $CH_2CHF_2$ |
| 3-105 | F | $CF_3$ | Me |
| 3-106 | F | $CF_3$ | Et |
| 3-107 | F | $CF_3$ | c-Pr |
| 3-108 | F | $CF_3$ | $CH_2$-c-Pr |
| 3-109 | F | $CF_3$ | $CH_2CF_3$ |
| 3-110 | F | $CF_3$ | $CH_2CHF_2$ |
| 3-111 | F | $CHF_2$ | Me |
| 3-112 | F | $CHF_2$ | Et |
| 3-113 | F | $CHF_2$ | c-Pr |
| 3-114 | F | $CHF_2$ | $CH_2$-c-Pr |
| 3-115 | F | $CHF_2$ | $CH_2CF_3$ |
| 3-116 | F | $CHF_2$ | $CH_2CHF_2$ |
| 3-117 | Cl | SMe | Me |
| 3-118 | Cl | SMe | Et |
| 3-119 | Cl | SMe | c-Pr |
| 3-120 | Cl | S(O)Me | Me |
| 3-121 | Cl | S(O)Me | Et |
| 3-122 | Cl | S(O)Me | c-Pr |
| 3-123 | Cl | $SO_2Me$ | Me |
| 3-124 | Cl | $SO_2Me$ | Et |
| 3-125 | Cl | $SO_2Me$ | c-Pr |
| 3-126 | Cl | SO,Me | $CH_2$-c-Pr |
| 3-127 | Cl | SO,Me | $CH_2cF_3$ |
| 3-128 | Cl | SO,Me | $CH_2CHF_2$ |
| 3-129 | Cl | $CF_3$ | Me |
| 3-130 | Cl | $CF_3$ | Et |
| 3-131 | Cl | $CF_3$ | c-Pr |
| 3-132 | Cl | $CF_3$ | $CH_2$-c-Pr |
| 3-133 | Cl | $CF_3$ | $CH_2cF_3$ |
| 3-134 | Cl | $CF_3$ | $CH_2CHF_2$ |
| 3-135 | Cl | $CF_3$ | CH(Me)-c-Pr |
| 3-136 | Cl | $CF_3$ | Pr |
| 3-137 | Cl | $CF_3$ | i-Pr |
| 3-138 | Cl | $CF_3$ | $CH_2CH_2OMe$ |
| 3-139 | Cl | $CF_3$ | $CH_2CH_2SMe$ |
| 3-140 | Cl | $CF_3$ | $CH_2CN$ |

TABLE 3-continued

Inventive compounds of the general formula (I) in which Q is $Q^1$ and $R^x$ is propyl, and the other substituents have the definitions given below.

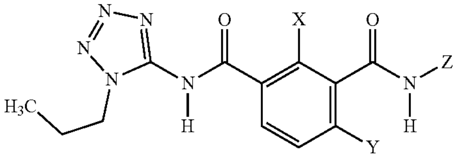

| No. | X | Y | Z |
|---|---|---|---|
| 3-141 | Cl | $CF_3$ | $CH_2$-(tetrahydrofuran-2-yl) |
| 3-142 | Cl | $CF_3$ | $CH_2C(O)NMe_2$ |
| 3-143 | Cl | $CF_3$ | Ph |
| 3-144 | Cl | $CF_3$ | $CH_2$-(thien-2-yl) |
| 3-145 | Cl | $CF_3$ | Oxetan-3-yl |
| 3-146 | Cl | $CF_3$ | c-Bu |
| 3-147 | Cl | $CHF_2$ | Me |
| 3-148 | Cl | $CHF_2$ | Et |
| 3-149 | Cl | $CHF_2$ | c-Pr |
| 3-150 | Cl | $CHF_2$ | $CH_2$-c-Pr |
| 3-151 | Cl | $CHF_2$ | $CH_2CF_3$ |
| 3-152 | Cl | $CHF_2$ | $CH_2CHF_2$ |
| 3-153 | Cl | $CHF_2$ | CH(Me)-c-Pr |
| 3-154 | Cl | $CHF_2$ | Pr |
| 3-155 | Cl | $CHF_2$ | i-Pr |
| 3-156 | Cl | $CHF_2$ | $CH_2CH_2OMe$ |
| 3-157 | Cl | $CHF_2$ | $CH_2CH_2SMe$ |
| 3-158 | Cl | $CHF_2$ | $CH_2CN$ |
| 3-159 | Cl | $CHF_2$ | $CH_2$-(tetrahydrofuran-2-yl) |
| 3-160 | Cl | $CHF_2$ | $CH_2C(O)NMe_2$ |
| 3-161 | Cl | $CHF_2$ | Ph |
| 3-162 | Cl | $CHF_2$ | $CH_2$-(thien-2-yl) |
| 3-163 | Cl | $CHF_2$ | Oxetan-3-yl |
| 3-164 | Cl | $CHF_2$ | c-Bu |
| 3-165 | Cl | $C_2F_5$ | Me |
| 3-166 | Cl | $C_2F_5$ | Et |
| 3-167 | Cl | $C_2F_5$ | c-Pr |
| 3-168 | Cl | $C_2F_5$ | $CH_2$-c-Pr |
| 3-169 | Cl | $C_2F_5$ | $CH_2CF_3$ |
| 3-170 | Cl | $C_2F_5$ | $CH_2CHF_2$ |
| 3-171 | Cl | Cl | Me |
| 3-172 | Cl | Cl | Et |
| 3-173 | Cl | Cl | c-Pr |
| 3-174 | Cl | Cl | $CH_2$-c-Pr |
| 3-175 | Cl | Cl | $CH_2CF_3$ |
| 3-176 | Cl | Cl | $CH_2CHF_2$ |
| 3-177 | Cl | Br | Me |
| 3-178 | Cl | Br | Et |
| 3-179 | Cl | Br | c-Pr |
| 3-180 | Cl | Br | $CH_2$-c-Pr |
| 3-181 | Cl | Br | $CH_2CF_3$ |
| 3-182 | Cl | Br | $CH_2CHF_2$ |
| 3-183 | Cl | Br | CH(Me)-c-Pr |
| 3-184 | Cl | Br | Pr |
| 3-185 | Cl | Br | iPr |
| 3-186 | Cl | Br | $CH_2CH_2OMe$ |
| 3-187 | Cl | Br | $CH_2CH_2SMe$ |
| 3-188 | Cl | Br | $CH_2CN$ |
| 3-189 | Cl | Br | $CH_2$-(tetrahydrofuran-2-yl) |
| 3-190 | Cl | Br | $CH_2C(O)NMe_2$ |
| 3-191 | Cl | Br | Ph |
| 3-192 | Cl | Br | $CH_2$-(thien-2-yl) |
| 3-193 | Cl | Br | Oxetan-3-yl |
| 3-194 | Cl | Br | cBu |
| 3-195 | Cl | I | Me |
| 3-196 | Cl | I | Et |
| 3-197 | Cl | I | c-Pr |
| 3-198 | Cl | I | $CH_2$-c-Pr |
| 3-199 | Cl | I | $CH_2cF_3$ |
| 3-200 | Cl | I | $CH_2CHF_2$ |
| 3-201 | Br | $SO_2Me$ | Me |
| 3-202 | Br | $SO_2Me$ | Et |
| 3-203 | Br | $SO_2Me$ | c-Pr |
| 3-204 | Br | $SO_2Me$ | $CH_2$-c-Pr |
| 3-205 | Br | $SO_2Me$ | $CH_2CF_3$ |

TABLE 3-continued

Inventive compounds of the general formula (I) in which Q is $Q^1$ and $R^x$ is propyl, and the other substituents have the definitions given below.

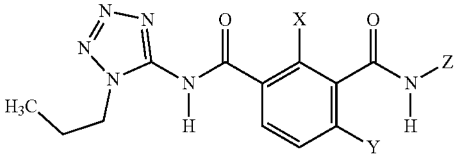

| No. | X | Y | Z |
|---|---|---|---|
| 3-206 | Br | $SO_2Me$ | $CH_2CHF_2$ |
| 3-207 | Br | $CF_3$ | Me |
| 3-208 | Br | $CF_3$ | Et |
| 3-209 | Br | $CF_3$ | c-Pr |
| 3-210 | Br | $CF_3$ | $CH_2$-c-Pr |
| 3-211 | Br | $CF_3$ | $CH_2CF_3$ |
| 3-212 | Br | $CF_3$ | $CH_2CHF_2$ |
| 3-213 | Br | $CF_3$ | CH(Me)-c-Pr |
| 3-214 | Br | $CF_3$ | Pr |
| 3-215 | Br | $CF_3$ | i-Pr |
| 3-216 | Br | $CF_3$ | $CH_2CH_2OMe$ |
| 3-217 | Br | $CF_3$ | $CH_2CH_2SMe$ |
| 3-218 | Br | $CF_3$ | $CH_2CN$ |
| 3-219 | Br | $CF_3$ | $CH_2$-(tetrahydrofuran-2-yl) |
| 3-220 | Br | $CF_3$ | $CH_2C(O)NMe_2$ |
| 3-221 | Br | $CF_3$ | Ph |
| 3-222 | Br | $CF_3$ | $CH_2$-(thien-2-yl) |
| 3-223 | Br | $CF_3$ | Oxetan-3-yl |
| 3-224 | Br | $CF_3$ | c-Bu |
| 3-225 | Br | $CHF_2$ | Me |
| 3-226 | Br | $CHF_2$ | Et |
| 3-227 | Br | $CHF_2$ | c-Pr |
| 3-228 | Br | $CHF_2$ | $CH_2$-c-Pr |
| 3-229 | Br | $CHF_2$ | $CH_2CF_3$ |
| 3-230 | Br | $CHF_2$ | $CH_2CHF_2$ |
| 3-231 | Br | $C_2F_5$ | Me |
| 3-232 | Br | $C_2F_5$ | Et |
| 3-233 | Br | $C_2F_5$ | c-Pr |
| 3-234 | Br | $C_2F_5$ | $CH_2$-c-Pr |
| 3-235 | Br | $C_2F_5$ | $CH_2cF_3$ |
| 3-236 | Br | $C_2F_5$ | $CH_2CHF_2$ |
| 3-237 | I | $SO_2Me$ | Me |
| 3-238 | I | $SO_2Me$ | Et |
| 3-239 | I | $SO_2Me$ | c-Pr |
| 3-240 | I | $CF_3$ | Me |
| 3-241 | I | $CF_3$ | Et |
| 3-242 | I | $CF_3$ | c-Pr |
| 3-243 | I | $CF_3$ | $CH_2$-c-Pr |
| 3-244 | I | $CF_3$ | $CH_2CF_3$ |
| 3-245 | I | $CF_3$ | $CH_2CHF_2$ |
| 3-246 | I | $CHF_2$ | Me |
| 3-247 | I | $CHF_2$ | Et |
| 3-248 | I | $CHF_2$ | c-Pr |
| 3-249 | I | $CHF_2$ | $CH_2$-c-Pr |
| 3-250 | I | $CHF_2$ | $CH_2CF_3$ |
| 3-251 | I | $CHF_2$ | $CH_2CHF_2$ |
| 3-252 | I | $C_2F_5$ | Me |
| 3-253 | I | $C_2F_5$ | Et |
| 3-254 | I | $C_2F_5$ | c-Pr |
| 3-255 | $CH_2OMe$ | $CF_3$ | Me |
| 3-256 | $CH_2OMe$ | $CF_3$ | Et |
| 3-257 | $CH_2OMe$ | $CF_3$ | c-Pr |
| 3-258 | $CH_2OMe$ | $CF_3$ | $CH_2$-c-Pr |
| 3-259 | $CH_2OMe$ | $CF_3$ | $CH_2CF_3$ |
| 3-260 | $CH_2OMe$ | $CF_3$ | $CH_2CHF_2$ |
| 3-261 | $CH_2OMe$ | $CHF_2$ | Me |
| 3-262 | $CH_2OMe$ | $CHF_2$ | Et |
| 3-263 | $CH_2OMe$ | $CHF_2$ | c-Pr |
| 3-264 | $CH_2OMe$ | $CHF_2$ | $CH_2$-c-Pr |
| 3-265 | $CH_2OMe$ | $CHF_2$ | $CH_2CF_3$ |
| 3-266 | $CH_2OMe$ | $CHF_2$ | $CH_2CHF_2$ |
| 3-267 | $CH_2OMe$ | $CHF_2$ | c-Pentyl |
| 3-268 | $CH_2OMe$ | $SO_2Me$ | Me |
| 3-269 | $CH_2OMe$ | $SO_2Me$ | Et |
| 3-270 | $CH_2OMe$ | $SO_2Me$ | c-Pr |

TABLE 3-continued

Inventive compounds of the general formula (I) in which Q is $Q^1$ and $R^x$ is propyl, and the other substituents have the definitions given below.

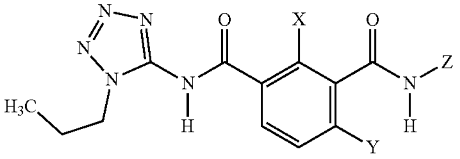

| No. | X | Y | Z |
|---|---|---|---|
| 3-271 | Et | $CF_3$ | Me |
| 3-272 | Et | $CF_3$ | Et |
| 3-273 | Et | $CF_3$ | c-Pr |
| 3-274 | Et | $CF_3$ | $CH_2$-c-Pr |
| 3-275 | Et | $CF_3$ | $CH_2CF_3$ |
| 3-276 | Et | $CF_3$ | $CH_2CHF_2$ |
| 3-277 | Et | $CHF_2$ | Me |
| 3-278 | Et | $CHF_2$ | Et |
| 3-279 | Et | $CHF_2$ | c-Pr |
| 3-280 | Et | $CHF_2$ | $CH_2$-c-Pr |
| 3-281 | Et | $CHF_2$ | $CH_2CF_3$ |
| 3-282 | Et | $CHF_2$ | $CH_2CHF_2$ |
| 3-283 | Et | $C_2F_5$ | Me |
| 3-284 | Et | $C_2F_5$ | Et |
| 3-285 | Et | $C_2F_5$ | c-Pr |
| 3-286 | c-Pr | $CF_3$ | Me |
| 3-287 | c-Pr | $CF_3$ | Et |
| 3-288 | c-Pr | $CF_3$ | c-Pr |
| 3-289 | c-Pr | $CF_3$ | $CH_2$-c-Pr |
| 3-290 | c-Pr | $CF_3$ | $CH_2CF_3$ |
| 3-291 | c-Pr | $CF_3$ | $CH_2CHF_2$ |
| 3-292 | c-Pr | $CF_3$ | CH(Me)-c-Pr |
| 3-293 | c-Pr | $CF_3$ | Pr |
| 3-294 | c-Pr | $CF_3$ | i-Pr |
| 3-295 | c-Pr | $CF_3$ | $CH_2CH_2OMe$ |
| 3-296 | c-Pr | $CF_3$ | $CH_2CH_2SMe$ |
| 3-297 | c-Pr | $CF_3$ | $CH_2CN$ |
| 3-298 | c-Pr | $CF_3$ | $CH_2$-(tetrahydrofuran-2-yl) |
| 3-299 | c-Pr | $CF_3$ | $CH_2C(O)NMe_2$ |
| 3-300 | c-Pr | $CF_3$ | Ph |
| 3-301 | c-Pr | $CF_3$ | $CH_2$-(thien-2-yl) |
| 3-302 | c-Pr | $CF_3$ | Oxetan-3-yl |
| 3-303 | c-Pr | $CF_3$ | c-Bu |
| 3-304 | c-Pr | $CHF_2$ | Me |
| 3-305 | c-Pr | $CHF_2$ | Et |
| 3-306 | c-Pr | $CHF_2$ | c-Pr |
| 3-307 | c-Pr | $CHF_2$ | $CH_2$-c-Pr |
| 3-308 | c-Pr | $CHF_2$ | $CH_2cF_3$ |
| 3-309 | c-Pr | $CHF_2$ | $CH_2CHF_2$ |
| 3-310 | c-Pr | $CHF_2$ | CH(Me)-c-Pr |
| 3-311 | c-Pr | $CHF_2$ | Pr |
| 3-312 | c-Pr | $CHF_2$ | i-Pr |
| 3-313 | c-Pr | $CHF_2$ | $CH_2CH_2OMe$ |
| 3-314 | c-Pr | $CHF_2$ | $CH_2CH_2SMe$ |
| 3-315 | c-Pr | $CHF_2$ | $CH_2CN$ |
| 3-316 | c-Pr | $CHF_2$ | $CH_2$-(tetrahydrofuran-2-yl) |
| 3-317 | c-Pr | $CHF_2$ | $CH_2C(O)NMe_2$ |
| 3-318 | c-Pr | $CHF_2$ | Ph |
| 3-319 | c-Pr | $CHF_2$ | $CH_2$-(thien-2-yl) |
| 3-320 | c-Pr | $CHF_2$ | Oxetan-3-yl |
| 3-321 | c-Pr | $CHF_2$ | c-Bu |
| 3-322 | c-Pr | $C_2F_5$ | Me |
| 3-323 | c-Pr | $C_2F_5$ | Et |
| 3-324 | c-Pr | $C_2F_5$ | c-Pr |
| 3-325 | c-Pr | $C_2F_5$ | $CH_2$-c-Pr |
| 3-326 | c-Pr | $C_2F_5$ | $CH_2CF_3$ |
| 3-327 | c-Pr | $C_2F_5$ | $CH_2CHF_2$ |
| 3-328 | c-Pr | $SO_2Me$ | Me |
| 3-329 | c-Pr | $SO_2Me$ | Et |
| 3-330 | c-Pr | $SO_2Me$ | c-Pr |
| 3-331 | $CF_3$ | $CF_3$ | Me |
| 3-332 | $CF_3$ | $CF_3$ | Et |
| 3-333 | $CF_3$ | $CF_3$ | c-Pr |
| 3-334 | $CF_3$ | $CF_3$ | $CH_2$-c-Pr |
| 3-335 | $CF_3$ | $CF_3$ | $CH_2CF_3$ |

TABLE 3-continued

Inventive compounds of the general formula (I) in which Q is $Q^1$ and $R^x$ is propyl, and the other substituents have the definitions given below.

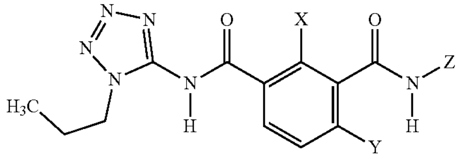

| No. | X | Y | Z |
|---|---|---|---|
| 3-336 | $CF_3$ | $CF_3$ | $CH_2CHF_2$ |
| 3-337 | Cl | $CF_3$ | Acetyl |
| 3-338 | Cl | $CF_3$ | H |

TABLE 4

Inventive compounds of the general formula (I) in which Q is $Q^2$ and $R^x$ is methyl, and the other substituents have the definitions given below.

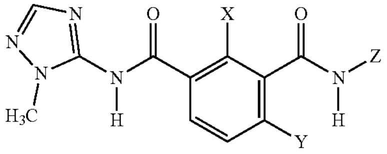

| No. | X | Y | Z |
|---|---|---|---|
| 4-1 | Me | F | Me |
| 4-2 | Me | F | Et |
| 4-3 | Me | F | c-Pr |
| 4-4 | Me | Cl | Me |
| 4-5 | Me | Cl | Et |
| 4-6 | Me | Cl | c-Pr |
| 4-7 | Me | Br | Me |
| 4-8 | Me | Br | Et |
| 4-9 | Me | Br | c-Pr |
| 4-10 | Me | I | Me |
| 4-11 | Me | I | Et |
| 4-12 | Me | I | c-Pr |
| 4-13 | Me | SMe | Me |
| 4-14 | Me | SMe | Et |
| 4-15 | Me | SMe | c-Pr |
| 4-16 | Me | S(O)Me | Me |
| 4-17 | Me | S(O)Me | Et |
| 4-18 | Me | S(O)Me | c-Pr |
| 4-19 | Me | $SO_2Me$ | Me |
| 4-20 | Me | $SO_2Me$ | Et |
| 4-21 | Me | $SO_2Me$ | c-Pr |
| 4-22 | Me | $SO_2Me$ | $CH_2$-c-Pr |
| 4-23 | Me | $SO_2Me$ | $CH_2CF_3$ |
| 4-24 | Me | $SO_2Me$ | $CH_2CHF_2$ |
| 4-25 | Me | $CF_3$ | Me |
| 4-26 | Me | $CF_3$ | Et |
| 4-27 | Me | $CF_3$ | c-Pr |
| 4-28 | Me | $CF_3$ | $CH_2$-c-Pr |
| 4-29 | Me | $CF_3$ | $CH_2CF_3$ |
| 4-30 | Me | $CF_3$ | $CH_2CHF_2$ |
| 4-31 | Me | $CHF_2$ | Me |
| 4-32 | Me | $CHF_2$ | Et |
| 4-33 | Me | $CHF_2$ | c-Pr |
| 4-34 | Me | $CHF_2$ | $CH_2$-c-Pr |
| 4-35 | Me | $CHF_2$ | $CH_2CF_3$ |
| 4-36 | Me | $CHF_2$ | $CH_2CHF_2$ |
| 4-37 | Me | $C_2F_5$ | Me |
| 4-38 | Me | $C_2F_5$ | Et |
| 4-39 | Me | $C_2F_5$ | c-Pr |
| 4-40 | OMe | Cl | Me |
| 4-41 | OMe | Cl | Et |
| 4-42 | OMe | Cl | c-Pr |
| 4-43 | OMe | $CF_3$ | Me |

TABLE 4-continued

Inventive compounds of the general formula (I) in which Q is $Q^2$ and $R^x$ is methyl, and the other substituents have the definitions given below.

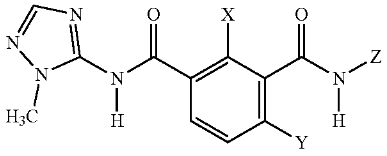

| No. | X | Y | Z |
|---|---|---|---|
| 4-44 | OMe | $CF_3$ | Et |
| 4-45 | OMe | $CF_3$ | c-Pr |
| 4-46 | OMe | $CF_3$ | $CH_2$-c-Pr |
| 4-47 | OMe | $CF_3$ | $CH_2CF_3$ |
| 4-48 | OMe | $CF_3$ | $CH_2CHF_2$ |
| 4-49 | OMe | $CHF_2$ | Me |
| 4-50 | OMe | $CHF_2$ | Et |
| 4-51 | OMe | $CHF_2$ | c-Pr |
| 4-52 | OMe | $CHF_2$ | $CH_2$-c-Pr |
| 4-53 | OMe | $CHF_2$ | $CH_2CF_3$ |
| 4-54 | OMe | $CHF_2$ | $CH_2CHF_2$ |
| 4-55 | SMe | $SO_2Me$ | Me |
| 4-56 | SMe | $SO_2Me$ | Et |
| 4-57 | SMe | $SO_2Me$ | c-Pr |
| 4-58 | SMe | $CF_3$ | Me |
| 4-59 | SMe | $CF_3$ | Et |
| 4-60 | SMe | $CF_3$ | c-Pr |
| 4-71 | SMe | $CF_3$ | $CH_2$-c-Pr |
| 4-72 | SMe | $CF_3$ | $CH_2CF_3$ |
| 4-73 | SMe | $CF_3$ | $CH_2CHF_2$ |
| 4-74 | SMe | $CHF_2$ | Me |
| 4-75 | SMe | $CHF_2$ | Et |
| 4-76 | SMe | $CHF_2$ | c-Pr |
| 4-77 | SMe | $CHF_2$ | $CH_2$-c-Pr |
| 4-78 | SMe | $CHF_2$ | $CH_2CF_3$ |
| 4-79 | SMe | $CHF_2$ | $CH_2CHF_2$ |
| 4-80 | SEt | $CF_3$ | Me |
| 4-81 | SEt | $CF_3$ | Et |
| 4-82 | SEt | $CF_3$ | c-Pr |
| 4-83 | SEt | $CF_3$ | $CH_2$-c-Pr |
| 4-84 | SEt | $CF_3$ | $CH_2CF_3$ |
| 4-85 | SEt | $CF_3$ | $CH_2CHF_2$ |
| 4-86 | SEt | $CHF_2$ | Me |
| 4-87 | SEt | $CHF_2$ | Et |
| 4-88 | SEt | $CHF_2$ | c-Pr |
| 4-89 | SEt | $CHF_2$ | $CH_2$-c-Pr |
| 4-90 | SEt | $CHF_2$ | $CH_2CF_3$ |
| 4-91 | SEt | $CHF_2$ | $CH_2CHF_2$ |
| 4-92 | F | $CF_3$ | Me |
| 4-93 | F | $CF_3$ | Et |
| 4-94 | F | $CF_3$ | c-Pr |
| 4-95 | F | $CF_3$ | $CH_2$-c-Pr |
| 4-96 | F | $CF_3$ | $CH_2CF_3$ |
| 4-97 | F | $CF_3$ | $CH_2CHF_2$ |
| 4-98 | F | $CHF_2$ | Me |
| 4-99 | F | $CHF_2$ | Et |
| 4-100 | F | $CHF_2$ | c-Pr |
| 4-101 | F | $CHF_2$ | $CH_2$-c-Pr |
| 4-102 | F | $CHF_2$ | $CH_2CF_3$ |
| 4-103 | F | $CHF_2$ | $CH_2CHF_2$ |
| 4-104 | Cl | SMe | Me |
| 4-105 | Cl | SMe | Et |
| 4-106 | Cl | SMe | c-Pr |
| 4-107 | Cl | S(O)Me | Me |
| 4-108 | Cl | S(O)Me | Et |
| 4-109 | Cl | S(O)Me | c-Pr |
| 4-110 | Cl | $SO_2Me$ | Me |
| 4-111 | Cl | $SO_2Me$ | Et |
| 4-112 | Cl | $SO_2Me$ | c-Pr |
| 4-113 | Cl | $SO_2Me$ | $CH_2$-c-Pr |
| 4-114 | Cl | $SO_2Me$ | $CH_2CF_3$ |
| 4-115 | Cl | $SO_2Me$ | $CH_2CHF_2$ |
| 4-116 | Cl | $CF_3$ | Me |
| 4-117 | Cl | $CF_3$ | Et |
| 4-118 | Cl | $CF_3$ | c-Pr |
| 4-119 | Cl | $CF_3$ | $CH_2$-c-Pr |

TABLE 4-continued

Inventive compounds of the general formula (I) in which Q is $Q^2$ and $R^x$ is methyl, and the other substituents have the definitions given below.

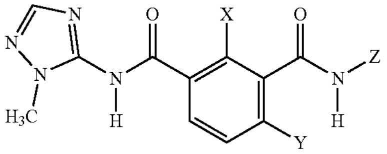

| No. | X | Y | Z |
|---|---|---|---|
| 4-120 | Cl | $CF_3$ | $CH_2CF_3$ |
| 4-121 | Cl | $CF_3$ | $CH_2CHF_2$ |
| 4-122 | Cl | $CHF_2$ | Me |
| 4-123 | Cl | $CHF_2$ | Et |
| 4-124 | Cl | $CHF_2$ | c-Pr |
| 4-125 | Cl | $CHF_2$ | $CH_2$-c-Pr |
| 4-126 | Cl | $CHF_2$ | $CH_2CF_3$ |
| 4-127 | Cl | $CHF_2$ | $CH_2CHF_2$ |
| 4-128 | Cl | $C_2F_5$ | Me |
| 4-129 | Cl | $C_2F_5$ | Et |
| 4-130 | Cl | $C_2F_5$ | c-Pr |
| 4-131 | Cl | $C_2F_5$ | $CH_2$-c-Pr |
| 4-132 | Cl | $C_2F_5$ | $CH_2CF_3$ |
| 4-133 | Cl | $C_2F_5$ | $CH_2CHF_2$ |
| 4-134 | Cl | Cl | Me |
| 4-135 | Cl | Cl | Et |
| 4-136 | Cl | Cl | c-Pr |
| 4-137 | Cl | Cl | $CH_2$-c-Pr |
| 4-138 | Cl | Cl | $CH_2CF_3$ |
| 4-139 | Cl | Cl | $CH_2CHF_2$ |
| 4-140 | Cl | Br | Me |
| 4-141 | Cl | Br | Et |
| 4-142 | Cl | Br | c-Pr |
| 4-143 | Cl | Br | $CH_2$-c-Pr |
| 4-144 | Cl | Br | $CH_2CF_3$ |
| 4-145 | Cl | Br | $CH_2CHF_2$ |
| 4-146 | Cl | I | Me |
| 4-147 | Cl | I | Et |
| 4-148 | Cl | I | c-Pr |
| 4-149 | Cl | I | $CH_2$-c-Pr |
| 4-150 | Cl | I | $CH_2CF_3$ |
| 4-151 | Cl | I | $CH_2CHF_2$ |
| 4-152 | Br | $SO_2Me$ | Me |
| 4-153 | Br | $SO_2Me$ | Et |
| 4-154 | Br | $SO_2Me$ | c-Pr |
| 4-155 | Br | $SO_2Me$ | $CH_2$-c-Pr |
| 4-156 | Br | $SO_2Me$ | $CH_2CF_3$ |
| 4-157 | Br | $SO_2Me$ | $CH_2CHF_2$ |
| 4-158 | Br | $CF_3$ | Me |
| 4-159 | Br | $CF_3$ | Et |
| 4-160 | Br | $CF_3$ | c-Pr |
| 4-161 | Br | $CF_3$ | $CH_2$-c-Pr |
| 4-162 | Br | $CF_3$ | $CH_2CF_3$ |
| 4-163 | Br | $CF_3$ | $CH_2CHF_2$ |
| 4-164 | Br | $CHF_2$ | Me |
| 4-165 | Br | $CHF_2$ | Et |
| 4-166 | Br | $CHF_2$ | c-Pr |
| 4-167 | Br | $CHF_2$ | $CH_2$-c-Pr |
| 4-168 | Br | $CHF_2$ | $CH_2CF_3$ |
| 4-169 | Br | $CHF_2$ | $CH_2CHF_2$ |
| 4-170 | Br | $C_2F_5$ | Me |
| 4-171 | Br | $C_2F_5$ | Et |
| 4-172 | Br | $C_2F_5$ | c-Pr |
| 4-173 | Br | $C_2F_5$ | $CH_2$-c-Pr |
| 4-174 | Br | $C_2F_5$ | $CH_2CF_3$ |
| 4-175 | Br | $C_2F_5$ | $CH_2CHF_2$ |
| 4-176 | I | $SO_2Me$ | Me |
| 4-177 | I | $SO_2Me$ | Et |
| 4-178 | I | $SO_2Me$ | c-Pr |
| 4-179 | I | $CF_3$ | Me |
| 4-180 | I | $CF_3$ | Et |
| 4-181 | I | $CF_3$ | c-Pr |
| 4-182 | I | $CF_3$ | $CH_2$-c-Pr |
| 4-183 | I | $CF_3$ | $CH_2CF_3$ |
| 4-184 | I | $CF_3$ | $CH_2CHF_2$ |
| 4-185 | I | $CHF_2$ | Me |

TABLE 4-continued

Inventive compounds of the general formula (I) in which Q is $Q^2$ and $R^x$ is methyl, and the other substituents have the definitions given below.

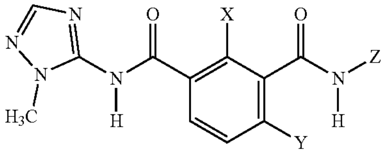

| No. | X | Y | Z |
|---|---|---|---|
| 4-186 | I | $CHF_2$ | Et |
| 4-187 | I | $CHF_2$ | c-Pr |
| 4-188 | I | $CHF_2$ | $CH_2$-c-Pr |
| 4-189 | I | $CHF_2$ | $CH_2CF_3$ |
| 4-190 | I | $CHF_2$ | $CH_2CHF_2$ |
| 4-191 | I | $C_2F_5$ | Me |
| 4-192 | I | $C_2F_5$ | Et |
| 4-193 | I | $C_2F_5$ | c-Pr |
| 4-194 | $CH_2OMe$ | $CF_3$ | Me |
| 4-195 | $CH_2OMe$ | $CF_3$ | Et |
| 4-196 | $CH_2OMe$ | $CF_3$ | c-Pr |
| 4-197 | $CH_2OMe$ | $CF_3$ | $CH_2$-c-Pr |
| 4-198 | $CH_2OMe$ | $CF_3$ | $CH_2CF_3$ |
| 4-199 | $CH_2OMe$ | $CF_3$ | $CH_2CHF_2$ |
| 4-200 | $CH_2OMe$ | $CHF_2$ | Me |
| 4-201 | $CH_2OMe$ | $CHF_2$ | Et |
| 4-202 | $CH_2OMe$ | $CHF_2$ | c-Pr |
| 4-203 | $CH_2OMe$ | $CHF_2$ | $CH_2$-c-Pr |
| 4-204 | $CH_2OMe$ | $CHF_2$ | $CH_2CF_3$ |
| 4-205 | $CH_2OMe$ | $CHF_2$ | $CH_2CHF_2$ |
| 4-206 | $CH_2OMe$ | $CHF_2$ | c-Pentyl |
| 4-207 | $CH_2OMe$ | $SO_2Me$ | Me |
| 4-208 | $CH_2OMe$ | $SO_2Me$ | Et |
| 4-209 | $CH_2OMe$ | $SO_2Me$ | c-Pr |
| 4-210 | Et | $CF_3$ | Me |
| 4-211 | Et | $CF_3$ | Et |
| 4-212 | Et | $CF_3$ | c-Pr |
| 4-213 | Et | $CF_3$ | $CH_2$-c-Pr |
| 4-214 | Et | $CF_3$ | $CH_2CF_3$ |
| 4-215 | Et | $CF_3$ | $CH_2CHF_2$ |
| 4-216 | Et | $CHF_2$ | Me |
| 4-217 | Et | $CHF_2$ | Et |
| 4-218 | Et | $CHF_2$ | c-Pr |
| 4-219 | Et | $CHF_2$ | $CH_2$-c-Pr |
| 4-220 | Et | $CHF_2$ | $CH_2CF_3$ |
| 4-221 | Et | $CHF_2$ | $CH_2CHF_2$ |
| 4-222 | Et | $C_2F_5$ | Me |
| 4-223 | Et | $C_2F_5$ | Et |
| 4-224 | Et | $C_2F_5$ | c-Pr |
| 4-225 | c-Pr | $CF_3$ | Me |
| 4-226 | c-Pr | $CF_3$ | Et |
| 4-227 | c-Pr | $CF_3$ | c-Pr |
| 4-228 | c-Pr | $CF_3$ | $CH_2$-c-Pr |
| 4-229 | c-Pr | $CF_3$ | $CH_2CF_3$ |
| 4-230 | c-Pr | $CF_3$ | $CH_2CHF_2$ |
| 4-231 | c-Pr | $CHF_2$ | Me |
| 4-232 | c-Pr | $CHF_2$ | Et |
| 4-233 | c-Pr | $CHF_2$ | c-Pr |
| 4-234 | c-Pr | $CHF_2$ | $CH_2$-c-Pr |
| 4-235 | c-Pr | $CHF_2$ | $CH_2CF_3$ |
| 4-236 | c-Pr | $CHF_2$ | $CH_2CHF_2$ |
| 4-237 | c-Pr | $C_2F_5$ | Me |
| 4-238 | c-Pr | $C_2F_5$ | Et |
| 4-239 | c-Pr | $C_2F_5$ | c-Pr |
| 4-240 | c-Pr | $C_2F_5$ | $CH_2$-c-Pr |
| 4-241 | c-Pr | $C_2F_5$ | $CH_2CF_3$ |
| 4-242 | c-Pr | $C_2F_5$ | $CH_2CHF_2$ |
| 4-243 | c-Pr | $SO_2Me$ | Me |
| 4-244 | c-Pr | $SO_2Me$ | Et |
| 4-245 | c-Pr | $SO_2Me$ | c-Pr |
| 4-246 | $CF_3$ | $CF_3$ | Me |
| 4-247 | $CF_3$ | $CF_3$ | Et |
| 4-248 | $CF_3$ | $CF_3$ | c-Pr |
| 4-249 | $CF_3$ | $CF_3$ | $CH_2$-c-Pr |
| 4-250 | $CF_3$ | $CF_3$ | $CH_2CF_3$ |

TABLE 4-continued

Inventive compounds of the general formula (I) in which Q is $Q^2$ and $R^x$ is methyl, and the other substituents have the definitions given below.

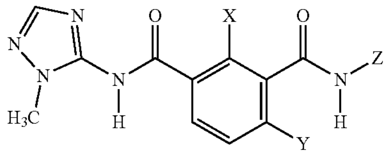

| No. | X | Y | Z |
|---|---|---|---|
| 4-251 | $CF_3$ | $CF_3$ | $CH_2CHF_2$ |
| 4-252 | Cl | $CF_3$ | H |

TABLE 5

Inventive compounds of the general formula (I) in which Q is $Q^4$ and $R^z$ is hydrogen, and the other substituents have the definitions given below.

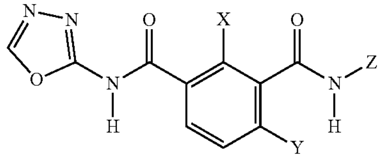

| No. | X | Y | Z |
|---|---|---|---|
| 5-1 | Me | F | Me |
| 5-2 | Me | F | Et |
| 5-3 | Me | F | c-Pr |
| 5-4 | Me | Cl | Me |
| 5-5 | Me | Cl | Et |
| 5-6 | Me | Cl | c-Pr |
| 5-7 | Me | Br | Me |
| 5-8 | Me | Br | Et |
| 5-9 | Me | Br | c-Pr |
| 5-10 | Me | I | Me |
| 5-11 | Me | I | Et |
| 5-12 | Me | I | c-Pr |
| 5-13 | Me | SMe | Me |
| 5-14 | Me | SMe | Et |
| 5-15 | Me | SMe | c-Pr |
| 5-16 | Me | S(O)Me | Me |
| 5-17 | Me | S(O)Me | Et |
| 5-18 | Me | S(O)Me | c-Pr |
| 5-19 | Me | $SO_2Me$ | Me |
| 5-20 | Me | $SO_2Me$ | Et |
| 5-21 | Me | $SO_2Me$ | c-Pr |
| 5-22 | Me | $SO_2Me$ | $CH_2$-c-Pr |
| 5-23 | Me | $SO_2Me$ | $CH_2CF_3$ |
| 5-24 | Me | $SO_2Me$ | $CH_2CHF_2$ |
| 5-25 | Me | $CF_3$ | Me |
| 5-26 | Me | $CF_3$ | Et |
| 5-27 | Me | $CF_3$ | c-Pr |
| 5-28 | Me | $CF_3$ | $CH_2$-c-Pr |
| 5-29 | Me | $CF_3$ | $CH_2CF_3$ |
| 5-30 | Me | $CF_3$ | $CH_2CHF_2$ |
| 5-31 | Me | $CHF_2$ | Me |
| 5-32 | Me | $CHF_2$ | Et |
| 5-33 | Me | $CHF_2$ | c-Pr |
| 5-34 | Me | $CHF_2$ | $CH_2$-c-Pr |
| 5-35 | Me | $CHF_2$ | $CH_2CF_3$ |
| 5-36 | Me | $CHF_2$ | $CH_2CHF_2$ |
| 5-37 | Me | $C_2F_5$ | Me |
| 5-38 | Me | $C_2F_5$ | Et |
| 5-39 | Me | $C_2F_5$ | c-Pr |
| 5-40 | OMe | Cl | Me |
| 5-41 | OMe | Cl | Et |
| 5-42 | OMe | Cl | c-Pr |
| 5-43 | OMe | $CF_3$ | Me |
| 5-44 | OMe | $CF_3$ | Et |

TABLE 5-continued

Inventive compounds of the general formula (I) in which Q is $Q^4$ and $R^z$ is hydrogen, and the other substituents have the definitions given below.

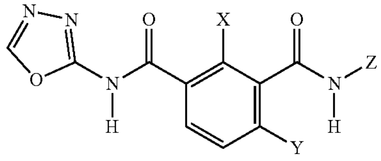

| No. | X | Y | Z |
|---|---|---|---|
| 5-45 | OMe | $CF_3$ | c-Pr |
| 5-46 | OMe | $CF_3$ | $CH_2$-c-Pr |
| 5-47 | OMe | $CF_3$ | $CH_2CF_3$ |
| 5-48 | OMe | $CF_3$ | $CH_2CHF_2$ |
| 5-49 | OMe | $CHF_2$ | Me |
| 5-50 | OMe | $CHF_2$ | Et |
| 5-51 | OMe | $CHF_2$ | c-Pr |
| 5-52 | OMe | $CHF_2$ | $CH_2$-c-Pr |
| 5-53 | OMe | $CHF_2$ | $CH_2CF_3$ |
| 5-54 | OMe | $CHF_2$ | $CH_2CHF_2$ |
| 5-55 | SMe | $SO_2Me$ | Me |
| 5-56 | SMe | $SO_2Me$ | Et |
| 5-57 | SMe | $SO_2Me$ | c-Pr |
| 5-58 | SMe | $CF_3$ | Me |
| 5-59 | SMe | $CF_3$ | Et |
| 5-60 | SMe | $CF_3$ | c-Pr |
| 5-71 | SMe | $CF_3$ | $CH_2$-c-Pr |
| 5-72 | SMe | $CF_3$ | $CH_2CF_3$ |
| 5-73 | SMe | $CF_3$ | $CH_2CHF_2$ |
| 5-74 | SMe | $CHF_2$ | Me |
| 5-75 | SMe | $CHF_2$ | Et |
| 5-76 | SMe | $CHF_2$ | c-Pr |
| 5-77 | SMe | $CHF_2$ | $CH_2$-c-Pr |
| 5-78 | SMe | $CHF_2$ | $CH_2CF_3$ |
| 5-79 | SMe | $CHF_2$ | $CH_2CHF_2$ |
| 5-80 | SEt | $CF_3$ | Me |
| 5-81 | SEt | $CF_3$ | Et |
| 5-82 | SEt | $CF_3$ | c-Pr |
| 5-83 | SEt | $CF_3$ | $CH_2$-c-Pr |
| 5-84 | SEt | $CF_3$ | $CH_2CF_3$ |
| 5-85 | SEt | $CF_3$ | $CH_2CHF_2$ |
| 5-86 | SEt | $CHF_2$ | Me |
| 5-87 | SEt | $CHF_2$ | Et |
| 5-88 | SEt | $CHF_2$ | c-Pr |
| 5-89 | SEt | $CHF_2$ | $CH_2$-c-Pr |
| 5-90 | SEt | $CHF_2$ | $CH_2CF_3$ |
| 5-91 | SEt | $CHF_2$ | $CH_2CHF_2$ |
| 5-92 | F | $CF_3$ | Me |
| 5-93 | F | $CF_3$ | Et |
| 5-94 | F | $CF_3$ | c-Pr |
| 5-95 | F | $CF_3$ | $CH_2$-c-Pr |
| 5-96 | F | $CF_3$ | $CH_2CF_3$ |
| 5-97 | F | $CF_3$ | $CH_2CHF_2$ |
| 5-98 | F | $CHF_2$ | Me |
| 5-99 | F | $CHF_2$ | Et |
| 5-100 | F | $CHF_2$ | c-Pr |
| 5-101 | F | $CHF_2$ | $CH_2$-c-Pr |
| 5-102 | F | $CHF_2$ | $CH_2CF_3$ |
| 5-103 | F | $CHF_2$ | $CH_2CHF_2$ |
| 5-104 | Cl | SMe | Me |
| 5-105 | Cl | SMe | Et |
| 5-106 | Cl | SMe | c-Pr |
| 5-107 | Cl | S(O)Me | Me |
| 5-108 | Cl | S(O)Me | Et |
| 5-109 | Cl | S(O)Me | c-Pr |
| 5-110 | Cl | $SO_2Me$ | Me |
| 5-111 | Cl | $SO_2Me$ | Et |
| 5-112 | Cl | $SO_2Me$ | c-Pr |
| 5-113 | Cl | $SO_2Me$ | $CH_2$-c-Pr |
| 5-114 | Cl | $SO_2Me$ | $CH_2CF_3$ |
| 5-115 | Cl | $SO_2Me$ | $CH_2CHF_2$ |
| 5-116 | Cl | $CF_3$ | Me |
| 5-117 | Cl | $CF_3$ | Et |
| 5-118 | Cl | $CF_3$ | c-Pr |
| 5-119 | Cl | $CF_3$ | $CH_2$-c-Pr |

TABLE 5-continued

Inventive compounds of the general formula (I) in which Q is $Q^4$ and $R^z$ is hydrogen, and the other substituents have the definitions given below.

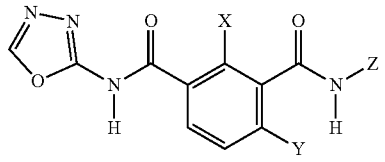

| No. | X | Y | Z |
|---|---|---|---|
| 5-120 | Cl | $CF_3$ | $CH_2CF_3$ |
| 5-121 | Cl | $CF_3$ | $CH_2CHF_2$ |
| 5-122 | Cl | $CHF_2$ | Me |
| 5-123 | Cl | $CHF_2$ | Et |
| 5-124 | Cl | $CHF_2$ | c-Pr |
| 5-125 | Cl | $CHF_2$ | $CH_2$-c-Pr |
| 5-126 | Cl | $CHF_2$ | $CH_2CF_3$ |
| 5-127 | Cl | $CHF_2$ | $CH_2CHF_2$ |
| 5-128 | Cl | $C_2F_5$ | Me |
| 5-129 | Cl | $C_2F_5$ | Et |
| 5-130 | Cl | $C_2F_5$ | c-Pr |
| 5-131 | Cl | $C_2F_5$ | $CH_2$-c-Pr |
| 5-132 | Cl | $C_2F_5$ | $CH_2CF_3$ |
| 5-133 | Cl | $C_2F_5$ | $CH_2CHF_2$ |
| 5-134 | Cl | Cl | Me |
| 5-135 | Cl | Cl | Et |
| 5-136 | Cl | Cl | c-Pr |
| 5-137 | Cl | Cl | $CH_2$-c-Pr |
| 5-138 | Cl | Cl | $CH_2CF_3$ |
| 5-139 | Cl | Cl | $CH_2CHF_2$ |
| 5-140 | Cl | Br | Me |
| 5-141 | Cl | Br | Et |
| 5-142 | Cl | Br | c-Pr |
| 5-143 | Cl | Br | $CH_2$-c-Pr |
| 5-144 | Cl | Br | $CH_2CF_3$ |
| 5-145 | Cl | Br | $CH_2CHF_2$ |
| 5-146 | Cl | I | Me |
| 5-147 | Cl | I | Et |
| 5-148 | Cl | I | c-Pr |
| 5-149 | Cl | I | $CH_2$-c-Pr |
| 5-150 | Cl | I | $CH_2CF_3$ |
| 5-151 | Cl | I | $CH_2CHF_2$ |
| 5-152 | Br | $SO_2Me$ | Me |
| 5-153 | Br | $SO_2Me$ | Et |
| 5-154 | Br | $SO_2Me$ | c-Pr |
| 5-155 | Br | $SO_2Me$ | $CH_2$-c-Pr |
| 5-156 | Br | $SO_2Me$ | $CH_2CF_3$ |
| 5-157 | Br | $SO_2Me$ | $CH_2CHF_2$ |
| 5-158 | Br | $CF_3$ | Me |
| 5-159 | Br | $CF_3$ | Et |
| 5-160 | Br | $CF_3$ | c-Pr |
| 5-161 | Br | $CF_3$ | $CH_2$-c-Pr |
| 5-162 | Br | $CF_3$ | $CH_2CF_3$ |
| 5-163 | Br | $CF_3$ | $CH_2CHF_2$ |
| 5-164 | Br | $CHF_2$ | Me |
| 5-165 | Br | $CHF_2$ | Et |
| 5-166 | Br | $CHF_2$ | c-Pr |
| 5-167 | Br | $CHF_2$ | $CH_2$-c-Pr |
| 5-168 | Br | $CHF_2$ | $CH_2CF_3$ |
| 5-169 | Br | $CHF_2$ | $CH_2CHF_2$ |
| 5-170 | Br | $C_2F_5$ | Me |
| 5-171 | Br | $C_2F_5$ | Et |
| 5-172 | Br | $C_2F_5$ | c-Pr |
| 5-173 | Br | $C_2F_5$ | $CH_2$-c-Pr |
| 5-174 | Br | $C_2F_5$ | $CH_2CF_3$ |
| 5-175 | Br | $C_2F_5$ | $CH_2CHF_2$ |
| 5-176 | I | $SO_2Me$ | Me |
| 5-177 | I | $SO_2Me$ | Et |
| 5-178 | I | $SO_2Me$ | c-Pr |
| 5-179 | I | $CF_3$ | Me |
| 5-180 | I | $CF_3$ | Et |
| 5-181 | I | $CF_3$ | c-Pr |
| 5-182 | I | $CF_3$ | $CH_2$-c-Pr |
| 5-183 | I | $CF_3$ | $CH_2CF_3$ |
| 5-184 | I | $CF_3$ | $CH_2CHF_2$ |

TABLE 5-continued

Inventive compounds of the general formula (I) in which Q is $Q^4$ and $R^z$ is hydrogen, and the other substituents have the definitions given below.

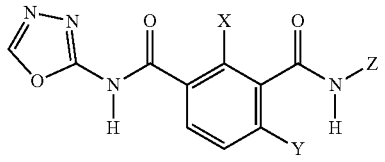

| No. | X | Y | Z |
|---|---|---|---|
| 5-185 | I | $CHF_2$ | Me |
| 5-186 | I | $CHF_2$ | Et |
| 5-187 | I | $CHF_2$ | c-Pr |
| 5-188 | I | $CHF_2$ | $CH_2$-c-Pr |
| 5-189 | I | $CHF_2$ | $CH_2CF_3$ |
| 5-190 | I | $CHF_2$ | $CH_2CHF_2$ |
| 5-191 | I | $C_2F_5$ | Me |
| 5-192 | I | $C_2F_5$ | Et |
| 5-193 | I | $C_2F_5$ | c-Pr |
| 5-194 | $CH_2OMe$ | $CF_3$ | Me |
| 5-195 | $CH_2OMe$ | $CF_3$ | Et |
| 5-196 | $CH_2OMe$ | $CF_3$ | c-Pr |
| 5-197 | $CH_2OMe$ | $CF_3$ | $CH_2$-c-Pr |
| 5-198 | $CH_2OMe$ | $CF_3$ | $CH_2CF_3$ |
| 5-199 | $CH_2OMe$ | $CF_3$ | $CH_2CHF_2$ |
| 5-200 | $CH_2OMe$ | $CHF_2$ | Me |
| 5-201 | $CH_2OMe$ | $CHF_2$ | Et |
| 5-202 | $CH_2OMe$ | $CHF_2$ | c-Pr |
| 5-203 | $CH_2OMe$ | $CHF_2$ | $CH_2$-c-Pr |
| 5-204 | $CH_2OMe$ | $CHF_2$ | $CH_2CF_3$ |
| 5-205 | $CH_2OMe$ | $CHF_2$ | $CH_2CHF_2$ |
| 5-206 | $CH_2OMe$ | $CHF_2$ | c-Pentyl |
| 5-207 | $CH_2OMe$ | $SO_2Me$ | Me |
| 5-208 | $CH_2OMe$ | $SO_2Me$ | Et |
| 5-209 | $CH_2OMe$ | $SO_2Me$ | c-Pr |
| 5-210 | Et | $CF_3$ | Me |
| 5-211 | Et | $CF_3$ | Et |
| 5-212 | Et | $CF_3$ | c-Pr |
| 5-213 | Et | $CF_3$ | $CH_2$-c-Pr |
| 5-214 | Et | $CF_3$ | $CH_2CF_3$ |
| 5-215 | Et | $CF_3$ | $CH_2CHF_2$ |
| 5-216 | Et | $CHF_2$ | Me |
| 5-217 | Et | $CHF_2$ | Et |
| 5-218 | Et | $CHF_2$ | c-Pr |
| 5-219 | Et | $CHF_2$ | $CH_2$-c-Pr |
| 5-220 | Et | $CHF_2$ | $CH_2CF_3$ |
| 5-221 | Et | $CHF_2$ | $CH_2CHF_2$ |
| 5-222 | Et | $C_2F_5$ | Me |
| 5-223 | Et | $C_2F_5$ | Et |
| 5-224 | Et | $C_2F_5$ | c-Pr |
| 5-225 | c-Pr | $CF_3$ | Me |
| 5-226 | c-Pr | $CF_3$ | Et |
| 5-227 | c-Pr | $CF_3$ | c-Pr |
| 5-228 | c-Pr | $CF_3$ | $CH_2$-c-Pr |
| 5-229 | c-Pr | $CF_3$ | $CH_2CF_3$ |
| 5-230 | c-Pr | $CF_3$ | $CH_2CHF_2$ |
| 5-231 | c-Pr | $CHF_2$ | Me |
| 5-232 | c-Pr | $CHF_2$ | Et |
| 5-233 | c-Pr | $CHF_2$ | c-Pr |
| 5-234 | c-Pr | $CHF_2$ | $CH_2$-c-Pr |
| 5-235 | c-Pr | $CHF_2$ | $CH_2CF_3$ |
| 5-236 | c-Pr | $CHF_2$ | $CH_2CHF_2$ |
| 5-237 | c-Pr | $C_2F_5$ | Me |
| 5-238 | c-Pr | $C_2F_5$ | Et |
| 5-239 | c-Pr | $C_2F_5$ | c-Pr |
| 5-240 | c-Pr | $C_2F_5$ | $CH_2$-c-Pr |
| 5-241 | c-Pr | $C_2F_5$ | $CH_2CF_3$ |
| 5-242 | c-Pr | $C_2F_5$ | $CH_2CHF_2$ |
| 5-243 | c-Pr | $SO_2Me$ | Me |
| 5-244 | c-Pr | $SO_2Me$ | Et |
| 5-245 | c-Pr | $SO_2Me$ | c-Pr |
| 5-246 | $CF_3$ | $CF_3$ | Me |
| 5-247 | $CF_3$ | $CF_3$ | Et |
| 5-248 | $CF_3$ | $CF_3$ | c-Pr |
| 5-249 | $CF_3$ | $CF_3$ | $CH_2$-c-Pr |

TABLE 5-continued

Inventive compounds of the general formula (I) in which Q is $Q^4$ and $R^z$ is hydrogen, and the other substituents have the definitions given below.

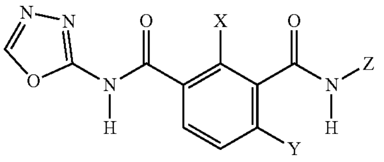

| No. | X | Y | Z |
|---|---|---|---|
| 5-250 | $CF_3$ | $CF_3$ | $CH_2CF_3$ |
| 5-251 | $CF_3$ | $CF_3$ | $CH_2CHF_2$ |
| 5-252 | Cl | $CF_3$ | Acetyl |
| 5-253 | Cl | $CF_3$ | H |
| 5-254 | Cl | $CF_3$ | $CH_2CN$ |
| 5-255 | Cl | CF | Ph |

TABLE 6

Inventive compounds of the general formula (I) in which Q is $Q^4$ and $R^z$ is methyl, and other substituents have the definitions given below.

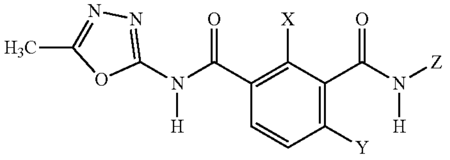

| No. | X | Y | Z |
|---|---|---|---|
| 6-1 | Me | F | Me |
| 6-2 | Me | F | Et |
| 6-3 | Me | F | c-Pr |
| 6-4 | Me | Cl | Me |
| 6-5 | Me | Cl | Et |
| 6-6 | Me | Cl | c-Pr |
| 6-7 | Me | Br | Me |
| 6-8 | Me | Br | Et |
| 6-9 | Me | Br | c-Pr |
| 6-10 | Me | I | Me |
| 6-11 | Me | I | Et |
| 6-12 | Me | I | c-Pr |
| 6-13 | Me | SMe | Me |
| 6-14 | Me | SMe | Et |
| 6-15 | Me | SMe | c-Pr |
| 6-16 | Me | S(O)Me | Me |
| 6-17 | Me | S(O)Me | Et |
| 6-18 | Me | S(O)Me | c-Pr |
| 6-19 | Me | $SO_2Me$ | Me |
| 6-20 | Me | $SO_2Me$ | Et |
| 6-21 | Me | $SO_2Me$ | c-Pr |
| 6-22 | Me | $SO_2Me$ | $CH_2$-c-Pr |
| 6-23 | Me | $SO_2Me$ | $CH_2CF_3$ |
| 6-24 | Me | $SO_2Me$ | $CH_2CHF_2$ |
| 6-25 | Me | $CF_3$ | Me |
| 6-26 | Me | $CF_3$ | Et |
| 6-27 | Me | $CF_3$ | c-Pr |
| 6-28 | Me | $CF_3$ | $CH_2$-c-Pr |
| 6-29 | Me | $CF_3$ | $CH_2CF_3$ |
| 6-30 | Me | $CF_3$ | $CH_2CHF_2$ |
| 6-31 | Me | $CHF_2$ | Me |
| 6-32 | Me | $CHF_2$ | Et |
| 6-33 | Me | $CHF_2$ | c-Pr |
| 6-34 | Me | $CHF_2$ | $CH_2$-c-Pr |
| 6-35 | Me | $CHF_2$ | $CH_2CF_3$ |
| 6-36 | Me | $CHF_2$ | $CH_2CHF_2$ |
| 6-37 | Me | $C_2F_5$ | Me |
| 6-38 | Me | $C_2F_5$ | Et |
| 6-39 | Me | $C_2F_5$ | c-Pr |
| 6-40 | OMe | Cl | Me |

TABLE 6-continued

Inventive compounds of the general formula (I) in which Q is $Q^4$ and $R^z$ is methyl, and other substituents have the definitions given below.

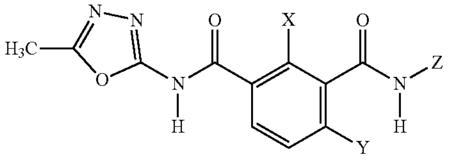

| No. | X | Y | Z |
|---|---|---|---|
| 6-41 | OMe | Cl | Et |
| 6-42 | OMe | Cl | c-Pr |
| 6-43 | OMe | $CF_3$ | Me |
| 6-44 | OMe | $CF_3$ | Et |
| 6-45 | OMe | $CF_3$ | c-Pr |
| 6-46 | OMe | $CF_3$ | $CH_2$-c-Pr |
| 6-47 | OMe | $CF_3$ | $CH_2CF_3$ |
| 6-48 | OMe | $CF_3$ | $CH_2CHF_2$ |
| 6-49 | OMe | $CHF_2$ | Me |
| 6-50 | OMe | $CHF_2$ | Et |
| 6-51 | OMe | $CHF_2$ | c-Pr |
| 6-52 | OMe | $CHF_2$ | $CH_2$-c-Pr |
| 6-53 | OMe | $CHF_2$ | $CH_2CF_3$ |
| 6-54 | OMe | $CHF_2$ | $CH_2CHF_2$ |
| 6-55 | SMe | $SO_2Me$ | Me |
| 6-56 | SMe | $SO_2Me$ | Et |
| 6-57 | SMe | $SO_2Me$ | c-Pr |
| 6-58 | SMe | $CF_3$ | Me |
| 6-59 | SMe | $CF_3$ | Et |
| 6-60 | SMe | $CF_3$ | c-Pr |
| 6-71 | SMe | $CF_3$ | $CH_2$-c-Pr |
| 6-72 | SMe | $CF_3$ | $CH_2CF_3$ |
| 6-73 | SMe | $CF_3$ | $CH_2CHF_2$ |
| 6-74 | SMe | $CHF_2$ | Me |
| 6-75 | SMe | $CHF_2$ | Et |
| 6-76 | SMe | $CHF_2$ | c-Pr |
| 6-77 | SMe | $CHF_2$ | $CH_2$-c-Pr |
| 6-78 | SMe | $CHF_2$ | $CH_2CF_3$ |
| 6-79 | SMe | $CHF_2$ | $CH_2CHF_2$ |
| 6-80 | SEt | $CF_3$ | Me |
| 6-81 | SEt | $CF_3$ | Et |
| 6-82 | SEt | $CF_3$ | c-Pr |
| 6-83 | SEt | $CF_3$ | $CH_2$-c-Pr |
| 6-84 | SEt | $CF_3$ | $CH_2CF_3$ |
| 6-85 | SEt | $CF_3$ | $CH_2CHF_2$ |
| 6-86 | SEt | $CHF_2$ | Me |
| 6-87 | SEt | $CHF_2$ | Et |
| 6-88 | SEt | $CHF_2$ | c-Pr |
| 6-89 | SEt | $CHF_2$ | $CH_2$-c-Pr |
| 6-90 | SEt | $CHF_2$ | $CH_2CF_3$ |
| 6-91 | SEt | $CHF_2$ | $CH_2CHF_2$ |
| 6-92 | F | $CF_3$ | Me |
| 6-93 | F | $CF_3$ | Et |
| 6-94 | F | $CF_3$ | c-Pr |
| 6-95 | F | $CF_3$ | $CH_2$-c-Pr |
| 6-96 | F | $CF_3$ | $CH_2CF_3$ |
| 6-97 | F | $CF_3$ | $CH_2CHF_2$ |
| 6-98 | F | $CHF_2$ | Me |
| 6-99 | F | $CHF_2$ | Et |
| 6-100 | F | $CHF_2$ | c-Pr |
| 6-101 | F | $CHF_2$ | $CH_2$-c-Pr |
| 6-102 | F | $CHF_2$ | $CH_2CF_3$ |
| 6-103 | F | $CHF_2$ | $CH_2CHF_2$ |
| 6-104 | Cl | SMe | Me |
| 6-105 | Cl | SMe | Et |
| 6-106 | Cl | SMe | c-Pr |
| 6-107 | Cl | S(O)Me | Me |
| 6-108 | Cl | S(O)Me | Et |
| 6-109 | Cl | S(O)Me | c-Pr |
| 6-110 | Cl | $SO_2Me$ | Me |
| 6-111 | Cl | $SO_2Me$ | Et |
| 6-112 | Cl | $SO_2Me$ | c-Pr |
| 6-113 | Cl | $SO_2Me$ | $CH_2$-c-Pr |
| 6-114 | Cl | $SO_2Me$ | $CH_2CF_3$ |
| 6-115 | Cl | $SO_2Me$ | $CH_2CHF_2$ |

TABLE 6-continued

Inventive compounds of the general formula (I) in which Q is $Q^4$ and $R^z$ is methyl, and other substituents have the definitions given below.

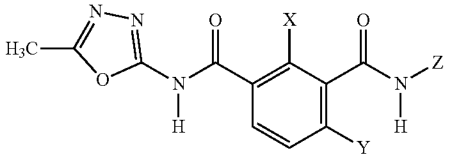

| No. | X | Y | Z |
|---|---|---|---|
| 6-116 | Cl | $CF_3$ | Me |
| 6-117 | Cl | $CF_3$ | Et |
| 6-118 | Cl | $CF_3$ | c-Pr |
| 6-119 | Cl | $CF_3$ | $CH_2$-c-Pr |
| 6-120 | Cl | $CF_3$ | $CH_2CF_3$ |
| 6-121 | Cl | $CF_3$ | $CH_2CHF_2$ |
| 6-122 | Cl | $CHF_2$ | Me |
| 6-123 | Cl | $CHF_2$ | Et |
| 6-124 | Cl | $CHF_2$ | c-Pr |
| 6-125 | Cl | $CHF_2$ | $CH_2$-c-Pr |
| 6-126 | Cl | $CHF_2$ | $CH_2CF_3$ |
| 6-127 | Cl | $CHF_2$ | $CH_2CHF_2$ |
| 6-128 | Cl | $C_2F_5$ | Me |
| 6-129 | Cl | $C_2F_5$ | Et |
| 6-130 | Cl | $C_2F_5$ | c-Pr |
| 6-131 | Cl | $C_2F_5$ | $CH_2$-c-Pr |
| 6-132 | Cl | $C_2F_5$ | $CH_2CF_3$ |
| 6-133 | Cl | $C_2F_5$ | $CH_2CHF_2$ |
| 6-134 | Cl | Cl | Me |
| 6-135 | Cl | Cl | Et |
| 6-136 | Cl | Cl | c-Pr |
| 6-137 | Cl | Cl | $CH_2$-c-Pr |
| 6-138 | Cl | Cl | $CH_2CF_3$ |
| 6-139 | Cl | Cl | $CH_2CHF_2$ |
| 6-140 | Cl | Br | Me |
| 6-141 | Cl | Br | Et |
| 6-142 | Cl | Br | c-Pr |
| 6-143 | Cl | Br | $CH_2$-c-Pr |
| 6-144 | Cl | Br | $CH_2CF_3$ |
| 6-145 | Cl | Br | $CH_2CHF_2$ |
| 6-146 | Cl | I | Me |
| 6-147 | Cl | I | Et |
| 6-148 | Cl | I | c-Pr |
| 6-149 | Cl | I | $CH_2$-c-Pr |
| 6-150 | Cl | I | $CH_2CF_3$ |
| 6-151 | Cl | I | $CH_2CHF_2$ |
| 6-152 | Br | $SO_2Me$ | Me |
| 6-153 | Br | $SO_2Me$ | Et |
| 6-154 | Br | $SO_2Me$ | c-Pr |
| 6-155 | Br | $SO_2Me$ | $CH_2$-c-Pr |
| 6-156 | Br | $SO_2Me$ | $CH_2CF_3$ |
| 6-157 | Br | $SO_2Me$ | $CH_2CHF_2$ |
| 6-158 | Br | $CF_3$ | Me |
| 6-159 | Br | $CF_3$ | Et |
| 6-160 | Br | $CF_3$ | c-Pr |
| 6-161 | Br | $CF_3$ | $CH_2$-c-Pr |
| 6-162 | Br | $CF_3$ | $CH_2CF_3$ |
| 6-163 | Br | $CF_3$ | $CH_2CHF_2$ |
| 6-164 | Br | $CHF_2$ | Me |
| 6-165 | Br | $CHF_2$ | Et |
| 6-166 | Br | $CHF_2$ | c-Pr |
| 6-167 | Br | $CHF_2$ | $CH_2$-c-Pr |
| 6-168 | Br | $CHF_2$ | $CH_2CF_3$ |
| 6-169 | Br | $CHF_2$ | $CH_2CHF_2$ |
| 6-170 | Br | $C_2F_5$ | Me |
| 6-171 | Br | $C_2F_5$ | Et |
| 6-172 | Br | $C_2F_5$ | c-Pr |
| 6-173 | Br | $C_2F_5$ | $CH_2$-c-Pr |
| 6-174 | Br | $C_2F_5$ | $CH_2CF_3$ |
| 6-175 | Br | $C_2F_5$ | $CH_2CHF_2$ |
| 6-176 | I | $SO_2Me$ | Me |
| 6-177 | I | $SO_2Me$ | Et |
| 6-178 | I | $SO_2Me$ | c-Pr |
| 6-179 | I | $CF_3$ | Me |
| 6-180 | I | $CF_3$ | Et |

TABLE 6-continued

Inventive compounds of the general formula (I) in which Q is $Q^4$ and $R^z$ is methyl, and other substituents have the definitions given below.

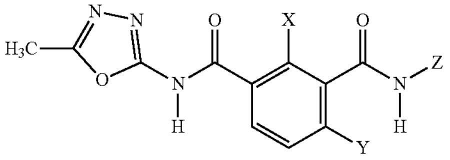

| No. | X | Y | Z |
|---|---|---|---|
| 6-181 | I | $CF_3$ | c-Pr |
| 6-182 | I | $CF_3$ | $CH_2$-c-Pr |
| 6-183 | I | $CF_3$ | $CH_2CF_3$ |
| 6-184 | I | $CF_3$ | $CH_2CHF_2$ |
| 6-185 | I | $CHF_2$ | Me |
| 6-186 | I | $CHF_2$ | Et |
| 6-187 | I | $CHF_2$ | c-Pr |
| 6-188 | I | $CHF_2$ | $CH_2$-c-Pr |
| 6-189 | I | $CHF_2$ | $CH_2CF_3$ |
| 6-190 | I | $CHF_2$ | $CH_2CHF_2$ |
| 6-191 | I | $C_2F_5$ | Me |
| 6-192 | I | $C_2F_5$ | Et |
| 6-193 | I | $C_2F_5$ | c-Pr |
| 6-194 | $CH_2OMe$ | $CF_3$ | Me |
| 6-195 | $CH_2OMe$ | $CF_3$ | Et |
| 6-196 | $CH_2OMe$ | $CF_3$ | c-Pr |
| 6-197 | $CH_2OMe$ | $CF_3$ | $CH_2$-c-Pr |
| 6-198 | $CH_2OMe$ | $CF_3$ | $CH_2CF_3$ |
| 6-199 | $CH_2OMe$ | $CF_3$ | $CH_2CHF_2$ |
| 6-200 | $CH_2OMe$ | $CHF_2$ | Me |
| 6-201 | $CH_2OMe$ | $CHF_2$ | Et |
| 6-202 | $CH_2OMe$ | $CHF_2$ | c-Pr |
| 6-203 | $CH_2OMe$ | $CHF_2$ | $CH_2$-c-Pr |
| 6-204 | $CH_2OMe$ | $CHF_2$ | $CH_2CF_3$ |
| 6-205 | $CH_2OMe$ | $CHF_2$ | $CH_2CHF_2$ |
| 6-206 | $CH_2OMe$ | $CHF_2$ | c-Pentyl |
| 6-207 | $CH_2OMe$ | $SO_2Me$ | Me |
| 6-208 | $CH_2OMe$ | $SO_2Me$ | Et |
| 6-209 | $CH_2OMe$ | $SO_2Me$ | c-Pr |
| 6-210 | Et | $CF_3$ | Me |
| 6-211 | Et | $CF_3$ | Et |
| 6-212 | Et | $CF_3$ | c-Pr |
| 6-213 | Et | $CF_3$ | $CH_2$-c-Pr |
| 6-214 | Et | $CF_3$ | $CH_2CF_3$ |
| 6-215 | Et | $CF_3$ | $CH_2CHF_2$ |
| 6-216 | Et | $CHF_2$ | Me |
| 6-217 | Et | $CHF_2$ | Et |
| 6-218 | Et | $CHF_2$ | c-Pr |
| 6-219 | Et | $CHF_2$ | $CH_2$-c-Pr |
| 6-220 | Et | $CHF_2$ | $CH_2CF_3$ |
| 6-221 | Et | $CHF_2$ | $CH_2CHF_2$ |
| 6-222 | Et | $C_2F_5$ | Me |
| 6-223 | Et | $C_2F_5$ | Et |
| 6-224 | Et | $C_2F_5$ | c-Pr |
| 6-225 | c-Pr | $CF_3$ | Me |
| 6-226 | c-Pr | $CF_3$ | Et |
| 6-227 | c-Pr | $CF_3$ | c-Pr |
| 6-228 | c-Pr | $CF_3$ | $CH_2$-c-Pr |
| 6-229 | c-Pr | $CF_3$ | $CH_2CF_3$ |
| 6-230 | c-Pr | $CF_3$ | $CH_2CHF_2$ |
| 6-231 | c-Pr | $CHF_2$ | Me |
| 6-232 | c-Pr | $CHF_2$ | Et |
| 6-233 | c-Pr | $CHF_2$ | c-Pr |
| 6-234 | c-Pr | $CHF_2$ | $CH_2$-c-Pr |
| 6-235 | c-Pr | $CHF_2$ | $CH_2CF_3$ |
| 6-236 | c-Pr | $CHF_2$ | $CH_2CHF_2$ |
| 6-237 | c-Pr | $C_2F_5$ | Me |
| 6-238 | c-Pr | $C_2F_5$ | Et |
| 6-239 | c-Pr | $C_2F_5$ | c-Pr |
| 6-240 | c-Pr | $C_2F_5$ | $CH_2$-c-Pr |
| 6-241 | c-Pr | $C_2F_5$ | $CH_2CF_3$ |
| 6-242 | c-Pr | $C_2F_5$ | $CH_2CHF_2$ |
| 6-243 | c-Pr | $SO_2Me$ | Me |
| 6-244 | c-Pr | $SO_2Me$ | Et |
| 6-245 | c-Pr | $SO_2Me$ | c-Pr |

TABLE 6-continued

Inventive compounds of the general formula (I) in which Q is $Q^4$ and $R^z$ is methyl, and other substituents have the definitions given below.

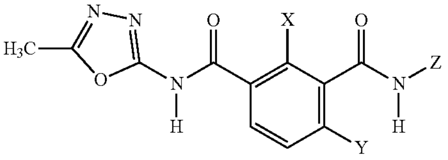

| No. | X | Y | Z |
|---|---|---|---|
| 6-246 | $CF_3$ | $CF_3$ | Me |
| 6-247 | $CF_3$ | $CF_3$ | Et |
| 6-248 | $CF_3$ | $CF_3$ | c-Pr |
| 6-249 | $CF_3$ | $CF_3$ | $CH_2$-c-Pr |
| 6-250 | $CF_3$ | $CF_3$ | $CH_2CF_3$ |
| 6-251 | $CF_3$ | $CF_3$ | $CH_2CHF_2$ |
| 6-252 | Cl | $CF_3$ | Acetyl |
| 6-253 | Cl | $CF_3$ | H |
| 6-254 | Cl | $CF_3$ | CH(Me)-c-Pr |
| 6-255 | Me | $CF_3$ | iPr |
| 6-256 | Me | $CF_3$ | cBu |
| 6-257 | Cl | Br | CH(Me)-c-Pr |
| 6-258 | Me | $CHF_2$ | CH(Me)-c-Pr |
| 6-259 | Cl | $CHF_2$ | Pr |
| 6-260 | Cl | $CHF_2$ | i-Pr |
| 6-261 | Cl | $CHF_2$ | c-Bu |
| 6-262 | Cl | $CHF_2$ | $CH_2CH_2OMe$ |
| 6-263 | Cl | $CHF_2$ | $CH_2$-(tetrahydrofuran-2-yl) |
| 6-264 | Cl | $CHF_2$ | $CH_2$-(thien-2-yl) |
| 6-265 | Cl | $CHF_2$ | $CH_2C(O)NMe_2$ |
| 6-266 | Cl | $CHF_2$ | Ph |
| 6-267 | Br | $CHF_2$ | CH(Me)-c-Pr |
| 6-268 | c-Pr | CF | CH(Me)-c-Pr |

NMR data for numerous inventive compounds of the formula (I) mentioned in tables above are disclosed below for further characterization:

Ex. no. 1-4: $^1$H-NMR (400 MHz, DMSO-$d_6$): δ=11.63 (br s, 1H); 8.50 (q, 1H); 7.67 (d, 1H); 7.50 (d, 1H); 3.98 (s, 3H); 2.80 (d, 3H); 2.33 (s, 3H);

Ex. no. 1-19: $^1$H-NMR (400 MHz, DMSO-$d_6$): δ=11.82 (br s, 1H); 8.57 (q, 1H); 7.94 (d, 1H); 7.89 (d, 1H); 4.01 (s, 3H); 3.27 (s, 3H); 2.78 (d, 3H); 2.35 (s, 3H);

Ex. no. 1-20: $^1$H-NMR (400 MHz, DMSO-$d_6$): δ=11.82 (br s, 1H); 8.63 (t, 1H); 7.94 (d, 1H); 7.88 (d, 1H); 4.01 (s, 3H); 3.27 (m, 2H); 3.27 (s, 3H); 2.38 (s, 3H); 1.13 (t, 3H);

Ex. no. 1-21: $^1$H-NMR (400 MHz, DMSO-$d_6$): δ=11.81 (br s, 1H); 8.70 (d, 1H); 7.93 (d, 1H); 7.88 (d, 1H); 4.00 (s, 3H); 3.27 (s, 3H); 2.78 (m, 1H); 2.35 (s, 3H); 0.69 (m, 2H); 0.62 (m, 1H); 0.51 (m, 1H);

Ex. no. 1-25: $^1$H-NMR (400 MHz, DMSO-$d_6$): δ=11.76 (br s, 1H); 8.51 (q, 1H); 7.83 (d, 1H); 7.76 (d, 1H); 4.00 (s, 3H); 2.79 (d, 3H); 2.34 (s, 3H);

Ex. no. 1-26: $^1$H-NMR (400 MHz, DMSO-$d_6$): δ=11.76 (br s, 1H); 8.49 (t, 1H); 7.83 (d, 1H); 7.75 (d, 1H); 4.00 (s, 3H); 3.28 (m, 2H); 2.36 (s, 3H); 1.11 (t, 3H);

Ex. no. 1-27: $^1$H-NMR (400 MHz, DMSO-$d_6$): δ=11.75 (br s, 1H); 8.66 (d, 1H); 7.83 (d, 1H); 7.75 (d, 1H); 4.00 (s, 3H); 2.81 (m, 1H); 2.34 (s, 3H); 0.71 (m, 2H); 0.49 (m, 2H);

Ex. no. 1-28: $^1$H-NMR (400 MHz, DMSO-$d_6$): δ=11.78 (br s, 1H); 8.72 (t, 1H); 7.83 (d, 1H); 7.76 (d, 1H); 4.01 (s, 3H); 3.13 (m, 2H); 2.38 (s, 3H); 1.01 (m, 1H); 0.45 (m, 2H); 0.23 (m, 2H);

Ex. no. 1-29: $^1$H-NMR (400 MHz, DMSO-$d_6$): δ=11.80 (br s, 1H); 9.38 (t, 1H); 7.88 (d, 1H); 7.80 (d, 1H); 4.13 (m, 2H); 4.01 (s, 3H); 2.35 (s, 3H);

Ex. no. 1-30: $^1$H-NMR (400 MHz, DMSO-$d_6$): δ=11.79 (br s, 1H); 9.09 (t, 1H); 7.86 (d, 1H); 7.78 (d, 1H); 6.13 (tt, 1H); 4.01 (s, 3H); 3.71 (2H); 2.36 (s, 3H);

Ex. no. 1-31: $^1$H-NMR (400 MHz, DMSO-$d_6$): δ=11.79 (br s, 1H); 8.62 (t, 1H); 7.82 (d, 1H); 7.75 (d, 1H); 4.01 (s, 3H); 3.40 (m, 1H); 2.39 (d, 3H); 1.20 (dd, 3H); 0.91 (m, 1H); 0.44 (m, 2H); 0.29 (m, 2H);

Ex. no. 1-32: $^1$H-NMR (400 MHz, DMSO-$d_6$): δ=11.94 (br s, 1H); 8.81 (t, 1H); 7.91 (d, 1H); 7.78 (d, 1H); 6.95 (t, 1H); 4.01 (s, 3H); 3.24 (m, 2H); 1.54 (m, 2H); 0.92 (t, 3H);

Ex. no. 1-33: $^1$H-NMR (400 MHz, DMSO-$d_6$): δ=11.77 (br s, 1H); 8.51 (d, 1H); 7.82 (d, 1H); 7.75 (d, 1H); 4.08 (m, 1H); 4.00 (s, 3H); 2.37 (s, 3H); 1.16 (d, 3H); 1.12 (d, 3H);

Ex. no. 1-34: $^1$H-NMR (400 MHz, DMSO-$d_6$): δ=11.78 (br s, 1H); 8.70 (d, 1H); 7.83 (d, 1H); 7.75 (d, 1H); 4.00 (s, 3H); 3.52-3.31 (m, 4H); 3.27 (s, 3H); 2.36 (s, 3H);

Ex. no. 1-36: $^1$H-NMR (400 MHz, DMSO-$d_6$): δ=11.81 (br s, 1H); 9.42 (t, 1H); 7.89 (d, 1H); 7.81 (d, 1H); 4.49 (m, 2H); 4.01 (s, 3H); 2.35 (s, 3H);

Ex. no. 1-37: $^1$H-NMR (400 MHz, DMSO-$d_6$): δ=11.77 (br s, 1H); 8.72 (br s, 1H); 7.83 (d, 1H); 7.75 (d, 1H); 4.00 (s, 3H); 3.97 (m, 1H); 3.77 (m, 1H); 3.63 (m, 1H); 3.35 (m, 1H); 3.27 (m, 1H); 2.36 (s, 3H); 1.92 (m, 1H); 1.83 (m, 2H); 1.60 (m, 1H);

Ex. no. 1-41: $^1$H-NMR (400 MHz, DMSO-$d_6$): δ=11.79 (br s, 1H); 9.41 (d, 1H); 7.87 (d, 1H); 7.80 (d, 1H); 4.98 (m, 1H); 4.80 (t, 2H); 4.54 (t, 1H); 4.48 (t, 1H); 4.01 (s, 3H); 2.36 (s, 3H);

Ex. no. 1-44: $^1$H-NMR (400 MHz, DMSO-$d_6$): δ=11.69 (br s, 1H); 8.56 (q, 1H); 7.80 (d, 1H); 7.63 (d, 1H); 6.91 (t, 1H); 4.00 (t, 1H); 2.80 (d, 3H); 2.33 (s, 3H);

Ex. no. 1-45: $^1$H-NMR (400 MHz, DMSO-$d_6$): δ=11.69 (br s, 1H); 8.65 (t, 1H); 7.79 (d, 1H); 7.63 (d, 1H); 6.91 (t, 1H); 4.00 (s, 3H); 3.30 (m, 2H); 2.35 (s, 3H); 1.13 (t, 3H);

Ex. no. 1-46: $^1$H-NMR (400 MHz, DMSO-$d_6$): δ=11.68 (br s, 1H); 8.71 (d, 1H); 7.79 (d, 1H); 7.62 (d, 1H); 6.90 (t, 1H); 3.99 (s, 3H); 2.85 (m, 1H); 2.33 (s, 3H); 0.71 (m, 1H); 0.54 (m, 2H);

Ex. no. 1-47: $^1$H-NMR (400 MHz, DMSO-$d_6$): δ=11.70 (br s, 1H); 8.79 (t, 1H); 7.80 (d, 1H); 7.64 (d, 1H); 6.92 (t, 1H); 4.00 (s, 3H); 3.15 (m, 2H); 2.38 (s, 3H); 1.04 (m, 1H); 0.46 (m, 2H); 0.24 (m, 2H);

Ex. no. 1-49: $^1$H-NMR (400 MHz, DMSO-$d_6$): δ=11.71 (br s, 1H); 9.12 (t, 1H); 7.82 (d, 1H); 7.66 (d, 1H); 6.93 (t, 1H); 6.19 (tt, 1H); 4.00 (s, 3H); 3.72 (m, 2H); 2.36 (s, 3H);

Ex. no. 1-56: $^1$H-NMR (400 MHz, DMSO-$d_6$): δ=11.66 (br s, 1H); 8.53 (q, 1H); 7.89 (d, 1H); 7.67 (d, 1H); 3.99 (s, 3H); 3.86 (s, 3H); 2.79 (d, 3H);

Ex. no. 1-57: $^1$H-NMR (400 MHz, DMSO-$d_6$): δ=11.65 (br s, 1H); 8.60 (t, 1H); 7.88 (d, 1H); 7.67 (d, 1H); 3.99 (s, 3H); 3.87 (s, 3H); 3.29 (m, 2H); 1.11 (t, 3H);

Ex. no. 1-58: $^1$H-NMR (400 MHz, DMSO-$d_6$): δ=11.65 (br s, 1H); 8.68 (d, 1H); 7.88 (d, 1H); 7.66 (d, 1H); 3.99 (s, 3H); 3.86 (s, 3H); 2.80 (m, 1H); 0.71 (m, 2H); 0.49 (m, 2H);

Ex. no. 1-72: $^1$H-NMR (400 MHz, DMSO-$d_6$): δ=11.53 (br s, 1H); 8.57 (q, 1H); 7.85 (d, 1H); 7.54 (d, 1H); 6.96 (t, 1H); 3.99 (s, 3H); 3.85 (s, 3H); 2.81 (d, 3H);

Ex. no. 1-73: $^1$H-NMR (400 MHz, DMSO-$d_6$): δ=11.52 (br s, 1H); 8.65 (t, 1H); 7.84 (d, 1H); 7.54 (d, 1H); 6.96 (t, 1H); 3.99 (s, 3H); 3.86 (s, 3H); 3.20 (m, 2H); 1.13 (t, 3H);

Ex. no. 1-74: $^1$H-NMR (400 MHz, DMSO-$d_6$): δ=11.51 (br s, 1H); 8.72 (d, 1H); 7.84 (d, 1H); 7.52 (d, 1H); 6.95 (t, 1H); 3.98 (s, 3H); 3.85 (s, 3H); 2.85 (m, 1H); 0.71 (m, 2H); 0.54 (m, 2H);

Ex. no. 1-81: $^1$H-NMR (400 MHz, DMSO-$d_6$): δ=11.82 (br s, 1H); 8.48 (q, 1H); 7.95 (d, 1H); 7.88 (d, 1H); 4.05 (s, 3H); 2.80 (d, 3H); 2.43 (s, 3H);

Ex. no. 1-82: $^1$H-NMR (400 MHz, DMSO-$d_6$): δ=11.82 (br s, 1H); 8.56 (t, 1H); 7.95 (d, 1H); 7.88 (d, 1H); 4.06 (s, 3H); 3.32 (m, 2H); 2.44 (s, 3H); 1.14 (t, 3H);

Ex. no. 1-83: $^1$H-NMR (400 MHz, DMSO-$d_6$): δ=11.83 (br s, 1H); 8.64 (d, 1H); 7.94 (d, 1H); 7.88 (d, 1H); 4.05 (s, 3H); 2.80 (m, 1H); 2.43 (s, 3H); 0.71 (m, 2H); 0.53 (br s, 2H);

Ex. no. 1-84: $^1$H-NMR (400 MHz, DMSO-$d_6$): δ=11.83 (br s, 1H); 8.68 (t, 1H); 7.95 (d, 1H); 7.87 (d, 1H); 4.05 (s, 3H); 3.16 (m, 2H); 2.45 (s, 3H); 1.02 (m, 1H); 0.45 (m, 2H); 0.24 (m, 2H);

Ex. no. 1-86: $^1$H-NMR (400 MHz, DMSO-$d_6$): δ=11.85 (br s, 1H); 9.10 (t, 1H); 7.98 (d, 1H); 7.92 (d, 1H); 6.11 (tt, 1H); 4.05 (s, 3H); 3.71 (m, 2H); 2.43 (s, 3H);

Ex. no. 1-87: $^1$H-NMR (400 MHz, DMSO-$d_6$): δ=11.76 (br s, 1H); 8.54 (q, 1H); 7.81 (s, 2H); 6.90 (t, 1H); 4.04 (s, 3H); 2.82 (d, 3H); 2.42 (s, 3H);

Ex. no. 1-88: $^1$H-NMR (400 MHz, DMSO-$d_6$): δ=11.76 (br s, 1H); 8.62 (t, 1H); 7.82 (s, 2H); 6.91 (t, 1H); 4.05 (s, 3H); 3.33 (m, 2H); 2.43 (s, 3H); 1.16 (t, 3H);

Ex. no. 1-89: $^1$H-NMR (400 MHz, DMSO-$d_6$): δ=11.77 (br s, 1H); 8.70 (d, 1H); 7.81 (br s, 2H); 6.90 (t, 1H); 4.05 (s, 3H); 2.85 (m, 1H); 2.41 (s, 3H); 0.71 (m, 2H); 0.58 (m, 2H);

Ex. no. 1-90: $^1$H-NMR (400 MHz, DMSO-$d_6$): δ=11.77 (br s, 1H); 8.76 (t, 1H); 7.82 (br s, 1H); 6.91 (t, 1H); 4.05 (s, 3H); 3.18 (m, 2H); 2.44 (s, 3H); 1.06 (m, 1H); 0.46 (m, 2H); 0.26 (m, 2H);

Ex. no. 1-92: $^1$H-NMR (400 MHz, DMSO-$d_6$): δ=11.79 (br s, 1H); 9.14 (t, 1H); 7.85 (br s, 2H); 6.92 (t, 1H); 6.18 (tt, 1H); 4.05 (s, 3H); 3.73 (m, 2H); 2.42 (s, 3H);

Ex. no. 1-123: $^1$H-NMR (400 MHz, DMSO-$d_6$): δ=12.03 (br s, 1H); 8.72 (q, 1); 8.07 (d, 1H); 8.02 (d, 1H); 4.01 (s, 3H); 3.31 (s, 3H); 2.79 (d, 3H);

Ex. no. 1-125: $^1$H-NMR (400 MHz, DMSO-$d_6$): δ=12.02 (br s, 1H); 8.85 (d, 1H); 8.06 (d, 1H); 8.02 (d, 1H); 4.01 (s, 3H); 3.31 (s, 3H); 2.78 (m, 1H); 0.70 (m, 2H); 0.60 (m, 1H); 0.56 (m, 1H);

Ex. no. 1-129: $^1$H-NMR (400 MHz, DMSO-$d_6$): δ=12.00 (br s, 1H); 8.69 (q, 1H); 7.97 (d, 1H); 7.93 (d, 1H); 4.01 (s, 3H); 2.79 (d, 3H);

Ex. no. 1-130: $^1$H-NMR (400 MHz, DMSO-$d_6$): δ=11.99 (br s, 1H); 8.76 (t, 1H); 7.97 (d, 1H); 7.93 (d, 1H); 4.01 (s, 3H); 3.29 (m, 2H); 1.11 (t, 3H);

Ex. no. 1-131: $^1$H-NMR (400 MHz, DMSO-$d_6$): δ=11.99 (br s, 1H); 8.82 (d, 1H); 7.97 (d, 1H); 7.92 (d, 1H); 4.01 (s, 3H); 2.80 (m, 1H); 0.72 (m, 2H); 0.50 (br s, 2H);

Ex. no. 1-132: $^1$H-NMR (400 MHz, DMSO-$d_6$): δ=12.02 (br s, 1H); 8.89 (t, 1H); 7.98 (d, 1H); 7.93 (d, 1H); 4.02 (s, 3H); 3.15 (m, 2H); 1.00 (m, 1H); 0.45 (m, 2H); 0.24 (m, 2H)

Ex. no. 1-133: $^1$H-NMR (400 MHz, DMSO-$d_6$): δ=12.06 (br s, 1H); 9.56 (t, 1H); 8.04 (d, 1H); 7.98 (d, 1H); 4.16 (m, 2H); 4.02 (s, 3H);

Ex. no. 1-134: $^1$H-NMR (400 MHz, DMSO-$d_6$): δ=12.05 (br s, 1H); 9.29 (t, 1H); 8.02 (d, 1H); 7.96 (d, 1H); 6.12 (tt, 1H); 4.02 (s, 3H); 3.72 (m, 2H);

Ex. no. 1-135: $^1$H-NMR (400 MHz, DMSO-$d_6$): δ=12.02 (br s, 1H); 8.77 (d, 1H); 7.97 (d, 1H); 7.93 (d, 1H); 4.02 (s, 3H); 3.44 (m, 1H); 1.20 (m, 3H); 0.90 (m, 1H); 0.43 (m, 2H); 0.29 (m, 2H);

Ex. no. 1-136: $^1$H-NMR (400 MHz, DMSO-$d_6$): δ=12.01 (br s, 1H); 8.78 (t, 1H); 7.97 (d, 1H); 7.93 (d, 1H); 4.02 (s, 3H); 3.22 (m, 2H); 1.53 (m, 2H); 0.92 (t, 3H);

Ex. no. 1-137: $^1$H-NMR (400 MHz, DMSO-$d_6$): δ=12.01 (br s, 1H); 8.66 (d, 1H); 7.96 (d, 1H); 7.92 (d, 1H); 4.07 (m, 1H); 4.01 (s, 3H); 1.14 (br s, 6H);

Ex. no. 1-138: $^1$H-NMR (400 MHz, DMSO-$d_6$): δ=12.00 (br s, 1H); 8.91 (t, 1H); 7.97 (d, 1H); 7.92 (d, 1); 4.01 (s, 3H); 3.43 (m, 4H); 3.27 (s, 3H);

Ex. no. 1-139: $^1$H-NMR (400 MHz, DMSO-$d_6$): δ=12.02 (br s, 1H); 8.99 (t, 1H); 7.98 (d, 1H); 7.94 (d, 1H); 4.01 (s, 3H); 3.45 (m, 2H); 2.63 (t, 2H); 2.11 (s, 3H);

Ex. no. 1-140: $^1$H-NMR (400 MHz, DMSO-$d_6$): δ=12.05 (br s, 1H); 9.61 (t, 1H); 8.04 (d, 1H); 7.99 (d, 1H); 4.42 (d, 2H); 4.01 (s, 3H);

Ex. no. 1-141: $^1$H-NMR (400 MHz, DMSO-$d_6$): δ=12.00 (br s, 1H); 8.90 (t, 1H); 7.97 (d, 1H); 7.92 (d, 1H); 4.01 (s, 3H); 3.95 (m, 1H); 3.77 (m, 1H); 3.63 (m, 1H); 3.30 (m, 2H); 1.95 (m, 1H); 1.83 (m, 2H); 1.63 (m, 1H);

Ex. no. 1-142: $^1$H-NMR (400 MHz, DMSO-$d_6$): δ=11.99 (br s, 1H); 8.90 (t, 1H); 7.96 (d, 1H); 7.91 (d, 1H); 4.18 (br d, 2H); 4.01 (s, 3H); 3.00 (s, 3H); 2.86 (s, 3H);

Ex. no. 1-143: $^1$H-NMR (400 MHz, DMSO-$d_6$): δ=12.08 (br s, 1H); 10.86 (br s, 1H); 8.04 (m, 2H); 7.65 (d, 2H); 7.38 (m, 2H); 7.15 (t, 1H); 4.02 (s, 3H);

Ex. no. 1-144: $^1$H-NMR (400 MHz, DMSO-$d_6$): δ=12.01 (br s, 1H); 9.36 (t, 1H); 7.98 (d, 1H); 7.94 (d, 1H); 7.45 (m, 1H); 7.07 (m, 1H); 6.98 (m, 1H); 4.66 (br s, 2H); 4.01 (s, 3H);

Ex. no. 1-146: $^1$H-NMR (400 MHz, DMSO-$d_6$): δ=12.01 (br s, 1H); 9.01 (d, 1H); 7.97 (d, 1H); 7.93 (d, 1H); 4.35 (m, 1H); 4.01 (s, 3H); 2.25 (m, 2H); 1.98 (m, 2H); 1.70 (m, 2H);

Ex. no. 1-147: $^1$H-NMR (400 MHz, DMSO-$d_6$): δ=11.93 (br s, 1H); 8.72 (q, 1H); 7.91 (d, 1H); 7.78 (d, 1H); 6.96 (t, 1H); 4.01 (s, 3H); 2.81 (d, 3H);

Ex. no. 1-148: $^1$H-NMR (400 MHz, DMSO-$d_6$): δ=11.93 (br s, 1H); 8.78 (t, 1H); 7.91 (d, 1H); 7.78 (d, 1H); 6.95 (t, 1H); 4.01 (s, 3H); 3.31 (m, 2H); 1.13 (t, 3H);

Ex. no. 1-149: $^1$H-NMR (400 MHz, DMSO-$d_6$): δ=11.92 (br s, 1H); 8.85 (d, 1H); 7.90 (d, 1H); 7.77 (d, 1H); 6.95 (t, 1H); 4.00 (s, 3H); 2.83 (m, 1H); 0.72 (m, 2H); 0.55 (m, 2H);

Ex. no. 1-155: $^1$H-NMR (400 MHz, DMSO-$d_6$): δ=11.94 (br s, 1H); 8.70 (d, 1H); 7.90 (d, 1H); 7.77 (d, 1H); 6.94 (t, 1H); 4.09 (m, 1H); 4.01 (s, 3H); 1.16 (d, 6H);

Ex. no. 1-156: $^1$H-NMR (400 MHz, DMSO-$d_6$): δ=11.94 (br s, 1H); 8.92 (t, 1H); 7.91 (d, 1H); 7.78 (d, 1H); 6.96 (t, 1H); 4.01 (s, 3H); 3.46 (m, 4H); 3.29 (s, 3H);

Ex. no. 1-157: $^1$H-NMR (400 MHz, DMSO-$d_6$): δ=11.95 (br s, 1H); 8.99 (t, 1H); 7.92 (d, 1H); 7.80 (d, 1H); 7.05 (t, 1H); 4.01 (s, 3H); 3.49 (m, 2H); 2.67 (m, 2H); 2.12 (s, 3H);

Ex. no. 1-158: $^1$H-NMR (400 MHz, DMSO-$d_6$): δ=11.98 (br s, 1H); 9.59 (t, 1H); 7.97 (d, 1H); 7.81 (d, 1H); 7.01 (t, 1H); 4.40 (d, 2H); 4.01 (s, 3H);

Ex. no. 1-159: $^1$H-NMR (400 MHz, DMSO-$d_6$): δ=11.94 (br s, 1H); 8.94 (t, 1H); 7.91 (d, 1H); 7.78 (d, 1H); 6.97 (t, 1H); 4.01 (s, 3H); 3.98 (m, 1H); 3.78 (m, 1H); 3.64 (m, 1H); 3.35 (m, 2H); 1.95 (m, 1H); 1.84 (m, 2H); 1.62 (m, 1H);

Ex. no. 1-160: $^1$H-NMR (400 MHz, DMSO-$d_6$): δ=11.95 (br s, 1H); 9.12 (t, 1H); 7.94 (d, 1H); 7.83 (d, 1H); 7.58 (t, 1H); 4.17 (d, 2H); 4.01 (t, 3H); 3.02 (s, 3H); 2.89 (s, 3H);

Ex. no. 1-161: $^1$H-NMR (400 MHz, DMSO-$d_6$): δ=11.99 (br s, 1H); 10.84 (br s, 1H); 7.99 (d, 1H); 7.85 (d, 1H); 7.69 (m, 2H); 7.38 (m, 2H); 7.15 (m, 1H); 7.12 (t, 1H); 4.02 (s, 3H);

Ex. no. 1-162: $^1$H-NMR (400 MHz, DMSO-$d_6$): δ=11.95 (br s, 1H); 9.45 (t, 1H); 7.93 (d, 1H); 7.79 (d, 1H); 7.45 (m, 1H); 7.08 (m, 1H); 6.99 (m, 1H); 6.92 (t, 1H); 4.68 (d, 2H); 4.00 (s, 3H);

Ex. no. 1-164: $^1$H-NMR (400 MHz, DMSO-$d_6$): δ=11.94 (br s, 1H); 9.05 (d, 1H); 7.91 (d, 1H); 7.78 (d, 1H); 6.93 (t, 1H); 4.37 (m, 1H); 4.01 (s, 3H); 2.26 (m, 2H); 2.01 (m, 2H); 1.72 (m, 2H);

Ex. no. 1-165: $^1$H-NMR (400 MHz, DMSO-$d_6$): δ=12.01 (br s, 1H); 8.61 (q, 1H); 8.00 (d, 1H); 7.85 (d, 1H); 4.01 (s, 3H); 2.78 (d, 3H);

Ex. no. 1-166: $^1$H-NMR (400 MHz, DMSO-$d_6$): δ=12.01 (br s, 1H); 8.67 (t, 1H); 7.99 (d, 1H); 7.85 (d, 1H); 4.01 (s, 3H); 3.29 (m, 1H); 1.11 (t, 3H);

Ex. no. 1-173: $^1$H-NMR (400 MHz, DMSO-$d_6$): δ=11.87 (br s, 1H); 8.79 (d, 1H); 7.77 (d, 1H); 7.66 (d, 1H); 3.99 (s, 3H); 2.82 (m, 1H); 0.72 (m, 2H); 0.52 (m, 2H);

Ex. no. 1-177: $^1$H-NMR (400 MHz, DMSO-$d_6$): δ=11.90 (br s, 1H); 8.65 (q, 1H); 7.81 (d, 1H); 7.69 (d, 1H); 3.99 (s, 3H); 2.79 (d, 3H);

Ex. no. 1-178: $^1$H-NMR (400 MHz, DMSO-$d_6$): δ=11.90 (br s, 1H); 8.71 (t, 1H); 7.81 (d, 1H); 7.68 (d, 1H); 3.99 (s, 3H); 3.28 (m, 2H); 1.14 (t, 3H);

Ex. no. 1-179: $^1$H-NMR (400 MHz, DMSO-$d_6$): δ=11.89 (br s, 1H); 8.77 (d, 1H); 7.80 (d, 1H); 7.68 (d, 1H); 3.99 (s, 3H); 2.81 (m, 1H); 0.72 (m, 2H); 0.54 (d, 2H);

Ex. no. 1-180: $^1$H-NMR (400 MHz, DMSO-$d_6$): δ=11.90 (br s, 1H); 8.80 (t, 1H); 7.81 (d, 1H); 7.68 (d, 1H); 3.99 (s, 3H); 3.16 (m, 2H); 1.02 (m, 1H); 0.46 (m, 2H); 0.26 (m, 2H);

Ex. no. 1-181: $^1$H-NMR (400 MHz, DMSO-$d_6$): δ=11.91 (br s, 1H); 9.49 (t, 1H); 7.85 (d, 1H); 7.74 (d, 1H); 4.14 (m, 2H); 3.99 (s, 3H);

Ex. no. 1-182: $^1$H-NMR (400 MHz, DMSO-$d_6$): δ=11.90 (br s, 1H); 9.23 (t, 1H); 7.83 (d, 1H); 7.72 (d, 1H); 6.14 (tt, 1H); 3.99 (s, 3H); 3.70 (m, 2H);

Ex. no. 1-183: $^1$H-NMR (400 MHz, DMSO-$d_6$): δ=11.99 (br s, 1H); 8.66 (d, 1H); 7.80 (d, 1H); 7.67 (d, 1H); 3.99 (s, 3H); 3.49 (m, 1H); 1.22 (d, 3H); 0.92 (m, 1H); 0.43 (m, 2H); 0.32 (m, 2H);

Ex. no. 1-184: $^1$H-NMR (400 MHz, DMSO-$d_6$): δ=11.88 (br s, 1H); 8.72 (t, 1H); 7.81 (d, 1H); 7.68 (d, 1H); 3.99 (s, 3H); 3.21 (m, 2H); 1.55 (m, 2H); 0.94 (t, 3H);

Ex. no. 1-185: $^1$H-NMR (400 MHz, DMSO-$d_6$): δ=11.88 (br s, 1H); 8.61 (d, 1H); 7.80 (d, 1H); 7.67 (d, 1H); 4.05 (m, 1H); 3.99 (s, 3H); 1.17 (d, 6H);

Ex. no. 1-186: $^1$H-NMR (400 MHz, DMSO-$d_6$): δ=11.88 (br s, 1H); 8.86 (t, 1H); 7.80 (d, 1H); 7.68 (d, 1H); 3.99 (s, 3H); 3.47 (m, 2H); 3.41 (m, 2H); 3.28 (s, 3H);

Ex. no. 1-187: $^1$H-NMR (400 MHz, DMSO-$d_6$): δ=11.89 (br s, 1H); 8.93 (t, 1H); 7.81 (d, 1H); 7.69 (d, 1H); 3.99 (s, 3H); 3.44 (m, 2H); 2.66 (m, 2H); 2.12 (s, 3H);

Ex. no. 1-195: $^1$H-NMR (400 MHz, DMSO-$d_6$): δ=11.86 (br s, 1H); 8.58 (q, 1H); 7.98 (d, 1H); 7.47 (d, 1H); 3.98 (s, 3H); 2.79 (d, 3H);

Ex. no. 1-196: $^1$H-NMR (400 MHz, DMSO-$d_6$): δ=11.85 (br s, 1H); 8.64 (t, 1H); 7.98 (d, 1H); 7.47 (d, 1H); 3.99 (s, 3H); 3.27 (m, 2H); 1.15 (t, 3H);

Ex. no. 1-197: $^1$H-NMR (400 MHz, DMSO-$d_6$): δ=11.86 (br s, 1H); 8.70 (d, 1H); 7.97 (d, 1H); 7.46 (d, 1H); 3.98 (s, 3H); 2.80 (m, 1H); 0.72 (m, 2H); 0.57 (br s, 2H);

Ex. no. 1-207: $^1$H-NMR (400 MHz, DMSO-$d_6$): δ=11.99 (br s, 1H); 8.67 (q, 1H); 7.96 (d, 1H); 7.92 (d, 1H); 4.03 (s, 3H); 2.79 (d, 3H);

Ex. no. 1-208: $^1$H-NMR (400 MHz, DMSO-$d_6$): δ=11.99 (br s, 1H); 8.72 (t, 1H); 7.91 (d, 1H); 7.96 (d, 1H); 4.03 (s, 3H); 3.29 (m, 2H); 1.12 (t, 3H);

Ex. no. 1-209: $^1$H-NMR (400 MHz, DMSO-$d_6$): δ=12.00 (br s, 1H); 8.81 (d, 1H); 7.96 (d, 1H); 7.91 (d, 1H); 4.03 (s, 3H); 2.79 (m, 1H); 0.72 (m, 2H); 0.57 (m, 1H); 0.48 (m, 1H);

Ex. no. 1-210: $^1$H-NMR (400 MHz, DMSO-$d_6$): δ=11.99 (br s, 1H); 8.84 (t, 1H); 7.96 (d, 1H); 7.91 (d, 1H); 4.03 (s, 3H); 3.14 (m, 2H); 1.01 (m, 1H); 0.45 (m, 2H); 0.24 (m, 2H);

Ex. no. 1-211: $^1$H-NMR (400 MHz, DMSO-$d_6$): δ=12.01 (br s, 1H); 9.52 (t, 1H); 8.01 (d, 1H); 7.97 (d, 1H); 4.20 (m, 1H); 4.08 (m, 1H); 4.04 (s, 3H);

Ex. no. 1-212: $^1$H-NMR (400 MHz, DMSO-$d_6$): δ=12.01 (br s, 1H); 9.26 (t, 1H); 7.99 (d, 1H); 7.95 (d, 1H); 6.12 (tt, 1H); 4.03 (s, 3H); 3.70 (m, 2H);

Ex. no. 1-225: $^1$H-NMR (400 MHz, DMSO-$d_6$): δ=11.91 (br s, 1H); 8.70 (q, 1H); 7.86 (d, 1H); 7.81 (d, 1H); 6.93 (t, 1H); 4.03 (s, 3H); 2.81 (d, 3H);

Ex. no. 1-226: $^1$H-NMR (400 MHz, DMSO-$d_6$): δ=11.91 (br s, 1H); 8.77 (t, 1H); 7.86 (d, 1H); 7.81 (d, 1H); 6.93 (t, 1H); 4.03 (s, 3H); 3.29 (m, 2H); 1.14 (t, 3H);

Ex. no. 1-227: $^1$H-NMR (400 MHz, DMSO-$d_6$): δ=11.92 (br s, 1H); 8.83 (d, 1H); 7.85 (d, 1H); 7.80 (d, 1H); 6.93 (t, 1H); 4.02 (s, 3H); 2.83 (m, 1H); 0.71 (m, 2H); 0.57 (m, 2H);

Ex. no. 1-228: $^1$H-NMR (400 MHz, DMSO-$d_6$): δ=11.93 (br s, 1H); 8.90 (t, 1H); 7.86 (d, 1H); 7.81 (d, 1H); 6.93 (t, 1H); 4.03 (s, 3H); 3.16 (m, 2H); 1.04 (m, 1H); 0.46 (m, 2H); 0.26 (m, 2H);

Ex. no. 1-229: $^1$H-NMR (400 MHz, DMSO-$d_6$): δ=11.96 (br s, 1H); 9.54 (t, 1H); 7.91 (d, 1H); 7.84 (d, 1H); 6.92 (t, 1H); 4.14 (m, 2H); 4.03 (s, 3H);

Ex. no. 1-230: $^1$H-NMR (400 MHz, DMSO-$d_6$): δ=11.95 (br s, 1H); 9.28 (t, 1H); 7.90 (d, 1H); 7.83 (d, 1H); 6.94 (t, 1H); 6.18 (tt, 1H); 4.03 (s, 3H); 3.72 (m, 2H);

Ex. no. 1-271: $^1$H-NMR (400 MHz, DMSO-$d_6$): δ=11.81 (br s, 1H); 8.52 (q, 1H); 7.85 (d, 1H); 7.78 (d, 1H); 4.01 (s, 3H); 2.79 (d, 3H); 2.72 (m, 2H); 1.17 (t, 3H);

Ex. no. 1-272: $^1$H-NMR (400 MHz, DMSO-$d_6$): δ=11.80 (br s, 1H); 8.62 (t, 1H); 7.84 (d, 1H); 7.77 (d, 1H); 4.01 (s, 3H); 3.29 (q, 2H); 2.77 (m, 2H); 1.18 (t, 3H); 1.11 (t, 3H);

Ex. no. 1-273: $^1$H-NMR (400 MHz, DMSO-$d_6$): δ=11.78 (br s, 1H); 8.68 (d, 1H); 7.84 (d, 1H); 7.76 (d, 1H); 4.01 (s, 3H); 2.81 (m, 2H) M 2.70 (m, 1H); 1.17 (t, 3H); 0.71 (m, 2H); 0.49 (m, 2H);

Ex. no. 1-274: $^1$H-NMR (400 MHz, DMSO-$d_6$): δ=11.80 (br s, 1H); 8.74 (t, 1H); 7.84 (d, 1H); 7.76 (d, 1H); 4.01 (s, 3H); 3.19 (m, 1H); 3.08 (m, 1H); 2.80 (m, 2H); 1.20 (t, 3H); 1.02 (m, 1H); 0.45 (m, 2H); 0.24 (m, 2H);

Ex. no. 1-276: $^1$H-NMR (400 MHz, DMSO-$d_6$): δ=11.82 (br s, 1H); 9.10 (t, 1H); 7.88 (d, 1H); 7.79 (d, 1H); 6.13 (tt, 1H); 4.01 (s, 3H); 3.77 (m, 1H); 3.63 (m, 1H); 2.77 (m, 2H); 1.17 (t, 3H);

Ex. no. 1-277: $^1$H-NMR (400 MHz, DMSO-$d_6$): δ=11.73 (br s, 1H); 8.57 (q, 3H); 7.80 (d, 1H); 7.64 (d, 1H); 6.89 (t, 1H); 4.00 (s, 3H); 2.81 (d, 3H); 2.74 (q, 2H); 1.15 (t, 3H);

Ex. no. 1-278: $^1$H-NMR (400 MHz, DMSO-$d_6$): δ=11.72 (br s, 1H); 8.67 (t, 1H); 7.80 (d, 1H); 7.64 (d, 1H); 6.90 (t, 1H); 4.00 (s, 3H); 3.21 (m, 2H); 2.76 (q, 2H); 1.15 (2×t, 6H)

Ex. no. 1-279: $^1$H-NMR (400 MHz, DMSO-$d_6$): δ=11.72 (br s, 1H); 8.75 (d, 1H); 7.80 (d, 1H); 7.63 (d, 1H); 6.89 (t, 1H); 4.00 (s, 3H); 2.86 (m, 1H); 2.75 (m, 2H); 1.15 (t, 3H); 0.71 (m, 2H); 0.53 (m, 2H);

Ex. no. 1-286: $^1$H-NMR (400 MHz, DMSO-$d_6$): δ=11.70 (br s, 1H); 8.44 (q, 1H); 7.77 (br s, 2H); 4.03 (s, 3H); 2.79 (d, 3H); 2.11 (m, 1H); 0.84 (m, 2H); 0.64 (m, 2H);

Ex. no. 1-287: $^1$H-NMR (400 MHz, DMSO-$d_6$): δ=11.70 (br s, 1H); 8.51 (t, 1H); 7.77 (br s, 2H); 4.03 (s, 3H); 3.29 (m, 2H); 2.14 (m, 1H); 1.13 (t, 3H); 0.84 (m, 2H); 0.66 (m, 2H);

Ex. no. 1-288: $^1$H-NMR (400 MHz, DMSO-$d_6$): δ=11.70 (br s, 1H); 8.59 (d, 1H); 7.77 (br s, 2H); 4.03 (s, 3H); 2.79 (m, 1H); 2.11 (m, 1H); 0.85 (m, 2H); 0.70 (m, 2H); 0.66 (m, 2H); 0.51 (m, 2H);

Ex. no. 1-289: $^1$H-NMR (400 MHz, DMSO-$d_6$): δ=11.70 (br s, 1H); 8.63 (t, 1H); 7.77 (br s, 2H); 4.03 (s, 3H); 3.13 (m, 2H); 2.15 (m, 1H); 1.03 (m, 1H); 0.85 (m, 2H); 0.68 (m, 2H); 0.45 (m, 2H); 0.23 (m, 2H);

Ex. no. 1-291: $^1$H-NMR (400 MHz, DMSO-$d_6$): δ=11.72 (br s, 1H); 9.03 (t, 1H); 7.80 (br s, 2H); 6.13 (tt, 1H); 4.04 (s, 3H); 3.69 (m, 2H); 2.13 (m, 1H); 0.87 (m, 2H); 0.64 (m, 2H);

Ex. no. 1-292: $^1$H-NMR (400 MHz, DMSO-$d_6$): δ=11.69 (br s, 1H); 8.55 (d, 1H); 7.76 (br s, 2H); 4.03 (s, 3H); 3.38 (m, 1H); 2.18 (m, 1H); 1.21 (d, 3H); 0.89 (m, 3H); 0.69 (m, 2H); 0.44 (m, 2H); 0.34 (m, 1H); 0.24 (m, 1H);

Ex. no. 1-304: $^1$H-NMR (400 MHz, DMSO-$d_6$): δ=11.64 (br s, 1H); 8.52 (q, 1H); 7.73 (d, 1H); 7.66 (d, 1H); 6.94 (t, 1H); 4.03 (s, 3H); 2.81 (d, 3H); 2.17 (m, 1H); 0.83 (m, 2H); 0.58 (m, 2H);

Ex. no. 1-305: $^1$H-NMR (400 MHz, DMSO-$d_6$): δ=11.62 (br s, 1H); 8.60 (t, 1H); 7.72 (d, 1H); 7.66 (d, 1H); 6.94 (t, 1H); 4.03 (s, 3H); 3.31 (m, 2H); 2.19 (m, 1H); 1.14 (t, 3H); 0.83 (m, 2H); 0.60 (m, 2H);

Ex. no. 1-306: $^1$H-NMR (400 MHz, DMSO-$d_6$): δ=11.61 (br s, 1H); 8.67 (d, 1H); 7.72 (d, 1H); 7.65 (d, 1H); 6.94 (t, 1H); 4.03 (s, 3H); 2.84 (m, 1H); 2.16 (m, 1H); 0.83 (m, 2H); 0.70 (m, 2H); 0.57 (m, 4H);

Ex. no. 1-337: $^1$H-NMR (400 MHz, DMSO-$d_6$): δ=12.03 (br s, 1H); 7.98 (br s, 2H); 4.02 (s, 3H); 3.91 (br s, 1H); 2.07 (br s, 3H);

Ex. no. 1-338: $^1$H-NMR (400 MHz, DMSO-$d_6$): δ=12.01 (br s, 1H); 8.22 (s, 1H); 8.00 (s, 1H); 7.97 (d, 1H); 7.94 (d, 1H); 4.03 (s, 3H);

Ex. no. 1-339: $^1$H-NMR (400 MHz, DMSO-$d_6$): δ=11.69 (br s, 1H); 8.70 (d, 1H); 7.79 (d, 1H); 7.64 (d, 1H); 6.90 (t, 1H); 4.00 (s, 3H); 3.45 (m, 1H); 2.38 (s, 3H); 1.22 (d, 3H); 0.93 (m, 1H); 0.46 (m, 2H); 0.35 (m, 1H); 0.28 (m, 1H);

Ex. no. 1-340: $^1$H-NMR (400 MHz, DMSO-$d_6$): δ=11.93 (br s, 1H); 8.79 (d, 1H); 7.85 (d, 1H); 7.81 (d, 1H); 6.91 (t, 1H); 4.03 (s, 3H); 3.45 (m, 1H); 1.23 (d, 3H); 0.92 (m, 1H); 0.44 (m, 2H); 0.38 (m, 1H); 0.29 (m, 1H);

Ex. no. 1-341: $^1$H-NMR (400 MHz, DMSO-$d_6$): δ=11.79 (br s, 1H); 8.66 (d, 1H); 7.83 (d, 1H); 7.76 (d, 1H); 4.01 (s, 3H); 3.40 (m, 1H); 2.84 (q, 2H); 2.78 (m, 1H); 1.22 (t, 3H); 1.17 (t, 3H); 0.91 (m, 1H); 0.43 (m, 2H); 0.29 (m, 2H);

Ex. no. 1-342: $^1$H-NMR (400 MHz, DMSO-$d_6$): δ=11.88 (br s, 1H); 8.62 (q, 1H); 7.84 (d, 1H); 7.64 (d, 1H); 4.01 (s, 3H); 2.79 (d, 3H);

Ex. no. 1-343: $^1$H-NMR (400 MHz, DMSO-$d_6$): δ=11.88 (br s, 1H); 8.68 (t, 1H); 7.83 (d, 1H); 7.63 (d, 1H); 4.01 (s, 3H); 3.28 (q, 2H); 1.14 (t, 3H);

Ex. no. 1-344: $^1$H-NMR (400 MHz, DMSO-$d_6$): δ=11.87 (br s, 1H); 8.74 (d, 1H); 7.82 (d, 1H); 7.63 (d, 1H); 4.01 (s, 3H); 2.80 (m, 1H); 0.72 (m, 2H); 0.56 (m, 2H);

Ex. no. 1-345: $^1$H-NMR (400 MHz, DMSO-$d_6$): δ=11.70 (br s, 1H); 8.67 (t, 1H); 7.79 (d, 1H); 7.64 (d, 1H); 6.90 (t, 1H); 4.00 (s, 3H); 3.24 (m, 2H); 2.36 (s, 3H); 1.54 (m, 2H); 0.91 (t, 3H);

Ex. no. 1-346: $^1$H-NMR (400 MHz, DMSO-$d_6$): δ=11.69 (br s, 1H); 8.57 (d, 1H); 7.79 (d, 1H); 7.63 (d, 1H); 6.91 (t, 1H); 4.11 (m, 1H); 4.00 (s, 3H); 2.36 (s, 3H); 1.16 (d, 6H);

Ex. no. 1-347: $^1$H-NMR (400 MHz, DMSO-$d_6$): δ=11.70 (br s, 1H); 8.74 (t, 1H); 7.79 (d, 1H); 7.62 (d, 1H); 6.93 (t, 1H); 4.00 (s, 3H); 3.47 (m, 4H); 3.28 (s, 3H); 2.36 (s, 3H);

Ex. no. 1-348: $^1$H-NMR (400 MHz, DMSO-$d_6$): δ=11.70 (br s, 1H); 8.81 (t, 1H); 7.80 (d, 1H); 7.65 (d, 1H); 7.01 (t, 1H); 4.00 (s, 3H); 3.49 (m, 2H); 2.68 (m, 2H); 2.38 (s, 3H); 2.11 (s, 3H);

Ex. no. 1-349: $^1$H-NMR (400 MHz, DMSO-$d_6$): δ=11.88 (br s, 1H); 8.65 (q, 1H); 7.73 (d, 1H); 7.70 (d, 1H); 4.01 (s, 3H); 2.79 (d, 3H);

Ex. no. 1-350: $^1$H-NMR (400 MHz, DMSO-$d_6$): δ=11.88 (br s, 1H); 8.71 (t, 1H); 7.73 (d, 1H); 7.69 (d, 1H); 4.01 (s, 3H); 3.28 (m, 2H); 1.14 (t, 3H);

Ex. no. 1-351: $^1$H-NMR (400 MHz, DMSO-$d_6$): δ=11.87 (br s, 1H); 8.77 (d, 1H); 7.72 (d, 1H); 7.68 (d, 1H); 4.01 (s, 3H); 2.80 (m, 1H); 0.72 (m, 2H); 0.55 (m, 2H);

Ex. no. 1-352: $^1$H-NMR (400 MHz, DMSO-$d_6$): δ=11.82 (br s, 1H); 8.56 (d, 1H); 7.94 (d, 1H); 7.86 (d, 1H); 4.06 (s, 3H); 3.47 (m, 1H); 2.45 (s, 3H); 1.21 (d, 3H); 0.91 (m, 1H); 0.41 (m, 2H); 0.33 (m, 2H);

Ex. no. 1-353: $^1$H-NMR (400 MHz, DMSO-$d_6$): δ=11.78 (br s, 1H); 8.65 (d, 1H); 7.82 (br s, 2H); 6.88 (t, 1H); 4.05 (s, 3H); 3.51 (m, 1H); 2.44 (s, 3H); 1.23 (d, 3H); 0.93 (m, 1H); 0.41 (m, 3H); 0.30 (m, 1H);

Ex. no. 1-354: $^1$H-NMR (400 MHz, DMSO-$d_6$): δ=11.65 (br s, 1H); 8.35 (q, 1H); 7.74 (d, 1H); 7.19 (d, 1H); 3.97 (s, 3H); 3.85 (s, 3H); 2.74 (d, 3H);

Ex. no. 1-355: $^1$H-NMR (400 MHz, DMSO-$d_6$): δ=11.64 (br s, 1H); 8.41 (t, 1H); 7.74 (d, 1H); 7.18 (d, 1H); 3.97 (s, 3H); 3.85 (s, 3H); 3.24 (m, 2H); 1.10 (t, 3H);

Ex. no. 1-356: $^1$H-NMR (400 MHz, DMSO-$d_6$): δ=11.64 (br s, 1H); 8.48 (d, 1H); 7.73 (d, 1H); 7.18 (d, 1H); 3.97 (s, 3H); 3.85 (s, 3H); 2.79 (m, 1H); 0.68 (m, 2H); 0.49 (m, 2H);

Ex. no. 1-357: $^1$H-NMR (400 MHz, DMSO-$d_6$): δ=12.05 (br s, 1H); 11.93 (br s, 1H); 8.06 (d, 1H); 7.99 (d, 1H); 4.02 (s, 3H); 3.74 (s, 3H);

Ex. no. 1-358: $^1$H-NMR (400 MHz, DMSO-$d_6$): δ=12.04 (br s, 1); 11.81 (br s, 1H); 8.05 (d, 1H); 7.99 (d, 1H); 4.02 (s, 3H); 3.97 (m, 2H); 1.23 (t, 3H);

Ex. no. 1-359: $^1$H-NMR (400 MHz, DMSO-$d_6$): δ=12.04 (br s, 1H); 11.81 (br s, 1H); 8.05 (d, 1H); 7.98 (d, 1H); 4.02 (s, 3H); 3.88 (m, 2H); 1.64 (m, 2H); 0.94 (t, 3H);

Ex. no. 1-360: $^1$H-NMR (400 MHz, DMSO-$d_6$): δ=12.04 (br s, 1H); 11.65 (br s, 1H); 8.04 (d, 1H); 7.98 (d, 1H); 4.18 (m, 1H); 4.02 (s, 3H); 1.22 (d, 6H);

Ex. no. 1-361: $^1$H-NMR (400 MHz, DMSO-$d_6$): δ=11.98 (br s, 1H); 11.92 (br s, 1H); 7.98 (d, 1H); 7.81 (d, 1H); 7.04 (t, 1H); 4.01 (s, 3H); 3.76 (s, 3H);

Ex. no. 1-362: $^1$H-NMR (400 MHz, DMSO-$d_6$): δ=11.98 (br s, 1H); 11.81 (br s, 1H); 7.97 (d, 1H); 7.81 (d, 1H); 7.02 (t, 1H); 4.01 (s, 3H); 3.99 (q, 2H); 1.23 (t, 3H);

Ex. no. 1-363: $^1$H-NMR (400 MHz, DMSO-$d_6$): δ=11.97 (br s, 1H); 11.81 (br s, 1H); 7.97 (d, 1H); 7.81 (d, 1H); 7.02 (t, 1H); 4.01 (s, 3H); 3.90 (t, 2H); 1.64 (m, 2H); 0.94 (t, 3H);

Ex. no. 1-364: $^1$H-NMR (400 MHz, DMSO-$d_6$): δ=11.97 (br s, 1H); 11.67 (br s, 1H); 7.97 (d, 1H); 7.81 (d, 1H); 7.01 (t, 1H); 4.21 (m, 1H); 4.01 (s, 3H); 1.23 (d, 6H);

Ex. no. 2-19: $^1$H-NMR (400 MHz, DMSO-$d_6$): δ=11.71 (br s, 1H); 8.57 (q, 1H); 7.94 (d, 1H); 7.88 (d, 1H); 4.36 (q, 2H); 3.27 (s, 3H); 2.78 (d, 3H); 2.35 (s, 3H); 1.47 (t, 3H);

Ex. no. 2-20: $^1$H-NMR (400 MHz, DMSO-$d_6$): δ=11.71 (br s, 1H); 8.63 (t, 1H); 7.94 (d, 1H); 7.87 (d, 1H); 4.35 (q, 2H); 3.27 (m, 2H); 3.27 (s, 3H); 2.37 (s, 3H); 1.47 (t, 3H); 1.13 (t, 3H);

Ex. no. 2-21: $^1$H-NMR (400 MHz, DMSO-$d_6$): δ=11.70 (br s, 1H); 8.70 (d, 1H); 7.93 (d, 1H); 7.87 (d, 1H); 4.35 (q, 2H); 3.27 (s, 3H); 2.77 (m, 1H); 2.35 (s, 3H); 1.47 (t, 3H); 0.69 (m, 2H); 0.62 (m, 1H); 0.51 (m, 1H);

Ex. no. 2-25: $^1$H-NMR (400 MHz, DMSO-$d_6$): δ=11.65 (br s, 1H); 8.51 (q, 1H) 7.82 (d, 1H); 7.76 (d, 1H); 4.35 (q, 2H); 2.79 (d, 3H); 2.33 (s, 3H); 1.47 (t, 3H);

Ex. no. 2-26: $^1$H-NMR (400 MHz, DMSO-$d_6$): δ=11.65 (br s, 1H); 8.60 (t, 1H); 7.83 (d, 1H); 7.76 (d, 1H); 4.35 (q, 2H); 3.30 (m, 2H); 2.35 (s, 3H); 1.47 (t, 3H); 1.11 (t, 3H);

Ex. no. 2-27: $^1$H-NMR (400 MHz, DMSO-$d_6$): δ=11.64 (br s, 1H); 8.66 (d, 1H); 7.82 (d, 1H); 7.75 (d, 1H); 4.35 (q, 2H); 2.81 (m, 1H); 2.34 (s, 3H); 1.47 (t, 3H); 0.71 (m, 2H); 0.49 (m, 2H);

Ex. no. 2-28: $^1$H-NMR (400 MHz, DMSO-$d_6$): δ=11.68 (br s, 1H); 8.72 (t, 1H); 7.82 (d, 1H); 7.76 (d, 1H); 4.35 (q, 2H); 3.13 (m, 2H); 2.38 (s, 3H); 1.47 (t, 3H); 1.01 (m, 1H); 0.45 (m, 2H); 0.23 (m, 2H);

Ex. no. 2-29: $^1$H-NMR (400 MHz, DMSO-$d_6$): δ=11.70 (br s, 1H); 9.38 (t, 1H); 7.87 (d, 1H); 7.80 (d, 1H); 4.35 (q, 2H); 4.13 (m, 2H); 2.35 (s, 3H); 1.47 (t, 3H);

Ex. no. 2-30: $^1$H-NMR (400 MHz, DMSO-$d_6$): δ=11.68 (br s, 1H); 9.08 (t, 1H); 7.85 (d, 1H); 7.78 (d, 1H); 6.14 (tt, 1H); 4.35 (q, 2H); 3.70 (m, 2H); 2.36 (s, 3H); 1.47 (t, 3H);

Ex. no. 2-31: $^1$H-NMR (400 MHz, DMSO-$d_6$): δ=11.66 (br s, 1H); 0.62 (t, 1H); 7.81 (d, 1H); 7.75 (d, 1H); 4.35 (q, 2H); 3.40 (m, 1H); 2.39 (d, 3H); 1.48 (t, 3H); 1.20 (dd, 3H); 0.90 (m, 1H); 0.45 (m, 2H); 0.30 (m, 2H);

Ex. no. 2-32: $^1$H-NMR (400 MHz, DMSO-$d_6$): δ=11.67 (br s, 1H); 8.62 (t, 1H); 7.82 (d, 1H); 7.76 (d, 1H); 4.35 (q, 2H); 3.21 (m, 2H); 2.36 (s, 3H); 1.51 (m, 2H); 1.47 (t, 3H); 0.91 (t, 3H);

Ex. no. 2-33: $^1$H-NMR (400 MHz, DMSO-$d_6$): δ=11.65 (br s, 1H); 8.50 (d, 1H); 7.81 (d, 1H); 7.75 (d, 1H); 4.35 (q, 2H); 4.09 (m, 1H); 2.36 (s, 3H); 1.47 (t, 3H); 1.16 (d, 3H); 1.12 (d, 3H);

Ex. no. 2-34: $^1$H-NMR (400 MHz, DMSO-$d_6$): δ=11.66 (br s, 1H); 8.70 (d, 1H); 4.35 (q, 2H); 3.52-3.30 (m, 4H); 3.27 (s, 3H); 2.36 (s, 3H); 1.47 (t, 3H);

Ex. no. 2-35: $^1$H-NMR (400 MHz, DMSO-$d_6$): δ=11.69 (br s, 1H); 8.78 (t, 1H); 7.83 (d, 1H); 7.76 (d, 1H); 4.35 (q, 2H); 3.50 (m, 1H); 3.40 (m, 1H); 2.64 (m, 2H); 2.39 (s, 3H); 2.11 (s, 3H); 1.47 (t, 3H);

Ex. no. 2-36: $^1$H-NMR (400 MHz, DMSO-$d_6$): δ=11.70 (br s, 1H); 9.42 (t, 1H); 7.89 (d, 1H); 7.81 (d, 1H); 4.49 (m, 2H); 4.36 (q, 2H); 2.35 (s, 3H); 1.47 (t, 3H);

Ex. no. 2-37: $^1$H-NMR (400 MHz, DMSO-$d_6$): δ=11.67 (br s, 1H); 8.72 (br s, 1H); 7.82 (d, 1H); 7.75 (d, 1H); 4.37 (q, 2H); 3.96 (m, 1H); 3.77 (m, 1H); 3.62 (m, 1H); 3.37 (m, 1H); 3.27 (m, 1H); 2.36 (s, 3H); 1.94 (m, 1H); 1.82 (m, 2H); 1.60 (m, 1H); 1.47 (t, 3H);

Ex. no. 2-42: $^1$H-NMR (400 MHz, DMSO-$d_6$): δ=11.66 (br s, 1H); 8.85 (d, 1H); 7.82 (d, 1H); 7.76 (d, 1H); 4.37 (m, 1H); 4.35 (q, 2H); 2.34 (s, 3H); 2.24 (m 2H); 1.97 (m, 2H); 1.69 (m, 2H); 1.47 (t, 3H);

Ex. no. 2-44: $^1$H-NMR (400 MHz, DMSO-$d_6$): δ=11.58 (br s, 1H); 8.56 (q, 1H); 7.79 (d, 1H); 7.64 (d, 1H); 6.91 (t, 1H); 4.34 (q, 2H); 2.81 (d, 3H); 2.33 (s, 3H); 1.47 (t, 3H);

Ex. no. 2-45: $^1$H-NMR (400 MHz, DMSO-$d_6$): δ=11.58 (br s, 1H); 8.65 (t, 1H); 7.78 (d, 1H); 7.64 (d, 1H); 6.91 (t, 1H); 4.34 (q, 2H); 3.31 (m, 2H); 2.35 (s, 3H); 1.47 (t, 3H); 1.13 (t, 3H);

Ex. no. 2-46: $^1$H-NMR (400 MHz, DMSO-$d_6$): δ=11.58 (br s, 1H); 8.71 (d, 1H); 7.78 (d, 1H); 7.63 (d, 1H); 6.91 (t, 1H); 4.34 (q, 2H); 2.85 (m, 1H); 2.33 (s, 3H); 1.47 (t, 3H); 0.71 (m, 2H); 0.53 (m, 2H);

Ex. no. 2-47: $^1$H-NMR (400 MHz, DMSO-$d_6$): δ=11.59 (br s, 1H); 8.79 (t, 1H); 7.79 (d, 1H); 7.64 (d, 1H); 6.92 (t, 1H); 4.35 (q, 2H); 3.16 (m, 2H); 2.38 (s, 3H); 1.47 (t, 3H); 1.05 (m, 1H); 0.46 (m, 2H); 0.24 (m, 2H);

Ex. no. 2-49: $^1$H-NMR (400 MHz, DMSO-$d_6$): δ=11.60 (br s, 1H); 9.12 (t, 1H); 7.82 (d, 1H); 7.66 (d, 1H); 6.93 (t, 1H); 6.19 (tt, 1H); 4.35 (q, 2H); 3.72 (m, 2H); 2.36 (s, 3H); 1.47 (t, 3H);

Ex. no. 2-56: $^1$H-NMR (400 MHz, DMSO-$d_6$): δ=11.56 (br s, 1H); 8.53 (q, 1H); 7.88 (d, 1H); 7.67 (d, 1H); 4.34 (q, 2H); 3.86 (s, 3H); 2.79 (d, 3H); 1.47 (t, 3H);

Ex. no. 2-57: $^1$H-NMR (400 MHz, DMSO-$d_6$): δ=11.54 (br s, 1H); 8.61 (t, 1H); 7.88 (d, 1H); 7.67 (d, 1H); 4.34 (q, 2H); 3.88 (s, 3H); 3.28 (m, 2H); 1.47 (t, 3H); 1.11 (t, 3H);

Ex. no. 2-58: $^1$H-NMR (400 MHz, DMSO-$d_6$): δ=11.54 (br s, 1H); 8.68 (d, 1H); 7.87 (d, 1H); 7.66 (d, 1H); 4.34 (q, 2H); 3.87 (s, 3H); 2.80 (m, 1H); 1.47 (t, 3H); 0.71 (m, 2H); 0.49 (m, 2H);

Ex. no. 2-72: $^1$H-NMR (400 MHz, DMSO-$d_6$): δ=11.42 (br s, 1H); 8.58 (q, 1H); 7.84 (d, 1H); 7.54 (d, 1H); 6.96 (t, 1H); 4.34 (q, 2H); 3.85 (s, 3H); 2.81 (d, 3H); 1.47 (t, 3H);

Ex. no. 2-73: $^1$H-NMR (400 MHz, DMSO-$d_6$): δ=11.42 (br s, 1H); 8.65 (t, 1H); 7.84 (d, 1H); 7.54 (d, 1H); 6.96 (t, 1H); 4.34 (q, 2H); 3.86 (s, 3H); 3.30 (m, 2H); 1.47 (t, 3H); 1.13 (t, 3H);

Ex. no. 2-74: $^1$H-NMR (400 MHz, DMSO-$d_6$): δ=11.40 (br s, 1H); 8.72 (d, 1H); 7.83 (d, 1H); 7.53 (d, 1H); 6.95 (t, 1H); 4.33 (q, 2H); 3.85 (s, 3H); 2.85 (m, 1H); 1.47 (t, 3H); 0.72 (m, 2H); 0.55 (m, 2H);

Ex. no. 2-81: $^1$H-NMR (400 MHz, DMSO-$d_6$): δ=11.71 (br s, 1H); 8.48 (q, 1H); 7.95 (d, 1H); 7.86 (d, 1H); 4.43 (q, 2H); 2.80 (d, 3H); 2.43 (s, 3H); 1.48 (t, 3H);

Ex. no. 2-82: $^1$H-NMR (400 MHz, DMSO-$d_6$): δ=11.70 (br s, 1H); 8.56 (t, 1H); 7.94 (d, 1H); 7.86 (d, 1H); 4.43 (q, 2H); 3.30 (m, 2H); 2.44 (s, 3H); 1.48 (t, 3H); 1.13 (s, 3H);

Ex. no. 2-83: $^1$H-NMR (400 MHz, DMSO-$d_6$): δ=11.72 (br s, 1H); 8.64 (d, 1H); 7.94 (d, 1H); 7.86 (d, 1H); 4.43 (q, 2H); 2.80 (m, 1H); 2.43 (s, 3H); 1.48 (t, 3H); 0.71 (m, 2H); 0.53 (br s, 2H);

Ex. no. 2-84: $^1$H-NMR (400 MHz, DMSO-$d_6$): δ=11.71 (br s, 1H); 8.68 (t, 1H); 7.95 (d, 1H); 7.86 (d, 1H); 4.44 (q, 2H); 3.16 (m, 2H); 2.45 (s, 3H); 1.47 (t, 3H); 1.02 (m, 1H); 0.45 (m, 2H); 0.25 (m, 2H);

Ex. no. 2-86: $^1$H-NMR (400 MHz, DMSO-$d_6$): δ=11.73 (br s, 1H); 9.10 (t, 1H); 7.98 (d, 1H); 7.91 (d, 1H); 6.12 (tt, 1H); 4.43 (q, 2H); 3.71 (m, 2H); 2.43 (s, 3H); 1.49 (t, 3H);

Ex. no. 2-87: $^1$H-NMR (400 MHz, DMSO-$d_6$): δ=11.65 (br s, 1H); 8.55 (q, 1H); 7.81 (s, 2H); 6.91 (t, 1H); 4.43 (q, 2H); 2.83 (d, 3H); 2.42 (s. 3H); 1.49 (t 3H);

Ex. no. 2-88: $^1$H-NMR (400 MHz, DMSO-$d_6$): δ=11.65 (br s, 1H); 8.62 (t, 1H); 7.81 (s, 2H); 6.90 (t, 1H); 4.43 (q, 2H); 3.32 (m, 2H); 2.43 (s, 3H); 1.48 (t, 3H); 1.15 (t, 3H);

Ex. no. 2-89: $^1$H-NMR (400 MHz, DMSO-$d_6$): δ=11.65 (br s, 1H); 8.70 (d, 1H); 7.80 (br s, 2H); 6.90 (t, 1H); 4.43 (q, 2H); 2.85 (m, 1H); 2.41 (s, 3H); 1.48 (t, 3H); 0.72 (m, 2H); 0.57 (m, 2H);

Ex. no. 2-90: $^1$H-NMR (400 MHz, DMSO-$d_6$): δ=11.66 (br s, 1H); 8.76 (t, 1H); 7.83 (m, 2H); 6.91 (t, 1H); 4.43 (q, 2H); 3.19 (m, 2H); 2.44 (s, 3H); 1.49 (t, 3H); 1.06 (m, 1H); 0.46 (m, 2H); 0.26 (m, 2H);

Ex. no. 2-92: $^1$H-NMR (400 MHz, DMSO-$d_6$): δ=11.68 (br s, 1H); 9.14 (t, 1H); 7.84 (br s, 2H); 6.92 (t, 1H); 6.18 (tt, 1H); 4.43 (q, 2H); 3.73 (m, 2H); 2.42 (s, 3H); 1.48 (t, 3H);

Ex. no. 2-123: $^1$H-NMR (400 MHz, DMSO-$d_6$): δ=11.92 (br s, 1H); 8.73 (q, 1H); 8.07 (d, 1H); 8.02 (d, 1H); 4.37 (q, 2H); 2.79 (d, 3H); 1.47 (t, 3H);

Ex. no. 2-125: $^1$H-NMR (400 MHz, DMSO-$d_6$): δ=11.91 (br s, 1H); 8.85 (d, 1H); 8.05 (d, 1H); 8.02 (d, 1H); 4.37 (q, 2H); 3.31 (s, 3H); 2.77 (m, 1H); 1.47 (t, 3H); 0.69 (m, 2H); 0.58 (m, 2H);

Ex. no. 2-129: $^1$H-NMR (400 MHz, DMSO-$d_6$): δ=11.89 (br s, 1H); 8.70 (q, 1H); 7.97 (d, 1H); 7.93 (d, 1H); 4.37 (q, 2H); 2.79 (d, 3H); 1.47 (t, 3H);

Ex. no. 2-130: $^1$H-NMR (400 MHz, DMSO-$d_6$): δ=11.89 (br s, 1H); 8.76 (t, 1H); 7.96 (d, 1H); 7.93 (d, 1H); 4.37 (q, 2H); 3.28 (m, 2H); 1.47 (t, 3H); 1.12 (t, 3H);

Ex. no. 2-131: $^1$H-NMR (400 MHz, DMSO-$d_6$): δ=11.89 (br s, 1H); 8.83 (d, 1H); 7.96 (d, 1H); 7.92 (d, 1H); 4.37 (q, 2H); 2.80 (m, 1H); 1.47 (t, 3H); 0.72 (m, 2H); 0.50 (br s, 2H);

Ex. no. 2-132: $^1$H-NMR (400 MHz, DMSO-$d_6$): δ=11.91 (br s, 1H); 8.89 (t, 1H); 7.97 (d, 1H); 7.93 (d, 1H); 4.38 (q, 2H); 3.15 (m, 3H); 1.47 (t, 3H); 0.46 (m, 2H); 0.23 (m, 2H);

Ex. no. 2-133: $^1$H-NMR (400 MHz, DMSO-$d_6$): δ=11.96 (br s, 1H); 9.56 (t, 1H); 8.03 (d, 1H); 7.98 (d, 1H); 4.38 (q, 2H); 4.15 (m, 2H); 1.47 (t, 3H);

Ex. no. 2-134: $^1$H-NMR (400 MHz, DMSO-$d_6$): δ=11.93 (br s, 1H); 9.29 (t, 1H); 8.01 (d, 1H); 7.96 (d, 1H); 6.12 (tt, 1H); 4.38 (q, 2H); 3.71 (m, 2H); 1.47 (t, 3H);

Ex. no. 2-135: $^1$H-NMR (400 MHz, DMSO-$d_6$): δ=11.91 (br s, 1H); 8.77 (d, 1H); 7.96 (d, 1H); 7.92 (d, 1H); 4.38 (q, 2H); 3.43 (m, 1H); 1.48 (t, 3H); 1.20 (m, 3H); 0.90 (m, 1H); 0.43 (m, 2H); 0.30 (m, 2H);

Ex. no. 2-138: $^1$H-NMR (400 MHz, DMSO-$d_6$): δ=11.90 (br s, 1H); 8.91 (t, 1H); 7.96 (d, 1H); 7.92 (d, 1H); 4.38 (q, 2H); 3.45 (m, 4H); 3.27 (s, 3H); 1.47 (t, 3H);

Ex. no. 2-139: $^1$H-NMR (400 MHz, DMSO-$d_6$): δ=11.91 (br s, 1H); 8.99 (t, 1H); 7.98 (d, 1H); 7.93 (d, 1H); 4.38 (q, 2H); 3.45 (m, 2H); 2.63 (t, 2H); 2.11 (s, 3H); 1.47 (t, 3H);

Ex. no. 2-141: $^1$H-NMR (400 MHz, DMSO-$d_6$): δ=11.90 (br s, 1H); 8.90 (t, 1H); 7.96 (d, 1H); 7.92 (d, 1H); 4.37 (q, 2H); 3.96 (m, 1H); 3.78 (m, 1H); 3.65 (m, 1H); 3.32 (br s, 2H); 1.93 (m, 1H); 1.83 (m, 2H); 1.62 (m, 1H); 1.47 (t, 3H);

Ex. no. 2-142: $^1$H-NMR (400 MHz, DMSO-$d_6$): δ=11.88 (br s, 1H); 8.90 (t, 1H); 7.95 (d, 1H); 7.90 (d, 1H); 4.37 (q, 2H); 4.18 (br d, 2H); 3.00 (s, 3H); 2.86 (s, 3H); 1.47 (t, 3H);

Ex. no. 2-143: $^1$H-NMR (400 MHz, DMSO-$d_6$): δ=11.98 (br s, 1H); 10.88 (br s, 1H); 8.06 (d, 1H); 8.02 (d, 1H); 7.65 (d, 2H); 7.38 (t, 2H); 7.16 (t, 1H); 4.38 (q, 2H); 1.47 (t, 3H);

Ex. no. 2-144: $^1$H-NMR (400 MHz, DMSO-$d_6$): δ=11.91 (br s, 1H); 9.37 (t, 1H); 7.98 (d, 1H); 7.93 (d, 1H); 7.45 (m, 1H); 7.07 (m, 1H); 6.99 (m, 1H); 4.66 (br s, 2H); 4.37 (q, 2H); 1.47 (t, 3H);

Ex. no. 2-146: $^1$H-NMR (400 MHz, DMSO-$d_6$): δ=11.61 (br s, 1H); 7.74 (d, 1H); 7.71 (d, 1H); 4.62 (m, 1H); 4.57 (q, 2H); 2.46 (m, 2H); 2.19 (m, 2H); 1.82 (m, 2H); 1.62 (t, 3H);

Ex. no. 2-147: $^1$H-NMR (400 MHz, DMSO-$d_6$): δ=11.83 (br s, 1H); 8.72 (q, 1H); 7.90 (d, 1H); 7.78 (d, 1H); 6.96 (t, 1H); 4.37 (q, 2H); 2.81 (d, 3H); 1.47 (t, 3H);

Ex. no. 2-148: $^1$H-NMR (400 MHz, DMSO-$d_6$): δ=11.82 (br s, 1H); 8.79 (t, 1H); 7.90 (d, 1H); 7.78 (d, 1H); 6.96 (t, 1H); 4.37 (q, 2H); 3.31 (m, 2H); 1.47 (t, 3H); 1.13 (t, 3H);

Ex. no. 2-149: $^1$H-NMR (400 MHz, DMSO-$d_6$): δ=11.82 (br s, 1H); 8.85 (d, 1H); 7.89 (d, 1H); 7.77 (d, 1H); 6.95 (t, 1H); 4.37 (q, 2H); 2.84 (m, 1H); 1.47 (t, 3H); 0.72 (m, 2H); 0.55 (m, 2H);

Ex. no. 2-154: $^1$H-NMR (400 MHz, DMSO-$d_6$): δ=11.84 (br s, 1H); 8.81 (t, 1H); 7.90 (d, 1H); 7.78 (d, 1H); 6.95 (t, 1H); 4.37 (q, 2H); 3.24 (m, 2H); 1.54 (m, 2H); 1.47 (t, 3H); 0.92 (t, 3H);

Ex. no. 2-155: $^1$H-NMR (400 MHz, DMSO-$d_6$): δ=11.83 (br s, 1H); 8.70 (d, 1H); 7.89 (d, 1H); 7.77 (d, 1H); 6.95 (t, 1H); 4.37 (q, 2H); 4.09 (m, 1H); 1.47 (t, 3H); 1.16 (d, 6H);

Ex. no. 2-156: $^1$H-NMR (400 MHz, DMSO-$d_6$): δ=11.84 (br s, 1H); 8.93 (t, 1H); 7.90 (d, 1H); 7.78 (d, 1H); 6.93 (t, 1H); 4.37 (q, 2H); 3.47 (m, 4H); 3.29 (s, 3H); 1.47 (t, 3H);

Ex. no. 2-157: $^1$H-NMR (400 MHz, DMSO-$d_6$): δ=11.85 (br s, 1H); 8.99 (t, 1H); 7.92 (d, 1H); 7.80 (d, 1H); 7.05 (t, 1H); 4.37 (q, 2H); 3.49 (m, 2H); 2.67 (m, 2H); 2.12 (s, 3H); 1.47 (t, 3H);

Ex. no. 2-158: $^1$H-NMR (400 MHz, DMSO-$d_6$): δ=11.87 (br s, 1H); 9.59 (t, 1H); 7.97 (d, 1H); 7.81 (d, 1H); 7.01 (t, 1H); 4.37 (m, 4H); 1.47 (t, 3H);

Ex. no. 2-159: $^1$H-NMR (400 MHz, DMSO-$d_6$): δ=11.84 (br s, 1H); 8.94 (t, 1H); 7.90 (d, 1H); 7.78 (d, 1H); 6.98 (t, 1H); 4.37 (q, 2H); 3.99 (m, 1H); 3.78 (m, 1H); 3.65 (m, 1H); 3.35 (m, 2H); 1.94 (m, 1H); 1.84 (m, 2H); 1.62 (m, 1H); 1.47 (t, 3H);

Ex. no. 2-160: $^1$H-NMR (400 MHz, DMSO-$d_6$): δ=11.84 (br s, 1H); 9.12 (t, 1H); 7.93 (d, 1H); 7.83 (d, 1H); 7.58 (t, 1H); 4.37 (q, 2H); 4.17 (d, 2H); 3.02 (s, 3H); 2.89 (s, 3H); 1.47 (t, 3H);

Ex. no. 2-161: $^1$H-NMR (400 MHz, DMSO-$d_6$): δ=11.88 (br s, 1H); 10.84 (br s, 1H); 7.98 (d, 1H); 7.85 (d, 1H); 7.69 (m, 2H); 7.38 (m, 2H); 7.16 (m, 1H); 7.12 (t, 1H); 4.38 (q, 2H); 1.48 (t, 3H);

Ex. no. 2-162: $^1$H-NMR (400 MHz, DMSO-$d_6$): δ=11.85 (br s, 1H); 9.45 (t, 1H); 7.92 (d, 1H); 7.79 (d, 1H); 7.45 (m, 1H); 7.07 (m, 1H); 6.99 (m, 1H); 6.92 (t, 1H); 4.68 (d, 2H); 4.36 (q, 2H); 1.47 (t, 3H);

Ex. no. 2-164: $^1$H-NMR (400 MHz, DMSO-$d_6$): δ=11.84 (br s, 1H); 9.05 (d, 1H); 7.90 (d, 1H); 7.78 (d, 1H); 6.93 (t, 1H); 4.37 (m, 3H); 2.25 (m, 2H); 2.01 (m, 2H); 1.71 (m, 2H); 1.47 (t, 3H);

Ex. no. 2-173: $^1$H-NMR (400 MHz, DMSO-$d_6$): δ=11.76 (br s, 1H); 8.79 (d, 1H); 7.76 (d, 1H); 7.66 (d, 1H); 4.35 (q, 2H); 2.82 (m, 1H); 1.47 (t, 3H); 0.73 (m, 2H); 0.53 (m, 2H);

Ex. no. 2-177: $^1$H-NMR (400 MHz, DMSO-$d_6$): δ=11.79 (br s, 1H); 8.65 (d, 1H); 7.81 (d, 1H); 7.68 (d, 1H); 4.35 (q, 2H); 2.79 (d, 3H); 1.46 (t, 3H);

Ex. no. 2-178: $^1$H-NMR (400 MHz, DMSO-$d_6$): δ=11.79 (br s, 1H); 8.71 (t, 1H); 7.81 (d, 1H); 7.67 (d, 1H); 4.35 (q, 1H); 3.28 (m, 2H); 1.46 (t, 3H); 1.14 (t, 3H);

Ex. no. 2-179: $^1$H-NMR (400 MHz, DMSO-$d_6$): δ=11.78 (br s, 1H); 8.77 (d, 1H); 7.80 (d, 1H); 7.67 (d, 1H); 4.35 (q, 2H); 2.81 (m, 1H); 1.46 (t, 3H); 0.72 (m, 2H); 0.54 (m, 2H);

Ex. no. 2-180: $^1$H-NMR (400 MHz, DMSO-$d_6$): δ=11.79 (br s, 1H); 8.80 (t, 1H); 7.81 (d, 1H); 7.67 (d, 1H); 4.35 (q, 2H); 3.16 (m, 2H); 1.46 (t, 3H); 1.02 (m, 1H); 0.46 (m, 2H); 0.26 (m, 2H);

Ex. no. 2-181: $^1$H-NMR (400 MHz, DMSO-$d_6$): δ=11.81 (br s, 1H); 9.50 (t, 1H); 7.85 (d, 1H); 7.73 (d, 1H); 4.35 (q, 2H); 4.13 (m, 2H); 1.46 (t, 3H);

Ex. no. 2-182: $^1$H-NMR (400 MHz, DMSO-$d_6$): δ=11.79 (br s, 1H); 9.23 (t, 1H); 7.83 (d, 1H); 7.71 (d, 1H); 6.14 (tt, 1H); 4.35 (q, 2H); 3.70 (m, 2H); 1.46 (t, 3H);

Ex. no. 2-183: $^1$H-NMR (400 MHz, DMSO-$d_6$): δ=11.79 (br s, 1H); 8.67 (d, 1H); 7.80 (d, 1H); 7.66 (d, 1H); 4.35 (q, 2H); 3.49 (m, 1H); 1.47 (t, 3H); 1.22 (d, 3H); 0.92 (m, 1H); 0.43 (m, 2H); 0.32 (m, 2H);

Ex. no. 2-184: $^1$H-NMR (400 MHz, DMSO-$d_6$): δ=11.78 (br s, 1H); 8.72 (t, 1H); 7.81 (d, 1H); 7.67 (d, 1H); 4.35 (q, 2H); 3.22 (m, 2H); 1.56 (m, 2H); 1.46 (t, 3H); 0.94 (t, 3H);

Ex. no. 2-185: $^1$H-NMR (400 MHz, DMSO-$d_6$): δ=11.77 (br s, 1H); 7.80 (d, 1H); 7.66 (d, 1H); 4.35 (q, 2H); 4.06 (m, 1H); 1.46 (t, 3H); 1.17 (d, 6H);

Ex. no. 2-186: $^1$H-NMR (400 MHz, DMSO-$d_6$): δ=11.78 (br s, 1H); 8.86 (t, 1H); 7.80 (d, 1H); 7.67 (d, 1H); 4.35 (q, 2H); 3.48 (m, 2H); 3.41 (m, 2H); 3.28 (s, 3H); 1.46 (s, 3H);

Ex. no. 2-187: $^1$H-NMR (400 MHz, DMSO-$d_6$): δ=11.80 (br s, 1H); 8.93 (t, 1H); 7.81 (d, 1H); 7.69 (d, 1H); 4.35 (q, 2H); 3.44 (m, 2H); 2.67 (m, 2H); 2.09 (s, 3H); 1.46 (t, 3H);

Ex. no. 2-195: $^1$H-NMR (400 MHz, DMSO-$d_6$): δ=11.74 (br s, 1H); 8.58 (q, 1H); 7.98 (d, 1H); 7.46 (d, 1H); 4.34 (q, 2H); 2.79 (d, 3H); 1.45 (t, 3H);

Ex. no. 2-196: $^1$H-NMR (400 MHz, DMSO-$d_6$): δ=11.75 (br s, 1H); 8.64 (t, 1H); 7.98 (d, 1H); 7.46 (d, 1H); 4.34 (q, 2H); 3.27 (m, 2H); 1.46 (t, 3H); 1.15 (t, 3H);

Ex. no. 2-197: $^1$H-NMR (400 MHz, DMSO-$d_6$): δ=11.72 (br s, 1H); 8.70 (d, 1H); 7.97 (d, 1H); 7.45 (d, 1H); 4.34 (q, 2H); 2.79 (m, 1H); 1.45 (t, 3H); 0.72 (m, 2H); 0.57 (br s, 2H);

Ex. no. 2-207: $^1$H-NMR (400 MHz, DMSO-$d_6$): δ=11.89 (br s, 1H); 8.67 (q, 1H); 7.96 (d, 1H); 7.91 (d, 1H); 4.39 (q, 2H); 2.79 (d, 3H); 1.48 (t, 3H);

Ex. no. 2-208: $^1H$-NMR (400 MHz, DMSO-$d_6$): δ=11.88 (br s, 1H); 8.73 (t, 1H); 7.95 (d, 1H); 7.90 (d, 1H); 4.39 (q, 2H); 3.29 (m, 2H); 1.48 (t, 3H); 1.12 (t, 3H);

Ex. no. 2-210: $^1H$-NMR (400 MHz, DMSO-$d_6$): δ=11.88 (br s, 1H); 8.84 (t, 1H); 7.96 (d, 1H); 7.90 (d, 1H); 4.40 (q, 2H); 3.14 (m, 2H); 1.48 (t, 3H); 1.01 (m, 1H); 0.46 (m, 2H); 0.24 (m, 2H);

Ex. no. 2-211: $^1H$-NMR (400 MHz, DMSO-$d_6$): δ=11.90 (br s, 1H); 9.52 (t, 1H); 8.00 (d, 1H); 7.96 (d, 1H); 4.40 (q, 2H); 4.19 (m, 1H); 4.08 (m, 1H); 1.48 (t, 3H);

Ex. no. 2-212: $^1H$-NMR (400 MHz, DMSO-$d_6$): δ=11.89 (br s, 1H); 9.26 (t, 1H); 7.99 (d, 2H); 7.94 (d, 1H); 6.12 (tt, 1H); 4.40 (q, 2H); 3.70 (m, 2H); 1.48 (t, 3H);

Ex. no. 2-213: $^1H$-NMR (400 MHz, DMSO-$d_6$): δ=11.87 (br s, 1H); 8.73 (t, 1H); 7.95 (d, 1H); 4.40 (q, 2H); 3.42 (m, 1H); 1.48 (t, 3H); 1.24 and 1.18 (2×d, 3H); 0.90 (m, 1H); 0.33 (m, 4H);

Ex. no. 2-225: $^1H$-NMR (400 MHz, DMSO-$d_6$): δ=11.82 (br s, 1H); 8.70 (q, 1H); 7.85 (d, 1H); 7.81 (d, 1H); 6.94 (t, 1H); 4.39 (q, 2H); 2.81 (d, 3H); 1.47 (t, 3H);

Ex. no. 2-226: $^1H$-NMR (400 MHz, DMSO-$d_6$): δ=11.82 (br s, 1H); 8.77 (t, 1H); 7.85 (d, 1H); 7.81 (d, 1H); 6.93 (t, 1H); 4.39 (q, 2H); 3.30 (m, 2H); 1.48 (t, 3H); 1.14 (t, 3H);

Ex. no. 2-227: $^1H$-NMR (400 MHz, DMSO-$d_6$): δ=11.81 (br s, 1H); 8.83 (d, 1H); 7.84 (d, 1H); 7.80 (d, 1H); 6.93 (t, 1H); 4.39 (q, 2H); 2.83 (m, 1H); 1.47 (t, 3H); 0.72 (m, 2H); 0.57 (m, 2H);

Ex. no. 2-228: $^1H$-NMR (400 MHz, DMSO-$d_6$): δ=11.82 (br s, 1H); 8.90 t, 1H); 7.85 (d, 1H); 7.81 (d, 1H); 6.93 (t, 1H); 4.39 (q, 2H); 3.16 (t, 2H); 1.48 (t, 3H); 1.04 (m, 1H); 0.48 (m, 2H); 0.25 (m, 2H);

Ex. no. 2-229: $^1H$-NMR (400 MHz, DMSO-$d_6$): δ=11.84 (br s, 1H); 9.54 (t, 1H); 7.90 (d, 1H); 7.84 (d, 1H); 6.93 (t, 1H); 4.39 (q, 2H); 4.14 (m, 2H); 1.48 (t, 3H);

Ex. no. 2-230: $^1H$-NMR (400 MHz, DMSO-$d_6$): δ=11.83 (br s, 1H); 9.28 (t, 1H); 7.89 (d, 1H); 7.83 (d, 1H); 6.94 (t, 1H); 6.18 (tt, 1H); 4.39 (q, 2H); 3.72 (m, 2H); 1.48 (t, 3H);

Ex. no. 2-271: $^1H$-NMR (400 MHz, DMSO-$d_6$): δ=11.69 (br s, 1H); 8.53 (q, 1H); 7.84 (d, 1H); 7.77 (d, 1H); 4.36 (q, 2H); 2.79 (d, 3H); 2.69 (m, 2H); 1.48 (t, 3H); 1.17 (t, 3H);

Ex. no. 2-272: $^1H$-NMR (400 MHz, DMSO-$d_6$): δ=11.69 (br s, 1H); 8.62 (t, 1H); 7.83 (d, 1H); 7.77 (d, 1H); 4.36 (q, 2H); 3.29 (m, 2H); 2.77 (m, 2H); 1.48 (t, 3H); 1.18 (t, 3H); 1.11 (t, 3H);

Ex. no. 2-273: $^1H$-NMR (400 MHz, DMSO-$d_6$): δ=11.67 (br s, 1H); 8.67 (d, 1H); 7.82 (d, 1H); 7.76 (d, 1H); 4.35 (q, 2H); 2.80 (m, 2H); 2.70 (m, 1H); 1.47 (t, 3H); 1.17 (t, 3H); 0.71 (m, 2H); 0.49 (m, 2H);

Ex. no. 2-276: $^1H$-NMR (400 MHz, DMSO-$d_6$): δ=11.71 (br s, 1H); 9.10 (t, 1H); 7.86 (d, 1H); 7.79 (d, 1H); 6.13 (tt, 1H); 4.36 (q, 2H); 3.78 (m, 1H); 3.63 (m, 1H); 2.77 (m, 2H); 1.48 (t, 3H); 1.17 (t, 3H);

Ex. no. 2-277: $^1H$-NMR (400 MHz, DMSO-$d_6$): δ=11.62 (br s, 1H); 8.58 (q, 1H); 7.79 (d, 1H); 7.65 (d, 1H); 6.90 (t, 1H); 4.35 (q, 2H); 2.81 (d, 3H); 2.74 (q, 2H); 1.47 (t, 3H); 1.15 (t, 3H);

Ex. no. 2-278: $^1H$-NMR (400 MHz, DMSO-$d_6$): δ=11.61 (br s, 1H); 8.67 (t, 1H); 7.79 (d, 1H); 7.65 (d, 1H); 6.90 (t, 1H); 4.35 (q, 2H); 3.31 (m, 2H); 2.76 (q, 2H); 1.48 (t, 3H); 1.15 (2×t, 6H);

Ex. no. 2-279: $^1H$-NMR (400 MHz, DMSO-$d_6$): δ=11.60 (br s, 1H); 8.74 (d, 1H); 7.78 (d, 1H); 7.64 (d, 1H); 6.89 (t, 1H); 4.35 (q, 2H); 2.86 (m, 1H); 2.73 (m, 2H); 1.47 (t, 3H); 1.15 (t, 3H); 0.72 (m, 2H); 0.53 (m, 2H);

Ex. no. 2-286: $^1H$-NMR (400 MHz, DMSO-$d_6$): δ=11.59 (br s, 1H); 8.45 (q, 1H); 7.77 (br s, 2H); 4.38 (q, 2H); 2.79 (d, 3H); 2.11 (m, 1H); 1.48 (t, 3H); 0.84 (m, 2H); 0.64 (m, 2H);

Ex. no. 2-287: $^1H$-NMR (400 MHz, DMSO-$d_6$): δ=11.58 (br s, 1H); 8.51 (t, 1H); 7.77 (br s, 2H); 4.38 (q, 2H); 3.29 (m, 2H); 2.14 (m, 1H); 1.48 (t, 3H); 1.13 (t, 3H); 0.84 (m, 2H); 0.67 (m, 2H);

Ex. no. 2-288: $^1H$-NMR (400 MHz, DMSO-$d_6$): δ=11.58 (br s, 1H); 8.59 (d, 1H); 7.76 (br s, 2H); 4.37 (q, 2H); 2.79 (m, 1H); 2.12 (m, 1H); 1.48 (t, 3H); 0.85 (m, 2H); 0.70 (m, 2H); 0.66 (m, 2H); 0.51 (br s, 2H);

Ex. no. 2-289: $^1H$-NMR (400 MHz, DMSO-$d_6$): δ=11.58 (br s, 1H); 8.64 (t, 1H); 7.77 (br s, 2H); 4.38 (q, 2H); 3.13 (m, 2H); 2.15 (m, 1H); 1.49 (t, 3H); 1.03 (m, 1H); 0.86 (m, 2H); 0.68 (m, 2H); 0.45 (m, 2H); 0.23 (m, 2H);

Ex. no. 2-291: $^1H$-NMR (400 MHz, DMSO-$d_6$): δ=11.60 (br s, 1H); 9.03 (t, 1H); 7.80 (br s, 2H); 6.13 (tt, 1H); 4.38 (q, 2H); 3.69 (m, 2H); 2.13 (m, 1H); 1.49 (t, 3H); 0.87 (m, 2H); 0.65 (m, 2H);

Ex. no. 2-292: $^1H$-NMR (400 MHz, DMSO-$d_6$): δ=11.58 (br s, 1H); 8.55 (d, 1H); 7.76 (br s, 2H); 4.38 (q, 2H); 3.37 (m, 1H); 2.17 (m, 1H); 1.49 (t, 3H); 1.20 (br s, 3H); 0.89 (m, 3H); 0.70 (br s, 2H); 0.45 (m, 2H); 0.24 (m, 1H);

Ex. no. 2-304: $^1H$-NMR (400 MHz, DMSO-$d_6$): δ=11.52 (br s, 1H); 8.53 (q, 1H); 7.72 (d, 1H); 7.66 (d, 1H); 6.94 (t, 1H); 4.37 (q, 2H); 2.81 (d, 3H); 2.16 (m, 1H); 1.49 (t, 3H); 0.83 (m, 2H); 0.58 (m, 2H);

Ex. no. 2-305: $^1H$-NMR (400 MHz, DMSO-$d_6$): δ=11.52 (br s, 1H); 8.61 (t, 1H); 7.72 (d, 1H); 7.66 (d, 1H); 6.95 (t, 1H); 4.38 (q, 2H); 2.32 (q, 2H); 2.19 (m, 1H); 1.49 (t, 3H); 1.14 (3H); 0.83 (m, 2H); 0.61 (m, 2H);

Ex. no. 2-306: $^1H$-NMR (400 MHz, DMSO-$d_6$): δ=11.51 (br s, 1H); 8.68 (d, 1H); 7.72 (d, 1H); 7.65 (d, 1H); 6.94 (t, 1H); 4.37 (q, 2H); 2.85 (m, 1H); 2.16 (m, 1H); 1.48 (t, 3H); 0.83 (m, 2H); 0.71 (m, 2H); 0.58 (m, 4H);

Ex. no. 2-337: $^1H$-NMR (400 MHz, DMSO-$d_6$): δ=11.93 (br s, 1H); 7.98 (br s, 2H); 4.37 (q, 2H); 3.81 (br s, 1H); 2.07 (br s, 3H); 1.47 (t, 3H);

Ex. no. 2-338: $^1H$-NMR (400 MHz, DMSO-$d_6$): δ=11.91 (br s, 1H); 8.22 (s, 1H); 8.00 (s, 1H); 7.96 (d, 1H); 7.93 (d, 1); 4.39 (q, 2H); 1.49 (t, 3H);

Ex. no. 2-339: $^1H$-NMR (400 MHz, DMSO-$d_6$): δ=11.59 (br s, 1H); 8.70 (d, 1H); 7.78 (d, 1H); 7.64 (d, 1H); 6.91 (t, 1H); 4.35 (q, 2H); 3.45 (m, 1H); 2.38 (s, 3H); 1.47 (t, 3H); 1.22 (d, 3H); 0.93 (m, 1H); 0.45 (m, 2H); 0.35 (m, 1H); 0.27 (m, 1H);

Ex. no. 2-340: $^1H$-NMR (400 MHz, DMSO-$d_6$): δ=11.81 (br s, 1H); 8.79 (d, 1H); 7.84 (d, 1H); 7.81 (d, 1H); 6.91 (t, 1H); 4.39 (q, 2H); 3.45 (m, 1H); 1.48 (s, 3H); 1.23 (d, 3H); 0.93 (m, 1H); 0.44 (m, 2H); 0.38 (m, 1H); 0.29 (m, 1H);

Ex. no. 2-341: $^1H$-NMR (400 MHz, DMSO-$d_6$): δ=11.68 (br s, 1H); 8.67 (d, 1H); 7.82 (d, 1H); 7.76 (d, 1H); 4.36 (q, 2H); 3.40 (m, 1H); 2.82 (q, 2H); 2.78 (m, 1H); 1.48 (t, 3H); 1.22 (t, 3H); 1.19 (t, 3H); 0.91 (m, 1H); 0.45 (m, 2H); 0.29 (m, 2H);

Ex. no. 2-342: $^1H$-NMR (400 MHz, DMSO-$d_6$): δ=11.76 (br s, 1H); 8.68 (t, 1H); 7.83 (d, 1H); 7.62 (d, 1H); 4.37 (q, 2H); 3.28 (m, 2H); 1.47 (s, 3H); 1.14 (t, 3H);

Ex. no. 2-343: $^1H$-NMR (400 MHz, DMSO-$d_6$): δ=11.75 (br s, 1H); 8.74 (d, 1H); 7.82 (d, 1H); 7.61 (d, 1H); 4.37 (q, 2H); 2.79 (m, 1H); 1.47 (t, 3H); 0.72 (m, 2H); 0.56 (m, 2H);

Ex. no. 2-344: $^1H$-NMR (400 MHz, DMSO-$d_6$): δ=11.59 (br s, 1H); 8.67 (t, 1H); 7.79 (d, 1H); 7.64 (d, 1H); 6.90 (t, 1H); 4.35 (q, 2H); 3.24 (m, 2H); 2.35 (s, 3H); 1.54 (m, 2H); 1.47 (t, 3H); 0.92 (t, 3H);

Ex. no. 2-345: $^1$H-NMR (400 MHz, DMSO-$d_6$): δ=11.58 (br s, 1H); 8.56 (d, 1H); 7.78 (d, 1H); 7.63 (d, 1H); 6.91 (t, 1H); 4.34 (q, 2H); 4.11 (m, 1H); 2.36 (s, 3H); 1.47 (t, 3H); 1.16 (d, 6H);

Ex. no. 2-346: $^1$H-NMR (400 MHz, DMSO-$d_6$): δ=11.59 (br s, 1H); 8.74 (t, 1H); 7.78 (d, 1H); 7.64 (d, 1H); 6.93 (t, 1H); 4.35 (q, 2H); 3.47 (m, 4H); 3.28 (s, 3H); 2.35 (s, 3H); 1.47 (t, 3H);

Ex. no. 2-347: $^1$H-NMR (400 MHz, DMSO-$d_6$): δ=11.59 (br s, 1H); 8.81 (t, 1H); 7.79 (d, 1H); 7.65 (d, 1H); 7.01 (t, 1H); 4.35 (q, 2H); 3.49 (m, 2H); 2.68 (m, 2H); 2.38 (s, 3H); 2.11 (s, 3H); 1.47 (t, 3H);

Ex. no. 2-348: $^1$H-NMR (400 MHz, DMSO-$d_6$): δ=11.77 (br s, 1H); 8.71 (t, 1H); 7.72 (d, 1H); 7.69 (d, 1H); 4.37 (q, 2H); 3.28 (m, 2H); 1.47 (t, 3H); 1.14 (t, 3H);

Ex. no. 2-349: $^1$H-NMR (400 MHz, DMSO-$d_6$): δ=11.76 (br s, 1H); 8.77 (d, 1H); 7.71 (d, 1H); 7.68 (d, 1H); 4.37 (q, 2H); 2.80 (m, 2H); 1.47 (t, 3H); 0.72 (m, 2H); 0.54 (m, 2H);

Ex. no. 2-350: $^1$H-NMR (400 MHz, DMSO-$d_6$): δ=11.71 (br s, 1H); 8.57 (d, 1H); 7.94 (d, 1H); 7.85 (d, 1H); 4.44 (q, 2H); 3.47 (m, 1H); 2.46 (s, 3H); 1.49 (t, 3H); 1.21 (d, 3H); 0.91 (m, 1H); 0.42 (m, 2H); 0.33 (m, 2H);

Ex. no. 2-351: $^1$H-NMR (400 MHz, DMSO-$d_6$): δ=11.65 (br s, 1H); 8.66 (d, 1H); 7.83 (d, 1H); 7.79 (d, 1H); 6.89 (t, 1H); 4.44 (q, 2H); 3.51 (m, 1H); 2.45 (s, 3H); 1.49 (t, 3H); 1.23 (d, 3H); 0.93 (m, 1H); 0.30 (m, 2H);

Ex. no. 2-352: $^1$H-NMR (400 MHz, DMSO-$d_6$): δ=11.54 (br s, 1H); 8.35 (q, 1H); 7.73 (d, 1H); 7.19 (d, 1H); 7.33 (m, 2H); 3.85 (s, 3H); 2.74 (d, 3H); 1.45 (t, 3H);

Ex. no. 2-353: $^1$H-NMR (400 MHz, DMSO-$d_6$): δ=11.53 (br s, 1H); 8.41 (t, 1H); 7.72 (d, 1H); 7.18 (d, 1H); 4.33 (q, 2H); 3.85 (s, 3H); 3.24 (m, 2H); 1.46 (t, 3H); 1.10 (t, 3H);

Ex. no. 2-354: $^1$H-NMR (400 MHz, DMSO-$d_6$): δ=11.53 (br s, 1H); 8.48 (d, 1H); 7.72 (d, 1H); 7.18 (d, 1H); 4.33 (q, 2H); 3.85 (s, 3H); 2.80 (m, 1H); 1.47 (t, 3H); 0.69 (m, 2H); 0.48 (m, 2H);

Ex. no. 2-357: $^1$H-NMR (400 MHz, DMSO-$d_6$): δ=11.94 (br s, 1H); 11.93 (br s, 1H); 8.05 (d, 1H); 7.99 (d, 1H); 4.38 (q, 2H); 3.74 (s, 3H); 1.47 (t, 3H);

Ex. no. 2-358: $^1$H-NMR (400 MHz, DMSO-$d_6$): δ=11.94 (br s, 1H); 11.81 (br s, 1H); 8.04 (d, 1H); 7.98 (d, 1H); 4.38 (q, 2H); 3.97 (m, 2H); 1.48 (t, 3H); 1.23 (t, 3H);

Ex. no. 2-359: $^1$H-NMR (400 MHz, DMSO-$d_6$): δ=11.93 (br s, 1H); 11.81 (br s, 1H); 8.04 (d, 1H); 7.98 (d, 1H); 4.38 (q, 2H); 3.88 (m, 2H); 1.64 (m, 2H); 1.47 (t, 3H); 0.94 (t, 3H);

Ex. no. 2-360: $^1$H-NMR (400 MHz, DMSO-$d_6$): δ=11.93 (br s, 1H); 11.65 (br s, 1H); 8.04 (d, 1H); 7.98 (d, 1H); 4.38 (q, 2H); 4.18 (m, 2H); 1.47 (t, 3H); 1.23 (d, 6H);

Ex. no. 2-361: $^1$H-NMR (400 MHz, DMSO-$d_6$): δ=11.92 (br s, 1H); 11.87 (br s, 1H); 7.97 (d, 1H); 7.81 (d, 1H); 7.04 (t, 1H); 4.37 (q, 2H); 3.76 (s, 3H); 1.47 (t, 3H);

Ex. no. 2-362: $^1$H-NMR (400 MHz, DMSO-$d_6$): δ=11.87 (br s, 1H); 11.81 (br s, 1H); 7.97 (d, 1H); 7.81 (d, 1H); 7.02 (t, 1H); 4.37 (q, 2H); 3.99 (q, 2H); 1.47 (t, 3H); 1.23 (t, 3H);

Ex. no. 2-363: $^1$H-NMR (400 MHz, DMSO-$d_6$): δ=11.87 (br s, 1H); 11.81 (br s, 1H); 7.96 (d, 1H); 7.81 (d, 1H); 7.02 (t, 1H); 4.38 (q, 2H); 3.91 (t, 2H); 1.65 (m, 2H); 1.48 (t, 3H); 0.95 (t, 3H);

Ex. no. 2-364: $^1$H-NMR (400 MHz, DMSO-$d_6$): δ=11.87 (br s, 1H); 11.67 (br s, 1H); 7.96 (d, 1H); 7.81 (d, 1H); 7.01 (t, 1H); 4.37 (q, 2H); 4.21 (m, 1H); 1.47 (t, 3H); 1.23 (d, 6H);

Ex. no. 3-26: $^1$H-NMR (400 MHz, DMSO-$d_6$): δ=11.63 (br s, 1H); 8.59 (t, 1H); 7.80 (d, 1H); 7.76 (d, 1H); 4.30 (t, 2H); 3.28 (m, 2H); 2.35 (s, 3H); 1.88 (m, 2H); 1.11 (t, 3H); 0.88 (t, 3H);

Ex. no. 3-27: $^1$H-NMR (400 MHz, DMSO-$d_6$): δ=11.62 (br s, 1H); 8.66 (d, 1H); 7.80 (d, 1H); 7.75 (d, 1H); 4.30 (t, 2H); 2.81 (m, 1H); 2.34 (s, 3H); 1.88 (m, 2H); 0.88 (t, 3H); 0.71 (m, 2H); 0.49 (m, 2H);

Ex. no. 3-125: $^1$H-NMR (400 MHz, DMSO-$d_6$): δ=11.90 (br s, 1H); 8.85 (d, 1H); 8.06 (d, 1H); 8.00 (d, 1H); 4.32 (t, 2H); 3.31 (s, 3H); 2.77 (m, 1H); 1.88 (m, 2H); 0.88 (t, 3H); 0.70 (m, 2H); 0.58 (m, 2H);

Ex. no. 3-129: $^1$H-NMR (400 MHz, DMSO-$d_6$): δ=11.88 (br s, 1H); 8.70 (q, 1 h); 7.96 (d, 1H); 7.93 (d, 1H); 4.32 (t, 2H); 2.80 (d, 3H); 1.88 (m, 2H); 0.88 (t, 3H);

Ex. no. 3-208: $^1$H-NMR (400 MHz, DMSO-$d_6$): δ=11.85 (br s, 1H); 8.73 (t, 1H); 7.95 (d, 1H); 7.89 (d, 1H); 4.34 (t, 2H); 3.29 (m, 2H); 1.89 (m 2H); 1.12 (t, 3H); 0.89 (t, 3H);

Ex. no. 3-273: $^1$H-NMR (400 MHz, DMSO-$d_6$): δ=11.65 (br s, 1H); 8.68 (d, 1H); 7.81 (d, 1H); 7.76 (d, 1H); 4.30 (t, 2H); 2.81 (m 2H); 2.70 (m, 1H); 1.89 (m, 2H); 1.17 (t, 3H); 0.89 (t, 3H); 0.71 (m, 2H); 0.49 (m, 2H);

Ex. no. 3-337: $^1$H-NMR (400 MHz, DMSO-$d_6$): δ=11.91 (br s, 1H); 7.97 (br s, 2H); 4.31 (t, 2H); 3.89 (br s, 1H); 2.07 (br s, 3H); 1.89 (m, 2H); 0.88 (t, 3H);

Ex. no. 3-338: $^1$H-NMR (400 MHz, DMSO-$d_6$): δ=11.89 (br s, 1H); 8.22 (s, 1H); 8.01 (s, 1H); 7.94 (s, 2H); 4.34 (t, 2H); 1.90 (m, 2H); 0-90 (t, 3H);

Ex. no. 4-212: $^1$H-NMR (400 MHz, DMSO-$d_6$): δ=11.22 (br s, 1H); 8.66 (d, 1H); 7.91 (s, 1H); 7.77 (d, 1H); 7.72 (d, 1H); 3.77 (s, 3H); 2.80 (m, 2H); 2.71 (m, 1H); 1.17 (t, 3H); 0.71 (m, 2H); 0.48 (m, 2H);

Ex. no. 5-58: $^1$H-NMR (400 MHz, DMSO-$d_6$): δ=12.45 (br s, 1H); 9.05 (s, 1H); 8.46 (q, 1H); 7.90 (d, 1H); 7.78 (d, 1H); 2.79 (d, 3H); 2.39 (s, 3H);

Ex. no. 5-59: $^1$H-NMR (400 MHz, DMSO-$d_6$): δ=12.42 (br s, 1H); 9.07 (s, 1H); 8.53 (t, 1H); 7.90 (d, 1H); 7.78 (d, 1H); 3.28 (m, 2H); 2.40 (s, 3H); 1.12 (t, 3H);

Ex. no. 5-74: $^1$H-NMR (400 MHz, DMSO-$d_6$): δ=12.38 (br s, 1H); 9.05 (s, 1H); 8.52 (q, 1H); 7.77 (d, 1H); 7.72 (d, 1H); 6.88 (t, 1H); 2.81 (d, 1H); 2.37 (s, 3H);

Ex. no. 5-75: $^1$H-NMR (400 MHz, DMSO-$d_6$): δ=12.35 (br s, 1H); 9.05 (s, 1H); 8.60 (t, 1H); 7.77 (d, 1H); 7.72 (d, 1H); 6.88 (t, 1H); 3.32 (m, 2H); 2.39 (s, 3H); 1.14 (t, 3H);

Ex. no. 5-117: $^1$H-NMR (400 MHz, DMSO-$d_6$): δ=12.62 (br s, 1H); 9.07 (s, 1H); 8.74 (t, 1H); 7.89 (s, 2H); 3.31 (m, 2H); 1.11 (t, 3H);

Ex. no. 5-122: $^1$H-NMR (400 MHz, DMSO-$d_6$): δ=12.55 (br s, 1H); 9.07 (s, 1H); 8.70 (q, 1H); 7.82 (d, 1H); 7.75 (d, 1H); 6.95 (t, 1H); 2.80 (d, 3H);

Ex. no. 5-123: $^1$H-NMR (400 MHz, DMSO-$d_6$): δ=12.56 (br s, 1H); 9.06 (s, 1H); 8.77 (t, 1H); 7.82 (d, 1H); 7.74 (d, 1H); 3.29 (m, 2H); 1.13 (t, 3H);

Ex. no. 5-253: $^1$H-NMR (400 MHz, DMSO-$d_6$): δ=12.61 (br s, 1H); 9.07 (s, 1H); 8.19 (s, 1H); 7.96 (s, 1H); 7.89 (d, 1H); 7.86 (d, 1H);

Ex. no. 5-254: $^1$H-NMR (400 MHz, DMSO-$d_6$): δ=12.67 (br s, 1H); 9.59 (t, 1H); 9.08 (s, 1H); 7.96 (s, 2H); 4.41 (d, 2H);

Ex. no. 5-255: $^1$H-NMR (400 MHz, DMSO-$d_6$): δ=12.71 (br s, 1H); 10.85 (br s, 1H); 9.08 (s, 1H); 7.98 (m, 2H); 7.65 (m, 2H); 7.38 (m, 2H); 7.15 (m, 1H);

Ex. no. 6-26: $^1$H-NMR (400 MHz, DMSO-$d_6$): δ=12.18 (br s, 1H); 8.58 (t, 1H); 7.71 (s, 2H); 3.29 (m, 2H); 2.50 (s, 3H); 2.31 (s, 3H); 1.10 (t, 3H);

Ex. no. 6-32: $^1$H-NMR (400 MHz, DMSO-$d_6$): δ=12.11 (br s, 1H); 8.64 (t, 1H); 7.67 (d, 1H); 7.59 (d, 1); 6.89 (t, 1H); 3.30 (m, 2H); 2.49 (s, 3H); 2.31 (s, 3H); 1.12 (t, 3H);

Ex. no. 6-33: $^1$H-NMR (400 MHz, DMSO-$d_6$): δ=12.10 (br s, 1H); 8.70 (d, 1H); 7.67 (d, 1H); 7.58 (d, 1H); 6.89 (t, 1H); 2.85 (m, 1H); 2.49 (s, 3H); 2.28 (s, 3H); 0.70 (m, 2H); 0.53 (m, 2H);

Ex. no. 6-34: $^1$H-NMR (400 MHz, DMSO-$d_6$): δ=12.11 (br s, 1H); 8.78 (t, 1H); 7.68 (d, 1H); 7.60 (d, 1H); 6.90 (t, 1H); 3.15 (m, 2H); 2.49 (s, 3H); 2.33 (s, 3H); 1.04 (m, 1H); 0.46 (m, 2H); 0.23 (m, 2H);

Ex. no. 6-43: $^1$H-NMR (400 MHz, DMSO-$d_6$): δ=12.19 (br s, 1H); 8.49 (q, 1H); 7.77 (d, 1H); 7.61 (d, 1H); 3.80 (s, 3H); 2.77 (d, 3H); 2.49 (s, 3H);

Ex. no. 6-44: $^1$H-NMR (400 MHz, DMSO-$d_6$): δ=12.17 (br s, 1H); 8.57 (t, 1H); 7.76 (d, 1H); 7.62 (d, 1H); 3.81 (s, 3H); 3.27 (m, 2H); 2.49 (s, 3H); 1.10 (t, 3H);

Ex. no. 6-45: $^1$H-NMR (400 MHz, DMSO-$d_6$): δ=12.17 (br s, 1H); 8.64 (d, 1H); 7.76 (d, 1H); 7.61 (d, 1H); 3.80 (s, 3H); 2.79 (m, 1H); 2.49 (s, 3H); 0.70 (m, 2H); 0.47 (m, 2H);

Ex. no. 6-49: $^1$H-NMR (400 MHz, DMSO-$d_6$): δ=12.01 (br s, 1H); 8.53 (q, 1H); 7.72 (d, 1H); 7.49 (d, 1H); 6.93 (t, 1H); 3.79 (s, 3H); 2.79 (d, 3H); 2.49 (s, 3H);

Ex. no. 6-50: $^1$H-NMR (400 MHz, DMSO-$d_6$): δ=12.02 (br s, 1H); 8.61 (t, 1H); 7.72 (d, 1H); 7.49 (d, 1H); 6.94 (t, 1H); 3.81 (s, 3H); 3.29 (m, 2H); 2.49 (s, 3H); 1.12 (t, 3H);

Ex. no. 6-51: $^1$H-NMR (400 MHz, DMSO-$d_6$): δ=12.02 (br s, 1H); 8.68 (d, 1H); 7.72 (d, 1H); 7.48 (d, 1H); 6.92 (t, 1H); 3.79 (s, 3H); 2.84 (m, 1H); 2.49 (s, 3H); 0.70 (m, 2H); 0.53 (m, 2H);

Ex. no. 6-58: $^1$H-NMR (400 MHz, DMSO-$d_6$): δ=12.24 (br s, 1H); 8.46 (q, 1H); 7.90 (d, 1H); 7.76 (d, 1H); 2.79 (d, 3H); 2.49 (s, 3H); 2.39 (s, 3H);

Ex. no. 6-60: $^1$H-NMR (400 MHz, DMSO-$d_6$): δ=12.25 br s, 1H); 8.61 (d, 1H); 7.89 (d, 1H); 7.76 (d, 1H); 2.79 (m, 1H); 2.49 (s, 3H); 2.39 (s, 3H); 0.71 (m, 2H); 0.52 (br s, 1H);

Ex. no. 6-74: $^1$H-NMR (400 MHz, DMSO-$d_6$): δ=12.18 (br s, 1H); 8.52 (q, 1H); 7.76 (d, 1H); 7.70 (d, 1H); 6.88 (t, 1H); 2.81 (d, 3H); 2.49 (s, 3H); 2.38 (s, 3H);

Ex. no. 6-75: $^1$H-NMR (400 MHz, DMSO-$d_6$): δ=12.16 (br s, 1H); 8.59 (t, 1H); 7.77 (d, 1H); 7.69 (d, 1H); 6.88 (t, 1H); 3.31 (m, 2H); 2.49 (s, 3H); 2.39 (s, 3H); 1.14 (t, 3H);

Ex. no. 6-76: $^1$H-NMR (400 MHz, DMSO-$d_6$): δ=12.17 (br s, 1H); 8.67 (d, 1H); 7.76 (d, 1H); 7.69 (d, 1H); 6.88 (t, 1H); 2.84 (m, 1H); 2.49 (s, 3H); 2.37 (s, 3H); 0.71 (m, 2H); 0.57 (m, 2H);

Ex. no. 6-116: $^1$H-NMR (400 MHz, DMSO-$d_6$): δ=12.44 (br s, 1H); 8.67 (q, 1H); 7.89 (d, 1H); 7.86 (d, 1H); 2.78 (d, 3H); 2.50 (s, 3H);

Ex. no. 6-117: $^1$H-NMR (400 MHz, DMSO-$d_6$): δ=12.44 (br s, 1H); 8.74 (t, 1H); 7.89 (d, 1H); 7.86 (d, 1H); 3.27 (m, 2H); 2.49 (s, 3H); 1.11 (t, 3H);

Ex. no. 6-118: $^1$H-NMR (400 MHz, DMSO-$d_6$): δ=12.44 (br s, 1H); 8.81 (d, 1H); 7.88 (d, 1H); 7.85 (d, 1H); 2.79 (m, 1H); 2.49 (s, 3H); 0.72 (m, 2H); 0.50 (br s, 2H);

Ex. no. 6-120: $^1$H-NMR (400 MHz, DMSO-$d_6$): δ=12.51 (br s, 1H); 9.54 (t, 1H); 7.93 (s, 2H); 4.14 (m, 2H); 2.52 (s, 3H);

Ex. no. 6-124: $^1$H-NMR (400 MHz, DMSO-$d_6$): δ=12.36 (br s, 1H); 8.83 (d, 1H); 7.80 (d, 1H); 7.72 (d, 1H); 6.93 (t, 1H); 2.83 (m, 1H); 2.48 (s, 3H); 0.71 (m, 2H); 0.54 (m, 2H);

Ex. no. 6-141: $^1$H-NMR (400 MHz, DMSO-$d_6$): δ=12.31 (br s, 1H); 8.69 (t, 1H); 7.76 (d, 1H); 7.57 (d, 1H); 3.27 (m, 2H); 2.48 (s, 3H); 1.13 (t, 3H);

Ex. no. 6-143: $^1$H-NMR (400 MHz, DMSO-$d_6$): δ=12.31 (br s, 1H); 8.79 (t, 1H); 7.76 (d, 1H); 7.57 (d, 1H); 3.15 (m, 2H); 2.49 (s, 3H); 1.01 (m, 1H); 0.44 (m, 2H); 0.25 (m, 2H);

Ex. no. 6-144: $^1$H-NMR (400 MHz, DMSO-$d_6$): δ=12.32 (br s, 1H); 9.48 (t, 1H); 7.80 (d, 1H); 7.63 (d, 1H); 4.12 (m, 2H); 2.49 (s, 3H);

Ex. no. 6-145: $^1$H-NMR (400 MHz, DMSO-$d_6$): δ=12.31 (br s, 1H); 9.21 (t, 1H); 7.78 (d, 1H); 7.61 (d, 1H); 6.13 (tt, 1H); 3.69 (m, 2H); 2.49 (s, 3H);

Ex. no. 6-159: $^1$H-NMR (400 MHz, DMSO-$d_6$): δ=12.41 (br s, 1H); 8.72 (t, 1H); 7.92 (d, 1H); 7.80 (d, 1H); 3.28 (m, 2H); 2.50 (s, 3H); 1.11 (t, 3H);

Ex. no. 6-161: $^1$H-NMR (400 MHz, DMSO-$d_6$): δ=12.42 (br s, 1H); 8.82 (t, 1H); 7.91 (d, 1H); 7.80 (d, 1H); 3.13 (m, 2H); 2.49 (s, 3H); 1.00 (m, 1H); 0.45 (m, 2H); 0.23 (m, 2H);

Ex. no. 6-165: $^1$H-NMR (400 MHz, DMSO-$d_6$): δ=12.35 (br s, 1H); 8.75 (t, 1H); 7.77 (d, 1H); 7.74 (d, 1H); 6.91 (t, 1H); 3.29 (m, 2H); 2.49 (s, 3H); 1.13 (t, 3H);

Ex. no. 6-166: $^1$H-NMR (400 MHz, DMSO-$d_6$): δ=12.36 (br s, 1H); 8.81 (d, 1H); 7.76 (d, 1H); 7.73 (d, 1H); 6.91 (t, 1H); 2.80 (m, 1H); 2.49 (s, 3H); 0.71 (m, 2H); 0.56 (m, 2H);

Ex. no. 6-167: $^1$H-NMR (400 MHz, DMSO-$d_6$): δ=12.35 (br s, 1H); 8.88 (t, 1H); 7.78 (d, 1H); 7.74 (d, 1H); 6.91 (t, 1H); 3.15 (m, 2H); 2.49 (s, 3H); 1.03 (m, 1H); 0.46 (m, 2H); 0.24 (m, 2H);

Ex. no. 6-168: $^1$H-NMR (400 MHz, DMSO-$d_6$): δ=12.38 (br s, 1H); 9.52 (t, 1H); 7.80 (s, 2H); 6.90 (t, 1H); 4.13 (m, 2H); 2.49 (s, 3H);

Ex. no. 6-169: $^1$H-NMR (400 MHz, DMSO-$d_6$): δ=12.37 (br s, 1H) M 9.26 (t, 1H); 7.80 (d, 1H); 7.78 (d, 1H); 6.92 (t, 1H); 6.17 (tt, 1H); 3.71 (m, 2H); 2.49 (s, 3H);

Ex. no. 6-210: $^1$H-NMR (400 MHz, DMSO-$d_6$): δ=12.22 (br s, 1H); 8.52 (q, 1H); 7.72 (s, 2H); 2.78 (d, 3H); 2.66 (m, 2H); 2.46 (s, 3H); 1.13 (t, 3H);

Ex. no. 6-211: $^1$H-NMR (400 MHz, DMSO-$d_6$): δ=12.21 (br s, 1H); 8.61 (t, 1H); 7.72 (br s, 2H); 3.28 (m, 2H); 2.78 (m, 1H); 2.69 (m, 1H); 2.49 (s, 3H); 1.15 (t, 3H); 1.10 (t, 3H);

Ex. no. 6-212: $^1$H-NMR (400 MHz, DMSO-$d_6$): δ=12.19 (br s, 1H); 8.66 (d, 1H); 7.71 (s, 2H); 2.80 (m, 2H); 2.68 (m, 1H); 2.52 (s, 3H); 1.13 (t, 3H); 0.71 (m, 2H); 0.48 (m, 2H);

Ex. no. 6-228: $^1$H-NMR (400 MHz, DMSO-$d_6$): δ=12.08 (br s, 1H); 8.61 (t, 1H); 7.73 (d, 1H); 7.63 (d, 1H); 3.12 (m, 2H); 2.49 (s, 3H); 2.11 (m, 1H); 1.02 (m, 1H); 0.80 (m, 2H); 0.62 (m, 2H); 0.46 (m, 2H); 0.22 (m, 2H);

Ex. no. 6-230: $^1$H-NMR (400 MHz, DMSO-$d_6$): δ=12.11 (br s, 1H); 9.01 (t, 1H); 7.76 (d, 1H); 7.67 (d, 1H); 6.12 (tt, 1H); 3.68 (m, 2H); 2.49 (s, 3H); 2.10 (m, 1H); 0.83 (m, 2H); 0.59 (m, 2H);

Ex. no. 6-231: $^1$H-NMR (400 MHz, DMSO-$d_6$): δ=12.01 (br s, 1H); 8.51 (q, 1H); 7.63 (d, 1H); 7.60 (d, 1H); 6.92 (t, 1H); 2.81 (d, 3H); 2.49 (s, 3H); 2.13 (m, 1H); 0.79 (m, 2H); 0.51 (m, 2H);

Ex. no. 6-233: $^1$H-NMR (400 MHz, DMSO-$d_6$): δ=12.01 (br s, 1H); 8.66 (d, 1H); 7.60 (m, 2H); 6.92 (t, 1H); 2.84 (m, 1H); 2.49 (s, 3H); 2.12 (m, 1H); 0.79 (m, 2H); 0.70 (m, 2H); 0.54 (m, 4H);

Ex. no. 6-252: $^1$H-NMR (400 MHz, DMSO-$d_6$): δ=11.82 (br s, 1H); 7.91 (br s, 2H); 4.30 (br s, 1H); 2.38 (s, 3H); 1.99 (s, 3H);

Ex. no. 6-253: $^1$H-NMR (400 MHz, DMSO-$d_6$): δ=12.45 (br s, 1H); 8.20 (s, 1H); 7.98 (s, 1H); 7.89 (d, 1H); 7.86 (d, 1H); 2.52 (s, 3H);

Ex. no. 6-254: $^1$H-NMR (400 MHz, DMSO-$d_6$): δ=12.44 (br s, 1H); 8.73 (d, 1H); 7.85 (d, 1H); 7.88 (d, 1H); 3.43 (m, 1H); 1.19 (m, 3H); 0.89 (m, 1H); 0.42 (m, 2H); 0.29 (m, 2H);

Ex. no. 6-255: $^1$H-NMR (400 MHz, DMSO-$d_6$): δ=12.19 (br s, 1H); 8.50 (d, 1H); 7.70 (s, 2H); 4.07 (m, 1H); 2.49 (s, 3H); 2.31 (s, 3H); 1.15 (d, 3H); 1.11 (d, 3H);

Ex. no. 6-256: $^1$H-NMR (400 MHz, DMSO-$d_6$): δ=12.20 (br s, 1H); 8.84 (d, 1H); 7.71 (s, 2H); 4.36 (m, 1H); 2.49 (s, 3H); 2.30 (s, 3H); 2.24 (m, 2H); 1.97 (m, 2H); 1.48 (m, 2H);

Ex. no. 6-257: $^1$H-NMR (400 MHz, DMSO-$d_6$): δ=12.31 (br s, 1H); 8.65 (d, 1H); 7.75 (d, 1H); 7.57 (d, 1H); 3.48 (m, 1H); 2.49 (s, 3H); 1.21 (d, 3H); 0.91 (m, 1H); 0.42 (m, 2H); 0.34 (m, 2H);

Ex. no. 6-258: $^1$H-NMR (400 MHz, DMSO-$d_6$): δ=12.11 (br s, 1H); 8.69 (d, 1H); 7.68 (d, 1H); 7.59 (d, 1H); 6.89 (t, 1H); 3.44 (m, 1H); 2.49 (s, 3H); 2.34 (s, 3H); 1.22 (d, 3H); 0.92 (m, 1H); 0.43 (m, 2H); 0.34 (m, 1H); 0.26 (m, 1H);

Ex. no. 6-259: $^1$H-NMR (400 MHz, DMSO-$d_6$): δ=12.38 (br s, 1H); 8.79 (t, 1H); 7.80 (d, 1H); 7.74 (d, 1H); 6.92 (t, 1H); 3.23 (m, 2H); 2.49 (s, 3H); 1.54 (m, 2H); 0.92 (t, 3H);

Ex. no. 6-260: $^1$H-NMR (400 MHz, DMSO-$d_6$): δ=12.38 (br s, 1H); 8.69 (d, 1H); 7.79 (d, 1H); 7.73 (d, 1H); 6.92 (t, 1H); 4.08 (m, 1H); 2.49 (s, 3H); 1.16 (d, 6H);

Ex. no. 6-261: $^1$H-NMR (400 MHz, DMSO-$d_6$): δ=12.38 (br s, 1H); 9.03 (d, 1H); 7.80 (d, 1H); 7.73 (d, 1H); 6.91 (t, 1H); 4.36 (m, 1H); 2.49 (s, 3H); 2.26 (m, 2H); 2.01 (m, 2H); 1.69 (m, 2H);

Ex. no. 6-262: $^1$H-NMR (400 MHz, DMSO-$d_6$): δ=12.38 (br s, 1H); 8.90 (t, 1H); 7.80 (d, 1H); 7.74 (d, 1H); 6.94 (t, 1H); 3.45 (m, 4H); 3.28 (s, 3H); 2.49 (s, 3H);

Ex. no. 6-263: $^1$H-NMR (400 MHz, DMSO-$d_6$): δ=12.35 (br s, 1H); 8.91 (t, 1H); 7.80 (d, 1H); 7.73 (d, 1H); 6.95 (t, 1H); 3.98 (m, 1H); 3.78 (m, 1H); 3.65 (m, 1H); 3.34 (m, 2H); 2.49 (s, 3H); 1.94 (m, 1H); 1.84 (m, 2H); 1.62 (m, 1H);

Ex. no. 6-264: $^1$H-NMR (400 MHz, DMSO-$d_6$): δ=12.38 (br s, 1H); 9.43 (t, 1H); 7.82 (d, 1H); 7.75 (d, 1H); 7.45 (m, 1H); 7.07 (m, 1H); 6.99 (m, 1H); 6.90 (t, 1H); 4.67 (d, 3H); 2.49 (s, 3H);

Ex. no. 6-265: $^1$H-NMR (400 MHz, DMSO-$d_6$): δ=12.39 (br s, 1H); 9.10 (t, 1H); 7.83 (d, 1H); 7.79 (d, 1H); 7.57 (t, 1H); 4.16 (d, 2H); 3.01 (s, 3H); 2.88 (s, 3H);

Ex. no. 6-266: $^1$H-NMR (400 MHz, DMSO-$d_6$): δ=12.41 (br s, 1H); 10.83 (br s, 1H); 7.88 (d, 1H); 7.80 (d, 1H); 7.69 (m, 2H); 7.37 (m, 2H); 7.15 (m, 1H); 7.10 (t, 1H); 2.49 (s, 3H);

Ex. no. 6-267: $^1$H-NMR (400 MHz, DMSO-$d_6$): δ=12.35 (br s, 1H); 8.77 (d, 1H); 7.75 (m, 2H); 6.89 (t, 1H); 3.45 (m, 1H); 2.49 (s, 3H); 1.22 (d, 3H); 0.92 (m, 1H); 0.41 (m, 3H); 0.28 (m, 1H);

Ex. no. 6-268: $^1$H-NMR (400 MHz, DMSO-$d_6$): δ=12.08 (br s, 1H); 8.53 (d, 1H); 7.73 (d, 1H); 7.62 (d, 1H); 3.36 (m, 1H); 2.49 (s, 3H); 2.21 (m, 1H); 1.20 (d, 3H); 0.89 (m, 1H); 0.83 (m, 2H); 0.63 (br s, 2H); 0.44 (m, 2H); 0.32 (m, 1H); 0.24 (m, 1H).

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (® Triton X 207), 3 parts by weight of isotridecanol polyglycol ether (8 EO) and 71 parts by weight of paraffinic mineral oil (boiling range for example about 255 to above 277° C.), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
 75 parts by weight of a compound of the formula (I) and/or salts thereof,
 10 parts by weight of calcium lignosulfonate,
 5 parts by weight of sodium lauryl sulfate,
 3 parts by weight of polyvinyl alcohol and
 7 parts by weight of kaolin,
 grinding the mixture in a pinned-disk mill, and granulating the powder in a fluidized bed by spray application of water as a granulating liquid.

f) Water-dispersible granules are also obtained by homogenizing and precomminuting, in a colloid mill,
 25 parts by weight of a compound of the formula (I) and/or salts thereof,
 5 parts by weight of sodium 2,2'-dinaphthylmethane-6,6'-disulfonate
 2 parts by weight of sodium oleoylmethyltaurate,
 1 part by weight of polyvinyl alcohol,
 17 parts by weight of calcium carbonate and
 50 parts by weight of water,
 then grinding the mixture in a bead mill and atomizing and drying the resulting suspension in a spray tower by means of a one-phase nozzle.

C. BIOLOGICAL EXAMPLES

The abbreviations used for the harmful plants mean:

| | | | |
|---|---|---|---|
| ABUTH | *Abutilon theophrasti* | ALOMY | *Alopecurus myosuroides* |
| AVEFA | *Avena fatua* | AMARE | *Amaranthus retroflexus* |
| CYPES | *Cyperus esculentus* | DIGSA | *Digitaria sanguinalis* |
| ECHCG | *Echinochloa crus-galli* | HORMU | *Hordeum murinum* |
| LOLMU | *Lolium multiflorum* | LOLRI | *Lolium rigidum* |
| MATIN | *Matricaria inodora* | PHBPU | *Pharbitis purpurea* |
| POLCO | *Polygonum convolvulus* | SETVI | *Setaria viridis* |
| STEME | *Stellaria media* | VERPE | *Veronica persica* |
| VIOTR | *Viola tricolor* | | |

1. Pre-Emergence Herbicidal Action Against Harmful Plants

Seeds of monocotyledonous and dicotyledonous weed plants and crop plants are laid out in sandy loam soil in wood-fiber pots and covered with soil. The compounds of the invention, formulated in the form of wettable powders (WP) or as emulsion concentrates (EC), are then applied to the surface of the covering soil in the form of an aqueous suspension or emulsion at a water application rate equivalent to 600 to 800 l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). Numerous compounds of the invention showed very good action against a multitude of important harmful plants. The tables below illustrate, in an illustrative manner, the post-emergence herbicidal action of the compounds of the invention, the herbicidal activity being stated in percent.

TABLE 1a

| Pre-emergence action at 20 g/ha against ABUTH in % | | |
|---|---|---|
| Example number | Dosage [g/ha] | ABUTH |
| 3-129 | 20 | 100 |
| 2-129 | 20 | 100 |
| 1-129 | 20 | 100 |
| 6-116 | 20 | 100 |
| 1-338 | 20 | 80 |
| 2-338 | 20 | 90 |
| 3-338 | 20 | 90 |
| 2-337 | 20 | 100 |
| 3-337 | 20 | 100 |
| 1-26 | 20 | 100 |
| 2-26 | 20 | 100 |
| 3-26 | 20 | 100 |
| 6-26 | 20 | 100 |
| 1-208 | 20 | 100 |
| 2-208 | 20 | 100 |
| 3-208 | 20 | 100 |
| 6-159 | 20 | 100 |
| 1-130 | 20 | 100 |
| 2-130 | 20 | 100 |
| 1-131 | 20 | 100 |
| 2-131 | 20 | 100 |
| 6-118 | 20 | 100 |
| 1-149 | 20 | 100 |
| 2-149 | 20 | 100 |
| 6-124 | 20 | 100 |
| 5-59 | 20 | 100 |
| 5-58 | 20 | 90 |
| 5-117 | 20 | 100 |
| 5-253 | 20 | 90 |
| 5-75 | 20 | 100 |
| 5-74 | 20 | 80 |
| 5-123 | 20 | 100 |
| 5-122 | 20 | 90 |
| 1-82 | 20 | 100 |
| 1-87 | 20 | 100 |
| 2-87 | 20 | 100 |
| 1-88 | 20 | 100 |
| 2-88 | 20 | 100 |
| 1-209 | 20 | 100 |
| 2-25 | 20 | 100 |
| 3-27 | 20 | 100 |
| 1-27 | 20 | 100 |
| 2-27 | 20 | 100 |
| 1-173 | 20 | 90 |
| 2-173 | 20 | 90 |
| 1-273 | 20 | 100 |
| 2-273 | 20 | 90 |
| 3-273 | 20 | 90 |
| 6-212 | 20 | 80 |
| 1-44 | 20 | 100 |
| 2-44 | 20 | 100 |
| 1-45 | 20 | 80 |
| 2-45 | 20 | 80 |
| 1-46 | 20 | 90 |
| 2-46 | 20 | 100 |
| 1-30 | 20 | 100 |
| 1-31 | 20 | 100 |
| 2-31 | 20 | 100 |
| 1-28 | 20 | 90 |
| 2-28 | 20 | 100 |
| 2-29 | 20 | 100 |
| 1-304 | 20 | 100 |
| 2-304 | 20 | 100 |
| 1-305 | 20 | 100 |
| 2-305 | 20 | 100 |
| 1-306 | 20 | 100 |
| 2-306 | 20 | 100 |
| 2-177 | 20 | 90 |
| 1-178 | 20 | 90 |
| 1-179 | 20 | 80 |
| 1-132 | 20 | 100 |
| 2-132 | 20 | 100 |
| 1-135 | 20 | 100 |
| 2-135 | 20 | 100 |
| 6-254 | 20 | 100 |
| 2-134 | 20 | 100 |

TABLE 1a-continued

| Pre-emergence action at 20 g/ha against ABUTH in % | | |
|---|---|---|
| Example number | Dosage [g/ha] | ABUTH |
| 6-120 | 20 | 80 |
| 1-277 | 20 | 90 |
| 2-277 | 20 | 90 |
| 1-278 | 20 | 90 |
| 2-278 | 20 | 100 |
| 1-279 | 20 | 100 |
| 2-279 | 20 | 80 |
| 2-195 | 20 | 100 |
| 2-225 | 20 | 100 |
| 1-197 | 20 | 100 |
| 2-227 | 20 | 100 |
| 1-227 | 20 | 100 |
| 2-226 | 20 | 80 |
| 2-196 | 20 | 100 |
| 2-57 | 20 | 100 |
| 2-58 | 20 | 100 |
| 2-56 | 20 | 100 |
| 1-57 | 20 | 100 |
| 1-207 | 20 | 100 |
| 2-207 | 20 | 100 |
| 2-271 | 20 | 100 |
| 2-32 | 20 | 100 |
| 1-34 | 20 | 80 |
| 2-34 | 20 | 80 |
| 6-255 | 20 | 100 |
| 2-33 | 20 | 100 |
| 2-42 | 20 | 100 |
| 1-146 | 20 | 100 |
| 1-72 | 20 | 100 |
| 2-72 | 20 | 100 |
| 1-73 | 20 | 100 |
| 2-73 | 20 | 100 |
| 1-74 | 20 | 100 |
| 2-74 | 20 | 100 |
| 1-138 | 20 | 100 |
| 2-138 | 20 | 80 |
| 1-137 | 20 | 100 |
| 1-136 | 20 | 90 |
| 1-180 | 20 | 90 |
| 2-180 | 20 | 100 |
| 6-143 | 20 | 100 |
| 1-183 | 20 | 100 |
| 2-183 | 20 | 100 |
| 1-182 | 20 | 100 |
| 2-182 | 20 | 100 |
| 6-145 | 20 | 100 |
| 1-181 | 20 | 90 |
| 2-181 | 20 | 100 |
| 2-36 | 20 | 90 |
| 1-228 | 20 | 100 |
| 2-228 | 20 | 100 |
| 6-167 | 20 | 90 |
| 1-230 | 20 | 90 |
| 2-230 | 20 | 100 |
| 2-286 | 20 | 100 |
| 1-287 | 20 | 100 |
| 2-287 | 20 | 100 |
| 2-288 | 20 | 100 |
| 1-210 | 20 | 100 |
| 2-210 | 20 | 100 |
| 1-212 | 20 | 80 |
| 2-213 | 20 | 100 |
| 1-288 | 20 | 100 |
| 1-289 | 20 | 100 |
| 2-289 | 20 | 100 |
| 1-291 | 20 | 100 |
| 2-291 | 20 | 100 |
| 2-292 | 20 | 100 |
| 1-271 | 20 | 100 |
| 2-47 | 20 | 100 |
| 1-339 | 20 | 90 |
| 2-339 | 20 | 100 |
| 6-258 | 20 | 100 |
| 1-49 | 20 | 80 |
| 2-49 | 20 | 100 |
| 1-229 | 20 | 90 |

TABLE 1a-continued

| Pre-emergence action at 20 g/ha against ABUTH in % | | |
|---|---|---|
| Example number | Dosage [g/ha] | ABUTH |
| 2-229 | 20 | 80 |
| 1-340 | 20 | 100 |
| 6-267 | 20 | 90 |
| 2-340 | 20 | 100 |
| 1-47 | 20 | 100 |
| 1-33 | 20 | 90 |
| 1-32 | 20 | 100 |
| 2-154 | 20 | 100 |
| 6-259 | 20 | 90 |
| 1-155 | 20 | 100 |
| 2-155 | 20 | 100 |
| 6-260 | 20 | 90 |
| 1-164 | 20 | 80 |
| 2-164 | 20 | 90 |
| 6-261 | 20 | 80 |
| 1-165 | 20 | 90 |
| 1-166 | 20 | 90 |
| 2-156 | 20 | 100 |
| 1-159 | 20 | 80 |
| 2-161 | 20 | 90 |
| 2-211 | 20 | 100 |
| 2-272 | 20 | 100 |
| 1-161 | 20 | 80 |
| 2-276 | 20 | 100 |
| 1-276 | 20 | 100 |
| 1-211 | 20 | 100 |
| 1-274 | 20 | 100 |
| 1-272 | 20 | 90 |
| 6-211 | 20 | 90 |
| 1-341 | 20 | 100 |
| 1-292 | 20 | 100 |
| 2-341 | 20 | 100 |
| 1-83 | 20 | 100 |
| 2-83 | 20 | 100 |
| 1-89 | 20 | 90 |
| 2-89 | 20 | 100 |
| 6-161 | 20 | 100 |
| 6-268 | 20 | 100 |
| 2-342 | 20 | 100 |
| 1-344 | 20 | 90 |
| 1-345 | 20 | 100 |
| 2-344 | 20 | 100 |
| 1-346 | 20 | 90 |
| 2-345 | 20 | 90 |
| 2-346 | 20 | 80 |
| 1-195 | 20 | 90 |
| 2-184 | 20 | 100 |
| 1-185 | 20 | 100 |
| 2-185 | 20 | 100 |
| 1-186 | 20 | 100 |
| 2-186 | 20 | 100 |
| 1-84 | 20 | 100 |
| 2-84 | 20 | 100 |
| 1-352 | 20 | 100 |
| 2-350 | 20 | 100 |
| 1-86 | 20 | 100 |
| 2-86 | 20 | 100 |
| 1-92 | 20 | 100 |
| 2-92 | 20 | 100 |
| 1-90 | 20 | 100 |
| 2-90 | 20 | 100 |
| 1-353 | 20 | 100 |
| 2-351 | 20 | 80 |
| 2-354 | 20 | 90 |

TABLE 1b

| Pre-emergence action at 80 g/ha against ABUTH in % | | |
|---|---|---|
| Example number | Dosage [g/ha] | ABUTH |
| 3-129 | 80 | 100 |
| 2-129 | 80 | 100 |

TABLE 1b-continued

| Pre-emergence action at 80 g/ha against ABUTH in % | | |
|---|---|---|
| Example number | Dosage [g/ha] | ABUTH |
| 1-129 | 80 | 100 |
| 6-116 | 80 | 100 |
| 1-338 | 80 | 100 |
| 2-338 | 80 | 100 |
| 3-338 | 80 | 100 |
| 6-253 | 80 | 90 |
| 1-337 | 80 | 100 |
| 2-337 | 80 | 100 |
| 3-337 | 80 | 100 |
| 6-252 | 80 | 80 |
| 1-123 | 80 | 100 |
| 2-123 | 80 | 100 |
| 1-26 | 80 | 100 |
| 2-26 | 80 | 100 |
| 3-26 | 80 | 100 |
| 6-26 | 80 | 100 |
| 1-208 | 80 | 100 |
| 2-208 | 80 | 100 |
| 3-208 | 80 | 100 |
| 6-159 | 80 | 100 |
| 2-125 | 80 | 100 |
| 3-125 | 80 | 100 |
| 1-130 | 80 | 100 |
| 2-130 | 80 | 100 |
| 6-117 | 80 | 100 |
| 1-81 | 80 | 100 |
| 2-81 | 80 | 100 |
| 2-82 | 80 | 100 |
| 6-58 | 80 | 100 |
| 1-147 | 80 | 90 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 100 |
| 1-149 | 80 | 100 |
| 2-149 | 80 | 100 |
| 6-124 | 80 | 100 |
| 5-59 | 80 | 100 |
| 5-58 | 80 | 100 |
| 5-117 | 80 | 100 |
| 5-253 | 80 | 100 |
| 5-75 | 80 | 100 |
| 5-74 | 80 | 100 |
| 5-123 | 80 | 100 |
| 5-122 | 80 | 100 |
| 1-82 | 80 | 100 |
| 1-87 | 80 | 100 |
| 2-87 | 80 | 100 |
| 1-88 | 80 | 100 |
| 2-88 | 80 | 100 |
| 1-209 | 80 | 100 |
| 1-4 | 80 | 100 |
| 1-25 | 80 | 100 |
| 2-25 | 80 | 100 |
| 3-27 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 90 |
| 3-273 | 80 | 100 |
| 6-212 | 80 | 90 |
| 4-212 | 80 | 90 |
| 1-44 | 80 | 100 |
| 2-44 | 80 | 100 |
| 1-45 | 80 | 100 |
| 2-45 | 80 | 100 |
| 6-32 | 80 | 80 |
| 1-46 | 80 | 100 |
| 2-46 | 80 | 100 |
| 6-33 | 80 | 90 |
| 1-30 | 80 | 100 |
| 2-30 | 80 | 100 |

TABLE 1b-continued

| Pre-emergence action at 80 g/ha against ABUTH in % | | |
|---|---|---|
| Example number | Dosage [g/ha] | ABUTH |
| 1-31 | 80 | 100 |
| 2-31 | 80 | 100 |
| 1-28 | 80 | 100 |
| 2-28 | 80 | 100 |
| 1-29 | 80 | 100 |
| 2-29 | 80 | 100 |
| 1-304 | 80 | 100 |
| 2-304 | 80 | 100 |
| 1-305 | 80 | 100 |
| 2-305 | 80 | 100 |
| 1-306 | 80 | 100 |
| 2-306 | 80 | 100 |
| 1-177 | 80 | 100 |
| 2-177 | 80 | 100 |
| 1-178 | 80 | 100 |
| 2-178 | 80 | 100 |
| 1-179 | 80 | 100 |
| 2-179 | 80 | 100 |
| 1-132 | 80 | 100 |
| 2-132 | 80 | 100 |
| 1-135 | 80 | 100 |
| 2-135 | 80 | 100 |
| 6-254 | 80 | 100 |
| 1-134 | 80 | 90 |
| 2-134 | 80 | 100 |
| 1-133 | 80 | 100 |
| 2-133 | 80 | 100 |
| 6-120 | 80 | 100 |
| 1-277 | 80 | 100 |
| 2-277 | 80 | 100 |
| 1-278 | 80 | 100 |
| 2-278 | 80 | 100 |
| 1-279 | 80 | 100 |
| 2-279 | 80 | 100 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 100 |
| 1-225 | 80 | 80 |
| 1-226 | 80 | 90 |
| 2-226 | 80 | 80 |
| 6-165 | 80 | 100 |
| 6-166 | 80 | 100 |
| 2-196 | 80 | 100 |
| 1-56 | 80 | 90 |
| 6-45 | 80 | 90 |
| 2-57 | 80 | 100 |
| 6-43 | 80 | 100 |
| 1-58 | 80 | 80 |
| 2-58 | 80 | 100 |
| 2-56 | 80 | 100 |
| 1-57 | 80 | 100 |
| 1-207 | 80 | 100 |
| 2-207 | 80 | 100 |
| 2-271 | 80 | 100 |
| 6-210 | 80 | 100 |
| 2-32 | 80 | 100 |
| 1-34 | 80 | 100 |
| 2-34 | 80 | 100 |
| 6-255 | 80 | 100 |
| 2-33 | 80 | 100 |
| 2-42 | 80 | 100 |
| 6-256 | 80 | 100 |
| 2-146 | 80 | 90 |
| 1-143 | 80 | 100 |
| 5-255 | 80 | 100 |
| 5-254 | 80 | 100 |
| 1-146 | 80 | 100 |
| 2-143 | 80 | 100 |
| 1-72 | 80 | 100 |
| 2-72 | 80 | 100 |
| 1-73 | 80 | 100 |
| 2-73 | 80 | 100 |
| 6-50 | 80 | 90 |

TABLE 1b-continued

| Pre-emergence action at 80 g/ha against ABUTH in % | | |
|---|---|---|
| Example number | Dosage [g/ha] | ABUTH |
| 1-74 | 80 | 100 |
| 2-74 | 80 | 100 |
| 6-51 | 80 | 100 |
| 1-138 | 80 | 100 |
| 2-138 | 80 | 100 |
| 1-137 | 80 | 100 |
| 1-136 | 80 | 100 |
| 1-180 | 80 | 100 |
| 2-180 | 80 | 100 |
| 6-143 | 80 | 100 |
| 1-183 | 80 | 100 |
| 2-183 | 80 | 100 |
| 6-257 | 80 | 100 |
| 1-182 | 80 | 100 |
| 2-182 | 80 | 100 |
| 6-145 | 80 | 100 |
| 1-181 | 80 | 100 |
| 2-181 | 80 | 100 |
| 6-144 | 80 | 90 |
| 1-36 | 80 | 100 |
| 2-36 | 80 | 100 |
| 1-228 | 80 | 100 |
| 2-228 | 80 | 100 |
| 6-167 | 80 | 100 |
| 1-230 | 80 | 100 |
| 2-230 | 80 | 100 |
| 6-169 | 80 | 90 |
| 2-286 | 80 | 100 |
| 1-287 | 80 | 100 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 100 |
| 2-213 | 80 | 100 |
| 1-288 | 80 | 100 |
| 1-289 | 80 | 100 |
| 2-289 | 80 | 100 |
| 6-228 | 80 | 90 |
| 1-291 | 80 | 100 |
| 2-291 | 80 | 100 |
| 6-230 | 80 | 90 |
| 2-292 | 80 | 100 |
| 1-271 | 80 | 100 |
| 2-47 | 80 | 100 |
| 6-34 | 80 | 100 |
| 1-339 | 80 | 100 |
| 2-339 | 80 | 100 |
| 6-258 | 80 | 100 |
| 1-49 | 80 | 100 |
| 2-49 | 80 | 100 |
| 1-41 | 80 | 100 |
| 1-229 | 80 | 100 |
| 2-229 | 80 | 100 |
| 1-340 | 80 | 100 |
| 6-267 | 80 | 100 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 100 |
| 1-155 | 80 | 100 |
| 2-155 | 80 | 100 |
| 6-260 | 80 | 100 |
| 1-164 | 80 | 80 |
| 2-164 | 80 | 100 |
| 6-261 | 80 | 100 |
| 1-165 | 80 | 100 |
| 1-166 | 80 | 100 |
| 1-156 | 80 | 100 |
| 2-156 | 80 | 100 |

TABLE 1b-continued

| Pre-emergence action at 80 g/ha against ABUTH in % | | |
|---|---|---|
| Example number | Dosage [g/ha] | ABUTH |
| 6-262 | 80 | 100 |
| 1-159 | 80 | 100 |
| 2-159 | 80 | 100 |
| 1-160 | 80 | 80 |
| 2-160 | 80 | 90 |
| 2-161 | 80 | 100 |
| 6-266 | 80 | 80 |
| 2-211 | 80 | 100 |
| 2-272 | 80 | 100 |
| 1-161 | 80 | 90 |
| 2-276 | 80 | 100 |
| 1-276 | 80 | 100 |
| 1-211 | 80 | 100 |
| 1-274 | 80 | 100 |
| 6-168 | 80 | 100 |
| 1-272 | 80 | 100 |
| 6-211 | 80 | 100 |
| 1-341 | 80 | 100 |
| 1-292 | 80 | 100 |
| 2-341 | 80 | 100 |
| 2-158 | 80 | 100 |
| 1-83 | 80 | 100 |
| 2-83 | 80 | 100 |
| 6-60 | 80 | 90 |
| 1-89 | 80 | 100 |
| 2-89 | 80 | 100 |
| 6-161 | 80 | 100 |
| 6-268 | 80 | 100 |
| 1-343 | 80 | 100 |
| 2-342 | 80 | 100 |
| 1-344 | 80 | 100 |
| 2-343 | 80 | 100 |
| 1-345 | 80 | 100 |
| 2-344 | 80 | 100 |
| 1-346 | 80 | 100 |
| 2-345 | 80 | 100 |
| 1-347 | 80 | 100 |
| 2-346 | 80 | 90 |
| 2-347 | 80 | 100 |
| 1-195 | 80 | 100 |
| 1-184 | 80 | 100 |
| 2-184 | 80 | 100 |
| 1-185 | 80 | 100 |
| 2-185 | 80 | 100 |
| 1-186 | 80 | 100 |
| 2-186 | 80 | 100 |
| 1-350 | 80 | 100 |
| 2-348 | 80 | 100 |
| 1-351 | 80 | 100 |
| 2-349 | 80 | 100 |
| 1-84 | 80 | 100 |
| 2-84 | 80 | 100 |
| 1-352 | 80 | 100 |
| 2-350 | 80 | 100 |
| 1-86 | 80 | 100 |
| 2-86 | 80 | 100 |
| 1-92 | 80 | 100 |
| 2-92 | 80 | 100 |
| 1-90 | 80 | 100 |
| 2-90 | 80 | 100 |
| 1-353 | 80 | 100 |
| 2-351 | 80 | 100 |
| 1-354 | 80 | 100 |
| 2-352 | 80 | 100 |
| 1-355 | 80 | 100 |
| 2-353 | 80 | 100 |
| 1-356 | 80 | 100 |
| 2-354 | 80 | 100 |

TABLE 1c

| Pre-emergence action at 3200 g/ha against ABUTH in % | | |
|---|---|---|
| Example number | Dosage [g/ha] | ABUTH |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 100 |
| 2-337 | 320 | 100 |
| 6-252 | 320 | 90 |
| 6-117 | 320 | 100 |
| 1-81 | 320 | 100 |
| 2-81 | 320 | 100 |
| 2-82 | 320 | 100 |
| 6-58 | 320 | 100 |
| 1-147 | 320 | 100 |
| 2-147 | 320 | 100 |
| 1-148 | 320 | 100 |
| 2-148 | 320 | 100 |

TABLE 2a

| Pre-emergence action at 20 g/ha against ALOMY in % | | |
|---|---|---|
| Example number | Dosage [g/ha] | ALOMY |
| 2-129 | 20 | 90 |
| 1-129 | 20 | 90 |
| 1-208 | 20 | 80 |
| 2-208 | 20 | 80 |
| 1-130 | 20 | 100 |
| 2-130 | 20 | 90 |
| 1-131 | 20 | 80 |
| 2-131 | 20 | 90 |
| 1-149 | 20 | 80 |
| 2-149 | 20 | 80 |
| 1-173 | 20 | 80 |
| 2-173 | 20 | 100 |
| 1-177 | 20 | 80 |
| 2-177 | 20 | 90 |
| 1-178 | 20 | 80 |
| 2-178 | 20 | 80 |
| 1-179 | 20 | 80 |
| 2-179 | 20 | 80 |
| 1-132 | 20 | 80 |
| 1-134 | 20 | 80 |
| 1-133 | 20 | 90 |
| 6-120 | 20 | 80 |
| 2-278 | 20 | 80 |
| 2-279 | 20 | 80 |
| 1-197 | 20 | 100 |
| 2-227 | 20 | 80 |
| 1-227 | 20 | 80 |
| 2-196 | 20 | 90 |
| 2-58 | 20 | 90 |
| 2-207 | 20 | 80 |
| 2-32 | 20 | 90 |
| 1-34 | 20 | 80 |
| 2-34 | 20 | 80 |
| 6-255 | 20 | 90 |
| 2-33 | 20 | 90 |
| 2-42 | 20 | 80 |
| 6-256 | 20 | 80 |
| 1-137 | 20 | 90 |
| 2-180 | 20 | 80 |
| 1-182 | 20 | 80 |
| 2-287 | 20 | 80 |
| 1-212 | 20 | 100 |
| 1-32 | 20 | 80 |
| 2-155 | 20 | 80 |
| 1-166 | 20 | 90 |
| 2-276 | 20 | 90 |
| 1-276 | 20 | 90 |

TABLE 2a-continued

| Pre-emergence action at 20 g/ha against ALOMY in % | | |
|---|---|---|
| Example number | Dosage [g/ha] | ALOMY |
| 1-211 | 20 | 90 |
| 1-274 | 20 | 80 |
| 1-272 | 20 | 90 |
| 1-341 | 20 | 80 |
| 1-292 | 20 | 80 |
| 2-341 | 20 | 80 |
| 1-83 | 20 | 80 |
| 2-83 | 20 | 90 |
| 1-342 | 20 | 90 |
| 2-342 | 20 | 90 |
| 1-344 | 20 | 90 |
| 2-343 | 20 | 80 |
| 1-345 | 20 | 80 |
| 2-344 | 20 | 80 |
| 1-195 | 20 | 90 |
| 1-184 | 20 | 90 |
| 2-184 | 20 | 90 |
| 1-185 | 20 | 90 |
| 2-348 | 20 | 90 |
| 1-351 | 20 | 100 |

TABLE 2b

| Pre-emergence action at 80 g/ha against ALOMY in % | | |
|---|---|---|
| Example number | Dosage [g/ha] | ALOMY |
| 3-129 | 80 | 80 |
| 2-129 | 80 | 100 |
| 1-129 | 80 | 100 |
| 6-116 | 80 | 100 |
| 2-338 | 80 | 90 |
| 3-338 | 80 | 80 |
| 2-337 | 80 | 90 |
| 3-337 | 80 | 100 |
| 1-26 | 80 | 100 |
| 2-26 | 80 | 100 |
| 3-26 | 80 | 80 |
| 6-26 | 80 | 80 |
| 1-208 | 80 | 100 |
| 2-208 | 80 | 90 |
| 3-208 | 80 | 90 |
| 6-159 | 80 | 80 |
| 1-130 | 80 | 100 |
| 2-130 | 80 | 100 |
| 1-81 | 80 | 80 |
| 1-147 | 80 | 90 |
| 2-147 | 80 | 90 |
| 1-148 | 80 | 90 |
| 2-148 | 80 | 90 |
| 1-131 | 80 | 100 |
| 2-131 | 80 | 100 |
| 6-118 | 80 | 100 |
| 1-149 | 80 | 90 |
| 2-149 | 80 | 90 |
| 6-124 | 80 | 90 |
| 5-117 | 80 | 90 |
| 5-123 | 80 | 80 |
| 5-122 | 80 | 80 |
| 1-82 | 80 | 80 |
| 1-87 | 80 | 90 |
| 2-87 | 80 | 80 |
| 1-88 | 80 | 90 |
| 2-88 | 80 | 90 |
| 1-209 | 80 | 80 |
| 1-4 | 80 | 80 |
| 1-25 | 80 | 90 |
| 2-25 | 80 | 90 |
| 3-27 | 80 | 90 |
| 1-27 | 80 | 90 |
| 2-27 | 80 | 100 |
| 1-173 | 80 | 100 |
| 2-173 | 80 | 100 |

TABLE 2b-continued

| Pre-emergence action at 80 g/ha against ALOMY in % | | |
|---|---|---|
| Example number | Dosage [g/ha] | ALOMY |
| 1-273 | 80 | 90 |
| 2-273 | 80 | 90 |
| 6-212 | 80 | 80 |
| 1-44 | 80 | 90 |
| 2-44 | 80 | 80 |
| 1-45 | 80 | 90 |
| 2-45 | 80 | 90 |
| 1-46 | 80 | 90 |
| 2-46 | 80 | 100 |
| 1-30 | 80 | 80 |
| 2-30 | 80 | 100 |
| 1-31 | 80 | 90 |
| 2-31 | 80 | 80 |
| 1-28 | 80 | 90 |
| 2-28 | 80 | 90 |
| 1-29 | 80 | 100 |
| 2-29 | 80 | 80 |
| 1-177 | 80 | 100 |
| 2-177 | 80 | 100 |
| 1-178 | 80 | 100 |
| 2-178 | 80 | 100 |
| 6-141 | 80 | 90 |
| 1-179 | 80 | 100 |
| 2-179 | 80 | 100 |
| 1-132 | 80 | 100 |
| 2-132 | 80 | 90 |
| 1-135 | 80 | 90 |
| 2-135 | 80 | 90 |
| 6-254 | 80 | 90 |
| 1-134 | 80 | 100 |
| 2-134 | 80 | 90 |
| 1-133 | 80 | 90 |
| 2-133 | 80 | 90 |
| 6-120 | 80 | 90 |
| 1-277 | 80 | 90 |
| 1-278 | 80 | 90 |
| 2-278 | 80 | 90 |
| 1-279 | 80 | 80 |
| 2-279 | 80 | 90 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 90 |
| 1-225 | 80 | 100 |
| 1-226 | 80 | 90 |
| 2-226 | 80 | 90 |
| 6-165 | 80 | 80 |
| 2-196 | 80 | 100 |
| 1-56 | 80 | 90 |
| 2-57 | 80 | 90 |
| 1-58 | 80 | 90 |
| 2-58 | 80 | 100 |
| 2-56 | 80 | 90 |
| 1-57 | 80 | 80 |
| 1-207 | 80 | 100 |
| 2-207 | 80 | 90 |
| 2-271 | 80 | 80 |
| 2-32 | 80 | 100 |
| 1-34 | 80 | 100 |
| 2-34 | 80 | 90 |
| 6-255 | 80 | 100 |
| 2-33 | 80 | 100 |
| 2-42 | 80 | 90 |
| 6-256 | 80 | 90 |
| 2-146 | 80 | 80 |
| 1-146 | 80 | 90 |
| 1-141 | 80 | 90 |
| 1-37 | 80 | 100 |
| 2-37 | 80 | 90 |
| 2-72 | 80 | 80 |
| 1-73 | 80 | 80 |
| 2-73 | 80 | 100 |
| 1-74 | 80 | 90 |
| 2-74 | 80 | 100 |

TABLE 2b-continued

| Example number | Dosage [g/ha] | ALOMY |
|---|---|---|
| Pre-emergence action at 80 g/ha against ALOMY in % | | |
| 1-138 | 80 | 90 |
| 2-138 | 80 | 90 |
| 2-141 | 80 | 90 |
| 1-137 | 80 | 90 |
| 1-136 | 80 | 90 |
| 1-180 | 80 | 100 |
| 2-180 | 80 | 100 |
| 1-183 | 80 | 90 |
| 2-183 | 80 | 90 |
| 1-182 | 80 | 100 |
| 2-182 | 80 | 80 |
| 6-145 | 80 | 90 |
| 1-181 | 80 | 100 |
| 2-181 | 80 | 80 |
| 1-228 | 80 | 90 |
| 2-228 | 80 | 80 |
| 1-230 | 80 | 90 |
| 2-286 | 80 | 80 |
| 2-287 | 80 | 90 |
| 2-288 | 80 | 90 |
| 1-210 | 80 | 80 |
| 2-210 | 80 | 100 |
| 1-212 | 80 | 100 |
| 2-212 | 80 | 100 |
| 1-288 | 80 | 90 |
| 1-289 | 80 | 90 |
| 2-289 | 80 | 90 |
| 1-291 | 80 | 80 |
| 2-291 | 80 | 80 |
| 2-292 | 80 | 90 |
| 1-271 | 80 | 90 |
| 2-47 | 80 | 100 |
| 6-34 | 80 | 80 |
| 1-339 | 80 | 90 |
| 2-339 | 80 | 90 |
| 6-258 | 80 | 90 |
| 1-49 | 80 | 80 |
| 2-49 | 80 | 90 |
| 1-229 | 80 | 90 |
| 2-229 | 80 | 90 |
| 1-340 | 80 | 90 |
| 6-267 | 80 | 80 |
| 1-47 | 80 | 90 |
| 1-33 | 80 | 100 |
| 1-32 | 80 | 100 |
| 2-154 | 80 | 100 |
| 6-259 | 80 | 80 |
| 1-155 | 80 | 90 |
| 2-155 | 80 | 100 |
| 6-260 | 80 | 90 |
| 1-164 | 80 | 100 |
| 1-165 | 80 | 100 |
| 1-166 | 80 | 100 |
| 1-156 | 80 | 90 |
| 2-156 | 80 | 100 |
| 2-159 | 80 | 80 |
| 1-162 | 80 | 90 |
| 2-211 | 80 | 90 |
| 2-272 | 80 | 90 |
| 2-276 | 80 | 90 |
| 1-276 | 80 | 100 |
| 1-211 | 80 | 100 |
| 1-274 | 80 | 90 |
| 6-168 | 80 | 80 |
| 1-272 | 80 | 100 |
| 6-211 | 80 | 90 |
| 1-341 | 80 | 90 |
| 1-292 | 80 | 90 |
| 2-341 | 80 | 90 |
| 1-83 | 80 | 100 |
| 2-83 | 80 | 90 |
| 1-89 | 80 | 90 |
| 2-89 | 80 | 100 |
| 6-161 | 80 | 90 |
| 1-342 | 80 | 100 |
| 1-343 | 80 | 100 |

TABLE 2b-continued

| Example number | Dosage [g/ha] | ALOMY |
|---|---|---|
| Pre-emergence action at 80 g/ha against ALOMY in % | | |
| 2-342 | 80 | 100 |
| 1-344 | 80 | 100 |
| 2-343 | 80 | 90 |
| 1-345 | 80 | 90 |
| 2-344 | 80 | 100 |
| 1-346 | 80 | 90 |
| 2-345 | 80 | 80 |
| 1-347 | 80 | 80 |
| 2-346 | 80 | 80 |
| 1-195 | 80 | 90 |
| 1-184 | 80 | 100 |
| 2-184 | 80 | 100 |
| 1-185 | 80 | 100 |
| 2-185 | 80 | 90 |
| 1-186 | 80 | 90 |
| 2-186 | 80 | 100 |
| 1-349 | 80 | 100 |
| 1-350 | 80 | 100 |
| 2-348 | 80 | 100 |
| 1-351 | 80 | 100 |
| 2-349 | 80 | 100 |
| 1-84 | 80 | 100 |
| 2-84 | 80 | 90 |
| 1-352 | 80 | 80 |
| 1-86 | 80 | 100 |
| 2-86 | 80 | 90 |
| 1-92 | 80 | 90 |
| 2-92 | 80 | 90 |
| 1-90 | 80 | 80 |
| 1-353 | 80 | 90 |
| 2-351 | 80 | 80 |
| 1-354 | 80 | 80 |
| 2-352 | 80 | 90 |
| 1-355 | 80 | 90 |
| 2-353 | 80 | 90 |
| 1-356 | 80 | 100 |
| 2-354 | 80 | 90 |

TABLE 2c

| Example number | Dosage [g/ha] | ALOMY |
|---|---|---|
| Pre-emergence action at 320 g/ha against ALOMY in % | | |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 90 |
| 2-337 | 320 | 100 |
| 6-117 | 320 | 90 |
| 1-81 | 320 | 100 |
| 2-81 | 320 | 90 |
| 2-82 | 320 | 100 |
| 1-147 | 320 | 100 |
| 2-147 | 320 | 100 |
| 1-148 | 320 | 100 |
| 2-148 | 320 | 100 |

TABLE 3a

| Example number | Dosage [g/ha] | AMARE |
|---|---|---|
| Pre-emergence action at 20 g/ha against AMARE in % | | |
| 3-129 | 20 | 100 |
| 2-129 | 20 | 100 |
| 1-129 | 20 | 100 |

TABLE 3a-continued

| Pre-emergence action at 20 g/ha against AMARE in % | | |
|---|---|---|
| Example number | Dosage [g/ha] | AMARE |
| 6-116 | 20 | 100 |
| 1-338 | 20 | 100 |
| 2-338 | 20 | 90 |
| 3-338 | 20 | 80 |
| 1-337 | 20 | 90 |
| 2-337 | 20 | 90 |
| 3-337 | 20 | 100 |
| 6-252 | 20 | 80 |
| 1-123 | 20 | 80 |
| 2-123 | 20 | 80 |
| 1-26 | 20 | 100 |
| 2-26 | 20 | 100 |
| 3-26 | 20 | 100 |
| 6-26 | 20 | 100 |
| 1-208 | 20 | 100 |
| 2-208 | 20 | 100 |
| 3-208 | 20 | 100 |
| 6-159 | 20 | 100 |
| 1-125 | 20 | 90 |
| 2-125 | 20 | 80 |
| 1-130 | 20 | 100 |
| 2-130 | 20 | 100 |
| 1-131 | 20 | 100 |
| 2-131 | 20 | 100 |
| 6-118 | 20 | 80 |
| 1-149 | 20 | 100 |
| 2-149 | 20 | 100 |
| 6-124 | 20 | 100 |
| 5-59 | 20 | 100 |
| 5-58 | 20 | 100 |
| 5-117 | 20 | 90 |
| 5-253 | 20 | 100 |
| 5-75 | 20 | 100 |
| 5-74 | 20 | 100 |
| 5-123 | 20 | 100 |
| 5-122 | 20 | 80 |
| 1-82 | 20 | 90 |
| 1-87 | 20 | 90 |
| 2-87 | 20 | 100 |
| 1-88 | 20 | 100 |
| 2-88 | 20 | 100 |
| 1-209 | 20 | 100 |
| 1-4 | 20 | 90 |
| 1-25 | 20 | 100 |
| 2-25 | 20 | 100 |
| 3-27 | 20 | 100 |
| 1-27 | 20 | 100 |
| 2-27 | 20 | 100 |
| 1-173 | 20 | 100 |
| 2-173 | 20 | 100 |
| 1-273 | 20 | 100 |
| 2-273 | 20 | 90 |
| 3-273 | 20 | 100 |
| 6-212 | 20 | 90 |
| 4-212 | 20 | 90 |
| 1-44 | 20 | 100 |
| 2-44 | 20 | 100 |
| 1-45 | 20 | 100 |
| 2-45 | 20 | 100 |
| 6-32 | 20 | 80 |
| 1-46 | 20 | 100 |
| 2-46 | 20 | 100 |
| 6-33 | 20 | 90 |
| 1-30 | 20 | 100 |
| 2-30 | 20 | 100 |
| 1-31 | 20 | 100 |
| 2-31 | 20 | 100 |
| 1-28 | 20 | 100 |
| 2-28 | 20 | 100 |
| 1-29 | 20 | 100 |
| 2-29 | 20 | 100 |
| 1-304 | 20 | 100 |
| 2-304 | 20 | 100 |
| 1-305 | 20 | 100 |
| 2-305 | 20 | 100 |
| 1-306 | 20 | 100 |

TABLE 3a-continued

| Pre-emergence action at 20 g/ha against AMARE in % | | |
|---|---|---|
| Example number | Dosage [g/ha] | AMARE |
| 2-306 | 20 | 90 |
| 1-177 | 20 | 100 |
| 2-177 | 20 | 100 |
| 1-178 | 20 | 100 |
| 2-178 | 20 | 100 |
| 1-179 | 20 | 100 |
| 2-179 | 20 | 100 |
| 1-132 | 20 | 100 |
| 2-132 | 20 | 100 |
| 1-135 | 20 | 100 |
| 2-135 | 20 | 100 |
| 6-254 | 20 | 100 |
| 1-134 | 20 | 100 |
| 2-134 | 20 | 100 |
| 1-133 | 20 | 90 |
| 2-133 | 20 | 90 |
| 6-120 | 20 | 100 |
| 1-277 | 20 | 100 |
| 2-277 | 20 | 100 |
| 1-278 | 20 | 100 |
| 2-278 | 20 | 100 |
| 1-279 | 20 | 100 |
| 2-279 | 20 | 100 |
| 2-195 | 20 | 100 |
| 2-225 | 20 | 100 |
| 1-197 | 20 | 100 |
| 2-227 | 20 | 100 |
| 1-227 | 20 | 100 |
| 2-197 | 20 | 100 |
| 1-225 | 20 | 100 |
| 1-226 | 20 | 100 |
| 2-226 | 20 | 100 |
| 6-165 | 20 | 100 |
| 6-166 | 20 | 90 |
| 2-196 | 20 | 100 |
| 1-56 | 20 | 100 |
| 6-45 | 20 | 80 |
| 6-44 | 20 | 80 |
| 2-57 | 20 | 100 |
| 1-58 | 20 | 100 |
| 2-58 | 20 | 100 |
| 2-56 | 20 | 100 |
| 1-57 | 20 | 100 |
| 1-207 | 20 | 100 |
| 2-207 | 20 | 100 |
| 2-271 | 20 | 100 |
| 2-32 | 20 | 100 |
| 1-34 | 20 | 100 |
| 2-34 | 20 | 90 |
| 6-255 | 20 | 100 |
| 2-33 | 20 | 100 |
| 2-42 | 20 | 100 |
| 6-256 | 20 | 90 |
| 2-146 | 20 | 100 |
| 5-255 | 20 | 90 |
| 1-146 | 20 | 100 |
| 1-141 | 20 | 100 |
| 1-37 | 20 | 100 |
| 2-37 | 20 | 90 |
| 1-72 | 20 | 100 |
| 2-72 | 20 | 100 |
| 6-49 | 20 | 80 |
| 1-73 | 20 | 100 |
| 2-73 | 20 | 100 |
| 6-50 | 20 | 100 |
| 1-74 | 20 | 100 |
| 2-74 | 20 | 100 |
| 6-51 | 20 | 80 |
| 1-144 | 20 | 90 |
| 2-144 | 20 | 80 |
| 1-138 | 20 | 100 |
| 2-138 | 20 | 100 |
| 2-141 | 20 | 100 |
| 1-137 | 20 | 100 |
| 1-136 | 20 | 100 |
| 1-180 | 20 | 100 |

TABLE 3a-continued

| Example number | Dosage [g/ha] | AMARE |
|---|---|---|
| Pre-emergence action at 20 g/ha against AMARE in % | | |
| 2-180 | 20 | 100 |
| 6-143 | 20 | 100 |
| 1-183 | 20 | 100 |
| 2-183 | 20 | 90 |
| 1-182 | 20 | 100 |
| 2-182 | 20 | 100 |
| 6-145 | 20 | 90 |
| 1-181 | 20 | 100 |
| 2-181 | 20 | 100 |
| 6-144 | 20 | 90 |
| 1-36 | 20 | 100 |
| 2-36 | 20 | 100 |
| 1-228 | 20 | 100 |
| 2-228 | 20 | 100 |
| 6-167 | 20 | 100 |
| 1-230 | 20 | 100 |
| 2-230 | 20 | 100 |
| 6-169 | 20 | 90 |
| 2-286 | 20 | 100 |
| 1-287 | 20 | 100 |
| 2-287 | 20 | 100 |
| 2-288 | 20 | 100 |
| 1-210 | 20 | 100 |
| 2-210 | 20 | 100 |
| 1-212 | 20 | 100 |
| 2-213 | 20 | 100 |
| 1-288 | 20 | 100 |
| 1-289 | 20 | 90 |
| 2-289 | 20 | 100 |
| 1-291 | 20 | 100 |
| 2-291 | 20 | 100 |
| 6-230 | 20 | 100 |
| 2-292 | 20 | 100 |
| 1-271 | 20 | 100 |
| 2-47 | 20 | 100 |
| 6-34 | 20 | 100 |
| 1-339 | 20 | 100 |
| 2-339 | 20 | 100 |
| 6-258 | 20 | 100 |
| 1-49 | 20 | 100 |
| 2-49 | 20 | 100 |
| 1-41 | 20 | 90 |
| 1-229 | 20 | 100 |
| 2-229 | 20 | 100 |
| 1-340 | 20 | 100 |
| 6-267 | 20 | 90 |
| 2-340 | 20 | 100 |
| 1-47 | 20 | 100 |
| 1-33 | 20 | 100 |
| 1-32 | 20 | 100 |
| 2-154 | 20 | 100 |
| 6-259 | 20 | 100 |
| 1-155 | 20 | 100 |
| 2-155 | 20 | 100 |
| 6-260 | 20 | 100 |
| 2-164 | 20 | 100 |
| 6-261 | 20 | 100 |
| 1-165 | 20 | 100 |
| 1-166 | 20 | 100 |
| 1-156 | 20 | 100 |
| 2-156 | 20 | 100 |
| 6-262 | 20 | 90 |
| 1-159 | 20 | 100 |
| 2-159 | 20 | 100 |
| 1-162 | 20 | 90 |
| 2-162 | 20 | 90 |
| 6-264 | 20 | 80 |
| 1-160 | 20 | 100 |
| 2-160 | 20 | 100 |
| 2-161 | 20 | 90 |
| 6-266 | 20 | 90 |
| 2-211 | 20 | 100 |
| 2-272 | 20 | 100 |
| 1-161 | 20 | 100 |
| 2-276 | 20 | 100 |
| 1-276 | 20 | 90 |

TABLE 3a-continued

| Example number | Dosage [g/ha] | AMARE |
|---|---|---|
| Pre-emergence action at 20 g/ha against AMARE in % | | |
| 1-211 | 20 | 100 |
| 1-274 | 20 | 100 |
| 6-168 | 20 | 90 |
| 1-272 | 20 | 100 |
| 6-211 | 20 | 100 |
| 1-341 | 20 | 100 |
| 1-292 | 20 | 100 |
| 2-341 | 20 | 100 |
| 1-158 | 20 | 100 |
| 2-83 | 20 | 100 |
| 1-89 | 20 | 100 |
| 2-89 | 20 | 90 |
| 6-161 | 20 | 100 |
| 1-342 | 20 | 100 |
| 1-343 | 20 | 100 |
| 2-342 | 20 | 90 |
| 1-344 | 20 | 100 |
| 2-343 | 20 | 100 |
| 1-345 | 20 | 100 |
| 2-344 | 20 | 100 |
| 1-346 | 20 | 100 |
| 2-345 | 20 | 100 |
| 2-346 | 20 | 100 |
| 1-195 | 20 | 90 |
| 1-184 | 20 | 100 |
| 2-184 | 20 | 100 |
| 1-185 | 20 | 100 |
| 2-185 | 20 | 100 |
| 1-186 | 20 | 80 |
| 2-186 | 20 | 100 |
| 1-349 | 20 | 100 |
| 1-350 | 20 | 100 |
| 2-348 | 20 | 100 |
| 1-351 | 20 | 100 |
| 2-349 | 20 | 100 |
| 1-84 | 20 | 100 |
| 2-84 | 20 | 100 |
| 1-352 | 20 | 100 |
| 2-350 | 20 | 100 |
| 1-86 | 20 | 100 |
| 2-86 | 20 | 100 |
| 1-92 | 20 | 100 |
| 2-92 | 20 | 100 |
| 1-90 | 20 | 100 |
| 2-90 | 20 | 100 |
| 1-353 | 20 | 100 |
| 2-351 | 20 | 100 |
| 2-352 | 20 | 100 |
| 1-355 | 20 | 100 |
| 2-353 | 20 | 100 |
| 1-356 | 20 | 100 |
| 2-354 | 20 | 100 |

TABLE 3b

| Example number | Dosage [g/ha] | AMARE |
|---|---|---|
| Pre-emergence action at 80 g/ha against AMARE in % | | |
| 3-129 | 80 | 100 |
| 2-129 | 80 | 100 |
| 1-129 | 80 | 100 |
| 6-116 | 80 | 100 |
| 1-338 | 80 | 100 |
| 2-338 | 80 | 100 |
| 3-338 | 80 | 100 |
| 6-253 | 80 | 80 |
| 1-337 | 80 | 100 |
| 2-337 | 80 | 100 |
| 3-337 | 80 | 100 |
| 6-252 | 80 | 90 |
| 1-123 | 80 | 100 |
| 2-123 | 80 | 100 |

TABLE 3b-continued

| Pre-emergence action at 80 g/ha against AMARE in % | | |
|---|---|---|
| Example number | Dosage [g/ha] | AMARE |
| 1-26 | 80 | 100 |
| 2-26 | 80 | 100 |
| 3-26 | 80 | 100 |
| 6-26 | 80 | 100 |
| 1-208 | 80 | 100 |
| 2-208 | 80 | 100 |
| 3-208 | 80 | 100 |
| 6-159 | 80 | 100 |
| 1-125 | 80 | 100 |
| 2-125 | 80 | 100 |
| 3-125 | 80 | 100 |
| 1-130 | 80 | 100 |
| 2-130 | 80 | 100 |
| 6-117 | 80 | 100 |
| 1-81 | 80 | 100 |
| 2-81 | 80 | 100 |
| 2-82 | 80 | 100 |
| 6-58 | 80 | 100 |
| 1-147 | 80 | 100 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 100 |
| 1-149 | 80 | 100 |
| 2-149 | 80 | 100 |
| 6-124 | 80 | 100 |
| 5-59 | 80 | 100 |
| 5-58 | 80 | 100 |
| 5-117 | 80 | 90 |
| 5-253 | 80 | 100 |
| 5-75 | 80 | 100 |
| 5-74 | 80 | 100 |
| 5-123 | 80 | 100 |
| 5-122 | 80 | 100 |
| 1-82 | 80 | 100 |
| 1-87 | 80 | 100 |
| 2-87 | 80 | 100 |
| 1-88 | 80 | 100 |
| 2-88 | 80 | 100 |
| 1-209 | 80 | 100 |
| 1-4 | 80 | 100 |
| 1-25 | 80 | 100 |
| 2-25 | 80 | 100 |
| 3-27 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 100 |
| 3-273 | 80 | 100 |
| 6-212 | 80 | 90 |
| 4-212 | 80 | 90 |
| 1-44 | 80 | 100 |
| 2-44 | 80 | 100 |
| 1-45 | 80 | 100 |
| 2-45 | 80 | 100 |
| 6-32 | 80 | 100 |
| 1-46 | 80 | 100 |
| 2-46 | 80 | 100 |
| 6-33 | 80 | 100 |
| 1-30 | 80 | 100 |
| 2-30 | 80 | 100 |
| 1-31 | 80 | 100 |
| 2-31 | 80 | 100 |
| 1-28 | 80 | 100 |
| 2-28 | 80 | 100 |
| 1-29 | 80 | 100 |
| 2-29 | 80 | 100 |
| 1-304 | 80 | 100 |
| 2-304 | 80 | 100 |
| 6-231 | 80 | 100 |
| 1-305 | 80 | 100 |
| 2-305 | 80 | 100 |

TABLE 3b-continued

| Pre-emergence action at 80 g/ha against AMARE in % | | |
|---|---|---|
| Example number | Dosage [g/ha] | AMARE |
| 1-306 | 80 | 100 |
| 2-306 | 80 | 100 |
| 6-233 | 80 | 80 |
| 1-177 | 80 | 100 |
| 2-177 | 80 | 100 |
| 1-178 | 80 | 100 |
| 2-178 | 80 | 100 |
| 6-141 | 80 | 100 |
| 1-179 | 80 | 100 |
| 2-179 | 80 | 100 |
| 1-132 | 80 | 100 |
| 2-132 | 80 | 100 |
| 1-135 | 80 | 100 |
| 2-135 | 80 | 100 |
| 6-254 | 80 | 100 |
| 1-134 | 80 | 100 |
| 2-134 | 80 | 100 |
| 1-133 | 80 | 100 |
| 2-133 | 80 | 100 |
| 6-120 | 80 | 100 |
| 1-277 | 80 | 100 |
| 2-277 | 80 | 100 |
| 1-278 | 80 | 100 |
| 2-278 | 80 | 100 |
| 1-279 | 80 | 100 |
| 2-279 | 80 | 100 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 100 |
| 1-225 | 80 | 100 |
| 1-226 | 80 | 100 |
| 2-226 | 80 | 100 |
| 6-165 | 80 | 100 |
| 6-166 | 80 | 100 |
| 2-196 | 80 | 100 |
| 1-56 | 80 | 100 |
| 6-45 | 80 | 100 |
| 6-44 | 80 | 100 |
| 2-57 | 80 | 100 |
| 6-43 | 80 | 100 |
| 1-58 | 80 | 100 |
| 2-58 | 80 | 100 |
| 2-56 | 80 | 100 |
| 1-57 | 80 | 100 |
| 1-207 | 80 | 100 |
| 2-207 | 80 | 100 |
| 2-271 | 80 | 100 |
| 6-210 | 80 | 100 |
| 2-32 | 80 | 100 |
| 1-34 | 80 | 100 |
| 2-34 | 80 | 100 |
| 6-255 | 80 | 100 |
| 2-33 | 80 | 100 |
| 2-42 | 80 | 100 |
| 6-256 | 80 | 100 |
| 2-146 | 80 | 100 |
| 2-142 | 80 | 100 |
| 1-143 | 80 | 100 |
| 5-255 | 80 | 100 |
| 1-142 | 80 | 100 |
| 5-254 | 80 | 100 |
| 1-140 | 80 | 100 |
| 1-146 | 80 | 100 |
| 1-141 | 80 | 100 |
| 1-37 | 80 | 100 |
| 2-37 | 80 | 100 |
| 2-143 | 80 | 100 |
| 1-72 | 80 | 100 |
| 2-72 | 80 | 100 |
| 6-49 | 80 | 100 |
| 1-73 | 80 | 100 |
| 2-73 | 80 | 100 |
| 6-50 | 80 | 100 |

TABLE 3b-continued

| Example number | Dosage [g/ha] | AMARE |
|---|---|---|
| Pre-emergence action at 80 g/ha against AMARE in % | | |
| 1-74 | 80 | 100 |
| 2-74 | 80 | 100 |
| 6-51 | 80 | 100 |
| 2-35 | 80 | 90 |
| 1-144 | 80 | 100 |
| 2-144 | 80 | 100 |
| 1-138 | 80 | 100 |
| 2-138 | 80 | 100 |
| 2-141 | 80 | 100 |
| 1-137 | 80 | 100 |
| 1-136 | 80 | 100 |
| 1-180 | 80 | 100 |
| 2-180 | 80 | 100 |
| 6-143 | 80 | 100 |
| 1-183 | 80 | 100 |
| 2-183 | 80 | 100 |
| 6-257 | 80 | 100 |
| 1-182 | 80 | 100 |
| 2-182 | 80 | 100 |
| 6-145 | 80 | 100 |
| 1-181 | 80 | 100 |
| 2-181 | 80 | 100 |
| 6-144 | 80 | 100 |
| 1-36 | 80 | 100 |
| 2-36 | 80 | 100 |
| 1-228 | 80 | 100 |
| 2-228 | 80 | 100 |
| 6-167 | 80 | 100 |
| 1-230 | 80 | 100 |
| 2-230 | 80 | 100 |
| 6-169 | 80 | 100 |
| 2-286 | 80 | 100 |
| 1-287 | 80 | 100 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 100 |
| 2-213 | 80 | 100 |
| 1-288 | 80 | 100 |
| 1-289 | 80 | 100 |
| 2-289 | 80 | 100 |
| 6-228 | 80 | 100 |
| 1-291 | 80 | 100 |
| 2-291 | 80 | 100 |
| 6-230 | 80 | 100 |
| 2-292 | 80 | 100 |
| 1-271 | 80 | 100 |
| 2-47 | 80 | 100 |
| 6-34 | 80 | 100 |
| 1-339 | 80 | 100 |
| 2-339 | 80 | 100 |
| 6-258 | 80 | 100 |
| 1-49 | 80 | 100 |
| 2-49 | 80 | 100 |
| 1-41 | 80 | 100 |
| 1-229 | 80 | 100 |
| 2-229 | 80 | 100 |
| 1-340 | 80 | 100 |
| 6-267 | 80 | 100 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 100 |
| 1-155 | 80 | 100 |
| 2-155 | 80 | 100 |
| 6-260 | 80 | 100 |
| 1-164 | 80 | 100 |
| 2-164 | 80 | 100 |
| 6-261 | 80 | 100 |
| 1-165 | 80 | 100 |
| 1-166 | 80 | 100 |
| 1-156 | 80 | 100 |

TABLE 3b-continued

| Example number | Dosage [g/ha] | AMARE |
|---|---|---|
| Pre-emergence action at 80 g/ha against AMARE in % | | |
| 2-156 | 80 | 100 |
| 6-262 | 80 | 100 |
| 1-157 | 80 | 100 |
| 2-157 | 80 | 90 |
| 1-159 | 80 | 100 |
| 2-159 | 80 | 100 |
| 1-162 | 80 | 100 |
| 2-162 | 80 | 100 |
| 6-264 | 80 | 100 |
| 1-160 | 80 | 100 |
| 2-160 | 80 | 100 |
| 6-265 | 80 | 80 |
| 2-161 | 80 | 100 |
| 6-266 | 80 | 100 |
| 2-211 | 80 | 100 |
| 2-272 | 80 | 100 |
| 1-161 | 80 | 100 |
| 2-276 | 80 | 100 |
| 1-276 | 80 | 100 |
| 1-211 | 80 | 100 |
| 1-274 | 80 | 100 |
| 6-168 | 80 | 100 |
| 1-272 | 80 | 100 |
| 6-211 | 80 | 100 |
| 1-341 | 80 | 100 |
| 1-292 | 80 | 100 |
| 2-341 | 80 | 100 |
| 1-158 | 80 | 100 |
| 2-158 | 80 | 100 |
| 1-83 | 80 | 100 |
| 2-83 | 80 | 100 |
| 6-60 | 80 | 100 |
| 1-89 | 80 | 100 |
| 2-89 | 80 | 100 |
| 6-76 | 80 | 100 |
| 6-161 | 80 | 100 |
| 6-268 | 80 | 100 |
| 1-342 | 80 | 100 |
| 1-343 | 80 | 100 |
| 2-342 | 80 | 100 |
| 1-344 | 80 | 100 |
| 2-343 | 80 | 100 |
| 1-345 | 80 | 100 |
| 2-344 | 80 | 100 |
| 1-346 | 80 | 100 |
| 2-345 | 80 | 100 |
| 1-347 | 80 | 100 |
| 2-346 | 80 | 100 |
| 1-195 | 80 | 100 |
| 1-184 | 80 | 100 |
| 2-184 | 80 | 100 |
| 1-185 | 80 | 100 |
| 2-185 | 80 | 100 |
| 1-186 | 80 | 100 |
| 2-186 | 80 | 100 |
| 1-349 | 80 | 100 |
| 1-350 | 80 | 100 |
| 2-348 | 80 | 100 |
| 1-351 | 80 | 100 |
| 2-349 | 80 | 100 |
| 1-84 | 80 | 100 |
| 2-84 | 80 | 100 |
| 1-352 | 80 | 100 |
| 2-350 | 80 | 100 |
| 1-86 | 80 | 100 |
| 2-86 | 80 | 100 |
| 1-92 | 80 | 100 |
| 2-92 | 80 | 100 |
| 1-90 | 80 | 100 |
| 2-90 | 80 | 100 |
| 1-353 | 80 | 100 |
| 2-351 | 80 | 100 |
| 1-354 | 80 | 100 |
| 2-352 | 80 | 100 |
| 1-355 | 80 | 100 |
| 2-353 | 80 | 100 |

TABLE 3b-continued

| Pre-emergence action at 80 g/ha against AMARE in % | | |
|---|---|---|
| Example number | Dosage [g/ha] | AMARE |
| 1-356 | 80 | 100 |
| 2-354 | 80 | 100 |

TABLE 3c

| Pre-emergence action at 320 g/ha against AMARE in % | | |
|---|---|---|
| Example number | Dosage [g/ha] | AMARE |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 90 |
| 2-337 | 320 | 100 |
| 6-252 | 320 | 90 |
| 6-117 | 320 | 100 |
| 1-81 | 320 | 100 |
| 2-81 | 320 | 100 |
| 2-82 | 320 | 100 |
| 6-58 | 320 | 100 |
| 1-147 | 320 | 100 |
| 2-147 | 320 | 100 |
| 1-148 | 320 | 100 |
| 2-148 | 320 | 100 |

TABLE 4a

| Pre-emergence action at 20 g/ha against AVEFA in % | | |
|---|---|---|
| Example number | Dosage [g/ha] | AVEFA |
| 2-129 | 20 | 100 |
| 1-129 | 20 | 100 |
| 2-337 | 20 | 90 |
| 2-26 | 20 | 80 |
| 3-26 | 20 | 80 |
| 1-208 | 20 | 80 |
| 1-130 | 20 | 100 |
| 2-130 | 20 | 90 |
| 1-131 | 20 | 80 |
| 1-149 | 20 | 80 |
| 2-149 | 20 | 80 |
| 2-27 | 20 | 80 |
| 2-173 | 20 | 90 |
| 1-29 | 20 | 80 |
| 1-177 | 20 | 80 |
| 2-178 | 20 | 90 |
| 1-135 | 20 | 80 |
| 1-134 | 20 | 80 |
| 2-134 | 20 | 80 |
| 2-197 | 20 | 80 |
| 1-225 | 20 | 80 |
| 1-226 | 20 | 80 |
| 2-196 | 20 | 80 |
| 1-207 | 20 | 80 |
| 2-32 | 20 | 90 |
| 2-33 | 20 | 80 |
| 2-42 | 20 | 80 |
| 2-288 | 20 | 80 |
| 1-212 | 20 | 80 |
| 2-291 | 20 | 80 |
| 1-164 | 20 | 100 |
| 2-276 | 20 | 80 |
| 1-211 | 20 | 80 |
| 1-274 | 20 | 80 |
| 1-341 | 20 | 80 |
| 1-343 | 20 | 80 |

TABLE 4a-continued

| Pre-emergence action at 20 g/ha against AVEFA in % | | |
|---|---|---|
| Example number | Dosage [g/ha] | AVEFA |
| 1-345 | 20 | 80 |
| 1-346 | 20 | 80 |
| 2-345 | 20 | 80 |
| 1-195 | 20 | 80 |
| 2-349 | 20 | 90 |
| 2-92 | 20 | 80 |
| 2-90 | 20 | 80 |

TABLE 4b

| Pre-emergence action at 80 g/ha against AVEFA in % | | |
|---|---|---|
| Example number | Dosage [g/ha] | AVEFA |
| 3-129 | 80 | 100 |
| 2-129 | 80 | 100 |
| 1-129 | 80 | 100 |
| 6-116 | 80 | 100 |
| 1-338 | 80 | 90 |
| 2-338 | 80 | 90 |
| 3-338 | 80 | 90 |
| 2-337 | 80 | 100 |
| 3-337 | 80 | 100 |
| 1-26 | 80 | 100 |
| 2-26 | 80 | 100 |
| 3-26 | 80 | 100 |
| 6-26 | 80 | 80 |
| 1-208 | 80 | 100 |
| 2-208 | 80 | 100 |
| 3-208 | 80 | 100 |
| 6-159 | 80 | 90 |
| 2-125 | 80 | 100 |
| 3-125 | 80 | 80 |
| 1-130 | 80 | 100 |
| 2-130 | 80 | 100 |
| 6-117 | 80 | 100 |
| 1-81 | 80 | 90 |
| 2-81 | 80 | 80 |
| 2-82 | 80 | 100 |
| 1-147 | 80 | 100 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 90 |
| 1-149 | 80 | 100 |
| 2-149 | 80 | 100 |
| 6-124 | 80 | 90 |
| 5-59 | 80 | 80 |
| 5-58 | 80 | 80 |
| 5-117 | 80 | 90 |
| 5-74 | 80 | 80 |
| 1-82 | 80 | 90 |
| 1-87 | 80 | 90 |
| 2-87 | 80 | 90 |
| 1-88 | 80 | 90 |
| 2-88 | 80 | 90 |
| 1-209 | 80 | 100 |
| 1-4 | 80 | 90 |
| 1-25 | 80 | 90 |
| 2-25 | 80 | 100 |
| 3-27 | 80 | 90 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 90 |
| 3-273 | 80 | 90 |

TABLE 4b-continued

| Pre-emergence action at 80 g/ha against AVEFA in % | | |
|---|---|---|
| Example number | Dosage [g/ha] | AVEFA |
| 1-44 | 80 | 90 |
| 2-44 | 80 | 90 |
| 1-45 | 80 | 90 |
| 2-45 | 80 | 100 |
| 1-46 | 80 | 100 |
| 2-46 | 80 | 100 |
| 1-30 | 80 | 100 |
| 2-30 | 80 | 100 |
| 1-31 | 80 | 90 |
| 2-31 | 80 | 100 |
| 1-28 | 80 | 100 |
| 2-28 | 80 | 90 |
| 1-29 | 80 | 90 |
| 2-29 | 80 | 100 |
| 1-306 | 80 | 80 |
| 1-177 | 80 | 100 |
| 2-177 | 80 | 90 |
| 1-178 | 80 | 100 |
| 2-178 | 80 | 100 |
| 6-141 | 80 | 80 |
| 1-179 | 80 | 100 |
| 2-179 | 80 | 100 |
| 1-132 | 80 | 100 |
| 2-132 | 80 | 90 |
| 1-135 | 80 | 100 |
| 2-135 | 80 | 90 |
| 6-254 | 80 | 90 |
| 1-134 | 80 | 90 |
| 2-134 | 80 | 90 |
| 1-133 | 80 | 100 |
| 2-133 | 80 | 90 |
| 6-120 | 80 | 90 |
| 1-277 | 80 | 90 |
| 1-278 | 80 | 90 |
| 2-278 | 80 | 90 |
| 1-279 | 80 | 90 |
| 2-279 | 80 | 100 |
| 2-195 | 80 | 80 |
| 2-225 | 80 | 80 |
| 1-197 | 80 | 100 |
| 2-227 | 80 | 90 |
| 1-227 | 80 | 90 |
| 2-197 | 80 | 100 |
| 1-225 | 80 | 80 |
| 1-226 | 80 | 90 |
| 2-226 | 80 | 100 |
| 2-196 | 80 | 100 |
| 1-56 | 80 | 80 |
| 2-57 | 80 | 90 |
| 1-58 | 80 | 80 |
| 2-58 | 80 | 90 |
| 1-57 | 80 | 90 |
| 1-207 | 80 | 90 |
| 2-207 | 80 | 90 |
| 2-32 | 80 | 90 |
| 2-34 | 80 | 90 |
| 6-255 | 80 | 80 |
| 2-33 | 80 | 90 |
| 2-42 | 80 | 90 |
| 6-256 | 80 | 80 |
| 2-73 | 80 | 80 |
| 2-74 | 80 | 80 |
| 1-137 | 80 | 90 |
| 1-136 | 80 | 80 |
| 1-180 | 80 | 80 |
| 2-180 | 80 | 80 |
| 1-183 | 80 | 90 |
| 2-183 | 80 | 80 |
| 1-182 | 80 | 90 |
| 2-182 | 80 | 90 |
| 1-181 | 80 | 80 |
| 2-181 | 80 | 90 |
| 1-228 | 80 | 90 |
| 2-228 | 80 | 80 |
| 1-230 | 80 | 90 |
| 2-230 | 80 | 80 |

TABLE 4b-continued

| Pre-emergence action at 80 g/ha against AVEFA in % | | |
|---|---|---|
| Example number | Dosage [g/ha] | AVEFA |
| 2-287 | 80 | 80 |
| 2-288 | 80 | 90 |
| 1-210 | 80 | 90 |
| 2-210 | 80 | 90 |
| 1-212 | 80 | 90 |
| 2-212 | 80 | 90 |
| 1-288 | 80 | 90 |
| 1-289 | 80 | 80 |
| 2-291 | 80 | 80 |
| 2-292 | 80 | 90 |
| 1-271 | 80 | 80 |
| 2-47 | 80 | 80 |
| 1-339 | 80 | 100 |
| 2-339 | 80 | 80 |
| 2-49 | 80 | 80 |
| 1-229 | 80 | 80 |
| 2-229 | 80 | 90 |
| 1-340 | 80 | 80 |
| 1-33 | 80 | 100 |
| 1-155 | 80 | 90 |
| 2-155 | 80 | 90 |
| 1-164 | 80 | 100 |
| 1-166 | 80 | 100 |
| 2-211 | 80 | 80 |
| 2-272 | 80 | 80 |
| 2-276 | 80 | 90 |
| 1-276 | 80 | 90 |
| 1-211 | 80 | 90 |
| 1-274 | 80 | 90 |
| 6-168 | 80 | 80 |
| 1-272 | 80 | 90 |
| 6-211 | 80 | 80 |
| 1-341 | 80 | 90 |
| 2-341 | 80 | 90 |
| 1-83 | 80 | 80 |
| 2-83 | 80 | 90 |
| 1-89 | 80 | 90 |
| 2-89 | 80 | 90 |
| 1-342 | 80 | 100 |
| 1-343 | 80 | 80 |
| 2-342 | 80 | 90 |
| 1-344 | 80 | 90 |
| 2-343 | 80 | 100 |
| 1-345 | 80 | 90 |
| 2-344 | 80 | 80 |
| 1-346 | 80 | 80 |
| 2-345 | 80 | 80 |
| 2-346 | 80 | 80 |
| 1-195 | 80 | 90 |
| 2-184 | 80 | 90 |
| 1-185 | 80 | 100 |
| 2-185 | 80 | 100 |
| 2-186 | 80 | 80 |
| 1-349 | 80 | 100 |
| 1-350 | 80 | 90 |
| 2-348 | 80 | 100 |
| 1-351 | 80 | 100 |
| 2-349 | 80 | 100 |
| 1-84 | 80 | 100 |
| 2-84 | 80 | 100 |
| 1-352 | 80 | 80 |
| 1-86 | 80 | 100 |
| 2-86 | 80 | 90 |
| 2-92 | 80 | 80 |
| 2-90 | 80 | 90 |
| 2-351 | 80 | 80 |
| 2-352 | 80 | 80 |
| 2-354 | 80 | 90 |

TABLE 4c

| Pre-emergence action at 320 g/ha against AVEFA in % | | |
|---|---|---|
| Example number | Dosage [g/ha] | AVEFA |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 90 |
| 2-337 | 320 | 100 |
| 6-117 | 320 | 100 |
| 1-81 | 320 | 100 |
| 2-81 | 320 | 100 |
| 2-82 | 320 | 100 |
| 1-147 | 320 | 100 |
| 2-147 | 320 | 100 |
| 1-148 | 320 | 100 |
| 2-148 | 320 | 100 |

TABLE 5a

| Pre-emergence action at 20 g/ha against CYPES in % | | |
|---|---|---|
| Example number | Dosage [g/ha] | CYPES |
| 2-129 | 20 | 100 |
| 1-129 | 20 | 90 |
| 6-116 | 20 | 100 |
| 6-253 | 20 | 80 |

TABLE 5b

| Pre-emergence action at 80 g/ha against CYPES in % | | |
|---|---|---|
| Example number | Dosage [g/ha] | CYPES |
| 3-129 | 80 | 100 |
| 2-129 | 80 | 100 |
| 1-129 | 80 | 90 |
| 6-116 | 80 | 100 |
| 1-338 | 80 | 90 |
| 2-338 | 80 | 90 |
| 3-338 | 80 | 90 |
| 6-253 | 80 | 90 |

TABLE 5c

| Pre-emergence action at 320 g/ha against CYPES in % | | |
|---|---|---|
| Example number | Dosage [g/ha] | CYPES |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 90 |
| 6-253 | 320 | 100 |

TABLE 6a

| Pre-emergence action at 20 g/ha against ECHCG in % | | |
|---|---|---|
| Example number | Dosage [g/ha] | ECHCG |
| 1-129 | 20 | 80 |
| 2-337 | 20 | 80 |

TABLE 6a-continued

| Pre-emergence action at 20 g/ha against ECHCG in % | | |
|---|---|---|
| Example number | Dosage [g/ha] | ECHCG |
| 1-26 | 20 | 80 |
| 1-130 | 20 | 90 |
| 2-130 | 20 | 80 |
| 6-124 | 20 | 80 |
| 5-59 | 20 | 80 |
| 5-117 | 20 | 80 |
| 5-123 | 20 | 90 |
| 5-122 | 20 | 80 |
| 2-87 | 20 | 80 |
| 1-88 | 20 | 90 |
| 2-27 | 20 | 90 |
| 1-273 | 20 | 90 |
| 1-31 | 20 | 90 |
| 2-28 | 20 | 80 |
| 1-305 | 20 | 80 |
| 2-305 | 20 | 80 |
| 1-177 | 20 | 80 |
| 1-178 | 20 | 80 |
| 1-132 | 20 | 90 |
| 1-135 | 20 | 80 |
| 6-254 | 20 | 90 |
| 2-134 | 20 | 80 |
| 1-278 | 20 | 90 |
| 1-227 | 20 | 80 |
| 1-225 | 20 | 90 |
| 1-226 | 20 | 80 |
| 2-226 | 20 | 100 |
| 2-57 | 20 | 90 |
| 1-58 | 20 | 100 |
| 1-57 | 20 | 90 |
| 2-42 | 20 | 90 |
| 6-256 | 20 | 80 |
| 1-137 | 20 | 80 |
| 1-183 | 20 | 90 |
| 1-228 | 20 | 90 |
| 2-287 | 20 | 90 |
| 2-288 | 20 | 90 |
| 1-210 | 20 | 80 |
| 2-210 | 20 | 80 |
| 1-288 | 20 | 80 |
| 1-289 | 20 | 80 |
| 1-271 | 20 | 90 |
| 1-32 | 20 | 80 |
| 1-164 | 20 | 100 |
| 1-166 | 20 | 90 |
| 1-211 | 20 | 90 |
| 6-161 | 20 | 80 |
| 1-345 | 20 | 90 |
| 2-344 | 20 | 90 |
| 2-84 | 20 | 90 |
| 2-350 | 20 | 80 |
| 1-86 | 20 | 90 |
| 2-86 | 20 | 80 |
| 2-90 | 20 | 90 |
| 1-353 | 20 | 90 |

TABLE 6b

| Pre-emergence action at 80 g/ha against ECHCG in % | | |
|---|---|---|
| Example number | Dosage [g/ha] | ECHCG |
| 3-129 | 80 | 80 |
| 2-129 | 80 | 100 |
| 1-129 | 80 | 100 |
| 6-116 | 80 | 100 |
| 1-338 | 80 | 90 |
| 2-338 | 80 | 90 |
| 2-337 | 80 | 100 |
| 3-337 | 80 | 90 |
| 1-26 | 80 | 100 |
| 2-26 | 80 | 100 |
| 6-26 | 80 | 100 |

TABLE 6b-continued

| Pre-emergence action at 80 g/ha against ECHCG in % | | |
|---|---|---|
| Example number | Dosage [g/ha] | ECHCG |
| 1-208 | 80 | 100 |
| 2-208 | 80 | 100 |
| 3-208 | 80 | 80 |
| 6-159 | 80 | 100 |
| 1-130 | 80 | 100 |
| 2-130 | 80 | 100 |
| 6-117 | 80 | 90 |
| 1-81 | 80 | 100 |
| 2-81 | 80 | 100 |
| 2-82 | 80 | 100 |
| 1-147 | 80 | 100 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 100 |
| 1-149 | 80 | 100 |
| 2-149 | 80 | 90 |
| 6-124 | 80 | 100 |
| 5-59 | 80 | 100 |
| 5-58 | 80 | 90 |
| 5-117 | 80 | 100 |
| 5-75 | 80 | 100 |
| 5-74 | 80 | 90 |
| 5-123 | 80 | 100 |
| 5-122 | 80 | 100 |
| 1-82 | 80 | 100 |
| 1-87 | 80 | 100 |
| 2-87 | 80 | 100 |
| 1-88 | 80 | 100 |
| 2-88 | 80 | 100 |
| 1-209 | 80 | 90 |
| 1-4 | 80 | 90 |
| 1-25 | 80 | 100 |
| 2-25 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 90 |
| 3-273 | 80 | 80 |
| 6-212 | 80 | 90 |
| 4-212 | 80 | 80 |
| 1-44 | 80 | 90 |
| 1-45 | 80 | 90 |
| 2-45 | 80 | 100 |
| 6-32 | 80 | 90 |
| 1-46 | 80 | 80 |
| 2-46 | 80 | 90 |
| 6-33 | 80 | 100 |
| 1-30 | 80 | 80 |
| 2-30 | 80 | 100 |
| 1-31 | 80 | 100 |
| 2-31 | 80 | 100 |
| 1-28 | 80 | 100 |
| 2-28 | 80 | 100 |
| 1-29 | 80 | 90 |
| 2-29 | 80 | 100 |
| 1-304 | 80 | 100 |
| 2-304 | 80 | 90 |
| 1-305 | 80 | 100 |
| 2-305 | 80 | 100 |
| 1-306 | 80 | 100 |
| 2-306 | 80 | 100 |
| 1-177 | 80 | 100 |
| 2-177 | 80 | 90 |
| 1-178 | 80 | 100 |
| 2-178 | 80 | 100 |
| 6-141 | 80 | 90 |
| 1-179 | 80 | 100 |
| 2-179 | 80 | 100 |
| 1-132 | 80 | 100 |
| 2-132 | 80 | 100 |
| 1-135 | 80 | 100 |

TABLE 6b-continued

| Pre-emergence action at 80 g/ha against ECHCG in % | | |
|---|---|---|
| Example number | Dosage [g/ha] | ECHCG |
| 2-135 | 80 | 100 |
| 6-254 | 80 | 100 |
| 1-134 | 80 | 100 |
| 2-134 | 80 | 100 |
| 1-133 | 80 | 100 |
| 2-133 | 80 | 100 |
| 6-120 | 80 | 100 |
| 1-277 | 80 | 90 |
| 2-277 | 80 | 90 |
| 1-278 | 80 | 100 |
| 2-278 | 80 | 100 |
| 1-279 | 80 | 100 |
| 2-279 | 80 | 100 |
| 2-195 | 80 | 80 |
| 2-225 | 80 | 90 |
| 1-197 | 80 | 90 |
| 2-227 | 80 | 100 |
| 1-227 | 80 | 90 |
| 2-197 | 80 | 100 |
| 1-225 | 80 | 100 |
| 1-226 | 80 | 100 |
| 2-226 | 80 | 100 |
| 6-165 | 80 | 100 |
| 6-166 | 80 | 80 |
| 1-56 | 80 | 90 |
| 6-45 | 80 | 80 |
| 6-44 | 80 | 100 |
| 2-57 | 80 | 100 |
| 6-43 | 80 | 100 |
| 1-58 | 80 | 100 |
| 2-58 | 80 | 100 |
| 2-56 | 80 | 90 |
| 1-57 | 80 | 90 |
| 1-207 | 80 | 90 |
| 2-207 | 80 | 100 |
| 2-271 | 80 | 100 |
| 6-210 | 80 | 90 |
| 2-32 | 80 | 100 |
| 1-34 | 80 | 90 |
| 2-34 | 80 | 90 |
| 6-255 | 80 | 100 |
| 2-33 | 80 | 100 |
| 2-42 | 80 | 100 |
| 6-256 | 80 | 100 |
| 1-146 | 80 | 100 |
| 1-141 | 80 | 90 |
| 1-37 | 80 | 80 |
| 2-37 | 80 | 80 |
| 1-72 | 80 | 80 |
| 2-72 | 80 | 100 |
| 1-73 | 80 | 100 |
| 2-73 | 80 | 100 |
| 1-74 | 80 | 100 |
| 2-74 | 80 | 100 |
| 1-144 | 80 | 100 |
| 2-144 | 80 | 80 |
| 1-138 | 80 | 100 |
| 2-138 | 80 | 90 |
| 2-141 | 80 | 80 |
| 1-137 | 80 | 100 |
| 1-136 | 80 | 90 |
| 1-180 | 80 | 100 |
| 2-180 | 80 | 100 |
| 1-183 | 80 | 100 |
| 2-183 | 80 | 90 |
| 6-257 | 80 | 80 |
| 1-182 | 80 | 100 |
| 2-182 | 80 | 100 |
| 6-145 | 80 | 90 |
| 1-181 | 80 | 100 |
| 2-181 | 80 | 100 |
| 6-144 | 80 | 100 |
| 1-228 | 80 | 100 |
| 2-228 | 80 | 100 |
| 6-167 | 80 | 100 |
| 1-230 | 80 | 90 |

TABLE 6b-continued

| Pre-emergence action at 80 g/ha against ECHCG in % | | |
|---|---|---|
| Example number | Dosage [g/ha] | ECHCG |
| 2-230 | 80 | 90 |
| 6-169 | 80 | 90 |
| 2-286 | 80 | 90 |
| 1-287 | 80 | 90 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 90 |
| 2-213 | 80 | 90 |
| 1-288 | 80 | 100 |
| 1-289 | 80 | 100 |
| 2-289 | 80 | 100 |
| 6-228 | 80 | 90 |
| 1-291 | 80 | 90 |
| 2-291 | 80 | 90 |
| 6-230 | 80 | 80 |
| 2-292 | 80 | 100 |
| 1-271 | 80 | 100 |
| 2-47 | 80 | 100 |
| 6-34 | 80 | 100 |
| 1-339 | 80 | 100 |
| 2-339 | 80 | 100 |
| 6-258 | 80 | 100 |
| 1-49 | 80 | 80 |
| 2-49 | 80 | 90 |
| 1-229 | 80 | 80 |
| 2-229 | 80 | 80 |
| 1-340 | 80 | 100 |
| 6-267 | 80 | 80 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 100 |
| 1-155 | 80 | 100 |
| 2-155 | 80 | 100 |
| 6-260 | 80 | 100 |
| 1-164 | 80 | 100 |
| 2-164 | 80 | 80 |
| 6-261 | 80 | 100 |
| 1-165 | 80 | 100 |
| 1-166 | 80 | 100 |
| 1-156 | 80 | 100 |
| 2-156 | 80 | 100 |
| 6-262 | 80 | 90 |
| 1-159 | 80 | 90 |
| 2-159 | 80 | 90 |
| 1-162 | 80 | 100 |
| 2-162 | 80 | 80 |
| 2-211 | 80 | 90 |
| 2-272 | 80 | 100 |
| 2-276 | 80 | 80 |
| 1-276 | 80 | 100 |
| 1-211 | 80 | 100 |
| 1-274 | 80 | 100 |
| 6-168 | 80 | 90 |
| 1-272 | 80 | 100 |
| 6-211 | 80 | 100 |
| 1-341 | 80 | 90 |
| 1-292 | 80 | 90 |
| 2-341 | 80 | 100 |
| 1-83 | 80 | 90 |
| 2-83 | 80 | 90 |
| 6-60 | 80 | 80 |
| 1-89 | 80 | 100 |
| 2-89 | 80 | 90 |
| 6-161 | 80 | 100 |
| 1-342 | 80 | 100 |
| 1-343 | 80 | 90 |
| 2-342 | 80 | 80 |
| 1-344 | 80 | 90 |
| 2-343 | 80 | 90 |
| 1-345 | 80 | 100 |

TABLE 6b-continued

| Pre-emergence action at 80 g/ha against ECHCG in % | | |
|---|---|---|
| Example number | Dosage [g/ha] | ECHCG |
| 2-344 | 80 | 100 |
| 1-346 | 80 | 90 |
| 2-345 | 80 | 90 |
| 2-346 | 80 | 90 |
| 1-195 | 80 | 100 |
| 1-184 | 80 | 100 |
| 2-184 | 80 | 100 |
| 1-185 | 80 | 100 |
| 2-185 | 80 | 90 |
| 1-186 | 80 | 80 |
| 2-186 | 80 | 100 |
| 1-349 | 80 | 90 |
| 1-350 | 80 | 100 |
| 2-348 | 80 | 100 |
| 1-351 | 80 | 100 |
| 2-349 | 80 | 90 |
| 1-84 | 80 | 100 |
| 2-84 | 80 | 100 |
| 1-352 | 80 | 100 |
| 2-350 | 80 | 100 |
| 1-86 | 80 | 100 |
| 2-86 | 80 | 100 |
| 1-92 | 80 | 100 |
| 2-92 | 80 | 100 |
| 1-90 | 80 | 100 |
| 2-90 | 80 | 100 |
| 1-353 | 80 | 100 |
| 2-351 | 80 | 100 |
| 2-352 | 80 | 80 |

TABLE 6c

| Pre-emergence action at 320 g/ha against ECHCG in % | | |
|---|---|---|
| Example number | Dosage [g/ha] | ECHCG |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 100 |
| 2-337 | 320 | 100 |
| 6-252 | 320 | 90 |
| 6-117 | 320 | 100 |
| 1-81 | 320 | 100 |
| 2-81 | 320 | 100 |
| 2-82 | 320 | 100 |
| 6-58 | 320 | 100 |
| 1-147 | 320 | 100 |
| 2-147 | 320 | 100 |
| 1-148 | 320 | 100 |
| 2-148 | 320 | 100 |

TABLE 7a

| Pre-emergence action at 20 g/ha against HORMU in % | | |
|---|---|---|
| Example number | Dosage [g/ha] | HORMU |
| 2-337 | 20 | 90 |
| 2-130 | 20 | 90 |

TABLE 7b

| Pre-emergence action at 80 g/ha against HORMU in % | | |
|---|---|---|
| Example number | Dosage [g/ha] | HORMU |
| 3-129 | 80 | 90 |
| 2-129 | 80 | 90 |
| 1-129 | 80 | 90 |
| 6-116 | 80 | 90 |
| 2-338 | 80 | 80 |
| 3-338 | 80 | 80 |
| 2-337 | 80 | 90 |
| 3-337 | 80 | 100 |
| 1-26 | 80 | 80 |
| 2-26 | 80 | 90 |
| 3-26 | 80 | 80 |
| 6-26 | 80 | 80 |
| 1-208 | 80 | 80 |
| 2-208 | 80 | 90 |
| 6-159 | 80 | 80 |
| 1-130 | 80 | 90 |
| 2-130 | 80 | 100 |
| 1-81 | 80 | 80 |
| 2-81 | 80 | 90 |
| 2-82 | 80 | 80 |
| 1-147 | 80 | 90 |
| 2-147 | 80 | 90 |
| 1-148 | 80 | 90 |
| 2-148 | 80 | 90 |
| 1-131 | 80 | 80 |
| 2-131 | 80 | 80 |
| 1-149 | 80 | 90 |
| 2-149 | 80 | 90 |
| 6-124 | 80 | 80 |
| 5-117 | 80 | 80 |
| 2-87 | 80 | 80 |
| 2-88 | 80 | 80 |
| 1-209 | 80 | 80 |
| 1-4 | 80 | 80 |
| 2-25 | 80 | 90 |
| 1-27 | 80 | 80 |
| 2-27 | 80 | 90 |
| 1-173 | 80 | 90 |
| 2-173 | 80 | 100 |
| 1-273 | 80 | 80 |
| 2-273 | 80 | 80 |
| 2-46 | 80 | 90 |

TABLE 7c

| Pre-emergence action at 320 g/ha against HORMU in % | | |
|---|---|---|
| Example number | Dosage [g/ha] | HORMU |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 90 |
| 2-337 | 320 | 100 |
| 6-117 | 320 | 100 |
| 1-81 | 320 | 100 |
| 2-81 | 320 | 100 |
| 2-82 | 320 | 100 |
| 6-58 | 320 | 90 |
| 1-147 | 320 | 100 |
| 2-147 | 320 | 100 |
| 1-148 | 320 | 100 |
| 2-148 | 320 | 100 |

TABLE 8a

| Pre-emergence action at 20 g/ha against LOLRI in % | | |
|---|---|---|
| Example number | Dosage [g/ha] | LOLRI |
| 1-173 | 20 | 80 |
| 1-164 | 20 | 100 |

TABLE 8b

| Pre-emergence action at 80 g/ha against LOLRI in % | | |
|---|---|---|
| Example number | Dosage [g/ha] | LOLRI |
| 1-129 | 80 | 90 |
| 2-337 | 80 | 80 |
| 1-26 | 80 | 80 |
| 2-208 | 80 | 80 |
| 1-130 | 80 | 100 |
| 2-130 | 80 | 100 |
| 1-131 | 80 | 80 |
| 1-149 | 80 | 90 |
| 2-149 | 80 | 90 |
| 5-117 | 80 | 80 |
| 1-82 | 80 | 80 |
| 1-87 | 80 | 80 |
| 2-87 | 80 | 80 |
| 2-88 | 80 | 80 |
| 1-25 | 80 | 80 |
| 2-25 | 80 | 80 |
| 1-27 | 80 | 80 |
| 2-27 | 80 | 80 |
| 1-173 | 80 | 90 |
| 2-173 | 80 | 90 |
| 1-273 | 80 | 80 |
| 2-273 | 80 | 80 |
| 1-45 | 80 | 80 |
| 2-45 | 80 | 80 |
| 1-46 | 80 | 90 |
| 2-46 | 80 | 90 |
| 1-177 | 80 | 90 |
| 2-177 | 80 | 90 |
| 1-178 | 80 | 80 |
| 2-178 | 80 | 80 |
| 1-179 | 80 | 90 |
| 2-179 | 80 | 80 |
| 1-132 | 80 | 80 |
| 2-132 | 80 | 90 |
| 2-135 | 80 | 80 |
| 1-134 | 80 | 80 |
| 2-134 | 80 | 80 |
| 2-133 | 80 | 80 |
| 2-279 | 80 | 80 |
| 2-195 | 80 | 90 |
| 1-197 | 80 | 80 |
| 1-227 | 80 | 90 |
| 2-197 | 80 | 90 |
| 1-225 | 80 | 80 |
| 2-196 | 80 | 100 |
| 2-32 | 80 | 90 |
| 1-34 | 80 | 80 |
| 6-255 | 80 | 80 |
| 2-33 | 80 | 80 |
| 2-42 | 80 | 80 |
| 1-138 | 80 | 90 |
| 1-137 | 80 | 90 |
| 1-136 | 80 | 90 |
| 1-182 | 80 | 80 |
| 2-182 | 80 | 80 |
| 1-181 | 80 | 80 |
| 2-288 | 80 | 90 |
| 1-212 | 80 | 80 |
| 2-212 | 80 | 90 |
| 1-288 | 80 | 80 |
| 1-289 | 80 | 80 |
| 1-271 | 80 | 100 |
| 2-47 | 80 | 80 |
| 1-339 | 80 | 100 |

TABLE 8b-continued

| Pre-emergence action at 80 g/ha against LOLRI in % | | |
|---|---|---|
| Example number | Dosage [g/ha] | LOLRI |
| 2-339 | 80 | 80 |
| 1-47 | 80 | 80 |
| 1-33 | 80 | 80 |
| 1-32 | 80 | 90 |
| 2-154 | 80 | 90 |
| 1-155 | 80 | 90 |
| 2-155 | 80 | 80 |
| 1-164 | 80 | 100 |
| 1-165 | 80 | 80 |
| 1-166 | 80 | 80 |
| 1-159 | 80 | 80 |
| 2-276 | 80 | 80 |
| 1-272 | 80 | 80 |
| 1-83 | 80 | 80 |
| 1-343 | 80 | 80 |
| 2-342 | 80 | 80 |
| 1-344 | 80 | 90 |
| 2-343 | 80 | 90 |
| 1-345 | 80 | 80 |
| 1-195 | 80 | 80 |
| 2-184 | 80 | 80 |
| 1-185 | 80 | 90 |
| 1-349 | 80 | 90 |
| 1-92 | 80 | 90 |

TABLE 8c

| Pre-emergence action at 320 g/ha against LOLRI in % | | |
|---|---|---|
| Example number | Dosage [g/ha] | LOLRI |
| 3-129 | 320 | 100 |
| 2-129 | 320 | 100 |
| 1-129 | 320 | 100 |
| 6-116 | 320 | 100 |
| 1-338 | 320 | 90 |
| 2-338 | 320 | 100 |
| 2-337 | 320 | 90 |
| 1-81 | 320 | 80 |
| 2-81 | 320 | 90 |
| 2-82 | 320 | 90 |
| 1-147 | 320 | 100 |
| 2-147 | 320 | 90 |
| 1-148 | 320 | 90 |
| 2-148 | 320 | 90 |

TABLE 9a

| Pre-emergence action at 20 g/ha against MATIN in % | | |
|---|---|---|
| Example number | Dosage [g/ha] | MATIN |
| 3-129 | 20 | 90 |
| 2-129 | 20 | 100 |
| 1-129 | 20 | 100 |
| 6-116 | 20 | 90 |
| 2-337 | 20 | 80 |
| 1-123 | 20 | 80 |
| 2-123 | 20 | 80 |
| 1-26 | 20 | 100 |
| 2-26 | 20 | 100 |
| 3-26 | 20 | 90 |
| 6-26 | 20 | 80 |
| 1-208 | 20 | 90 |
| 2-208 | 20 | 100 |
| 3-208 | 20 | 100 |
| 6-159 | 20 | 100 |
| 1-125 | 20 | 80 |
| 2-125 | 20 | 80 |
| 3-125 | 20 | 100 |
| 1-130 | 20 | 100 |

TABLE 9a-continued

| Pre-emergence action at 20 g/ha against MATIN in % | | |
|---|---|---|
| Example number | Dosage [g/ha] | MATIN |
| 2-130 | 20 | 100 |
| 1-131 | 20 | 100 |
| 2-131 | 20 | 90 |
| 6-118 | 20 | 90 |
| 1-149 | 20 | 100 |
| 2-149 | 20 | 90 |
| 6-124 | 20 | 90 |
| 5-59 | 20 | 80 |
| 5-58 | 20 | 90 |
| 5-117 | 20 | 90 |
| 5-75 | 20 | 80 |
| 5-74 | 20 | 80 |
| 1-82 | 20 | 100 |
| 1-87 | 20 | 80 |
| 2-87 | 20 | 90 |
| 1-88 | 20 | 100 |
| 2-88 | 20 | 100 |
| 1-209 | 20 | 80 |
| 1-25 | 20 | 90 |
| 2-25 | 20 | 100 |
| 3-27 | 20 | 100 |
| 1-27 | 20 | 100 |
| 2-27 | 20 | 100 |
| 1-173 | 20 | 80 |
| 2-173 | 20 | 100 |
| 1-273 | 20 | 100 |
| 2-273 | 20 | 100 |
| 3-273 | 20 | 90 |
| 6-212 | 20 | 80 |
| 4-212 | 20 | 80 |
| 1-44 | 20 | 90 |
| 2-44 | 20 | 90 |
| 1-45 | 20 | 100 |
| 2-45 | 20 | 90 |
| 1-46 | 20 | 90 |
| 2-46 | 20 | 90 |
| 6-33 | 20 | 80 |
| 1-30 | 20 | 100 |
| 2-30 | 20 | 100 |
| 1-31 | 20 | 100 |
| 2-31 | 20 | 100 |
| 1-28 | 20 | 100 |
| 2-28 | 20 | 100 |
| 1-29 | 20 | 100 |
| 2-29 | 20 | 100 |
| 1-304 | 20 | 90 |
| 2-304 | 20 | 90 |
| 1-305 | 20 | 100 |
| 2-305 | 20 | 100 |
| 1-306 | 20 | 100 |
| 2-306 | 20 | 90 |
| 1-177 | 20 | 90 |
| 2-177 | 20 | 90 |
| 1-178 | 20 | 90 |
| 2-178 | 20 | 90 |
| 1-179 | 20 | 90 |
| 2-179 | 20 | 100 |
| 1-132 | 20 | 100 |
| 2-132 | 20 | 100 |
| 1-135 | 20 | 90 |
| 2-135 | 20 | 90 |
| 6-254 | 20 | 80 |
| 1-134 | 20 | 90 |
| 2-134 | 20 | 90 |
| 1-133 | 20 | 90 |
| 2-133 | 20 | 90 |
| 6-120 | 20 | 90 |
| 1-277 | 20 | 90 |
| 2-277 | 20 | 90 |
| 1-278 | 20 | 100 |
| 2-278 | 20 | 100 |
| 1-279 | 20 | 100 |
| 2-279 | 20 | 90 |
| 2-195 | 20 | 100 |
| 2-225 | 20 | 80 |
| 1-197 | 20 | 90 |

TABLE 9a-continued

| Pre-emergence action at 20 g/ha against MATIN in % | | |
|---|---|---|
| Example number | Dosage [g/ha] | MATIN |
| 2-227 | 20 | 100 |
| 1-227 | 20 | 80 |
| 2-197 | 20 | 80 |
| 1-225 | 20 | 90 |
| 1-226 | 20 | 100 |
| 2-226 | 20 | 90 |
| 6-165 | 20 | 80 |
| 2-196 | 20 | 100 |
| 1-56 | 20 | 90 |
| 2-57 | 20 | 90 |
| 1-58 | 20 | 90 |
| 2-58 | 20 | 100 |
| 2-56 | 20 | 90 |
| 1-57 | 20 | 90 |
| 1-207 | 20 | 90 |
| 2-207 | 20 | 90 |
| 2-271 | 20 | 100 |
| 6-210 | 20 | 80 |
| 2-32 | 20 | 100 |
| 2-34 | 20 | 90 |
| 2-33 | 20 | 100 |
| 2-42 | 20 | 100 |
| 2-146 | 20 | 100 |
| 2-142 | 20 | 80 |
| 1-143 | 20 | 80 |
| 5-255 | 20 | 80 |
| 1-146 | 20 | 100 |
| 2-143 | 20 | 90 |
| 1-72 | 20 | 80 |
| 2-72 | 20 | 100 |
| 1-73 | 20 | 90 |
| 2-73 | 20 | 100 |
| 1-74 | 20 | 100 |
| 2-74 | 20 | 100 |
| 1-144 | 20 | 90 |
| 1-138 | 20 | 90 |
| 2-138 | 20 | 90 |
| 2-141 | 20 | 80 |
| 1-137 | 20 | 100 |
| 1-136 | 20 | 90 |
| 1-180 | 20 | 90 |
| 2-180 | 20 | 100 |
| 1-183 | 20 | 90 |
| 2-183 | 20 | 90 |
| 6-257 | 20 | 80 |
| 1-182 | 20 | 90 |
| 2-182 | 20 | 90 |
| 1-181 | 20 | 90 |
| 2-181 | 20 | 90 |
| 1-228 | 20 | 80 |
| 2-228 | 20 | 90 |
| 1-230 | 20 | 90 |
| 2-230 | 20 | 90 |
| 2-286 | 20 | 100 |
| 1-287 | 20 | 100 |
| 2-287 | 20 | 100 |
| 2-288 | 20 | 90 |
| 1-210 | 20 | 100 |
| 2-210 | 20 | 100 |
| 1-212 | 20 | 90 |
| 2-213 | 20 | 100 |
| 1-288 | 20 | 100 |
| 1-289 | 20 | 90 |
| 2-289 | 20 | 90 |
| 1-291 | 20 | 90 |
| 2-291 | 20 | 90 |
| 2-292 | 20 | 90 |
| 1-271 | 20 | 100 |
| 2-47 | 20 | 100 |
| 2-339 | 20 | 100 |
| 1-49 | 20 | 90 |
| 2-49 | 20 | 100 |
| 1-229 | 20 | 100 |
| 2-229 | 20 | 100 |
| 1-340 | 20 | 100 |
| 6-267 | 20 | 90 |

TABLE 9a-continued

| Pre-emergence action at 20 g/ha against MATIN in % | | |
|---|---|---|
| Example number | Dosage [g/ha] | MATIN |
| 2-340 | 20 | 100 |
| 1-47 | 20 | 80 |
| 1-33 | 20 | 100 |
| 1-32 | 20 | 100 |
| 2-154 | 20 | 100 |
| 6-259 | 20 | 90 |
| 1-155 | 20 | 100 |
| 2-155 | 20 | 100 |
| 6-260 | 20 | 100 |
| 2-164 | 20 | 100 |
| 6-261 | 20 | 90 |
| 1-165 | 20 | 100 |
| 1-166 | 20 | 100 |
| 1-156 | 20 | 90 |
| 2-156 | 20 | 100 |
| 2-161 | 20 | 80 |
| 2-211 | 20 | 90 |
| 2-272 | 20 | 100 |
| 1-161 | 20 | 90 |
| 2-276 | 20 | 100 |
| 1-276 | 20 | 90 |
| 1-211 | 20 | 90 |
| 1-274 | 20 | 100 |
| 6-168 | 20 | 80 |
| 1-272 | 20 | 90 |
| 1-341 | 20 | 100 |
| 1-292 | 20 | 100 |
| 2-341 | 20 | 100 |
| 1-83 | 20 | 90 |
| 2-83 | 20 | 100 |
| 1-89 | 20 | 90 |
| 2-89 | 20 | 90 |
| 6-161 | 20 | 100 |
| 1-342 | 20 | 80 |
| 2-342 | 20 | 90 |
| 1-344 | 20 | 90 |
| 2-343 | 20 | 80 |
| 1-345 | 20 | 100 |
| 2-344 | 20 | 100 |
| 1-346 | 20 | 90 |
| 2-345 | 20 | 100 |
| 2-346 | 20 | 90 |
| 1-195 | 20 | 90 |
| 1-184 | 20 | 80 |
| 2-184 | 20 | 90 |
| 1-185 | 20 | 100 |
| 2-185 | 20 | 100 |
| 2-186 | 20 | 80 |
| 2-348 | 20 | 90 |
| 2-349 | 20 | 90 |
| 1-84 | 20 | 100 |
| 2-84 | 20 | 100 |
| 1-352 | 20 | 100 |
| 2-350 | 20 | 100 |
| 1-86 | 20 | 100 |
| 2-86 | 20 | 100 |
| 1-92 | 20 | 100 |
| 2-92 | 20 | 100 |
| 1-90 | 20 | 100 |
| 2-90 | 20 | 100 |
| 1-353 | 20 | 100 |
| 2-351 | 20 | 100 |
| 1-354 | 20 | 80 |
| 2-352 | 20 | 90 |
| 1-355 | 20 | 80 |
| 2-353 | 20 | 90 |
| 2-354 | 20 | 100 |

TABLE 9b

| Pre-emergence action at 80 g/ha against MATIN in % | | |
|---|---|---|
| Example number | Dosage [g/ha] | MATIN |
| 3-129 | 80 | 100 |
| 2-129 | 80 | 100 |
| 1-129 | 80 | 100 |
| 6-116 | 80 | 90 |
| 1-338 | 80 | 80 |
| 2-338 | 80 | 90 |
| 3-338 | 80 | 90 |
| 2-337 | 80 | 100 |
| 3-337 | 80 | 100 |
| 1-123 | 80 | 100 |
| 2-123 | 80 | 100 |
| 1-26 | 80 | 100 |
| 2-26 | 80 | 100 |
| 3-26 | 80 | 100 |
| 6-26 | 80 | 90 |
| 1-208 | 80 | 100 |
| 2-208 | 80 | 100 |
| 3-208 | 80 | 100 |
| 6-159 | 80 | 100 |
| 1-125 | 80 | 100 |
| 2-125 | 80 | 100 |
| 3-125 | 80 | 100 |
| 1-130 | 80 | 100 |
| 2-130 | 80 | 100 |
| 6-117 | 80 | 100 |
| 1-81 | 80 | 100 |
| 2-81 | 80 | 100 |
| 2-82 | 80 | 100 |
| 6-58 | 80 | 80 |
| 1-147 | 80 | 90 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 100 |
| 1-149 | 80 | 100 |
| 2-149 | 80 | 100 |
| 6-124 | 80 | 100 |
| 5-59 | 80 | 90 |
| 5-58 | 80 | 100 |
| 5-117 | 80 | 100 |
| 5-75 | 80 | 100 |
| 5-74 | 80 | 90 |
| 5-122 | 80 | 90 |
| 1-82 | 80 | 100 |
| 1-87 | 80 | 90 |
| 2-87 | 80 | 90 |
| 1-88 | 80 | 100 |
| 2-88 | 80 | 100 |
| 1-209 | 80 | 100 |
| 1-4 | 80 | 100 |
| 1-25 | 80 | 100 |
| 2-25 | 80 | 100 |
| 3-27 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 100 |
| 3-273 | 80 | 100 |
| 6-212 | 80 | 90 |
| 4-212 | 80 | 80 |
| 4-212 | 80 | 90 |
| 1-44 | 80 | 90 |
| 2-44 | 80 | 100 |
| 1-45 | 80 | 100 |
| 2-45 | 80 | 100 |
| 6-32 | 80 | 90 |
| 1-46 | 80 | 100 |
| 2-46 | 80 | 100 |
| 6-33 | 80 | 90 |
| 1-30 | 80 | 100 |
| 2-30 | 80 | 100 |
| 1-31 | 80 | 100 |

TABLE 9b-continued

| Pre-emergence action at 80 g/ha against MATIN in % | | |
|---|---|---|
| Example number | Dosage [g/ha] | MATIN |
| 2-31 | 80 | 100 |
| 1-28 | 80 | 100 |
| 2-28 | 80 | 100 |
| 1-29 | 80 | 100 |
| 2-29 | 80 | 100 |
| 1-304 | 80 | 100 |
| 2-304 | 80 | 100 |
| 6-231 | 80 | 80 |
| 1-305 | 80 | 100 |
| 2-305 | 80 | 100 |
| 1-306 | 80 | 100 |
| 2-306 | 80 | 100 |
| 1-177 | 80 | 100 |
| 2-177 | 80 | 100 |
| 1-178 | 80 | 100 |
| 2-178 | 80 | 100 |
| 6-141 | 80 | 80 |
| 1-179 | 80 | 100 |
| 2-179 | 80 | 100 |
| 1-132 | 80 | 100 |
| 2-132 | 80 | 100 |
| 1-135 | 80 | 100 |
| 2-135 | 80 | 100 |
| 6-254 | 80 | 100 |
| 1-134 | 80 | 100 |
| 2-134 | 80 | 100 |
| 1-133 | 80 | 100 |
| 2-133 | 80 | 100 |
| 6-120 | 80 | 90 |
| 1-277 | 80 | 100 |
| 2-277 | 80 | 100 |
| 1-278 | 80 | 100 |
| 2-278 | 80 | 100 |
| 1-279 | 80 | 100 |
| 2-279 | 80 | 100 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 100 |
| 1-225 | 80 | 100 |
| 1-226 | 80 | 100 |
| 2-226 | 80 | 100 |
| 6-165 | 80 | 100 |
| 6-166 | 80 | 100 |
| 2-196 | 80 | 100 |
| 1-56 | 80 | 90 |
| 6-45 | 80 | 90 |
| 6-44 | 80 | 80 |
| 2-57 | 80 | 100 |
| 6-43 | 80 | 80 |
| 1-58 | 80 | 100 |
| 2-58 | 80 | 100 |
| 2-56 | 80 | 100 |
| 1-57 | 80 | 100 |
| 1-207 | 80 | 100 |
| 2-207 | 80 | 100 |
| 2-271 | 80 | 100 |
| 6-210 | 80 | 90 |
| 2-32 | 80 | 100 |
| 1-34 | 80 | 90 |
| 2-34 | 80 | 100 |
| 6-255 | 80 | 100 |
| 2-33 | 80 | 100 |
| 2-42 | 80 | 100 |
| 6-256 | 80 | 90 |
| 2-146 | 80 | 100 |
| 2-142 | 80 | 100 |
| 1-143 | 80 | 100 |
| 5-255 | 80 | 100 |
| 1-142 | 80 | 90 |
| 1-146 | 80 | 100 |
| 1-141 | 80 | 100 |
| 1-37 | 80 | 90 |
| 2-143 | 80 | 100 |

TABLE 9b-continued

| Pre-emergence action at 80 g/ha against MATIN in % | | |
|---|---|---|
| Example number | Dosage [g/ha] | MATIN |
| 1-72 | 80 | 100 |
| 2-72 | 80 | 100 |
| 1-73 | 80 | 100 |
| 2-73 | 80 | 100 |
| 6-50 | 80 | 80 |
| 1-74 | 80 | 100 |
| 2-74 | 80 | 100 |
| 2-35 | 80 | 80 |
| 1-144 | 80 | 90 |
| 2-144 | 80 | 90 |
| 1-138 | 80 | 100 |
| 2-138 | 80 | 100 |
| 2-141 | 80 | 90 |
| 1-137 | 80 | 100 |
| 1-136 | 80 | 100 |
| 1-180 | 80 | 100 |
| 2-180 | 80 | 100 |
| 1-183 | 80 | 100 |
| 2-183 | 80 | 100 |
| 6-257 | 80 | 90 |
| 1-182 | 80 | 100 |
| 2-182 | 80 | 100 |
| 1-181 | 80 | 100 |
| 2-181 | 80 | 100 |
| 6-144 | 80 | 80 |
| 2-36 | 80 | 90 |
| 1-228 | 80 | 100 |
| 2-228 | 80 | 100 |
| 6-167 | 80 | 90 |
| 1-230 | 80 | 100 |
| 2-230 | 80 | 100 |
| 6-169 | 80 | 80 |
| 2-286 | 80 | 100 |
| 1-287 | 80 | 100 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 100 |
| 2-213 | 80 | 100 |
| 1-288 | 80 | 100 |
| 1-289 | 80 | 100 |
| 2-289 | 80 | 100 |
| 6-228 | 80 | 80 |
| 1-291 | 80 | 100 |
| 2-291 | 80 | 100 |
| 6-230 | 80 | 80 |
| 2-292 | 80 | 100 |
| 1-271 | 80 | 100 |
| 2-47 | 80 | 100 |
| 6-34 | 80 | 90 |
| 1-339 | 80 | 100 |
| 2-339 | 80 | 100 |
| 6-258 | 80 | 90 |
| 1-49 | 80 | 100 |
| 2-49 | 80 | 100 |
| 1-41 | 80 | 100 |
| 1-229 | 80 | 100 |
| 2-229 | 80 | 100 |
| 1-340 | 80 | 100 |
| 6-267 | 80 | 100 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 100 |
| 1-155 | 80 | 100 |
| 2-155 | 80 | 100 |
| 6-260 | 80 | 100 |
| 1-164 | 80 | 100 |
| 2-164 | 80 | 100 |
| 6-261 | 80 | 100 |
| 1-165 | 80 | 100 |
| 1-166 | 80 | 100 |

TABLE 9b-continued

| Pre-emergence action at 80 g/ha against MATIN in % | | |
|---|---|---|
| Example number | Dosage [g/ha] | MATIN |
| 1-156 | 80 | 100 |
| 2-156 | 80 | 100 |
| 6-262 | 80 | 100 |
| 1-159 | 80 | 90 |
| 2-159 | 80 | 90 |
| 1-162 | 80 | 90 |
| 2-162 | 80 | 90 |
| 1-160 | 80 | 80 |
| 2-160 | 80 | 90 |
| 2-161 | 80 | 90 |
| 6-266 | 80 | 80 |
| 2-211 | 80 | 100 |
| 2-272 | 80 | 100 |
| 1-161 | 80 | 100 |
| 2-276 | 80 | 100 |
| 1-276 | 80 | 100 |
| 1-211 | 80 | 100 |
| 1-274 | 80 | 100 |
| 6-168 | 80 | 90 |
| 1-272 | 80 | 100 |
| 6-211 | 80 | 90 |
| 1-341 | 80 | 100 |
| 1-292 | 80 | 100 |
| 2-341 | 80 | 100 |
| 2-158 | 80 | 90 |
| 1-83 | 80 | 100 |
| 2-83 | 80 | 100 |
| 6-60 | 80 | 90 |
| 1-89 | 80 | 100 |
| 2-89 | 80 | 100 |
| 6-76 | 80 | 90 |
| 6-161 | 80 | 100 |
| 1-342 | 80 | 100 |
| 1-343 | 80 | 100 |
| 2-342 | 80 | 100 |
| 1-344 | 80 | 100 |
| 2-343 | 80 | 100 |
| 1-345 | 80 | 100 |
| 2-344 | 80 | 100 |
| 1-346 | 80 | 100 |
| 2-345 | 80 | 100 |
| 1-347 | 80 | 90 |
| 2-346 | 80 | 90 |
| 1-195 | 80 | 100 |
| 1-184 | 80 | 100 |
| 2-184 | 80 | 100 |
| 1-185 | 80 | 100 |
| 2-185 | 80 | 100 |
| 1-186 | 80 | 90 |
| 2-186 | 80 | 100 |
| 1-349 | 80 | 90 |
| 1-350 | 80 | 90 |
| 2-348 | 80 | 90 |
| 1-351 | 80 | 100 |
| 2-349 | 80 | 100 |
| 1-84 | 80 | 100 |
| 2-84 | 80 | 100 |
| 1-352 | 80 | 100 |
| 2-350 | 80 | 100 |
| 1-86 | 80 | 100 |
| 2-86 | 80 | 100 |
| 1-92 | 80 | 100 |
| 2-92 | 80 | 100 |
| 1-90 | 80 | 100 |
| 2-90 | 80 | 100 |
| 1-353 | 80 | 100 |
| 2-351 | 80 | 100 |
| 1-354 | 80 | 80 |
| 2-352 | 80 | 90 |
| 1-355 | 80 | 100 |
| 2-353 | 80 | 100 |
| 1-356 | 80 | 100 |
| 2-354 | 80 | 100 |

TABLE 9c

| Pre-emergence action at 320 g/ha against MATIN in % | | |
|---|---|---|
| Example number | Dosage [g/ha] | MATIN |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 100 |
| 2-337 | 320 | 100 |
| 6-117 | 320 | 100 |
| 1-81 | 320 | 100 |
| 2-81 | 320 | 100 |
| 2-82 | 320 | 100 |
| 6-58 | 320 | 100 |
| 1-147 | 320 | 100 |
| 2-147 | 320 | 100 |
| 1-148 | 320 | 100 |
| 2-148 | 320 | 100 |

TABLE 10a

| Pre-emergence action at 20 g/ha against PHBPU in % | | |
|---|---|---|
| Example number | Dosage [g/ha] | PHBPU |
| 3-129 | 20 | 80 |
| 2-26 | 20 | 90 |
| 2-27 | 20 | 80 |
| 2-134 | 20 | 80 |
| 1-277 | 20 | 80 |
| 2-279 | 20 | 80 |
| 2-197 | 20 | 80 |
| 2-196 | 20 | 80 |
| 1-56 | 20 | 80 |
| 1-57 | 20 | 80 |
| 2-33 | 20 | 80 |
| 2-42 | 20 | 80 |
| 1-138 | 20 | 80 |
| 1-137 | 20 | 80 |
| 2-287 | 20 | 80 |
| 2-210 | 20 | 80 |
| 1-212 | 20 | 80 |
| 2-213 | 20 | 80 |
| 2-291 | 20 | 80 |
| 2-292 | 20 | 80 |
| 1-271 | 20 | 80 |
| 1-339 | 20 | 100 |
| 2-154 | 20 | 80 |
| 2-86 | 20 | 80 |

TABLE 10b

| Pre-emergence action at 80 g/ha against PHBPU in % | | |
|---|---|---|
| Example number | Dosage [g/ha] | PHBPU |
| 3-129 | 80 | 90 |
| 2-129 | 80 | 90 |
| 1-129 | 80 | 90 |
| 3-337 | 80 | 90 |
| 2-26 | 80 | 100 |
| 2-131 | 80 | 80 |
| 2-149 | 80 | 80 |
| 5-59 | 80 | 80 |
| 5-117 | 80 | 100 |
| 1-82 | 80 | 80 |
| 1-87 | 80 | 80 |
| 2-87 | 80 | 80 |
| 1-88 | 80 | 90 |

TABLE 10b-continued

| Pre-emergence action at 80 g/ha against PHBPU in % | | |
|---|---|---|
| Example number | Dosage [g/ha] | PHBPU |
| 2-88 | 80 | 90 |
| 1-209 | 80 | 80 |
| 1-25 | 80 | 90 |
| 2-25 | 80 | 80 |
| 3-27 | 80 | 90 |
| 1-27 | 80 | 100 |
| 2-27 | 80 | 90 |
| 1-173 | 80 | 90 |
| 2-173 | 80 | 90 |
| 1-273 | 80 | 100 |
| 2-273 | 80 | 90 |
| 3-273 | 80 | 90 |
| 1-44 | 80 | 80 |
| 1-45 | 80 | 90 |
| 2-45 | 80 | 80 |
| 1-46 | 80 | 80 |
| 2-46 | 80 | 90 |
| 1-30 | 80 | 100 |
| 2-30 | 80 | 80 |
| 1-31 | 80 | 80 |
| 2-31 | 80 | 80 |
| 2-29 | 80 | 80 |
| 1-304 | 80 | 80 |
| 2-304 | 80 | 90 |
| 1-305 | 80 | 90 |
| 2-305 | 80 | 90 |
| 1-306 | 80 | 90 |
| 2-306 | 80 | 100 |
| 1-177 | 80 | 80 |
| 2-177 | 80 | 80 |
| 1-178 | 80 | 80 |
| 2-179 | 80 | 80 |
| 1-132 | 80 | 80 |
| 2-132 | 80 | 90 |
| 1-135 | 80 | 80 |
| 2-135 | 80 | 80 |
| 1-134 | 80 | 80 |
| 2-134 | 80 | 90 |
| 2-133 | 80 | 80 |
| 6-120 | 80 | 80 |
| 1-277 | 80 | 90 |
| 2-277 | 80 | 80 |
| 1-278 | 80 | 90 |
| 2-278 | 80 | 90 |
| 1-279 | 80 | 90 |
| 2-279 | 80 | 90 |
| 2-225 | 80 | 90 |
| 2-227 | 80 | 90 |
| 1-227 | 80 | 80 |
| 2-197 | 80 | 90 |
| 1-225 | 80 | 100 |
| 2-226 | 80 | 100 |
| 2-196 | 80 | 90 |
| 1-56 | 80 | 80 |
| 2-57 | 80 | 80 |
| 1-58 | 80 | 90 |
| 2-58 | 80 | 90 |
| 2-56 | 80 | 80 |
| 1-57 | 80 | 80 |
| 1-207 | 80 | 80 |
| 2-207 | 80 | 80 |
| 2-271 | 80 | 100 |
| 2-32 | 80 | 90 |
| 2-34 | 80 | 80 |
| 6-255 | 80 | 90 |
| 2-33 | 80 | 80 |
| 2-42 | 80 | 90 |
| 6-256 | 80 | 80 |
| 2-146 | 80 | 90 |
| 1-146 | 80 | 80 |
| 1-141 | 80 | 80 |
| 2-37 | 80 | 80 |
| 2-73 | 80 | 80 |
| 1-74 | 80 | 100 |

TABLE 10b-continued

| Pre-emergence action at 80 g/ha against PHBPU in % | | |
|---|---|---|
| Example number | Dosage [g/ha] | PHBPU |
| 2-74 | 80 | 90 |
| 1-138 | 80 | 90 |
| 2-138 | 80 | 80 |
| 2-141 | 80 | 80 |
| 1-137 | 80 | 90 |
| 1-136 | 80 | 80 |
| 2-180 | 80 | 100 |
| 1-183 | 80 | 90 |
| 2-183 | 80 | 90 |
| 1-182 | 80 | 90 |
| 2-182 | 80 | 90 |
| 1-181 | 80 | 80 |
| 2-181 | 80 | 80 |
| 1-228 | 80 | 90 |
| 2-228 | 80 | 100 |
| 1-230 | 80 | 90 |
| 2-230 | 80 | 80 |
| 2-286 | 80 | 90 |
| 1-287 | 80 | 100 |
| 2-287 | 80 | 80 |
| 2-288 | 80 | 90 |
| 1-210 | 80 | 80 |
| 2-210 | 80 | 90 |
| 1-212 | 80 | 80 |
| 2-212 | 80 | 80 |
| 2-213 | 80 | 90 |
| 1-288 | 80 | 100 |
| 1-289 | 80 | 80 |
| 2-289 | 80 | 80 |
| 6-228 | 80 | 80 |
| 1-291 | 80 | 80 |
| 2-291 | 80 | 90 |
| 2-292 | 80 | 90 |
| 1-271 | 80 | 90 |
| 2-47 | 80 | 90 |
| 1-339 | 80 | 100 |
| 2-339 | 80 | 80 |
| 6-258 | 80 | 90 |
| 2-49 | 80 | 80 |
| 1-229 | 80 | 90 |
| 1-340 | 80 | 90 |
| 2-340 | 80 | 80 |
| 1-33 | 80 | 100 |
| 1-32 | 80 | 80 |
| 2-154 | 80 | 100 |
| 6-259 | 80 | 80 |
| 1-155 | 80 | 100 |
| 2-155 | 80 | 100 |
| 1-164 | 80 | 100 |
| 2-164 | 80 | 100 |
| 1-165 | 80 | 100 |
| 1-166 | 80 | 80 |
| 1-156 | 80 | 80 |
| 2-159 | 80 | 90 |
| 2-272 | 80 | 80 |
| 1-161 | 80 | 80 |
| 2-276 | 80 | 90 |
| 1-276 | 80 | 90 |
| 1-211 | 80 | 80 |
| 1-274 | 80 | 90 |
| 1-272 | 80 | 80 |
| 1-341 | 80 | 80 |
| 1-292 | 80 | 80 |
| 2-341 | 80 | 80 |
| 1-89 | 80 | 80 |
| 2-344 | 80 | 90 |
| 2-345 | 80 | 80 |
| 1-184 | 80 | 80 |
| 2-184 | 80 | 90 |
| 1-185 | 80 | 80 |
| 2-185 | 80 | 100 |
| 1-186 | 80 | 80 |

TABLE 10b-continued

| Pre-emergence action at 80 g/ha against PHBPU in % | | |
|---|---|---|
| Example number | Dosage [g/ha] | PHBPU |
| 2-348 | 80 | 80 |
| 2-84 | 80 | 90 |
| 1-86 | 80 | 80 |
| 2-86 | 80 | 90 |
| 1-92 | 80 | 90 |
| 2-92 | 80 | 90 |
| 2-351 | 80 | 80 |

TABLE 10c

| Pre-emergence action at 320 g/ha against PHBPU in % | | |
|---|---|---|
| Example number | Dosage [g/ha] | PHBPU |
| 3-129 | 320 | 100 |
| 2-129 | 320 | 100 |
| 1-129 | 320 | 100 |
| 6-116 | 320 | 80 |
| 1-338 | 320 | 80 |
| 2-338 | 320 | 80 |
| 3-338 | 320 | 100 |
| 2-337 | 320 | 90 |

TABLE 11a

| Pre-emergence action at 20 g/ha against POLCO in % | | |
|---|---|---|
| Example number | Dosage [g/ha] | POLCO |
| 2-129 | 20 | 100 |
| 1-337 | 20 | 80 |
| 3-26 | 20 | 80 |
| 1-208 | 20 | 80 |
| 1-125 | 20 | 80 |
| 5-74 | 20 | 80 |
| 2-25 | 20 | 100 |
| 2-27 | 20 | 80 |
| 2-173 | 20 | 90 |
| 2-44 | 20 | 80 |
| 1-45 | 20 | 90 |
| 2-30 | 20 | 80 |
| 2-31 | 20 | 80 |
| 1-278 | 20 | 90 |
| 2-278 | 20 | 80 |
| 1-279 | 20 | 80 |
| 2-279 | 20 | 80 |
| 1-58 | 20 | 80 |
| 2-146 | 20 | 80 |
| 2-72 | 20 | 80 |
| 2-144 | 20 | 80 |
| 1-137 | 20 | 80 |
| 2-183 | 20 | 90 |
| 1-166 | 20 | 100 |
| 1-276 | 20 | 80 |
| 1-274 | 20 | 80 |
| 1-272 | 20 | 80 |

TABLE 11b

| Pre-emergence action at 80 g/ha against POLCO in % | | |
|---|---|---|
| Example number | Dosage [g/ha] | POLCO |
| 3-129 | 80 | 80 |
| 2-129 | 80 | 100 |
| 1-129 | 80 | 100 |
| 3-338 | 80 | 80 |
| 1-337 | 80 | 80 |
| 2-123 | 80 | 80 |
| 1-26 | 80 | 90 |
| 2-26 | 80 | 80 |
| 3-26 | 80 | 90 |
| 6-26 | 80 | 100 |
| 1-208 | 80 | 90 |
| 2-208 | 80 | 90 |
| 3-208 | 80 | 80 |
| 6-159 | 80 | 80 |
| 1-125 | 80 | 80 |
| 1-131 | 80 | 80 |
| 2-131 | 80 | 90 |
| 6-118 | 80 | 80 |
| 1-149 | 80 | 80 |
| 2-149 | 80 | 100 |
| 5-117 | 80 | 80 |
| 5-74 | 80 | 80 |
| 5-123 | 80 | 80 |
| 1-82 | 80 | 90 |
| 1-87 | 80 | 90 |
| 1-88 | 80 | 80 |
| 2-88 | 80 | 90 |
| 1-25 | 80 | 80 |
| 2-25 | 80 | 100 |
| 2-27 | 80 | 100 |
| 1-173 | 80 | 80 |
| 2-173 | 80 | 100 |
| 1-273 | 80 | 90 |
| 2-44 | 80 | 90 |
| 1-45 | 80 | 90 |
| 2-45 | 80 | 90 |
| 6-32 | 80 | 80 |
| 1-46 | 80 | 80 |
| 2-46 | 80 | 90 |
| 2-30 | 80 | 80 |
| 2-31 | 80 | 80 |
| 2-28 | 80 | 90 |
| 1-304 | 80 | 80 |
| 2-304 | 80 | 80 |
| 1-305 | 80 | 80 |
| 1-306 | 80 | 90 |
| 2-306 | 80 | 80 |
| 1-132 | 80 | 80 |
| 2-132 | 80 | 80 |
| 1-277 | 80 | 90 |
| 2-277 | 80 | 90 |
| 1-278 | 80 | 100 |
| 2-278 | 80 | 80 |
| 1-279 | 80 | 90 |
| 2-279 | 80 | 90 |
| 2-195 | 80 | 80 |
| 2-225 | 80 | 90 |
| 1-227 | 80 | 90 |
| 2-197 | 80 | 100 |
| 1-225 | 80 | 90 |
| 1-226 | 80 | 90 |
| 2-226 | 80 | 80 |
| 6-165 | 80 | 80 |
| 6-166 | 80 | 80 |
| 2-196 | 80 | 90 |
| 1-56 | 80 | 90 |
| 2-57 | 80 | 90 |
| 1-58 | 80 | 90 |
| 2-58 | 80 | 80 |
| 2-56 | 80 | 90 |
| 1-207 | 80 | 90 |
| 2-207 | 80 | 90 |
| 2-271 | 80 | 80 |
| 2-32 | 80 | 90 |

TABLE 11b-continued

| Pre-emergence action at 80 g/ha against POLCO in % | | |
|---|---|---|
| Example number | Dosage [g/ha] | POLCO |
| 2-34 | 80 | 90 |
| 2-42 | 80 | 80 |
| 2-146 | 80 | 80 |
| 1-146 | 80 | 80 |
| 2-72 | 80 | 80 |
| 2-73 | 80 | 80 |
| 1-74 | 80 | 80 |
| 2-74 | 80 | 80 |
| 2-35 | 80 | 80 |
| 2-144 | 80 | 90 |
| 1-138 | 80 | 90 |
| 2-138 | 80 | 90 |
| 2-141 | 80 | 80 |
| 1-137 | 80 | 100 |
| 1-180 | 80 | 100 |
| 2-180 | 80 | 90 |
| 1-183 | 80 | 80 |
| 2-183 | 80 | 90 |
| 2-182 | 80 | 90 |
| 6-169 | 80 | 100 |
| 2-287 | 80 | 80 |
| 2-288 | 80 | 90 |
| 1-212 | 80 | 80 |
| 2-212 | 80 | 80 |
| 1-288 | 80 | 80 |
| 1-289 | 80 | 80 |
| 2-289 | 80 | 80 |
| 1-291 | 80 | 80 |
| 2-291 | 80 | 80 |
| 2-292 | 80 | 100 |
| 1-271 | 80 | 80 |
| 2-47 | 80 | 80 |
| 1-339 | 80 | 80 |
| 2-339 | 80 | 80 |
| 6-258 | 80 | 80 |
| 1-49 | 80 | 90 |
| 2-49 | 80 | 90 |
| 1-229 | 80 | 80 |
| 1-340 | 80 | 90 |
| 1-47 | 80 | 100 |
| 1-33 | 80 | 90 |
| 1-32 | 80 | 100 |
| 2-154 | 80 | 90 |
| 6-259 | 80 | 90 |
| 1-155 | 80 | 90 |
| 2-155 | 80 | 90 |
| 2-164 | 80 | 90 |
| 1-165 | 80 | 90 |
| 1-166 | 80 | 100 |
| 2-156 | 80 | 90 |
| 2-272 | 80 | 80 |
| 1-161 | 80 | 80 |
| 2-276 | 80 | 90 |
| 1-276 | 80 | 90 |
| 1-211 | 80 | 90 |
| 1-274 | 80 | 90 |
| 1-272 | 80 | 90 |
| 6-211 | 80 | 90 |
| 1-341 | 80 | 80 |
| 1-292 | 80 | 90 |
| 2-83 | 80 | 90 |
| 1-89 | 80 | 80 |
| 2-342 | 80 | 80 |
| 2-343 | 80 | 90 |
| 1-345 | 80 | 90 |
| 2-344 | 80 | 90 |
| 1-346 | 80 | 80 |
| 2-345 | 80 | 90 |
| 1-184 | 80 | 80 |
| 2-348 | 80 | 90 |
| 2-350 | 80 | 100 |

TABLE 11b-continued

| Pre-emergence action at 80 g/ha against POLCO in % | | |
|---|---|---|
| Example number | Dosage [g/ha] | POLCO |
| 1-86 | 80 | 80 |
| 1-354 | 80 | 80 |
| 1-355 | 80 | 80 |

TABLE 11c

| Pre-emergence action at 320 g/ha against POLCO in % | | |
|---|---|---|
| Example number | Dosage [g/ha] | POLCO |
| 3-129 | 320 | 100 |
| 2-129 | 320 | 100 |
| 1-129 | 320 | 100 |
| 6-116 | 320 | 90 |
| 1-338 | 320 | 80 |
| 2-338 | 320 | 90 |
| 3-338 | 320 | 80 |
| 2-337 | 320 | 80 |
| 2-81 | 320 | 100 |
| 2-82 | 320 | 90 |
| 1-147 | 320 | 90 |
| 2-147 | 320 | 80 |
| 1-148 | 320 | 80 |
| 2-148 | 320 | 100 |

TABLE 12a

| Pre-emergence action at 20 g/ha against SETVI in % | | |
|---|---|---|
| Example number | Dosage [g/ha] | SETVI |
| 2-129 | 20 | 100 |
| 2-337 | 20 | 90 |
| 1-26 | 20 | 80 |
| 2-26 | 20 | 80 |
| 1-208 | 20 | 100 |
| 2-208 | 20 | 80 |
| 1-130 | 20 | 90 |
| 2-130 | 20 | 90 |
| 1-131 | 20 | 80 |
| 2-131 | 20 | 80 |
| 1-149 | 20 | 90 |
| 6-124 | 20 | 80 |
| 1-82 | 20 | 80 |
| 1-209 | 20 | 90 |
| 1-25 | 20 | 80 |
| 2-25 | 20 | 100 |
| 1-27 | 20 | 100 |
| 1-173 | 20 | 90 |
| 1-273 | 20 | 100 |
| 2-273 | 20 | 80 |
| 1-30 | 20 | 90 |
| 2-30 | 20 | 100 |
| 1-304 | 20 | 90 |
| 1-305 | 20 | 80 |
| 2-177 | 20 | 100 |
| 1-179 | 20 | 80 |
| 1-132 | 20 | 80 |
| 1-134 | 20 | 90 |
| 2-134 | 20 | 80 |
| 2-133 | 20 | 100 |
| 1-279 | 20 | 80 |
| 2-279 | 20 | 80 |
| 2-195 | 20 | 80 |
| 1-197 | 20 | 100 |

TABLE 12a-continued

| Pre-emergence action at 20 g/ha against SETVI in % | | |
|---|---|---|
| Example number | Dosage [g/ha] | SETVI |
| 2-227 | 20 | 100 |
| 2-197 | 20 | 90 |
| 1-225 | 20 | 90 |
| 1-226 | 20 | 100 |
| 2-226 | 20 | 80 |
| 6-165 | 20 | 90 |
| 2-196 | 20 | 90 |
| 1-56 | 20 | 90 |
| 2-57 | 20 | 80 |
| 1-58 | 20 | 100 |
| 2-58 | 20 | 100 |
| 2-56 | 20 | 100 |
| 1-57 | 20 | 90 |
| 1-207 | 20 | 100 |
| 2-207 | 20 | 100 |
| 2-271 | 20 | 100 |
| 2-32 | 20 | 100 |
| 2-34 | 20 | 100 |
| 6-255 | 20 | 100 |
| 2-33 | 20 | 80 |
| 2-42 | 20 | 80 |
| 6-256 | 20 | 80 |
| 1-141 | 20 | 90 |
| 1-37 | 20 | 90 |
| 1-74 | 20 | 100 |
| 2-141 | 20 | 90 |
| 1-182 | 20 | 100 |
| 2-182 | 20 | 90 |
| 6-167 | 20 | 80 |
| 1-230 | 20 | 90 |
| 2-286 | 20 | 80 |
| 1-287 | 20 | 90 |
| 2-287 | 20 | 90 |
| 2-288 | 20 | 90 |
| 1-212 | 20 | 80 |
| 1-288 | 20 | 100 |
| 1-340 | 20 | 90 |
| 1-155 | 20 | 80 |
| 1-166 | 20 | 80 |
| 1-272 | 20 | 80 |
| 1-341 | 20 | 80 |
| 1-89 | 20 | 90 |
| 1-346 | 20 | 100 |
| 1-195 | 20 | 90 |
| 1-349 | 20 | 90 |
| 1-351 | 20 | 100 |
| 1-86 | 20 | 80 |
| 2-92 | 20 | 100 |

TABLE 12b

| Pre-emergence action at 80 g/ha against SETVI in % | | |
|---|---|---|
| Example number | Dosage [g/ha] | SETVI |
| 3-129 | 80 | 90 |
| 2-129 | 80 | 100 |
| 1-129 | 80 | 100 |
| 6-116 | 80 | 100 |
| 1-338 | 80 | 90 |
| 2-338 | 80 | 90 |
| 1-337 | 80 | 90 |
| 2-337 | 80 | 100 |
| 6-252 | 80 | 90 |
| 1-26 | 80 | 100 |
| 2-26 | 80 | 100 |
| 6-26 | 80 | 100 |
| 1-208 | 80 | 100 |
| 2-208 | 80 | 100 |

TABLE 12b-continued

| Pre-emergence action at 80 g/ha against SETVI in % | | |
|---|---|---|
| Example number | Dosage [g/ha] | SETVI |
| 3-208 | 80 | 100 |
| 6-159 | 80 | 100 |
| 1-130 | 80 | 100 |
| 2-130 | 80 | 100 |
| 6-117 | 80 | 100 |
| 1-81 | 80 | 100 |
| 2-81 | 80 | 100 |
| 2-82 | 80 | 100 |
| 6-58 | 80 | 100 |
| 1-147 | 80 | 100 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 100 |
| 1-149 | 80 | 100 |
| 2-149 | 80 | 100 |
| 6-124 | 80 | 100 |
| 5-59 | 80 | 100 |
| 5-58 | 80 | 100 |
| 5-117 | 80 | 90 |
| 5-253 | 80 | 80 |
| 5-75 | 80 | 100 |
| 5-74 | 80 | 90 |
| 5-123 | 80 | 100 |
| 5-122 | 80 | 100 |
| 1-82 | 80 | 100 |
| 1-87 | 80 | 100 |
| 2-87 | 80 | 100 |
| 1-88 | 80 | 100 |
| 2-88 | 80 | 100 |
| 1-209 | 80 | 100 |
| 1-4 | 80 | 100 |
| 1-25 | 80 | 100 |
| 2-25 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 90 |
| 3-273 | 80 | 100 |
| 6-212 | 80 | 90 |
| 1-44 | 80 | 100 |
| 2-44 | 80 | 100 |
| 1-45 | 80 | 100 |
| 2-45 | 80 | 100 |
| 1-46 | 80 | 100 |
| 2-46 | 80 | 100 |
| 6-33 | 80 | 100 |
| 1-30 | 80 | 100 |
| 2-30 | 80 | 100 |
| 1-31 | 80 | 100 |
| 2-31 | 80 | 100 |
| 1-28 | 80 | 100 |
| 2-28 | 80 | 100 |
| 1-29 | 80 | 100 |
| 2-29 | 80 | 100 |
| 1-304 | 80 | 100 |
| 2-304 | 80 | 90 |
| 1-305 | 80 | 100 |
| 2-305 | 80 | 80 |
| 1-306 | 80 | 100 |
| 2-306 | 80 | 100 |
| 1-177 | 80 | 100 |
| 2-177 | 80 | 100 |
| 1-178 | 80 | 100 |
| 2-178 | 80 | 100 |
| 1-179 | 80 | 100 |
| 2-179 | 80 | 100 |
| 1-132 | 80 | 100 |
| 2-132 | 80 | 100 |
| 1-135 | 80 | 100 |

TABLE 12b-continued

| Pre-emergence action at 80 g/ha against SETVI in % | | |
|---|---|---|
| Example number | Dosage [g/ha] | SETVI |
| 2-135 | 80 | 100 |
| 6-254 | 80 | 80 |
| 1-134 | 80 | 100 |
| 2-134 | 80 | 100 |
| 1-133 | 80 | 100 |
| 2-133 | 80 | 100 |
| 6-120 | 80 | 100 |
| 1-277 | 80 | 100 |
| 2-277 | 80 | 80 |
| 1-278 | 80 | 100 |
| 2-278 | 80 | 100 |
| 1-279 | 80 | 100 |
| 2-279 | 80 | 100 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 100 |
| 1-225 | 80 | 100 |
| 1-226 | 80 | 100 |
| 2-226 | 80 | 100 |
| 6-165 | 80 | 100 |
| 6-166 | 80 | 100 |
| 2-196 | 80 | 100 |
| 1-56 | 80 | 100 |
| 6-45 | 80 | 100 |
| 6-44 | 80 | 90 |
| 2-57 | 80 | 100 |
| 6-43 | 80 | 90 |
| 1-58 | 80 | 100 |
| 2-58 | 80 | 100 |
| 2-56 | 80 | 100 |
| 1-57 | 80 | 100 |
| 1-207 | 80 | 100 |
| 2-207 | 80 | 100 |
| 2-271 | 80 | 100 |
| 6-210 | 80 | 100 |
| 2-32 | 80 | 100 |
| 1-34 | 80 | 100 |
| 2-34 | 80 | 100 |
| 6-255 | 80 | 100 |
| 2-33 | 80 | 100 |
| 2-42 | 80 | 100 |
| 6-256 | 80 | 100 |
| 2-146 | 80 | 100 |
| 1-146 | 80 | 80 |
| 1-141 | 80 | 100 |
| 1-37 | 80 | 100 |
| 2-37 | 80 | 100 |
| 1-72 | 80 | 100 |
| 2-72 | 80 | 100 |
| 1-73 | 80 | 100 |
| 2-73 | 80 | 100 |
| 1-74 | 80 | 100 |
| 2-74 | 80 | 100 |
| 1-144 | 80 | 80 |
| 1-138 | 80 | 100 |
| 2-138 | 80 | 80 |
| 2-141 | 80 | 100 |
| 1-137 | 80 | 100 |
| 1-136 | 80 | 80 |
| 1-180 | 80 | 90 |
| 2-180 | 80 | 100 |
| 1-183 | 80 | 100 |
| 2-183 | 80 | 100 |
| 1-182 | 80 | 100 |
| 2-182 | 80 | 100 |
| 6-145 | 80 | 100 |
| 1-181 | 80 | 100 |
| 2-181 | 80 | 100 |
| 6-144 | 80 | 90 |
| 1-228 | 80 | 100 |
| 2-228 | 80 | 90 |

TABLE 12b-continued

| Pre-emergence action at 80 g/ha against SETVI in % | | |
|---|---|---|
| Example number | Dosage [g/ha] | SETVI |
| 6-167 | 80 | 80 |
| 1-230 | 80 | 100 |
| 2-230 | 80 | 90 |
| 6-169 | 80 | 100 |
| 2-286 | 80 | 100 |
| 1-287 | 80 | 100 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 100 |
| 2-213 | 80 | 100 |
| 1-288 | 80 | 100 |
| 1-289 | 80 | 80 |
| 2-289 | 80 | 90 |
| 6-228 | 80 | 80 |
| 1-291 | 80 | 100 |
| 2-291 | 80 | 100 |
| 2-292 | 80 | 100 |
| 1-271 | 80 | 100 |
| 2-47 | 80 | 100 |
| 2-339 | 80 | 100 |
| 6-258 | 80 | 80 |
| 1-49 | 80 | 80 |
| 2-49 | 80 | 100 |
| 1-229 | 80 | 100 |
| 2-229 | 80 | 100 |
| 1-340 | 80 | 100 |
| 6-267 | 80 | 80 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 100 |
| 1-155 | 80 | 100 |
| 2-155 | 80 | 90 |
| 6-260 | 80 | 100 |
| 2-164 | 80 | 80 |
| 6-261 | 80 | 100 |
| 1-165 | 80 | 100 |
| 1-166 | 80 | 100 |
| 1-156 | 80 | 100 |
| 2-156 | 80 | 100 |
| 6-262 | 80 | 100 |
| 1-162 | 80 | 80 |
| 6-264 | 80 | 80 |
| 2-211 | 80 | 100 |
| 2-272 | 80 | 100 |
| 2-276 | 80 | 100 |
| 1-276 | 80 | 100 |
| 1-211 | 80 | 100 |
| 1-274 | 80 | 100 |
| 6-168 | 80 | 90 |
| 1-272 | 80 | 100 |
| 6-211 | 80 | 100 |
| 1-341 | 80 | 100 |
| 1-292 | 80 | 100 |
| 2-341 | 80 | 90 |
| 1-83 | 80 | 100 |
| 2-83 | 80 | 100 |
| 1-89 | 80 | 100 |
| 2-89 | 80 | 100 |
| 6-76 | 80 | 80 |
| 6-161 | 80 | 100 |
| 1-343 | 80 | 100 |
| 2-342 | 80 | 100 |
| 1-344 | 80 | 100 |
| 2-343 | 80 | 100 |
| 1-345 | 80 | 100 |
| 2-344 | 80 | 80 |
| 1-346 | 80 | 100 |
| 2-345 | 80 | 100 |

TABLE 12b-continued

| Pre-emergence action at 80 g/ha against SETVI in % | | |
|---|---|---|
| Example number | Dosage [g/ha] | SETVI |
| 1-195 | 80 | 100 |
| 1-185 | 80 | 100 |
| 2-185 | 80 | 100 |
| 1-186 | 80 | 80 |
| 1-349 | 80 | 100 |
| 1-350 | 80 | 100 |
| 2-348 | 80 | 100 |
| 1-351 | 80 | 100 |
| 2-349 | 80 | 100 |
| 1-84 | 80 | 100 |
| 2-84 | 80 | 100 |
| 1-352 | 80 | 100 |
| 2-350 | 80 | 100 |
| 1-86 | 80 | 100 |
| 2-86 | 80 | 100 |
| 1-92 | 80 | 100 |
| 2-92 | 80 | 100 |
| 1-90 | 80 | 100 |
| 2-90 | 80 | 100 |
| 1-353 | 80 | 100 |
| 2-351 | 80 | 100 |
| 1-354 | 80 | 90 |
| 2-352 | 80 | 100 |
| 1-355 | 80 | 90 |

TABLE 12c

| Pre-emergence action at 320 g/ha against SETVI in % | | |
|---|---|---|
| Example number | Dosage [g/ha] | SETVI |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 100 |
| 2-337 | 320 | 100 |
| 6-252 | 320 | 90 |
| 6-117 | 320 | 100 |
| 1-81 | 320 | 100 |
| 2-81 | 320 | 100 |
| 2-82 | 320 | 100 |
| 6-58 | 320 | 100 |
| 1-147 | 320 | 100 |
| 2-147 | 320 | 100 |
| 1-148 | 320 | 100 |
| 2-148 | 320 | 100 |

TABLE 13a

| Pre-emergence action at 20 g/ha against STEME in % | | |
|---|---|---|
| Example number | Dosage [g/ha] | STEME |
| 3-129 | 20 | 90 |
| 2-129 | 20 | 80 |
| 1-129 | 20 | 100 |
| 6-116 | 20 | 90 |
| 2-337 | 20 | 90 |
| 1-26 | 20 | 100 |
| 2-26 | 20 | 100 |
| 3-26 | 20 | 80 |

TABLE 13a-continued

| Pre-emergence action at 20 g/ha against STEME in % | | |
|---|---|---|
| Example number | Dosage [g/ha] | STEME |
| 6-26 | 20 | 80 |
| 1-208 | 20 | 100 |
| 2-208 | 20 | 100 |
| 3-208 | 20 | 90 |
| 6-159 | 20 | 80 |
| 2-125 | 20 | 80 |
| 3-125 | 20 | 90 |
| 1-130 | 20 | 100 |
| 2-130 | 20 | 100 |
| 1-131 | 20 | 100 |
| 2-131 | 20 | 100 |
| 6-118 | 20 | 90 |
| 1-149 | 20 | 90 |
| 2-149 | 20 | 100 |
| 6-124 | 20 | 80 |
| 5-59 | 20 | 90 |
| 5-58 | 20 | 100 |
| 5-117 | 20 | 90 |
| 5-75 | 20 | 100 |
| 5-74 | 20 | 90 |
| 5-123 | 20 | 90 |
| 5-122 | 20 | 90 |
| 1-82 | 20 | 100 |
| 1-87 | 20 | 90 |
| 2-87 | 20 | 100 |
| 1-88 | 20 | 100 |
| 2-88 | 20 | 100 |
| 1-25 | 20 | 80 |
| 2-25 | 20 | 90 |
| 3-27 | 20 | 100 |
| 1-27 | 20 | 90 |
| 2-27 | 20 | 100 |
| 1-173 | 20 | 80 |
| 2-173 | 20 | 100 |
| 1-273 | 20 | 100 |
| 2-273 | 20 | 90 |
| 3-273 | 20 | 90 |
| 6-212 | 20 | 80 |
| 1-44 | 20 | 90 |
| 2-44 | 20 | 90 |
| 1-45 | 20 | 90 |
| 2-45 | 20 | 90 |
| 1-46 | 20 | 90 |
| 2-46 | 20 | 90 |

TABLE 13b

| Pre-emergence action at 80 g/ha against STEME in % | | |
|---|---|---|
| Example number | Dosage [g/ha] | STEME |
| 3-129 | 80 | 100 |
| 2-129 | 80 | 80 |
| 1-129 | 80 | 100 |
| 6-116 | 80 | 100 |
| 1-338 | 80 | 90 |
| 2-338 | 80 | 90 |
| 3-338 | 80 | 90 |
| 2-337 | 80 | 90 |
| 3-337 | 80 | 100 |
| 1-123 | 80 | 90 |
| 2-123 | 80 | 80 |
| 1-26 | 80 | 100 |
| 2-26 | 80 | 100 |
| 3-26 | 80 | 100 |
| 6-26 | 80 | 100 |
| 1-208 | 80 | 100 |
| 2-208 | 80 | 100 |
| 3-208 | 80 | 100 |

TABLE 13b-continued

| Pre-emergence action at 80 g/ha against STEME in % | | |
|---|---|---|
| Example number | Dosage [g/ha] | STEME |
| 6-159 | 80 | 100 |
| 1-125 | 80 | 100 |
| 2-125 | 80 | 100 |
| 3-125 | 80 | 100 |
| 1-130 | 80 | 100 |
| 2-130 | 80 | 100 |
| 6-117 | 80 | 100 |
| 1-81 | 80 | 100 |
| 2-81 | 80 | 90 |
| 2-82 | 80 | 100 |
| 6-58 | 80 | 90 |
| 1-147 | 80 | 100 |
| 2-147 | 80 | 100 |
| 1-148 | 80 | 100 |
| 2-148 | 80 | 90 |
| 1-131 | 80 | 100 |
| 2-131 | 80 | 100 |
| 6-118 | 80 | 100 |
| 1-149 | 80 | 100 |
| 2-149 | 80 | 100 |
| 6-124 | 80 | 90 |
| 5-59 | 80 | 100 |
| 5-58 | 80 | 100 |
| 5-117 | 80 | 90 |
| 5-253 | 80 | 90 |
| 5-75 | 80 | 100 |
| 5-74 | 80 | 100 |
| 5-123 | 80 | 90 |
| 5-122 | 80 | 90 |
| 1-82 | 80 | 100 |
| 1-87 | 80 | 100 |
| 2-87 | 80 | 100 |
| 1-88 | 80 | 100 |
| 2-88 | 80 | 100 |
| 1-209 | 80 | 90 |
| 1-4 | 80 | 90 |
| 1-25 | 80 | 90 |
| 2-25 | 80 | 100 |
| 3-27 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 90 |
| 3-273 | 80 | 100 |
| 6-212 | 80 | 90 |
| 4-212 | 80 | 90 |
| 1-44 | 80 | 90 |
| 2-44 | 80 | 100 |
| 1-45 | 80 | 90 |
| 2-45 | 80 | 100 |
| 6-32 | 80 | 90 |
| 1-46 | 80 | 100 |
| 2-46 | 80 | 100 |

TABLE 13c

| Pre-emergence action at 320 g/ha against STEME in % | | |
|---|---|---|
| Example number | Dosage [g/ha] | STEME |
| 3-129 | 320 | 100 |
| 2-129 | 320 | 100 |
| 1-129 | 320 | 100 |
| 6-116 | 320 | 100 |
| 1-338 | 320 | 90 |
| 2-338 | 320 | 100 |
| 3-338 | 320 | 100 |
| 6-253 | 320 | 100 |
| 2-337 | 320 | 100 |

TABLE 13c-continued

| Pre-emergence action at 320 g/ha against STEME in % | | |
|---|---|---|
| Example number | Dosage [g/ha] | STEME |
| 6-252 | 320 | 90 |
| 6-117 | 320 | 100 |
| 1-81 | 320 | 100 |
| 2-81 | 320 | 100 |
| 2-82 | 320 | 100 |
| 6-58 | 320 | 90 |
| 1-147 | 320 | 100 |
| 2-147 | 320 | 100 |
| 1-148 | 320 | 100 |
| 2-148 | 320 | 100 |

TABLE 14a

| Pre-emergence action at 20 g/ha against VERPE in % | | |
|---|---|---|
| Example number | Dosage [g/ha] | VERPE |
| 2-337 | 20 | 80 |
| 1-125 | 20 | 80 |
| 1-209 | 20 | 90 |
| 1-4 | 20 | 80 |
| 1-25 | 20 | 80 |
| 1-27 | 20 | 80 |
| 2-27 | 20 | 80 |
| 1-178 | 20 | 80 |
| 2-56 | 20 | 80 |
| 2-32 | 20 | 90 |
| 2-34 | 20 | 90 |
| 2-33 | 20 | 80 |
| 6-256 | 20 | 80 |
| 2-37 | 20 | 80 |
| 1-73 | 20 | 80 |
| 2-73 | 20 | 90 |
| 1-183 | 20 | 90 |
| 2-286 | 20 | 80 |
| 2-287 | 20 | 90 |
| 2-292 | 20 | 90 |
| 1-271 | 20 | 90 |
| 1-339 | 20 | 100 |
| 2-339 | 20 | 80 |
| 6-258 | 20 | 90 |
| 1-340 | 20 | 100 |
| 1-32 | 20 | 80 |
| 2-155 | 20 | 80 |
| 1-165 | 20 | 80 |
| 1-166 | 20 | 80 |
| 2-156 | 20 | 80 |
| 1-161 | 20 | 80 |
| 1-274 | 20 | 90 |
| 1-341 | 20 | 80 |
| 1-292 | 20 | 100 |
| 1-158 | 20 | 80 |
| 2-158 | 20 | 80 |
| 2-342 | 20 | 80 |
| 1-344 | 20 | 80 |
| 1-349 | 20 | 90 |
| 1-84 | 20 | 80 |
| 2-84 | 20 | 80 |
| 1-352 | 20 | 90 |
| 1-356 | 20 | 100 |
| 2-354 | 20 | 80 |

TABLE 14b

| Pre-emergence action at 80 g/ha against VERPE in % | | |
|---|---|---|
| Example number | Dosage [g/ha] | VERPE |
| 1-129 | 80 | 100 |
| 1-338 | 80 | 90 |
| 2-338 | 80 | 100 |

TABLE 14b-continued

| Pre-emergence action at 80 g/ha against VERPE in % | | |
|---|---|---|
| Example number | Dosage [g/ha] | VERPE |
| 3-338 | 80 | 90 |
| 1-337 | 80 | 90 |
| 2-337 | 80 | 90 |
| 3-337 | 80 | 100 |
| 1-26 | 80 | 80 |
| 1-125 | 80 | 80 |
| 3-125 | 80 | 80 |
| 1-130 | 80 | 80 |
| 2-130 | 80 | 80 |
| 2-81 | 80 | 90 |
| 1-148 | 80 | 80 |
| 2-148 | 80 | 80 |
| 1-149 | 80 | 100 |
| 2-149 | 80 | 80 |
| 5-58 | 80 | 80 |
| 5-75 | 80 | 90 |
| 5-122 | 80 | 100 |
| 1-82 | 80 | 90 |
| 1-87 | 80 | 90 |
| 2-87 | 80 | 90 |
| 1-88 | 80 | 100 |
| 2-88 | 80 | 100 |
| 1-209 | 80 | 100 |
| 1-4 | 80 | 90 |
| 1-25 | 80 | 100 |
| 2-25 | 80 | 100 |
| 3-27 | 80 | 90 |
| 1-27 | 80 | 90 |
| 2-27 | 80 | 100 |
| 2-173 | 80 | 80 |
| 1-273 | 80 | 90 |
| 2-273 | 80 | 100 |
| 3-273 | 80 | 100 |
| 2-44 | 80 | 90 |
| 1-45 | 80 | 90 |
| 2-45 | 80 | 90 |
| 1-46 | 80 | 90 |
| 2-46 | 80 | 90 |
| 1-31 | 80 | 100 |
| 2-28 | 80 | 80 |
| 1-304 | 80 | 100 |
| 2-304 | 80 | 100 |
| 1-305 | 80 | 100 |
| 2-305 | 80 | 100 |
| 1-306 | 80 | 90 |
| 2-306 | 80 | 100 |
| 1-177 | 80 | 100 |
| 2-177 | 80 | 80 |
| 1-178 | 80 | 80 |
| 2-178 | 80 | 90 |
| 2-179 | 80 | 90 |
| 1-132 | 80 | 100 |
| 1-135 | 80 | 90 |
| 2-135 | 80 | 100 |
| 6-254 | 80 | 100 |
| 1-277 | 80 | 90 |
| 2-277 | 80 | 100 |
| 1-278 | 80 | 100 |
| 2-278 | 80 | 100 |
| 1-279 | 80 | 90 |
| 2-279 | 80 | 90 |
| 2-225 | 80 | 100 |
| 2-227 | 80 | 100 |
| 1-227 | 80 | 100 |
| 2-197 | 80 | 90 |
| 1-225 | 80 | 80 |
| 1-226 | 80 | 90 |
| 2-226 | 80 | 100 |
| 2-196 | 80 | 80 |
| 1-56 | 80 | 90 |
| 2-57 | 80 | 90 |
| 1-58 | 80 | 100 |
| 2-56 | 80 | 100 |
| 1-57 | 80 | 80 |
| 1-207 | 80 | 100 |
| 2-207 | 80 | 90 |

TABLE 14b-continued

| Pre-emergence action at 80 g/ha against VERPE in % | | |
|---|---|---|
| Example number | Dosage [g/ha] | VERPE |
| 2-271 | 80 | 100 |
| 2-32 | 80 | 100 |
| 1-34 | 80 | 100 |
| 2-34 | 80 | 90 |
| 6-255 | 80 | 90 |
| 2-33 | 80 | 90 |
| 2-42 | 80 | 90 |
| 6-256 | 80 | 80 |
| 2-146 | 80 | 80 |
| 2-37 | 80 | 80 |
| 2-143 | 80 | 80 |
| 2-72 | 80 | 90 |
| 1-73 | 80 | 100 |
| 2-73 | 80 | 90 |
| 1-74 | 80 | 100 |
| 2-74 | 80 | 90 |
| 1-144 | 80 | 80 |
| 2-144 | 80 | 100 |
| 1-138 | 80 | 90 |
| 2-138 | 80 | 100 |
| 1-137 | 80 | 90 |
| 1-136 | 80 | 90 |
| 1-180 | 80 | 80 |
| 1-183 | 80 | 100 |
| 2-183 | 80 | 90 |
| 2-181 | 80 | 100 |
| 1-36 | 80 | 90 |
| 1-228 | 80 | 90 |
| 2-228 | 80 | 90 |
| 1-230 | 80 | 100 |
| 2-230 | 80 | 100 |
| 2-286 | 80 | 100 |
| 1-287 | 80 | 90 |
| 2-287 | 80 | 100 |
| 2-288 | 80 | 100 |
| 1-210 | 80 | 80 |
| 2-213 | 80 | 90 |
| 1-288 | 80 | 100 |
| 1-289 | 80 | 100 |
| 2-289 | 80 | 100 |
| 2-291 | 80 | 90 |
| 2-292 | 80 | 100 |
| 1-271 | 80 | 100 |
| 2-47 | 80 | 100 |
| 1-339 | 80 | 100 |
| 2-339 | 80 | 100 |
| 6-258 | 80 | 100 |
| 1-49 | 80 | 100 |
| 2-49 | 80 | 100 |
| 1-41 | 80 | 90 |
| 1-229 | 80 | 100 |
| 2-229 | 80 | 80 |
| 1-340 | 80 | 100 |
| 6-267 | 80 | 90 |
| 2-340 | 80 | 100 |
| 1-47 | 80 | 100 |
| 1-33 | 80 | 100 |
| 1-32 | 80 | 100 |
| 2-154 | 80 | 100 |
| 1-155 | 80 | 100 |
| 2-155 | 80 | 100 |
| 6-260 | 80 | 90 |
| 1-164 | 80 | 90 |
| 2-164 | 80 | 100 |
| 1-165 | 80 | 100 |
| 1-166 | 80 | 100 |
| 2-156 | 80 | 100 |
| 1-159 | 80 | 80 |
| 2-159 | 80 | 80 |
| 6-264 | 80 | 90 |
| 2-160 | 80 | 80 |
| 2-161 | 80 | 80 |
| 2-272 | 80 | 90 |
| 1-161 | 80 | 90 |
| 2-276 | 80 | 80 |
| 1-211 | 80 | 100 |

TABLE 14b-continued

| Pre-emergence action at 80 g/ha against VERPE in % | | |
|---|---|---|
| Example number | Dosage [g/ha] | VERPE |
| 1-274 | 80 | 90 |
| 1-272 | 80 | 90 |
| 6-211 | 80 | 80 |
| 1-341 | 80 | 90 |
| 1-292 | 80 | 100 |
| 2-341 | 80 | 90 |
| 1-158 | 80 | 80 |
| 2-158 | 80 | 90 |
| 1-83 | 80 | 80 |
| 1-89 | 80 | 90 |
| 2-89 | 80 | 90 |
| 6-268 | 80 | 90 |
| 1-343 | 80 | 80 |
| 2-342 | 80 | 80 |
| 1-344 | 80 | 90 |
| 1-345 | 80 | 80 |
| 2-344 | 80 | 80 |
| 1-346 | 80 | 80 |
| 2-345 | 80 | 100 |
| 2-346 | 80 | 80 |
| 1-184 | 80 | 90 |
| 2-184 | 80 | 100 |
| 2-186 | 80 | 90 |
| 1-349 | 80 | 90 |
| 1-350 | 80 | 80 |
| 2-348 | 80 | 80 |
| 1-351 | 80 | 90 |
| 2-349 | 80 | 80 |
| 1-84 | 80 | 100 |
| 2-84 | 80 | 80 |
| 1-352 | 80 | 100 |
| 2-350 | 80 | 100 |
| 1-86 | 80 | 100 |
| 2-86 | 80 | 90 |
| 1-92 | 80 | 100 |
| 2-92 | 80 | 100 |
| 1-90 | 80 | 90 |
| 2-90 | 80 | 90 |
| 1-353 | 80 | 100 |
| 2-351 | 80 | 100 |
| 1-355 | 80 | 100 |
| 1-356 | 80 | 100 |
| 2-354 | 80 | 80 |

TABLE 14c

| Pre-emergence action at 320 g/ha against VERPE in % | | |
|---|---|---|
| Example number | Dosage [g/ha] | VERPE |
| 3-129 | 320 | 100 |
| 2-129 | 320 | 100 |
| 1-129 | 320 | 100 |
| 6-116 | 320 | 80 |
| 1-338 | 320 | 100 |
| 2-338 | 320 | 100 |
| 3-338 | 320 | 100 |
| 6-253 | 320 | 100 |
| 2-337 | 320 | 90 |
| 6-117 | 320 | 90 |
| 1-81 | 320 | 100 |
| 2-81 | 320 | 90 |
| 2-82 | 320 | 90 |
| 1-147 | 320 | 90 |
| 2-147 | 320 | 90 |
| 1-148 | 320 | 100 |
| 2-148 | 320 | 100 |

TABLE 15a

| Example number | Dosage [g/ha] | VIOTR |
|---|---|---|
| Pre-emergence action at 20 g/ha against VIOTR in % | | |
| 3-129 | 20 | 100 |
| 2-129 | 20 | 100 |
| 1-129 | 20 | 100 |
| 1-337 | 20 | 80 |
| 2-337 | 20 | 90 |
| 3-337 | 20 | 100 |
| 1-26 | 20 | 90 |
| 2-26 | 20 | 100 |
| 3-26 | 20 | 100 |
| 1-208 | 20 | 100 |
| 2-208 | 20 | 100 |
| 1-130 | 20 | 100 |
| 2-130 | 20 | 100 |
| 1-131 | 20 | 100 |
| 2-131 | 20 | 100 |
| 6-118 | 20 | 90 |
| 1-149 | 20 | 100 |
| 2-149 | 20 | 100 |
| 5-59 | 20 | 100 |
| 5-58 | 20 | 90 |
| 5-117 | 20 | 100 |
| 5-75 | 20 | 100 |
| 5-123 | 20 | 90 |
| 5-122 | 20 | 80 |
| 1-82 | 20 | 100 |
| 1-87 | 20 | 80 |
| 2-87 | 20 | 90 |
| 1-88 | 20 | 100 |
| 2-88 | 20 | 100 |
| 1-25 | 20 | 80 |
| 3-27 | 20 | 90 |
| 1-27 | 20 | 100 |
| 2-27 | 20 | 100 |
| 1-173 | 20 | 80 |
| 1-273 | 20 | 100 |
| 2-273 | 20 | 90 |
| 3-273 | 20 | 100 |
| 2-44 | 20 | 100 |
| 1-45 | 20 | 80 |
| 2-45 | 20 | 90 |
| 1-46 | 20 | 90 |
| 2-46 | 20 | 100 |
| 1-30 | 20 | 100 |
| 2-30 | 20 | 100 |
| 1-31 | 20 | 100 |
| 2-31 | 20 | 100 |
| 1-28 | 20 | 100 |
| 2-28 | 20 | 100 |
| 1-29 | 20 | 100 |
| 2-29 | 20 | 100 |
| 1-304 | 20 | 100 |
| 2-304 | 20 | 90 |
| 1-305 | 20 | 100 |
| 2-305 | 20 | 90 |
| 1-306 | 20 | 100 |
| 2-306 | 20 | 100 |
| 2-177 | 20 | 100 |
| 2-178 | 20 | 100 |
| 1-179 | 20 | 100 |
| 2-179 | 20 | 100 |
| 1-132 | 20 | 100 |
| 2-132 | 20 | 100 |
| 2-135 | 20 | 100 |
| 1-134 | 20 | 90 |
| 2-134 | 20 | 100 |
| 1-133 | 20 | 100 |
| 1-277 | 20 | 100 |
| 2-277 | 20 | 100 |
| 1-278 | 20 | 100 |
| 2-278 | 20 | 100 |
| 1-279 | 20 | 100 |
| 2-279 | 20 | 100 |
| 2-195 | 20 | 100 |
| 2-225 | 20 | 80 |
| 1-197 | 20 | 100 |
| 2-227 | 20 | 100 |

TABLE 15a-continued

| Example number | Dosage [g/ha] | VIOTR |
|---|---|---|
| Pre-emergence action at 20 g/ha against VIOTR in % | | |
| 1-227 | 20 | 100 |
| 2-197 | 20 | 100 |
| 1-226 | 20 | 80 |
| 2-226 | 20 | 100 |
| 6-165 | 20 | 80 |
| 2-196 | 20 | 90 |
| 1-56 | 20 | 100 |
| 2-57 | 20 | 100 |
| 1-58 | 20 | 100 |
| 2-58 | 20 | 100 |
| 2-56 | 20 | 80 |
| 1-57 | 20 | 100 |
| 1-207 | 20 | 100 |
| 2-207 | 20 | 90 |
| 2-271 | 20 | 100 |
| 2-32 | 20 | 100 |
| 1-34 | 20 | 100 |
| 2-34 | 20 | 100 |
| 6-255 | 20 | 80 |
| 2-33 | 20 | 100 |
| 2-42 | 20 | 100 |
| 6-256 | 20 | 90 |
| 2-146 | 20 | 100 |
| 1-141 | 20 | 80 |
| 2-72 | 20 | 100 |
| 6-49 | 20 | 80 |
| 1-73 | 20 | 100 |
| 2-73 | 20 | 90 |
| 1-74 | 20 | 100 |
| 2-74 | 20 | 100 |
| 1-144 | 20 | 80 |
| 1-138 | 20 | 100 |
| 2-138 | 20 | 90 |
| 1-137 | 20 | 90 |
| 1-136 | 20 | 90 |
| 1-180 | 20 | 80 |
| 2-180 | 20 | 100 |
| 1-183 | 20 | 100 |
| 1-182 | 20 | 90 |
| 2-182 | 20 | 100 |
| 1-181 | 20 | 100 |
| 1-228 | 20 | 90 |
| 2-228 | 20 | 100 |
| 6-167 | 20 | 90 |
| 1-230 | 20 | 100 |
| 2-230 | 20 | 90 |
| 2-286 | 20 | 90 |
| 1-287 | 20 | 100 |
| 2-287 | 20 | 100 |
| 2-288 | 20 | 100 |
| 1-210 | 20 | 100 |
| 2-210 | 20 | 100 |
| 1-212 | 20 | 100 |
| 2-213 | 20 | 100 |
| 1-288 | 20 | 100 |
| 1-289 | 20 | 100 |
| 2-289 | 20 | 100 |
| 1-291 | 20 | 100 |
| 2-291 | 20 | 100 |
| 2-292 | 20 | 100 |
| 1-271 | 20 | 100 |
| 2-47 | 20 | 80 |
| 1-339 | 20 | 100 |
| 2-339 | 20 | 100 |
| 2-49 | 20 | 90 |
| 1-340 | 20 | 100 |
| 2-340 | 20 | 100 |
| 1-33 | 20 | 100 |
| 2-155 | 20 | 90 |
| 1-165 | 20 | 90 |
| 1-166 | 20 | 100 |
| 2-272 | 20 | 90 |
| 2-276 | 20 | 100 |
| 1-276 | 20 | 80 |
| 1-274 | 20 | 90 |
| 1-272 | 20 | 90 |

TABLE 15a-continued

| Pre-emergence action at 20 g/ha against VIOTR in % | | |
|---|---|---|
| Example number | Dosage [g/ha] | VIOTR |
| 1-341 | 20 | 100 |
| 1-292 | 20 | 90 |
| 2-341 | 20 | 90 |
| 1-83 | 20 | 90 |
| 2-89 | 20 | 90 |
| 2-342 | 20 | 90 |
| 2-343 | 20 | 90 |
| 2-344 | 20 | 80 |
| 1-346 | 20 | 80 |
| 2-345 | 20 | 80 |
| 2-346 | 20 | 80 |
| 1-195 | 20 | 100 |
| 1-185 | 20 | 80 |
| 2-185 | 20 | 80 |
| 1-351 | 20 | 100 |
| 2-349 | 20 | 90 |
| 2-84 | 20 | 80 |
| 1-352 | 20 | 100 |
| 2-350 | 20 | 100 |
| 1-86 | 20 | 100 |
| 2-92 | 20 | 90 |
| 1-90 | 20 | 90 |
| 2-90 | 20 | 80 |
| 1-353 | 20 | 100 |
| 2-351 | 20 | 100 |
| 2-352 | 20 | 80 |
| 2-353 | 20 | 90 |
| 2-354 | 20 | 80 |

TABLE 15b

| Pre-emergence action at 80 g/ha against VIOTR in % | | |
|---|---|---|
| Example number | Dosage [g/ha] | VIOTR |
| 3-129 | 80 | 100 |
| 2-129 | 80 | 100 |
| 1-129 | 80 | 100 |
| 6-116 | 80 | 100 |
| 1-338 | 80 | 80 |
| 2-338 | 80 | 100 |
| 3-338 | 80 | 90 |
| 1-337 | 80 | 80 |
| 2-337 | 80 | 100 |
| 3-337 | 80 | 100 |
| 1-123 | 80 | 80 |
| 2-123 | 80 | 80 |
| 1-26 | 80 | 100 |
| 2-26 | 80 | 100 |
| 3-26 | 80 | 100 |
| 6-26 | 80 | 100 |
| 1-208 | 80 | 100 |
| 2-208 | 80 | 100 |
| 3-208 | 80 | 100 |
| 6-159 | 80 | 100 |
| 1-125 | 80 | 100 |
| 2-125 | 80 | 100 |
| 3-125 | 80 | 100 |
| 1-130 | 80 | 100 |
| 2-130 | 80 | 100 |
| 6-117 | 80 | 80 |
| 1-81 | 80 | 90 |
| 2-81 | 80 | 90 |
| 2-82 | 80 | 100 |
| 1-147 | 80 | 100 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 90 |
| 1-149 | 80 | 100 |
| 2-149 | 80 | 100 |

TABLE 15b-continued

| Pre-emergence action at 80 g/ha against VIOTR in % | | |
|---|---|---|
| Example number | Dosage [g/ha] | VIOTR |
| 6-124 | 80 | 100 |
| 5-59 | 80 | 100 |
| 5-58 | 80 | 100 |
| 5-117 | 80 | 100 |
| 5-253 | 80 | 90 |
| 5-75 | 80 | 100 |
| 5-74 | 80 | 100 |
| 5-123 | 80 | 100 |
| 5-122 | 80 | 100 |
| 1-82 | 80 | 100 |
| 1-87 | 80 | 100 |
| 2-87 | 80 | 90 |
| 1-88 | 80 | 100 |
| 2-88 | 80 | 100 |
| 1-209 | 80 | 100 |
| 1-25 | 80 | 100 |
| 2-25 | 80 | 100 |
| 3-27 | 80 | 100 |
| 1-27 | 80 | 100 |
| 2-27 | 80 | 100 |
| 1-173 | 80 | 90 |
| 2-173 | 80 | 100 |
| 1-273 | 80 | 100 |
| 2-273 | 80 | 100 |
| 3-273 | 80 | 100 |
| 4-212 | 80 | 90 |
| 1-44 | 80 | 90 |
| 2-44 | 80 | 100 |
| 1-45 | 80 | 100 |
| 2-45 | 80 | 100 |
| 1-46 | 80 | 100 |
| 2-46 | 80 | 100 |
| 6-33 | 80 | 100 |
| 1-30 | 80 | 100 |
| 2-30 | 80 | 100 |
| 1-31 | 80 | 100 |
| 2-31 | 80 | 100 |
| 1-28 | 80 | 100 |
| 2-28 | 80 | 100 |
| 1-29 | 80 | 100 |
| 2-29 | 80 | 100 |
| 1-304 | 80 | 100 |
| 2-304 | 80 | 100 |
| 1-305 | 80 | 100 |
| 2-305 | 80 | 100 |
| 1-306 | 80 | 100 |
| 2-306 | 80 | 100 |
| 1-177 | 80 | 100 |
| 2-177 | 80 | 100 |
| 1-178 | 80 | 100 |
| 2-178 | 80 | 100 |
| 1-179 | 80 | 100 |
| 2-179 | 80 | 100 |
| 1-132 | 80 | 100 |
| 2-132 | 80 | 100 |
| 1-135 | 80 | 100 |
| 2-135 | 80 | 100 |
| 6-254 | 80 | 90 |
| 1-134 | 80 | 100 |
| 2-134 | 80 | 100 |
| 1-133 | 80 | 100 |
| 2-133 | 80 | 90 |
| 6-120 | 80 | 90 |
| 1-277 | 80 | 100 |
| 2-277 | 80 | 100 |
| 1-278 | 80 | 100 |
| 2-278 | 80 | 100 |
| 1-279 | 80 | 100 |
| 2-279 | 80 | 100 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 100 |
| 1-225 | 80 | 100 |

TABLE 15b-continued

| Pre-emergence action at 80 g/ha against VIOTR in % | | |
|---|---|---|
| Example number | Dosage [g/ha] | VIOTR |
| 1-226 | 80 | 100 |
| 2-226 | 80 | 100 |
| 6-165 | 80 | 90 |
| 6-166 | 80 | 100 |
| 2-196 | 80 | 100 |
| 1-56 | 80 | 100 |
| 6-45 | 80 | 90 |
| 2-57 | 80 | 100 |
| 1-58 | 80 | 100 |
| 2-58 | 80 | 100 |
| 2-56 | 80 | 90 |
| 1-57 | 80 | 100 |
| 1-207 | 80 | 100 |
| 2-207 | 80 | 100 |
| 2-271 | 80 | 100 |
| 6-210 | 80 | 90 |
| 2-32 | 80 | 100 |
| 1-34 | 80 | 100 |
| 2-34 | 80 | 100 |
| 6-255 | 80 | 90 |
| 2-33 | 80 | 100 |
| 2-42 | 80 | 100 |
| 6-256 | 80 | 90 |
| 2-146 | 80 | 100 |
| 2-142 | 80 | 100 |
| 5-255 | 80 | 100 |
| 1-142 | 80 | 90 |
| 5-254 | 80 | 90 |
| 1-140 | 80 | 90 |
| 1-146 | 80 | 100 |
| 1-141 | 80 | 100 |
| 1-37 | 80 | 100 |
| 2-37 | 80 | 100 |
| 2-143 | 80 | 80 |
| 1-72 | 80 | 100 |
| 2-72 | 80 | 100 |
| 6-49 | 80 | 80 |
| 1-73 | 80 | 100 |
| 2-73 | 80 | 100 |
| 1-74 | 80 | 100 |
| 2-74 | 80 | 100 |
| 1-144 | 80 | 100 |
| 2-144 | 80 | 90 |
| 1-138 | 80 | 100 |
| 2-138 | 80 | 100 |
| 2-141 | 80 | 90 |
| 1-137 | 80 | 100 |
| 1-136 | 80 | 100 |
| 1-180 | 80 | 100 |
| 2-180 | 80 | 100 |
| 1-183 | 80 | 100 |
| 2-183 | 80 | 100 |
| 1-182 | 80 | 100 |
| 2-182 | 80 | 100 |
| 1-181 | 80 | 100 |
| 2-181 | 80 | 80 |
| 2-36 | 80 | 100 |
| 1-228 | 80 | 100 |
| 2-228 | 80 | 100 |
| 6-167 | 80 | 100 |
| 1-230 | 80 | 100 |
| 2-230 | 80 | 100 |
| 2-286 | 80 | 100 |
| 1-287 | 80 | 100 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 100 |
| 2-213 | 80 | 100 |
| 1-288 | 80 | 100 |
| 1-289 | 80 | 100 |
| 2-289 | 80 | 100 |
| 1-291 | 80 | 100 |
| 2-291 | 80 | 100 |

TABLE 15b-continued

| Pre-emergence action at 80 g/ha against VIOTR in % | | |
|---|---|---|
| Example number | Dosage [g/ha] | VIOTR |
| 2-292 | 80 | 100 |
| 1-271 | 80 | 100 |
| 2-47 | 80 | 100 |
| 1-339 | 80 | 100 |
| 2-339 | 80 | 100 |
| 6-258 | 80 | 80 |
| 1-49 | 80 | 100 |
| 2-49 | 80 | 100 |
| 1-41 | 80 | 100 |
| 1-229 | 80 | 100 |
| 2-229 | 80 | 100 |
| 1-340 | 80 | 100 |
| 6-267 | 80 | 80 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 80 |
| 1-155 | 80 | 100 |
| 2-155 | 80 | 100 |
| 2-164 | 80 | 100 |
| 1-165 | 80 | 100 |
| 1-166 | 80 | 100 |
| 1-156 | 80 | 100 |
| 2-156 | 80 | 100 |
| 6-262 | 80 | 90 |
| 2-159 | 80 | 80 |
| 2-162 | 80 | 80 |
| 1-160 | 80 | 80 |
| 2-160 | 80 | 100 |
| 2-161 | 80 | 100 |
| 2-211 | 80 | 80 |
| 2-272 | 80 | 100 |
| 2-276 | 80 | 100 |
| 1-276 | 80 | 100 |
| 1-211 | 80 | 100 |
| 1-274 | 80 | 90 |
| 1-272 | 80 | 100 |
| 6-211 | 80 | 80 |
| 1-341 | 80 | 100 |
| 1-292 | 80 | 100 |
| 2-341 | 80 | 100 |
| 1-158 | 80 | 90 |
| 2-158 | 80 | 100 |
| 1-83 | 80 | 100 |
| 2-83 | 80 | 100 |
| 1-89 | 80 | 100 |
| 2-89 | 80 | 100 |
| 6-161 | 80 | 80 |
| 1-343 | 80 | 100 |
| 2-342 | 80 | 100 |
| 1-344 | 80 | 100 |
| 2-343 | 80 | 100 |
| 1-345 | 80 | 100 |
| 2-344 | 80 | 100 |
| 1-346 | 80 | 100 |
| 2-345 | 80 | 100 |
| 1-347 | 80 | 80 |
| 2-346 | 80 | 80 |
| 1-195 | 80 | 100 |
| 1-184 | 80 | 90 |
| 2-184 | 80 | 100 |
| 1-185 | 80 | 100 |
| 2-185 | 80 | 100 |
| 2-186 | 80 | 90 |
| 1-349 | 80 | 100 |
| 1-350 | 80 | 100 |
| 2-348 | 80 | 100 |
| 1-351 | 80 | 100 |
| 2-349 | 80 | 100 |
| 1-84 | 80 | 100 |
| 2-84 | 80 | 100 |
| 1-352 | 80 | 100 |
| 2-350 | 80 | 100 |
| 1-86 | 80 | 100 |

TABLE 15b-continued

| Pre-emergence action at 80 g/ha against VIOTR in % | | |
|---|---|---|
| Example number | Dosage [g/ha] | VIOTR |
| 2-86 | 80 | 100 |
| 1-92 | 80 | 100 |
| 2-92 | 80 | 100 |
| 1-90 | 80 | 100 |
| 2-90 | 80 | 100 |
| 1-353 | 80 | 100 |
| 2-351 | 80 | 100 |
| 2-352 | 80 | 80 |
| 1-355 | 80 | 100 |
| 2-353 | 80 | 100 |
| 1-356 | 80 | 100 |
| 2-354 | 80 | 100 |

TABLE 15c

| Pre-emergence action at 320 g/ha against VIOTR in % | | |
|---|---|---|
| Example number | Dosage [g/ha] | VIOTR |
| 3-129 | 320 | 100 |
| 2-129 | 320 | 100 |
| 1-129 | 320 | 100 |
| 6-116 | 320 | 100 |
| 1-338 | 320 | 100 |
| 2-338 | 320 | 100 |
| 3-338 | 320 | 100 |
| 6-253 | 320 | 100 |
| 2-337 | 320 | 100 |
| 6-117 | 320 | 100 |
| 1-81 | 320 | 100 |
| 2-81 | 320 | 100 |
| 2-82 | 320 | 100 |
| 6-58 | 320 | 90 |
| 1-147 | 320 | 100 |
| 2-147 | 320 | 100 |
| 1-148 | 320 | 100 |
| 2-148 | 320 | 100 |

TABLE 16a

| Pre-emergence action at 20 g/ha against DIGSA in % | | |
|---|---|---|
| Example number | Dosage [g/ha] | DIGSA |
| 2-337 | 20 | 90 |
| 3-337 | 20 | 90 |
| 2-123 | 20 | 80 |
| 1-26 | 20 | 100 |
| 2-26 | 20 | 100 |
| 6-26 | 20 | 100 |
| 1-208 | 20 | 100 |
| 2-208 | 20 | 90 |
| 6-159 | 20 | 90 |
| 1-130 | 20 | 100 |
| 2-130 | 20 | 100 |
| 1-131 | 20 | 100 |
| 2-131 | 20 | 90 |
| 6-118 | 20 | 90 |
| 1-149 | 20 | 100 |
| 2-149 | 20 | 90 |
| 5-59 | 20 | 100 |
| 5-58 | 20 | 90 |
| 5-117 | 20 | 100 |
| 5-253 | 20 | 80 |
| 5-75 | 20 | 100 |
| 5-74 | 20 | 90 |
| 5-123 | 20 | 100 |
| 5-122 | 20 | 100 |
| 1-82 | 20 | 100 |
| 1-87 | 20 | 100 |
| 2-87 | 20 | 100 |

TABLE 16a-continued

| Pre-emergence action at 20 g/ha against DIGSA in % | | |
|---|---|---|
| Example number | Dosage [g/ha] | DIGSA |
| 1-88 | 20 | 100 |
| 2-88 | 20 | 100 |
| 1-209 | 20 | 100 |
| 1-25 | 20 | 90 |
| 2-25 | 20 | 100 |
| 1-27 | 20 | 100 |
| 2-27 | 20 | 100 |
| 1-173 | 20 | 100 |
| 2-173 | 20 | 100 |
| 1-273 | 20 | 100 |
| 2-273 | 20 | 100 |
| 3-273 | 20 | 90 |
| 6-212 | 20 | 100 |
| 4-212 | 20 | 80 |
| 4-212 | 20 | 80 |
| 1-44 | 20 | 90 |
| 2-44 | 20 | 100 |
| 1-45 | 20 | 100 |
| 2-45 | 20 | 90 |
| 6-32 | 20 | 90 |
| 1-46 | 20 | 90 |
| 2-46 | 20 | 100 |
| 6-33 | 20 | 80 |
| 1-30 | 20 | 100 |
| 2-30 | 20 | 100 |
| 1-31 | 20 | 100 |
| 2-31 | 20 | 100 |
| 1-28 | 20 | 100 |
| 2-28 | 20 | 100 |
| 1-29 | 20 | 100 |
| 2-29 | 20 | 90 |
| 1-304 | 20 | 100 |
| 2-304 | 20 | 90 |
| 6-231 | 20 | 80 |
| 1-305 | 20 | 100 |
| 2-305 | 20 | 100 |
| 1-306 | 20 | 100 |
| 2-306 | 20 | 100 |
| 1-177 | 20 | 100 |
| 2-177 | 20 | 100 |
| 1-178 | 20 | 100 |
| 2-178 | 20 | 100 |
| 6-141 | 20 | 90 |
| 1-179 | 20 | 100 |
| 2-179 | 20 | 100 |
| 1-132 | 20 | 100 |
| 2-132 | 20 | 80 |
| 1-135 | 20 | 90 |
| 2-135 | 20 | 100 |
| 6-254 | 20 | 90 |
| 1-134 | 20 | 90 |
| 2-134 | 20 | 80 |
| 1-133 | 20 | 90 |
| 1-277 | 20 | 100 |
| 2-277 | 20 | 90 |
| 1-278 | 20 | 100 |
| 2-278 | 20 | 100 |
| 1-279 | 20 | 100 |
| 2-279 | 20 | 90 |
| 2-195 | 20 | 90 |
| 2-225 | 20 | 100 |
| 1-197 | 20 | 100 |
| 2-227 | 20 | 90 |
| 1-227 | 20 | 100 |
| 2-197 | 20 | 100 |
| 6-165 | 20 | 90 |
| 6-166 | 20 | 80 |
| 2-196 | 20 | 90 |
| 6-45 | 20 | 90 |
| 2-57 | 20 | 100 |
| 2-58 | 20 | 100 |
| 2-56 | 20 | 100 |
| 1-57 | 20 | 100 |
| 1-207 | 20 | 100 |
| 2-207 | 20 | 90 |
| 2-271 | 20 | 100 |

TABLE 16a-continued

| Pre-emergence action at 20 g/ha against DIGSA in % | | |
|---|---|---|
| Example number | Dosage [g/ha] | DIGSA |
| 6-210 | 20 | 100 |
| 2-32 | 20 | 100 |
| 1-34 | 20 | 100 |
| 2-34 | 20 | 100 |
| 6-255 | 20 | 100 |
| 2-33 | 20 | 100 |
| 2-42 | 20 | 100 |
| 6-256 | 20 | 90 |
| 1-146 | 20 | 100 |
| 1-141 | 20 | 90 |
| 1-37 | 20 | 80 |
| 1-72 | 20 | 90 |
| 2-72 | 20 | 100 |
| 1-73 | 20 | 90 |
| 2-73 | 20 | 90 |
| 1-74 | 20 | 100 |
| 2-74 | 20 | 100 |
| 1-144 | 20 | 90 |
| 1-138 | 20 | 100 |
| 2-138 | 20 | 100 |
| 1-137 | 20 | 100 |
| 1-136 | 20 | 100 |
| 1-180 | 20 | 100 |
| 2-180 | 20 | 100 |
| 1-183 | 20 | 100 |
| 2-183 | 20 | 90 |
| 1-182 | 20 | 100 |
| 2-182 | 20 | 100 |
| 6-145 | 20 | 90 |
| 1-181 | 20 | 100 |
| 6-144 | 20 | 90 |
| 1-228 | 20 | 100 |
| 2-228 | 20 | 100 |
| 1-230 | 20 | 90 |
| 2-230 | 20 | 100 |
| 2-286 | 20 | 100 |
| 1-287 | 20 | 100 |
| 2-287 | 20 | 100 |
| 2-288 | 20 | 100 |
| 1-210 | 20 | 100 |
| 2-210 | 20 | 100 |
| 1-212 | 20 | 100 |
| 2-213 | 20 | 80 |
| 1-288 | 20 | 100 |
| 1-289 | 20 | 100 |
| 2-289 | 20 | 100 |
| 6-228 | 20 | 90 |
| 1-291 | 20 | 100 |
| 2-291 | 20 | 100 |
| 2-292 | 20 | 100 |
| 1-271 | 20 | 100 |
| 2-47 | 20 | 100 |
| 6-34 | 20 | 100 |
| 1-339 | 20 | 100 |
| 2-339 | 20 | 100 |
| 6-258 | 20 | 100 |
| 1-49 | 20 | 90 |
| 2-49 | 20 | 100 |
| 1-229 | 20 | 100 |
| 1-340 | 20 | 100 |
| 2-340 | 20 | 100 |
| 1-47 | 20 | 100 |
| 1-33 | 20 | 100 |
| 1-32 | 20 | 100 |
| 2-154 | 20 | 100 |
| 6-259 | 20 | 100 |
| 1-155 | 20 | 100 |
| 2-155 | 20 | 100 |
| 6-260 | 20 | 100 |
| 6-261 | 20 | 80 |
| 1-165 | 20 | 100 |
| 1-156 | 20 | 100 |
| 2-156 | 20 | 100 |
| 6-262 | 20 | 100 |

TABLE 16b

| Pre-emergence action at 80 g/ha against DIGSA in % | | |
|---|---|---|
| Example number | Dosage [g/ha] | DIGSA |
| 1-337 | 80 | 100 |
| 2-337 | 80 | 100 |
| 3-337 | 80 | 100 |
| 6-252 | 80 | 90 |
| 1-123 | 80 | 90 |
| 2-123 | 80 | 90 |
| 1-26 | 80 | 100 |
| 2-26 | 80 | 100 |
| 3-26 | 80 | 100 |
| 6-26 | 80 | 100 |
| 1-208 | 80 | 100 |
| 2-208 | 80 | 100 |
| 3-208 | 80 | 80 |
| 6-159 | 80 | 100 |
| 1-125 | 80 | 90 |
| 3-125 | 80 | 80 |
| 1-130 | 80 | 100 |
| 2-130 | 80 | 100 |
| 6-117 | 80 | 100 |
| 1-81 | 80 | 100 |
| 2-81 | 80 | 100 |
| 2-82 | 80 | 100 |
| 6-58 | 80 | 100 |
| 1-147 | 80 | 100 |
| 2-147 | 80 | 100 |
| 1-148 | 80 | 100 |
| 2-148 | 80 | 100 |
| 1-131 | 80 | 100 |
| 2-131 | 80 | 100 |
| 6-118 | 80 | 100 |
| 1-149 | 80 | 100 |
| 2-149 | 80 | 100 |
| 6-124 | 80 | 100 |
| 5-59 | 80 | 100 |
| 5-58 | 80 | 100 |
| 5-117 | 80 | 100 |
| 5-253 | 80 | 90 |
| 5-75 | 80 | 100 |
| 5-74 | 80 | 100 |
| 5-123 | 80 | 100 |
| 5-122 | 80 | 100 |
| 1-82 | 80 | 100 |
| 1-87 | 80 | 100 |
| 2-87 | 80 | 100 |
| 1-88 | 80 | 100 |
| 2-88 | 80 | 100 |
| 6-75 | 80 | 80 |
| 1-209 | 80 | 100 |
| 1-4 | 80 | 100 |
| 1-25 | 80 | 100 |
| 2-25 | 80 | 100 |
| 3-27 | 80 | 100 |
| 1-27 | 80 | 100 |
| 2-27 | 80 | 100 |
| 1-173 | 80 | 100 |
| 2-173 | 80 | 100 |
| 1-273 | 80 | 100 |
| 2-273 | 80 | 100 |
| 3-273 | 80 | 100 |
| 6-212 | 80 | 100 |
| 4-212 | 80 | 90 |
| 4-212 | 80 | 90 |
| 1-44 | 80 | 100 |
| 2-44 | 80 | 100 |
| 1-45 | 80 | 100 |
| 2-45 | 80 | 100 |
| 6-32 | 80 | 100 |
| 1-46 | 80 | 100 |
| 2-46 | 80 | 100 |
| 6-33 | 80 | 100 |
| 1-30 | 80 | 100 |
| 2-30 | 80 | 100 |
| 1-31 | 80 | 100 |
| 2-31 | 80 | 100 |

TABLE 16b-continued

| Pre-emergence action at 80 g/ha against DIGSA in % | | |
|---|---|---|
| Example number | Dosage [g/ha] | DIGSA |
| 1-28 | 80 | 100 |
| 2-28 | 80 | 100 |
| 1-29 | 80 | 100 |
| 2-29 | 80 | 100 |
| 1-304 | 80 | 100 |
| 2-304 | 80 | 100 |
| 6-231 | 80 | 90 |
| 1-305 | 80 | 100 |
| 2-305 | 80 | 100 |
| 1-306 | 80 | 100 |
| 2-306 | 80 | 100 |
| 6-233 | 80 | 90 |
| 1-177 | 80 | 100 |
| 2-177 | 80 | 100 |
| 1-178 | 80 | 100 |
| 2-178 | 80 | 100 |
| 6-141 | 80 | 100 |
| 1-179 | 80 | 100 |
| 2-179 | 80 | 100 |
| 1-132 | 80 | 100 |
| 2-132 | 80 | 100 |
| 1-135 | 80 | 100 |
| 2-135 | 80 | 100 |
| 6-254 | 80 | 100 |
| 1-134 | 80 | 100 |
| 2-134 | 80 | 100 |
| 1-133 | 80 | 100 |
| 2-133 | 80 | 90 |
| 6-120 | 80 | 90 |
| 1-277 | 80 | 100 |
| 2-277 | 80 | 100 |
| 1-278 | 80 | 100 |
| 2-278 | 80 | 100 |
| 1-279 | 80 | 100 |
| 2-279 | 80 | 100 |
| 2-195 | 80 | 100 |
| 2-225 | 80 | 100 |
| 1-197 | 80 | 100 |
| 2-227 | 80 | 100 |
| 1-227 | 80 | 100 |
| 2-197 | 80 | 100 |
| 1-225 | 80 | 90 |
| 1-226 | 80 | 90 |
| 6-165 | 80 | 100 |
| 6-166 | 80 | 100 |
| 2-196 | 80 | 100 |
| 1-56 | 80 | 80 |
| 6-45 | 80 | 100 |
| 2-57 | 80 | 100 |
| 6-43 | 80 | 100 |
| 1-58 | 80 | 80 |
| 2-58 | 80 | 100 |
| 2-56 | 80 | 100 |
| 1-57 | 80 | 100 |
| 1-207 | 80 | 100 |
| 2-207 | 80 | 100 |
| 2-271 | 80 | 100 |
| 6-210 | 80 | 100 |
| 2-32 | 80 | 100 |
| 1-34 | 80 | 100 |
| 2-34 | 80 | 100 |
| 6-255 | 80 | 100 |
| 2-33 | 80 | 100 |
| 2-42 | 80 | 100 |
| 6-256 | 80 | 100 |
| 2-146 | 80 | 100 |
| 1-143 | 80 | 80 |
| 1-146 | 80 | 100 |
| 1-141 | 80 | 100 |
| 1-37 | 80 | 100 |
| 2-37 | 80 | 100 |
| 1-72 | 80 | 100 |
| 2-72 | 80 | 100 |
| 1-73 | 80 | 100 |

TABLE 16b-continued

| Pre-emergence action at 80 g/ha against DIGSA in % | | |
|---|---|---|
| Example number | Dosage [g/ha] | DIGSA |
| 2-73 | 80 | 100 |
| 6-50 | 80 | 100 |
| 1-74 | 80 | 100 |
| 2-74 | 80 | 100 |
| 6-51 | 80 | 100 |
| 1-144 | 80 | 90 |
| 2-144 | 80 | 100 |
| 1-138 | 80 | 100 |
| 2-138 | 80 | 100 |
| 2-141 | 80 | 90 |
| 1-137 | 80 | 100 |
| 1-136 | 80 | 100 |
| 1-180 | 80 | 100 |
| 2-180 | 80 | 100 |
| 6-143 | 80 | 100 |
| 1-183 | 80 | 100 |
| 2-183 | 80 | 100 |
| 6-257 | 80 | 100 |
| 1-182 | 80 | 100 |
| 2-182 | 80 | 100 |
| 6-145 | 80 | 100 |
| 1-181 | 80 | 100 |
| 2-181 | 80 | 100 |
| 6-144 | 80 | 100 |
| 2-36 | 80 | 90 |
| 1-228 | 80 | 100 |
| 2-228 | 80 | 100 |
| 6-167 | 80 | 90 |
| 1-230 | 80 | 100 |
| 2-230 | 80 | 100 |
| 6-169 | 80 | 90 |
| 2-286 | 80 | 100 |
| 1-287 | 80 | 100 |
| 2-287 | 80 | 100 |
| 2-288 | 80 | 100 |
| 1-210 | 80 | 100 |
| 2-210 | 80 | 100 |
| 1-212 | 80 | 100 |
| 2-212 | 80 | 100 |
| 2-213 | 80 | 100 |
| 1-288 | 80 | 100 |
| 1-289 | 80 | 100 |
| 2-289 | 80 | 100 |
| 6-228 | 80 | 100 |
| 1-291 | 80 | 100 |
| 2-291 | 80 | 100 |
| 6-230 | 80 | 80 |
| 2-292 | 80 | 100 |
| 1-271 | 80 | 100 |
| 2-47 | 80 | 100 |
| 6-34 | 80 | 100 |
| 1-339 | 80 | 100 |
| 2-339 | 80 | 100 |
| 6-258 | 80 | 100 |
| 1-49 | 80 | 100 |
| 2-49 | 80 | 100 |
| 1-41 | 80 | 100 |
| 1-229 | 80 | 100 |
| 2-229 | 80 | 100 |
| 1-340 | 80 | 100 |
| 2-340 | 80 | 100 |
| 1-47 | 80 | 100 |
| 1-33 | 80 | 100 |
| 1-32 | 80 | 100 |
| 2-154 | 80 | 100 |
| 6-259 | 80 | 100 |
| 1-155 | 80 | 100 |
| 2-155 | 80 | 100 |
| 6-260 | 80 | 100 |
| 1-164 | 80 | 80 |
| 2-164 | 80 | 100 |
| 6-261 | 80 | 100 |
| 1-165 | 80 | 100 |
| 1-166 | 80 | 90 |

TABLE 16b-continued

| Pre-emergence action at 80 g/ha against DIGSA in % | | |
|---|---|---|
| Example number | Dosage [g/ha] | DIGSA |
| 1-156 | 80 | 100 |
| 2-156 | 80 | 100 |
| 6-262 | 80 | 100 |

TABLE 16c

| Pre-emergence action at 320 g/ha against DIGSA in % | | |
|---|---|---|
| Example number | Dosage [g/ha] | DIGSA |
| 2-337 | 320 | 100 |
| 6-252 | 320 | 90 |
| 6-117 | 320 | 100 |
| 1-81 | 320 | 100 |
| 2-81 | 320 | 100 |
| 2-82 | 320 | 100 |
| 6-58 | 320 | 100 |
| 1-147 | 320 | 100 |
| 2-147 | 320 | 100 |
| 1-148 | 320 | 100 |
| 2-148 | 320 | 100 |

2. Post-Emergence Herbicidal Action Against Harmful Plants

Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equivalent to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). Numerous compounds of the invention showed very good action against a multitude of important harmful plants. The tables below illustrate, in an illustrative manner, the post-emergence herbicidal action of the compounds of the invention, the herbicidal activity being stated in percent.

TABLE 17a

| Post-emergence action at 5 g/ha against ABUTH in % | | |
|---|---|---|
| Example number | Dosage [g/ha] | ABUTH |
| 3-129 | 5 | 100 |
| 2-129 | 5 | 100 |
| 1-129 | 5 | 100 |
| 6-116 | 5 | 90 |
| 1-338 | 5 | 90 |
| 2-338 | 5 | 100 |
| 3-338 | 5 | 90 |
| 6-253 | 5 | 100 |
| 3-337 | 5 | 80 |
| 1-26 | 5 | 90 |

TABLE 17a-continued

| Post-emergence action at 5 g/ha against ABUTH in % | | |
|---|---|---|
| Example number | Dosage [g/ha] | ABUTH |
| 2-26 | 5 | 100 |
| 3-26 | 5 | 80 |
| 6-26 | 5 | 90 |
| 1-208 | 5 | 80 |
| 2-208 | 5 | 90 |
| 3-208 | 5 | 90 |
| 6-159 | 5 | 90 |
| 1-130 | 5 | 90 |
| 2-130 | 5 | 90 |
| 1-131 | 5 | 90 |
| 6-118 | 5 | 80 |
| 1-149 | 5 | 80 |
| 2-149 | 5 | 80 |
| 6-124 | 5 | 80 |
| 5-59 | 5 | 90 |
| 5-58 | 5 | 90 |
| 5-117 | 5 | 80 |
| 5-253 | 5 | 90 |
| 5-75 | 5 | 90 |
| 5-74 | 5 | 90 |
| 5-123 | 5 | 90 |
| 5-122 | 5 | 80 |
| 1-82 | 5 | 90 |
| 1-87 | 5 | 90 |
| 2-87 | 5 | 90 |
| 1-88 | 5 | 90 |
| 2-88 | 5 | 90 |
| 1-209 | 5 | 90 |
| 1-4 | 5 | 90 |
| 1-25 | 5 | 100 |
| 2-25 | 5 | 100 |
| 1-27 | 5 | 100 |
| 2-27 | 5 | 100 |
| 2-173 | 5 | 90 |
| 1-273 | 5 | 90 |
| 2-273 | 5 | 90 |
| 3-273 | 5 | 80 |
| 6-212 | 5 | 80 |
| 1-44 | 5 | 90 |
| 2-44 | 5 | 80 |
| 1-45 | 5 | 80 |
| 2-45 | 5 | 80 |
| 6-32 | 5 | 80 |
| 1-46 | 5 | 90 |
| 2-46 | 5 | 80 |
| 1-30 | 5 | 80 |
| 2-30 | 5 | 80 |
| 1-31 | 5 | 80 |
| 1-28 | 5 | 80 |
| 2-28 | 5 | 80 |
| 1-304 | 5 | 90 |
| 2-304 | 5 | 90 |
| 1-305 | 5 | 90 |
| 2-305 | 5 | 80 |
| 1-306 | 5 | 80 |
| 1-177 | 5 | 90 |
| 2-177 | 5 | 80 |
| 1-178 | 5 | 80 |
| 2-178 | 5 | 90 |
| 1-277 | 5 | 90 |
| 2-277 | 5 | 80 |
| 1-278 | 5 | 80 |
| 2-278 | 5 | 80 |
| 1-279 | 5 | 80 |
| 2-195 | 5 | 100 |
| 2-225 | 5 | 100 |
| 2-227 | 5 | 100 |
| 1-227 | 5 | 100 |
| 1-225 | 5 | 80 |
| 1-226 | 5 | 90 |
| 1-56 | 5 | 80 |
| 6-45 | 5 | 80 |
| 2-57 | 5 | 90 |
| 1-58 | 5 | 90 |

TABLE 17a-continued

| Post-emergence action at 5 g/ha against ABUTH in % | | |
|---|---|---|
| Example number | Dosage [g/ha] | ABUTH |
| 2-58 | 5 | 100 |
| 2-56 | 5 | 100 |
| 1-57 | 5 | 90 |
| 1-207 | 5 | 80 |
| 2-271 | 5 | 100 |
| 2-32 | 5 | 90 |
| 1-34 | 5 | 90 |
| 2-34 | 5 | 90 |
| 6-255 | 5 | 90 |
| 2-33 | 5 | 90 |
| 2-42 | 5 | 80 |
| 6-256 | 5 | 80 |
| 1-72 | 5 | 80 |
| 2-72 | 5 | 80 |
| 1-73 | 5 | 80 |
| 2-73 | 5 | 80 |
| 1-74 | 5 | 80 |
| 2-74 | 5 | 80 |
| 2-286 | 5 | 90 |
| 1-287 | 5 | 90 |
| 2-287 | 5 | 80 |
| 2-288 | 5 | 80 |
| 1-210 | 5 | 80 |
| 2-210 | 5 | 80 |
| 1-288 | 5 | 80 |
| 1-289 | 5 | 80 |
| 1-291 | 5 | 80 |
| 2-291 | 5 | 80 |
| 1-271 | 5 | 80 |
| 2-47 | 5 | 90 |
| 2-47 | 5 | 80 |
| 6-34 | 5 | 80 |
| 2-339 | 5 | 80 |
| 6-258 | 5 | 80 |
| 1-49 | 5 | 90 |
| 2-49 | 5 | 90 |
| 1-41 | 5 | 80 |
| 1-32 | 5 | 90 |
| 2-154 | 5 | 80 |
| 1-155 | 5 | 80 |
| 2-155 | 5 | 80 |
| 1-164 | 5 | 80 |
| 1-165 | 5 | 90 |
| 1-166 | 5 | 90 |
| 1-156 | 5 | 90 |
| 6-262 | 5 | 80 |
| 2-211 | 5 | 80 |
| 2-272 | 5 | 90 |
| 2-276 | 5 | 80 |
| 1-276 | 5 | 80 |
| 1-272 | 5 | 80 |
| 6-211 | 5 | 80 |
| 1-83 | 5 | 90 |
| 2-83 | 5 | 90 |
| 1-89 | 5 | 90 |
| 2-89 | 5 | 90 |
| 1-342 | 5 | 90 |
| 1-343 | 5 | 90 |
| 2-342 | 5 | 80 |
| 1-345 | 5 | 80 |
| 2-344 | 5 | 90 |
| 1-346 | 5 | 80 |
| 2-345 | 5 | 90 |
| 1-347 | 5 | 80 |
| 2-346 | 5 | 90 |
| 1-184 | 5 | 80 |
| 2-184 | 5 | 90 |
| 1-185 | 5 | 80 |
| 2-185 | 5 | 90 |
| 1-186 | 5 | 90 |
| 2-186 | 5 | 80 |
| 1-349 | 5 | 80 |
| 2-348 | 5 | 90 |
| 1-86 | 5 | 100 |

TABLE 17a-continued

| Post-emergence action at 5 g/ha against ABUTH in % | | |
|---|---|---|
| Example number | Dosage [g/ha] | ABUTH |
| 2-86 | 5 | 80 |
| 1-92 | 5 | 90 |
| 2-92 | 5 | 80 |
| 1-90 | 5 | 80 |
| 1-354 | 5 | 90 |
| 1-355 | 5 | 80 |
| 2-353 | 5 | 90 |
| 2-354 | 5 | 90 |

TABLE 17b

| Post-emergence action at 20 g/ha against ABUTH in % | | |
|---|---|---|
| Example number | Dosage [g/ha] | ABUTH |
| 3-129 | 20 | 100 |
| 2-129 | 20 | 100 |
| 1-129 | 20 | 100 |
| 6-116 | 20 | 100 |
| 1-338 | 20 | 90 |
| 2-338 | 20 | 100 |
| 3-338 | 20 | 90 |
| 6-253 | 20 | 100 |
| 1-337 | 20 | 80 |
| 2-337 | 20 | 100 |
| 3-337 | 20 | 80 |
| 6-252 | 20 | 80 |
| 1-123 | 20 | 80 |
| 1-26 | 20 | 100 |
| 2-26 | 20 | 100 |
| 3-26 | 20 | 90 |
| 6-26 | 20 | 90 |
| 1-208 | 20 | 90 |
| 2-208 | 20 | 90 |
| 3-208 | 20 | 90 |
| 6-159 | 20 | 100 |
| 3-125 | 20 | 80 |
| 1-130 | 20 | 90 |
| 2-130 | 20 | 90 |
| 6-117 | 20 | 80 |
| 1-81 | 20 | 80 |
| 2-81 | 20 | 90 |
| 2-82 | 20 | 90 |
| 6-58 | 20 | 80 |
| 1-147 | 20 | 90 |
| 2-147 | 20 | 90 |
| 1-148 | 20 | 90 |
| 2-148 | 20 | 90 |
| 1-131 | 20 | 90 |
| 2-131 | 20 | 90 |
| 6-118 | 20 | 90 |
| 1-149 | 20 | 100 |
| 2-149 | 20 | 100 |
| 6-124 | 20 | 80 |
| 5-59 | 20 | 90 |
| 5-58 | 20 | 90 |
| 5-117 | 20 | 90 |
| 5-253 | 20 | 90 |
| 5-75 | 20 | 90 |
| 5-74 | 20 | 90 |
| 5-123 | 20 | 90 |
| 5-122 | 20 | 90 |
| 1-82 | 20 | 90 |
| 1-87 | 20 | 90 |
| 2-87 | 20 | 90 |
| 1-88 | 20 | 90 |
| 2-88 | 20 | 90 |
| 1-209 | 20 | 100 |
| 1-4 | 20 | 90 |

TABLE 17b-continued

| Post-emergence action at 20 g/ha against ABUTH in % | | |
|---|---|---|
| Example number | Dosage [g/ha] | ABUTH |
| 1-25 | 20 | 100 |
| 2-25 | 20 | 100 |
| 3-27 | 20 | 100 |
| 1-27 | 20 | 100 |
| 2-27 | 20 | 100 |
| 1-173 | 20 | 90 |
| 2-173 | 20 | 100 |
| 1-273 | 20 | 90 |
| 2-273 | 20 | 90 |
| 3-273 | 20 | 90 |
| 6-212 | 20 | 90 |
| 4-212 | 20 | 80 |
| 1-44 | 20 | 100 |
| 2-44 | 20 | 90 |
| 1-45 | 20 | 90 |
| 2-45 | 20 | 80 |
| 6-32 | 20 | 80 |
| 1-46 | 20 | 90 |
| 2-46 | 20 | 80 |
| 6-33 | 20 | 80 |
| 1-30 | 20 | 80 |
| 2-30 | 20 | 80 |
| 1-31 | 20 | 80 |
| 2-31 | 20 | 80 |
| 1-28 | 20 | 80 |
| 2-28 | 20 | 80 |
| 1-29 | 20 | 80 |
| 2-29 | 20 | 80 |
| 1-304 | 20 | 90 |
| 2-304 | 20 | 90 |
| 1-305 | 20 | 90 |
| 2-305 | 20 | 90 |
| 1-306 | 20 | 80 |
| 2-306 | 20 | 80 |
| 1-177 | 20 | 90 |
| 2-177 | 20 | 90 |
| 1-178 | 20 | 80 |
| 2-178 | 20 | 90 |
| 6-141 | 20 | 80 |
| 1-179 | 20 | 80 |
| 2-179 | 20 | 90 |
| 1-132 | 20 | 80 |
| 2-132 | 20 | 80 |
| 1-135 | 20 | 80 |
| 2-135 | 20 | 80 |
| 6-254 | 20 | 80 |
| 1-277 | 20 | 90 |
| 2-277 | 20 | 90 |
| 1-278 | 20 | 90 |
| 2-278 | 20 | 90 |
| 1-279 | 20 | 90 |
| 2-279 | 20 | 80 |
| 2-195 | 20 | 100 |
| 2-225 | 20 | 100 |
| 1-197 | 20 | 100 |
| 2-227 | 20 | 100 |
| 1-227 | 20 | 100 |
| 2-197 | 20 | 80 |
| 1-225 | 20 | 80 |
| 1-226 | 20 | 90 |
| 2-226 | 20 | 90 |
| 6-165 | 20 | 90 |
| 6-166 | 20 | 80 |
| 2-196 | 20 | 100 |
| 1-56 | 20 | 100 |
| 6-45 | 20 | 90 |
| 6-44 | 20 | 80 |
| 2-57 | 20 | 100 |
| 1-58 | 20 | 90 |
| 2-58 | 20 | 100 |
| 2-56 | 20 | 100 |
| 1-57 | 20 | 90 |
| 1-207 | 20 | 90 |
| 2-207 | 20 | 90 |

TABLE 17b-continued

| Post-emergence action at 20 g/ha against ABUTH in % | | |
|---|---|---|
| Example number | Dosage [g/ha] | ABUTH |
| 2-271 | 20 | 100 |
| 6-210 | 20 | 90 |
| 2-32 | 20 | 90 |
| 1-34 | 20 | 100 |
| 2-34 | 20 | 90 |
| 6-255 | 20 | 90 |
| 2-33 | 20 | 90 |
| 2-42 | 20 | 90 |
| 6-256 | 20 | 90 |
| 2-146 | 20 | 80 |
| 1-146 | 20 | 80 |
| 2-143 | 20 | 80 |
| 1-72 | 20 | 90 |
| 2-72 | 20 | 80 |
| 6-49 | 20 | 80 |
| 1-73 | 20 | 80 |
| 2-73 | 20 | 80 |
| 6-50 | 20 | 80 |
| 1-74 | 20 | 80 |
| 2-74 | 20 | 80 |
| 2-230 | 20 | 80 |
| 2-286 | 20 | 90 |
| 1-287 | 20 | 100 |
| 2-287 | 20 | 80 |
| 2-288 | 20 | 80 |
| 1-210 | 20 | 90 |
| 2-210 | 20 | 80 |
| 1-212 | 20 | 80 |
| 2-213 | 20 | 80 |
| 1-288 | 20 | 80 |
| 1-289 | 20 | 80 |
| 2-289 | 20 | 80 |
| 1-291 | 20 | 90 |
| 2-291 | 20 | 80 |
| 2-292 | 20 | 80 |
| 1-271 | 20 | 90 |
| 2-47 | 20 | 90 |
| 2-47 | 20 | 90 |
| 6-34 | 20 | 80 |
| 2-339 | 20 | 80 |
| 6-258 | 20 | 90 |
| 1-49 | 20 | 90 |
| 2-49 | 20 | 90 |
| 1-41 | 20 | 80 |
| 2-229 | 20 | 80 |
| 1-340 | 20 | 80 |
| 6-267 | 20 | 80 |
| 1-47 | 20 | 80 |
| 1-33 | 20 | 90 |
| 1-32 | 20 | 90 |
| 2-154 | 20 | 90 |
| 6-259 | 20 | 80 |
| 1-155 | 20 | 90 |
| 2-155 | 20 | 80 |
| 6-260 | 20 | 90 |
| 1-164 | 20 | 80 |
| 6-261 | 20 | 80 |
| 1-165 | 20 | 90 |
| 1-166 | 20 | 90 |
| 1-156 | 20 | 90 |
| 2-156 | 20 | 90 |
| 6-262 | 20 | 90 |
| 1-159 | 20 | 80 |
| 2-160 | 20 | 90 |
| 2-161 | 20 | 80 |
| 2-211 | 20 | 80 |
| 2-272 | 20 | 90 |
| 2-276 | 20 | 80 |
| 1-276 | 20 | 80 |
| 1-211 | 20 | 80 |
| 1-274 | 20 | 80 |
| 1-272 | 20 | 90 |
| 6-211 | 20 | 90 |
| 1-341 | 20 | 80 |

TABLE 17b-continued

| Post-emergence action at 20 g/ha against ABUTH in % | | |
|---|---|---|
| Example number | Dosage [g/ha] | ABUTH |
| 1-292 | 20 | 80 |
| 2-341 | 20 | 80 |
| 1-158 | 20 | 80 |
| 1-83 | 20 | 90 |
| 2-83 | 20 | 90 |
| 6-60 | 20 | 90 |
| 1-89 | 20 | 90 |
| 2-89 | 20 | 90 |
| 6-161 | 20 | 90 |
| 1-342 | 20 | 90 |
| 1-343 | 20 | 90 |
| 2-342 | 20 | 90 |
| 1-344 | 20 | 90 |
| 2-343 | 20 | 80 |
| 1-345 | 20 | 90 |
| 2-344 | 20 | 90 |
| 1-346 | 20 | 100 |
| 2-345 | 20 | 90 |
| 1-347 | 20 | 90 |
| 2-346 | 20 | 90 |
| 1-195 | 20 | 80 |
| 1-184 | 20 | 80 |
| 2-184 | 20 | 90 |
| 1-185 | 20 | 90 |
| 2-185 | 20 | 100 |
| 1-186 | 20 | 90 |
| 2-186 | 20 | 90 |
| 1-349 | 20 | 90 |
| 2-348 | 20 | 90 |
| 1-351 | 20 | 80 |
| 2-349 | 20 | 80 |
| 2-84 | 20 | 90 |
| 1-352 | 20 | 100 |
| 2-350 | 20 | 80 |
| 1-86 | 20 | 100 |
| 2-86 | 20 | 100 |
| 1-92 | 20 | 100 |
| 2-92 | 20 | 90 |
| 1-90 | 20 | 90 |
| 2-90 | 20 | 90 |
| 1-353 | 20 | 80 |
| 2-351 | 20 | 80 |
| 1-354 | 20 | 100 |
| 2-352 | 20 | 80 |
| 1-355 | 20 | 100 |
| 2-353 | 20 | 100 |
| 1-356 | 20 | 100 |
| 2-354 | 20 | 90 |

TABLE 17c

| Post-emergence action at 80 g/ha against ABUTH in % | | |
|---|---|---|
| Example number | Dosage [g/ha] | ABUTH |
| 3-129 | 80 | 100 |
| 2-129 | 80 | 100 |
| 1-129 | 80 | 100 |
| 6-116 | 80 | 100 |
| 1-338 | 80 | 100 |
| 2-338 | 80 | 100 |
| 3-338 | 80 | 100 |
| 6-253 | 80 | 100 |
| 2-337 | 80 | 100 |
| 6-252 | 80 | 100 |
| 6-117 | 80 | 80 |
| 1-81 | 80 | 90 |
| 2-81 | 80 | 90 |
| 2-82 | 80 | 90 |

TABLE 17c-continued

| Post-emergence action at 80 g/ha against ABUTH in % | | |
|---|---|---|
| Example number | Dosage [g/ha] | ABUTH |
| 6-58 | 80 | 80 |
| 1-147 | 80 | 90 |
| 2-147 | 80 | 90 |
| 1-148 | 80 | 90 |
| 2-148 | 80 | 90 |

TABLE 18a

| Post-emergence action at 5 g/ha against ALOMY in % | | |
|---|---|---|
| Example number | Dosage [g/ha] | ALOMY |
| 2-129 | 5 | 100 |
| 1-129 | 5 | 90 |
| 2-27 | 5 | 80 |
| 1-273 | 5 | 80 |
| 2-177 | 5 | 80 |
| 1-178 | 5 | 90 |
| 2-178 | 5 | 80 |
| 1-179 | 5 | 90 |
| 1-132 | 5 | 80 |
| 2-195 | 5 | 80 |
| 1-226 | 5 | 80 |
| 2-32 | 5 | 90 |
| 2-33 | 5 | 90 |
| 2-42 | 5 | 90 |
| 1-136 | 5 | 80 |
| 1-182 | 5 | 90 |
| 2-182 | 5 | 80 |
| 1-181 | 5 | 80 |
| 1-210 | 5 | 80 |
| 1-212 | 5 | 80 |
| 2-291 | 5 | 80 |
| 1-271 | 5 | 80 |
| 2-47 | 5 | 80 |
| 1-47 | 5 | 80 |
| 1-32 | 5 | 80 |
| 1-165 | 5 | 90 |
| 1-166 | 5 | 80 |
| 1-342 | 5 | 90 |
| 1-343 | 5 | 90 |
| 2-342 | 5 | 90 |
| 2-343 | 5 | 80 |
| 1-345 | 5 | 80 |
| 2-344 | 5 | 80 |
| 1-346 | 5 | 80 |
| 2-345 | 5 | 80 |
| 1-195 | 5 | 90 |
| 1-184 | 5 | 80 |
| 2-184 | 5 | 80 |
| 1-186 | 5 | 80 |
| 2-348 | 5 | 80 |
| 1-351 | 5 | 90 |
| 2-352 | 5 | 80 |

TABLE 18b

| Post-emergence action at 20 g/ha against ALOMY in % | | |
|---|---|---|
| Example number | Dosage [g/ha] | ALOMY |
| 3-129 | 20 | 80 |
| 2-129 | 20 | 100 |
| 1-129 | 20 | 100 |
| 6-116 | 20 | 80 |

TABLE 18b-continued

| Post-emergence action at 20 g/ha against ALOMY in % | | |
|---|---|---|
| Example number | Dosage [g/ha] | ALOMY |
| 2-338 | 20 | 80 |
| 1-26 | 20 | 90 |
| 2-26 | 20 | 80 |
| 3-26 | 20 | 80 |
| 1-208 | 20 | 80 |
| 2-208 | 20 | 80 |
| 6-159 | 20 | 80 |
| 1-130 | 20 | 80 |
| 2-130 | 20 | 80 |
| 6-117 | 20 | 80 |
| 1-81 | 20 | 80 |
| 2-81 | 20 | 80 |
| 1-147 | 20 | 80 |
| 2-147 | 20 | 80 |
| 1-148 | 20 | 80 |
| 2-148 | 20 | 80 |
| 1-131 | 20 | 90 |
| 2-131 | 20 | 80 |
| 6-118 | 20 | 80 |
| 1-149 | 20 | 80 |
| 2-149 | 20 | 80 |
| 6-124 | 20 | 90 |
| 5-59 | 20 | 80 |
| 5-58 | 20 | 80 |
| 5-117 | 20 | 80 |
| 5-75 | 20 | 80 |
| 5-123 | 20 | 80 |
| 5-122 | 20 | 80 |
| 1-82 | 20 | 90 |
| 1-87 | 20 | 80 |
| 2-87 | 20 | 80 |
| 1-88 | 20 | 80 |
| 2-88 | 20 | 80 |
| 1-209 | 20 | 80 |
| 1-4 | 20 | 80 |
| 1-25 | 20 | 100 |
| 2-25 | 20 | 90 |
| 1-27 | 20 | 100 |
| 2-27 | 20 | 90 |
| 1-173 | 20 | 80 |
| 2-173 | 20 | 100 |
| 1-273 | 20 | 100 |
| 2-273 | 20 | 80 |
| 6-212 | 20 | 80 |
| 1-46 | 20 | 90 |
| 2-46 | 20 | 80 |
| 1-30 | 20 | 80 |
| 2-31 | 20 | 80 |
| 1-177 | 20 | 90 |
| 2-177 | 20 | 100 |
| 1-178 | 20 | 100 |
| 2-178 | 20 | 90 |
| 6-141 | 20 | 90 |
| 1-179 | 20 | 90 |
| 2-179 | 20 | 90 |
| 1-132 | 20 | 90 |
| 1-135 | 20 | 90 |
| 2-134 | 20 | 80 |
| 1-133 | 20 | 90 |
| 2-133 | 20 | 80 |
| 2-278 | 20 | 80 |
| 2-195 | 20 | 100 |
| 2-197 | 20 | 90 |
| 1-225 | 20 | 90 |
| 1-226 | 20 | 100 |
| 2-226 | 20 | 90 |
| 6-165 | 20 | 80 |
| 2-196 | 20 | 90 |
| 2-57 | 20 | 90 |
| 2-58 | 20 | 80 |
| 2-56 | 20 | 80 |
| 1-57 | 20 | 80 |
| 1-207 | 20 | 90 |
| 2-207 | 20 | 90 |

TABLE 18b-continued

| Post-emergence action at 20 g/ha against ALOMY in % | | |
|---|---|---|
| Example number | Dosage [g/ha] | ALOMY |
| 2-271 | 20 | 100 |
| 2-32 | 20 | 100 |
| 1-34 | 20 | 90 |
| 2-34 | 20 | 100 |
| 6-255 | 20 | 90 |
| 2-33 | 20 | 100 |
| 2-42 | 20 | 100 |
| 2-142 | 20 | 80 |
| 1-142 | 20 | 90 |
| 2-74 | 20 | 80 |
| 1-138 | 20 | 90 |
| 1-137 | 20 | 90 |
| 1-136 | 20 | 90 |
| 2-180 | 20 | 90 |
| 1-183 | 20 | 90 |
| 2-183 | 20 | 80 |
| 1-182 | 20 | 100 |
| 2-182 | 20 | 100 |
| 6-145 | 20 | 80 |
| 1-181 | 20 | 100 |
| 2-181 | 20 | 90 |
| 2-36 | 20 | 90 |
| 1-228 | 20 | 90 |
| 2-228 | 20 | 80 |
| 1-230 | 20 | 90 |
| 2-230 | 20 | 90 |
| 2-287 | 20 | 90 |
| 2-288 | 20 | 90 |
| 1-210 | 20 | 100 |
| 2-210 | 20 | 90 |
| 1-212 | 20 | 90 |
| 1-288 | 20 | 90 |
| 2-289 | 20 | 90 |
| 1-291 | 20 | 90 |
| 2-291 | 20 | 80 |
| 2-292 | 20 | 80 |
| 1-271 | 20 | 90 |
| 2-47 | 20 | 90 |
| 2-47 | 20 | 90 |
| 1-339 | 20 | 80 |
| 2-339 | 20 | 80 |
| 6-258 | 20 | 80 |
| 2-49 | 20 | 80 |
| 1-229 | 20 | 80 |
| 1-340 | 20 | 80 |
| 1-47 | 20 | 90 |
| 1-33 | 20 | 90 |
| 1-32 | 20 | 90 |
| 2-154 | 20 | 80 |
| 1-155 | 20 | 90 |
| 2-155 | 20 | 90 |
| 1-165 | 20 | 100 |
| 1-166 | 20 | 90 |
| 1-156 | 20 | 80 |
| 2-156 | 20 | 90 |
| 1-160 | 20 | 80 |
| 2-160 | 20 | 80 |
| 2-211 | 20 | 80 |
| 2-272 | 20 | 90 |
| 2-276 | 20 | 80 |
| 1-276 | 20 | 80 |
| 1-274 | 20 | 80 |
| 1-272 | 20 | 90 |
| 1-341 | 20 | 80 |
| 1-292 | 20 | 80 |
| 1-83 | 20 | 100 |
| 2-83 | 20 | 100 |
| 1-89 | 20 | 90 |
| 2-89 | 20 | 90 |
| 6-161 | 20 | 90 |
| 1-342 | 20 | 100 |
| 1-343 | 20 | 100 |
| 2-342 | 20 | 90 |
| 1-344 | 20 | 100 |

TABLE 18b-continued

| Post-emergence action at 20 g/ha against ALOMY in % | | |
|---|---|---|
| Example number | Dosage [g/ha] | ALOMY |
| 2-343 | 20 | 100 |
| 1-345 | 20 | 90 |
| 2-344 | 20 | 90 |
| 1-346 | 20 | 90 |
| 2-345 | 20 | 80 |
| 1-347 | 20 | 80 |
| 2-346 | 20 | 80 |
| 1-195 | 20 | 100 |
| 1-184 | 20 | 80 |
| 2-184 | 20 | 100 |
| 1-185 | 20 | 90 |
| 2-185 | 20 | 90 |
| 1-186 | 20 | 90 |
| 2-186 | 20 | 80 |
| 1-349 | 20 | 80 |
| 2-348 | 20 | 90 |
| 1-351 | 20 | 90 |
| 2-349 | 20 | 80 |
| 1-84 | 20 | 100 |
| 2-84 | 20 | 90 |
| 1-352 | 20 | 80 |
| 2-350 | 20 | 80 |
| 1-86 | 20 | 100 |
| 2-86 | 20 | 80 |
| 1-92 | 20 | 90 |
| 2-92 | 20 | 80 |
| 1-90 | 20 | 80 |
| 1-353 | 20 | 80 |
| 2-351 | 20 | 80 |
| 1-354 | 20 | 80 |
| 2-352 | 20 | 90 |
| 1-355 | 20 | 80 |
| 1-356 | 20 | 80 |
| 2-354 | 20 | 80 |

TABLE 18c

| Post-emergence action at 80 g/ha against ALOMY in % | | |
|---|---|---|
| Example number | Dosage [g/ha] | ALOMY |
| 3-129 | 80 | 100 |
| 2-129 | 80 | 100 |
| 1-129 | 80 | 100 |
| 6-116 | 80 | 100 |
| 1-338 | 80 | 100 |
| 2-338 | 80 | 100 |
| 3-338 | 80 | 100 |
| 6-253 | 80 | 80 |
| 2-337 | 80 | 90 |
| 6-117 | 80 | 90 |
| 1-81 | 80 | 90 |
| 2-81 | 80 | 90 |
| 2-82 | 80 | 90 |
| 1-147 | 80 | 90 |
| 2-147 | 80 | 90 |
| 1-148 | 80 | 90 |
| 2-148 | 80 | 90 |

TABLE 19a

| Post-emergence action at 5 g/ha against AMARE in % | | |
|---|---|---|
| Example number | Dosage [g/ha] | ALOMY |
| 3-129 | 5 | 90 |
| 2-129 | 5 | 100 |
| 1-129 | 5 | 100 |
| 6-116 | 5 | 100 |
| 1-338 | 5 | 90 |
| 2-338 | 5 | 80 |
| 3-338 | 5 | 90 |
| 2-337 | 5 | 80 |
| 3-337 | 5 | 90 |
| 2-123 | 5 | 80 |
| 1-26 | 5 | 90 |
| 2-26 | 5 | 100 |
| 3-26 | 5 | 90 |
| 6-26 | 5 | 100 |
| 1-208 | 5 | 100 |
| 2-208 | 5 | 90 |
| 3-208 | 5 | 80 |
| 6-159 | 5 | 90 |
| 1-130 | 5 | 90 |
| 2-130 | 5 | 90 |
| 1-131 | 5 | 100 |
| 2-131 | 5 | 100 |
| 6-118 | 5 | 100 |
| 1-149 | 5 | 90 |
| 2-149 | 5 | 100 |
| 6-124 | 5 | 100 |
| 5-59 | 5 | 90 |
| 5-58 | 5 | 90 |
| 5-117 | 5 | 100 |
| 5-253 | 5 | 80 |
| 5-75 | 5 | 90 |
| 5-74 | 5 | 90 |
| 5-123 | 5 | 90 |
| 5-122 | 5 | 90 |
| 1-82 | 5 | 90 |
| 1-87 | 5 | 90 |
| 2-87 | 5 | 90 |
| 1-88 | 5 | 90 |
| 2-88 | 5 | 90 |
| 1-209 | 5 | 90 |
| 1-4 | 5 | 80 |
| 1-25 | 5 | 100 |
| 1-27 | 5 | 100 |
| 2-27 | 5 | 100 |
| 1-173 | 5 | 100 |
| 2-173 | 5 | 100 |
| 1-273 | 5 | 90 |
| 6-212 | 5 | 80 |
| 1-44 | 5 | 100 |
| 2-44 | 5 | 100 |
| 1-45 | 5 | 90 |
| 2-45 | 5 | 100 |
| 6-32 | 5 | 80 |
| 1-46 | 5 | 100 |
| 2-46 | 5 | 100 |
| 6-33 | 5 | 90 |
| 1-304 | 5 | 90 |
| 2-304 | 5 | 90 |
| 6-231 | 5 | 80 |
| 1-305 | 5 | 90 |
| 2-305 | 5 | 100 |
| 1-306 | 5 | 100 |
| 2-306 | 5 | 90 |
| 1-177 | 5 | 90 |
| 2-177 | 5 | 100 |
| 1-178 | 5 | 90 |
| 2-178 | 5 | 100 |
| 6-141 | 5 | 90 |
| 1-179 | 5 | 100 |
| 2-179 | 5 | 100 |
| 1-132 | 5 | 100 |
| 2-132 | 5 | 80 |
| 1-135 | 5 | 90 |
| 2-135 | 5 | 90 |

TABLE 19a-continued

| Post-emergence action at 5 g/ha against AMARE in % | | |
|---|---|---|
| Example number | Dosage [g/ha] | ALOMY |
| 6-254 | 5 | 80 |
| 1-134 | 5 | 90 |
| 2-134 | 5 | 80 |
| 1-133 | 5 | 90 |
| 2-133 | 5 | 80 |
| 6-120 | 5 | 80 |
| 1-277 | 5 | 100 |
| 2-277 | 5 | 90 |
| 1-278 | 5 | 90 |
| 2-278 | 5 | 90 |
| 1-279 | 5 | 90 |
| 2-195 | 5 | 100 |
| 2-225 | 5 | 100 |
| 1-197 | 5 | 100 |
| 2-227 | 5 | 100 |
| 1-227 | 5 | 100 |
| 2-197 | 5 | 80 |
| 1-225 | 5 | 90 |
| 1-226 | 5 | 90 |
| 2-226 | 5 | 90 |
| 1-56 | 5 | 100 |
| 2-57 | 5 | 100 |
| 1-58 | 5 | 100 |
| 2-58 | 5 | 100 |
| 2-56 | 5 | 100 |
| 1-57 | 5 | 100 |
| 1-207 | 5 | 100 |
| 2-207 | 5 | 100 |
| 2-271 | 5 | 100 |
| 6-210 | 5 | 100 |
| 2-32 | 5 | 100 |
| 1-34 | 5 | 100 |
| 2-34 | 5 | 100 |
| 6-255 | 5 | 100 |
| 2-33 | 5 | 100 |
| 2-42 | 5 | 100 |
| 6-256 | 5 | 80 |
| 2-146 | 5 | 80 |
| 1-141 | 5 | 90 |
| 1-144 | 5 | 80 |
| 1-138 | 5 | 80 |
| 2-138 | 5 | 90 |
| 2-141 | 5 | 80 |
| 1-137 | 5 | 90 |
| 1-136 | 5 | 90 |
| 1-181 | 5 | 100 |
| 1-228 | 5 | 90 |
| 6-167 | 5 | 80 |
| 2-286 | 5 | 90 |
| 2-287 | 5 | 90 |
| 2-288 | 5 | 90 |
| 1-212 | 5 | 90 |
| 1-288 | 5 | 90 |
| 1-289 | 5 | 90 |
| 2-289 | 5 | 90 |
| 1-291 | 5 | 80 |
| 6-230 | 5 | 90 |
| 2-292 | 5 | 80 |
| 1-271 | 5 | 90 |
| 2-47 | 5 | 90 |
| 2-47 | 5 | 100 |
| 6-34 | 5 | 90 |
| 1-339 | 5 | 80 |
| 2-339 | 5 | 80 |
| 6-258 | 5 | 90 |
| 1-49 | 5 | 90 |
| 2-49 | 5 | 90 |
| 1-41 | 5 | 80 |
| 1-229 | 5 | 90 |
| 2-229 | 5 | 80 |
| 1-340 | 5 | 90 |
| 6-267 | 5 | 90 |
| 2-340 | 5 | 90 |
| 1-47 | 5 | 90 |

TABLE 19a-continued

| Post-emergence action at 5 g/ha against AMARE in % | | |
|---|---|---|
| Example number | Dosage [g/ha] | ALOMY |
| 1-33 | 5 | 80 |
| 1-32 | 5 | 90 |
| 2-154 | 5 | 90 |
| 6-259 | 5 | 80 |
| 1-155 | 5 | 90 |
| 2-155 | 5 | 90 |
| 1-164 | 5 | 90 |
| 2-164 | 5 | 80 |
| 6-261 | 5 | 80 |
| 1-165 | 5 | 90 |
| 1-166 | 5 | 80 |
| 1-156 | 5 | 80 |
| 2-156 | 5 | 90 |
| 1-159 | 5 | 90 |
| 2-159 | 5 | 90 |
| 1-162 | 5 | 90 |
| 2-162 | 5 | 80 |
| 1-160 | 5 | 90 |
| 2-160 | 5 | 90 |
| 2-161 | 5 | 90 |
| 6-266 | 5 | 80 |
| 2-211 | 5 | 90 |
| 2-272 | 5 | 90 |
| 1-161 | 5 | 80 |
| 2-276 | 5 | 80 |
| 1-276 | 5 | 100 |
| 1-211 | 5 | 90 |
| 1-274 | 5 | 100 |
| 6-168 | 5 | 80 |
| 1-272 | 5 | 90 |
| 6-211 | 5 | 80 |
| 1-341 | 5 | 80 |
| 1-292 | 5 | 80 |
| 2-341 | 5 | 90 |
| 1-158 | 5 | 80 |
| 1-83 | 5 | 100 |
| 2-83 | 5 | 100 |
| 6-60 | 5 | 80 |
| 1-89 | 5 | 100 |
| 2-89 | 5 | 100 |
| 6-76 | 5 | 100 |
| 6-161 | 5 | 100 |
| 6-268 | 5 | 90 |
| 1-342 | 5 | 100 |
| 1-343 | 5 | 100 |
| 2-342 | 5 | 100 |
| 1-344 | 5 | 100 |
| 2-343 | 5 | 90 |
| 1-345 | 5 | 100 |
| 2-344 | 5 | 100 |
| 1-346 | 5 | 100 |
| 2-345 | 5 | 90 |
| 1-347 | 5 | 100 |
| 2-346 | 5 | 100 |
| 1-195 | 5 | 100 |
| 1-184 | 5 | 100 |
| 2-184 | 5 | 100 |
| 1-185 | 5 | 100 |
| 2-185 | 5 | 100 |
| 1-186 | 5 | 90 |
| 2-186 | 5 | 100 |
| 1-349 | 5 | 100 |
| 1-350 | 5 | 90 |
| 2-348 | 5 | 90 |
| 1-351 | 5 | 100 |
| 2-349 | 5 | 90 |
| 1-84 | 5 | 100 |
| 2-84 | 5 | 100 |
| 1-352 | 5 | 100 |
| 2-350 | 5 | 100 |
| 1-86 | 5 | 100 |
| 2-86 | 5 | 100 |
| 1-92 | 5 | 100 |
| 2-92 | 5 | 100 |

TABLE 19a-continued

| Post-emergence action at 5 g/ha against AMARE in % | | |
|---|---|---|
| Example number | Dosage [g/ha] | ALOMY |
| 1-90 | 5 | 100 |
| 2-90 | 5 | 100 |
| 1-353 | 5 | 100 |
| 2-351 | 5 | 100 |
| 1-354 | 5 | 90 |
| 2-352 | 5 | 100 |
| 1-355 | 5 | 100 |
| 2-353 | 5 | 100 |
| 1-356 | 5 | 100 |
| 2-354 | 5 | 100 |

TABLE 19b

| Post-emergence action at 20 g/ha against AMARE in % | | |
|---|---|---|
| Example number | Dosage [g/ha] | AMARE |
| 3-129 | 20 | 100 |
| 2-129 | 20 | 100 |
| 1-129 | 20 | 100 |
| 6-116 | 20 | 100 |
| 1-338 | 20 | 90 |
| 2-338 | 20 | 100 |
| 3-338 | 20 | 90 |
| 2-337 | 20 | 100 |
| 3-337 | 20 | 100 |
| 1-123 | 20 | 80 |
| 2-123 | 20 | 80 |
| 1-26 | 20 | 100 |
| 2-26 | 20 | 100 |
| 3-26 | 20 | 90 |
| 6-26 | 20 | 100 |
| 1-208 | 20 | 100 |
| 2-208 | 20 | 100 |
| 3-208 | 20 | 90 |
| 6-159 | 20 | 100 |
| 1-125 | 20 | 80 |
| 2-125 | 20 | 80 |
| 3-125 | 20 | 90 |
| 1-130 | 20 | 90 |
| 2-130 | 20 | 100 |
| 1-81 | 20 | 90 |
| 2-81 | 20 | 90 |
| 2-82 | 20 | 90 |
| 1-147 | 20 | 90 |
| 2-147 | 20 | 90 |
| 1-148 | 20 | 90 |
| 2-148 | 20 | 90 |
| 1-131 | 20 | 100 |
| 2-131 | 20 | 100 |
| 6-118 | 20 | 100 |
| 1-149 | 20 | 100 |
| 2-149 | 20 | 100 |
| 6-124 | 20 | 100 |
| 5-59 | 20 | 90 |
| 5-58 | 20 | 90 |
| 5-117 | 20 | 100 |
| 5-253 | 20 | 80 |
| 5-75 | 20 | 90 |
| 5-74 | 20 | 100 |
| 5-123 | 20 | 90 |
| 5-122 | 20 | 90 |
| 1-82 | 20 | 90 |
| 1-87 | 20 | 100 |
| 2-87 | 20 | 90 |
| 1-88 | 20 | 90 |
| 2-88 | 20 | 90 |
| 1-209 | 20 | 100 |
| 1-4 | 20 | 90 |

TABLE 19b-continued

| Post-emergence action at 20 g/ha against AMARE in % | | |
|---|---|---|
| Example number | Dosage [g/ha] | AMARE |
| 1-25 | 20 | 100 |
| 1-27 | 20 | 100 |
| 2-27 | 20 | 100 |
| 1-173 | 20 | 100 |
| 2-173 | 20 | 100 |
| 1-273 | 20 | 100 |
| 2-273 | 20 | 90 |
| 6-212 | 20 | 90 |
| 4-212 | 20 | 80 |
| 1-44 | 20 | 100 |
| 2-44 | 20 | 100 |
| 1-45 | 20 | 90 |
| 2-45 | 20 | 100 |
| 6-32 | 20 | 100 |
| 1-46 | 20 | 100 |
| 2-46 | 20 | 100 |
| 6-33 | 20 | 90 |
| 2-31 | 20 | 80 |
| 1-304 | 20 | 90 |
| 2-304 | 20 | 100 |
| 6-231 | 20 | 90 |
| 1-305 | 20 | 90 |
| 2-305 | 20 | 100 |
| 1-306 | 20 | 100 |
| 2-306 | 20 | 90 |
| 1-177 | 20 | 100 |
| 2-177 | 20 | 100 |
| 1-178 | 20 | 100 |
| 2-178 | 20 | 100 |
| 6-141 | 20 | 100 |
| 1-179 | 20 | 100 |
| 2-179 | 20 | 100 |
| 1-132 | 20 | 100 |
| 2-132 | 20 | 90 |
| 1-135 | 20 | 90 |
| 2-135 | 20 | 90 |
| 6-254 | 20 | 100 |
| 1-134 | 20 | 90 |
| 2-134 | 20 | 100 |
| 1-133 | 20 | 100 |
| 2-133 | 20 | 90 |
| 6-120 | 20 | 90 |
| 1-277 | 20 | 100 |
| 2-277 | 20 | 90 |
| 1-278 | 20 | 90 |
| 2-278 | 20 | 100 |
| 1-279 | 20 | 100 |
| 2-279 | 20 | 100 |
| 2-195 | 20 | 100 |
| 2-225 | 20 | 100 |
| 1-197 | 20 | 100 |
| 2-227 | 20 | 100 |
| 1-227 | 20 | 100 |
| 2-197 | 20 | 90 |
| 1-225 | 20 | 100 |
| 1-226 | 20 | 100 |
| 2-226 | 20 | 100 |
| 6-165 | 20 | 80 |
| 6-166 | 20 | 90 |
| 1-56 | 20 | 100 |
| 6-45 | 20 | 80 |
| 6-44 | 20 | 90 |
| 2-57 | 20 | 100 |
| 1-58 | 20 | 100 |
| 2-58 | 20 | 100 |
| 2-56 | 20 | 100 |
| 1-57 | 20 | 100 |
| 1-207 | 20 | 100 |
| 2-207 | 20 | 100 |
| 2-271 | 20 | 100 |
| 6-210 | 20 | 100 |
| 2-32 | 20 | 100 |
| 1-34 | 20 | 100 |
| 2-34 | 20 | 100 |

TABLE 19b-continued

| Post-emergence action at 20 g/ha against AMARE in % | | |
|---|---|---|
| Example number | Dosage [g/ha] | AMARE |
| 6-255 | 20 | 100 |
| 2-33 | 20 | 100 |
| 2-42 | 20 | 100 |
| 6-256 | 20 | 90 |
| 2-146 | 20 | 80 |
| 2-142 | 20 | 100 |
| 5-255 | 20 | 90 |
| 1-142 | 20 | 90 |
| 5-254 | 20 | 80 |
| 1-140 | 20 | 80 |
| 1-146 | 20 | 100 |
| 1-141 | 20 | 100 |
| 1-144 | 20 | 90 |
| 1-138 | 20 | 90 |
| 2-138 | 20 | 90 |
| 2-141 | 20 | 80 |
| 1-137 | 20 | 90 |
| 1-136 | 20 | 90 |
| 1-181 | 20 | 100 |
| 1-36 | 20 | 100 |
| 2-36 | 20 | 90 |
| 1-228 | 20 | 90 |
| 2-228 | 20 | 90 |
| 6-167 | 20 | 100 |
| 1-230 | 20 | 100 |
| 2-230 | 20 | 100 |
| 6-169 | 20 | 90 |
| 2-286 | 20 | 100 |
| 2-287 | 20 | 100 |
| 2-288 | 20 | 100 |
| 2-210 | 20 | 100 |
| 1-212 | 20 | 100 |
| 1-288 | 20 | 100 |
| 1-289 | 20 | 90 |
| 2-289 | 20 | 100 |
| 6-228 | 20 | 90 |
| 1-291 | 20 | 90 |
| 2-291 | 20 | 90 |
| 6-230 | 20 | 90 |
| 2-292 | 20 | 90 |
| 1-271 | 20 | 90 |
| 2-47 | 20 | 90 |
| 2-47 | 20 | 100 |
| 6-34 | 20 | 100 |
| 1-339 | 20 | 90 |
| 2-339 | 20 | 90 |
| 6-258 | 20 | 90 |
| 1-49 | 20 | 90 |
| 2-49 | 20 | 100 |
| 1-41 | 20 | 90 |
| 1-229 | 20 | 90 |
| 2-229 | 20 | 90 |
| 1-340 | 20 | 90 |
| 6-267 | 20 | 90 |
| 2-340 | 20 | 100 |
| 1-47 | 20 | 90 |
| 1-33 | 20 | 100 |
| 1-32 | 20 | 90 |
| 2-154 | 20 | 90 |
| 6-259 | 20 | 100 |
| 1-155 | 20 | 90 |
| 2-155 | 20 | 90 |
| 6-260 | 20 | 80 |
| 1-164 | 20 | 90 |
| 2-164 | 20 | 90 |
| 6-261 | 20 | 90 |
| 1-165 | 20 | 90 |
| 1-166 | 20 | 90 |
| 1-156 | 20 | 90 |
| 2-156 | 20 | 90 |
| 6-262 | 20 | 90 |
| 2-157 | 20 | 90 |
| 1-159 | 20 | 100 |
| 2-159 | 20 | 100 |

TABLE 19b-continued

| Post-emergence action at 20 g/ha against AMARE in % | | |
|---|---|---|
| Example number | Dosage [g/ha] | AMARE |
| 1-162 | 20 | 90 |
| 2-162 | 20 | 100 |
| 6-264 | 20 | 80 |
| 1-160 | 20 | 100 |
| 2-160 | 20 | 100 |
| 2-161 | 20 | 100 |
| 6-266 | 20 | 100 |
| 2-211 | 20 | 90 |
| 2-272 | 20 | 100 |
| 1-161 | 20 | 90 |
| 2-276 | 20 | 90 |
| 1-276 | 20 | 100 |
| 1-211 | 20 | 90 |
| 1-274 | 20 | 100 |
| 6-168 | 20 | 100 |
| 1-272 | 20 | 100 |
| 6-211 | 20 | 90 |
| 1-341 | 20 | 100 |
| 1-292 | 20 | 100 |
| 2-341 | 20 | 100 |
| 1-158 | 20 | 90 |
| 1-83 | 20 | 100 |
| 2-83 | 20 | 100 |
| 6-60 | 20 | 100 |
| 1-89 | 20 | 100 |
| 2-89 | 20 | 100 |
| 6-76 | 20 | 100 |
| 6-161 | 20 | 100 |
| 6-268 | 20 | 100 |
| 1-342 | 20 | 100 |
| 1-343 | 20 | 100 |
| 2-342 | 20 | 100 |
| 1-344 | 20 | 100 |
| 2-343 | 20 | 100 |
| 1-345 | 20 | 100 |
| 2-344 | 20 | 100 |
| 1-346 | 20 | 100 |
| 2-345 | 20 | 100 |
| 1-347 | 20 | 100 |
| 2-346 | 20 | 100 |
| 1-195 | 20 | 100 |
| 1-184 | 20 | 100 |
| 2-184 | 20 | 100 |
| 1-185 | 20 | 100 |
| 2-185 | 20 | 100 |
| 1-186 | 20 | 100 |
| 2-186 | 20 | 100 |
| 1-349 | 20 | 100 |
| 1-350 | 20 | 100 |
| 2-348 | 20 | 100 |
| 1-351 | 20 | 100 |
| 2-349 | 20 | 100 |
| 1-84 | 20 | 100 |
| 2-84 | 20 | 100 |
| 1-352 | 20 | 100 |
| 2-350 | 20 | 100 |
| 1-86 | 20 | 100 |
| 2-86 | 20 | 100 |
| 1-92 | 20 | 100 |
| 2-92 | 20 | 100 |
| 1-90 | 20 | 100 |
| 2-90 | 20 | 100 |
| 1-353 | 20 | 100 |
| 2-351 | 20 | 100 |
| 1-354 | 20 | 100 |
| 2-352 | 20 | 100 |
| 1-355 | 20 | 100 |
| 2-353 | 20 | 100 |
| 1-356 | 20 | 100 |
| 2-354 | 20 | 100 |

TABLE 19c

| Post-emergence action at 80 g/ha against AMARE in % | | |
|---|---|---|
| Example number | Dosage [g/ha] | AMARE |
| 3-129 | 80 | 100 |
| 2-129 | 80 | 100 |
| 1-129 | 80 | 100 |
| 6-116 | 80 | 100 |
| 1-338 | 80 | 100 |
| 2-338 | 80 | 100 |
| 3-338 | 80 | 100 |
| 6-253 | 80 | 100 |
| 2-337 | 80 | 100 |
| 6-117 | 80 | 80 |
| 1-81 | 80 | 90 |
| 2-81 | 80 | 90 |
| 2-82 | 80 | 90 |
| 6-58 | 80 | 90 |
| 1-147 | 80 | 90 |
| 2-147 | 80 | 90 |
| 1-148 | 80 | 90 |
| 2-148 | 80 | 90 |

TABLE 20a

| Post-emergence action at 5 g/ha against AVEFA in % | | |
|---|---|---|
| Example number | Dosage [g/ha] | AVEFA |
| 2-129 | 5 | 100 |
| 6-116 | 5 | 100 |
| 2-208 | 5 | 80 |
| 2-131 | 5 | 80 |
| 5-117 | 5 | 80 |
| 2-27 | 5 | 90 |
| 1-173 | 5 | 90 |
| 1-28 | 5 | 80 |
| 2-28 | 5 | 80 |
| 1-29 | 5 | 80 |
| 1-132 | 5 | 80 |
| 2-32 | 5 | 90 |
| 2-34 | 5 | 80 |

TABLE 20b

| Post-emergence action at 20 g/ha against AVEFA in % | | |
|---|---|---|
| Example number | Dosage [g/ha] | AVEFA |
| 3-129 | 20 | 100 |
| 2-129 | 20 | 100 |
| 1-129 | 20 | 100 |
| 6-116 | 20 | 100 |
| 1-338 | 20 | 80 |
| 2-338 | 20 | 80 |
| 3-337 | 20 | 80 |
| 2-26 | 20 | 80 |
| 1-208 | 20 | 90 |
| 2-208 | 20 | 90 |
| 3-208 | 20 | 80 |
| 1-130 | 20 | 80 |
| 2-130 | 20 | 90 |
| 2-81 | 20 | 90 |
| 2-82 | 20 | 90 |
| 6-58 | 20 | 80 |
| 1-147 | 20 | 90 |
| 2-147 | 20 | 90 |
| 1-148 | 20 | 100 |
| 2-148 | 20 | 90 |

TABLE 20b-continued

| Post-emergence action at 20 g/ha against AVEFA in % | | |
|---|---|---|
| Example number | Dosage [g/ha] | AVEFA |
| 1-131 | 20 | 80 |
| 2-131 | 20 | 80 |
| 1-149 | 20 | 100 |
| 5-117 | 20 | 90 |
| 5-75 | 20 | 80 |
| 5-74 | 20 | 80 |
| 5-123 | 20 | 80 |
| 5-122 | 20 | 80 |
| 1-82 | 20 | 90 |
| 1-87 | 20 | 80 |
| 2-87 | 20 | 80 |
| 1-88 | 20 | 80 |
| 2-88 | 20 | 80 |
| 1-4 | 20 | 80 |
| 2-25 | 20 | 100 |
| 3-27 | 20 | 90 |
| 1-27 | 20 | 100 |
| 2-27 | 20 | 100 |
| 1-173 | 20 | 100 |
| 2-173 | 20 | 100 |
| 1-273 | 20 | 90 |
| 3-273 | 20 | 80 |
| 1-44 | 20 | 80 |
| 2-44 | 20 | 80 |
| 1-46 | 20 | 80 |
| 1-30 | 20 | 80 |
| 1-31 | 20 | 90 |
| 2-31 | 20 | 80 |
| 1-28 | 20 | 80 |
| 2-28 | 20 | 90 |
| 1-29 | 20 | 90 |
| 2-29 | 20 | 80 |
| 1-178 | 20 | 80 |
| 2-178 | 20 | 80 |
| 1-179 | 20 | 90 |
| 1-132 | 20 | 90 |
| 2-135 | 20 | 80 |
| 1-277 | 20 | 80 |
| 2-195 | 20 | 80 |
| 1-227 | 20 | 80 |
| 1-225 | 20 | 80 |
| 1-226 | 20 | 80 |
| 2-226 | 20 | 80 |
| 2-57 | 20 | 80 |
| 1-58 | 20 | 90 |
| 2-58 | 20 | 80 |
| 2-271 | 20 | 80 |
| 2-32 | 20 | 100 |
| 2-34 | 20 | 80 |
| 2-33 | 20 | 100 |
| 1-137 | 20 | 80 |
| 2-182 | 20 | 80 |
| 1-181 | 20 | 90 |
| 2-230 | 20 | 80 |
| 2-288 | 20 | 80 |
| 1-212 | 20 | 80 |
| 1-291 | 20 | 80 |
| 2-291 | 20 | 90 |
| 2-292 | 20 | 80 |
| 1-271 | 20 | 80 |
| 2-47 | 20 | 80 |
| 1-49 | 20 | 80 |
| 1-165 | 20 | 90 |
| 2-272 | 20 | 80 |
| 2-341 | 20 | 90 |
| 2-83 | 20 | 90 |
| 2-89 | 20 | 80 |
| 1-344 | 20 | 80 |
| 2-345 | 20 | 80 |
| 1-349 | 20 | 80 |
| 1-351 | 20 | 80 |
| 2-349 | 20 | 90 |
| 1-84 | 20 | 80 |
| 2-84 | 20 | 100 |

TABLE 20b-continued

| Post-emergence action at 20 g/ha against AVEFA in % | | |
|---|---|---|
| Example number | Dosage [g/ha] | AVEFA |
| 1-352 | 20 | 80 |
| 2-350 | 20 | 90 |
| 1-86 | 20 | 100 |
| 2-86 | 20 | 80 |
| 1-92 | 20 | 90 |
| 2-92 | 20 | 80 |
| 2-90 | 20 | 80 |
| 1-353 | 20 | 80 |
| 2-351 | 20 | 80 |

TABLE 20c

| Post-emergence action at 80 g/ha against AVEFA in % | | |
|---|---|---|
| Example number | Dosage [g/ha] | AVEFA |
| 3-129 | 80 | 100 |
| 2-129 | 80 | 100 |
| 1-129 | 80 | 100 |
| 6-116 | 80 | 100 |
| 1-338 | 80 | 100 |
| 2-338 | 80 | 100 |
| 3-338 | 80 | 100 |
| 6-253 | 80 | 80 |
| 2-337 | 80 | 90 |
| 6-117 | 80 | 90 |
| 1-81 | 80 | 90 |
| 2-81 | 80 | 100 |
| 2-82 | 80 | 90 |
| 6-58 | 80 | 90 |
| 1-147 | 80 | 90 |
| 2-147 | 80 | 100 |
| 1-148 | 80 | 100 |
| 2-148 | 80 | 90 |

TABLE 21a

| Post-emergence action at 20 g/ha against CYPES in % | | |
|---|---|---|
| Example number | Dosage [g/ha] | CYPES |
| 1-338 | 20 | 80 |

TABLE 21b

| Post-emergence action at 80 g/ha against CYPES in % | | |
|---|---|---|
| Example number | Dosage [g/ha] | CYPES |
| 2-129 | 80 | 90 |
| 1-129 | 80 | 80 |
| 1-338 | 80 | 90 |
| 6-253 | 80 | 80 |

TABLE 22a

| Post-emergence action at 5 g/ha against ECHCG in % | | |
|---|---|---|
| Example number | Dosage [g/ha] | ECHCG |
| 1-129 | 5 | 100 |
| 2-26 | 5 | 80 |
| 6-26 | 5 | 80 |
| 6-159 | 5 | 80 |
| 1-130 | 5 | 80 |
| 5-59 | 5 | 80 |
| 5-58 | 5 | 80 |
| 5-117 | 5 | 80 |
| 5-75 | 5 | 80 |
| 5-74 | 5 | 80 |
| 5-123 | 5 | 90 |
| 5-122 | 5 | 90 |
| 1-82 | 5 | 80 |
| 1-87 | 5 | 80 |
| 2-87 | 5 | 80 |
| 1-88 | 5 | 80 |
| 2-88 | 5 | 80 |
| 2-27 | 5 | 80 |
| 2-173 | 5 | 80 |
| 1-273 | 5 | 80 |
| 2-273 | 5 | 80 |
| 3-273 | 5 | 80 |
| 6-212 | 5 | 90 |
| 1-45 | 5 | 80 |
| 1-46 | 5 | 80 |
| 2-30 | 5 | 80 |
| 1-31 | 5 | 80 |
| 2-31 | 5 | 80 |
| 1-28 | 5 | 80 |
| 2-28 | 5 | 80 |
| 2-305 | 5 | 90 |
| 1-306 | 5 | 90 |
| 2-306 | 5 | 90 |
| 1-135 | 5 | 80 |
| 2-135 | 5 | 80 |
| 1-278 | 5 | 90 |
| 1-279 | 5 | 80 |
| 1-225 | 5 | 90 |
| 1-226 | 5 | 100 |
| 6-165 | 5 | 90 |
| 6-166 | 5 | 80 |
| 1-56 | 5 | 80 |
| 2-57 | 5 | 100 |
| 1-58 | 5 | 90 |
| 2-58 | 5 | 90 |
| 1-57 | 5 | 80 |
| 2-32 | 5 | 80 |
| 1-34 | 5 | 90 |
| 2-34 | 5 | 90 |
| 6-255 | 5 | 90 |
| 2-33 | 5 | 90 |
| 2-42 | 5 | 90 |
| 6-256 | 5 | 90 |
| 1-37 | 5 | 80 |
| 2-72 | 5 | 80 |
| 1-73 | 5 | 80 |
| 2-73 | 5 | 80 |
| 1-74 | 5 | 80 |
| 2-74 | 5 | 80 |
| 1-138 | 5 | 80 |
| 2-138 | 5 | 80 |
| 1-137 | 5 | 90 |
| 1-136 | 5 | 80 |
| 6-257 | 5 | 80 |
| 2-182 | 5 | 90 |
| 1-181 | 5 | 80 |
| 2-228 | 5 | 80 |
| 1-230 | 5 | 80 |
| 6-169 | 5 | 80 |
| 2-287 | 5 | 80 |
| 2-288 | 5 | 80 |
| 1-212 | 5 | 80 |
| 2-213 | 5 | 80 |
| 1-288 | 5 | 80 |

TABLE 22a-continued

| Post-emergence action at 5 g/ha against ECHCG in % | | |
|---|---|---|
| Example number | Dosage [g/ha] | ECHCG |
| 2-289 | 5 | 80 |
| 1-291 | 5 | 80 |
| 2-291 | 5 | 80 |
| 2-292 | 5 | 80 |
| 1-271 | 5 | 80 |
| 2-47 | 5 | 80 |
| 2-47 | 5 | 80 |
| 6-34 | 5 | 80 |
| 1-339 | 5 | 90 |
| 6-258 | 5 | 80 |
| 1-49 | 5 | 80 |
| 1-229 | 5 | 90 |
| 1-47 | 5 | 90 |
| 1-33 | 5 | 80 |
| 6-259 | 5 | 80 |
| 1-155 | 5 | 90 |
| 6-260 | 5 | 90 |
| 1-164 | 5 | 80 |
| 1-156 | 5 | 80 |
| 2-156 | 5 | 90 |
| 2-272 | 5 | 80 |
| 1-211 | 5 | 80 |
| 1-274 | 5 | 80 |
| 6-168 | 5 | 80 |
| 1-272 | 5 | 80 |
| 1-341 | 5 | 80 |
| 1-292 | 5 | 80 |
| 2-341 | 5 | 80 |
| 6-161 | 5 | 90 |
| 1-343 | 5 | 80 |
| 2-344 | 5 | 80 |
| 1-346 | 5 | 80 |
| 2-346 | 5 | 80 |
| 1-185 | 5 | 90 |
| 2-84 | 5 | 100 |
| 1-352 | 5 | 100 |
| 1-86 | 5 | 80 |
| 2-86 | 5 | 100 |
| 1-92 | 5 | 100 |
| 2-92 | 5 | 80 |
| 1-353 | 5 | 100 |
| 2-351 | 5 | 100 |

TABLE 22b

| Post-emergence action at 20 G/ha against ECHCG in % | | |
|---|---|---|
| Example number | Dosage [g/ha] | ECHCG |
| 2-129 | 20 | 100 |
| 1-129 | 20 | 100 |
| 6-116 | 20 | 100 |
| 1-338 | 20 | 90 |
| 2-338 | 20 | 80 |
| 1-26 | 20 | 80 |
| 2-26 | 20 | 80 |
| 6-26 | 20 | 90 |
| 2-208 | 20 | 80 |
| 6-159 | 20 | 90 |
| 1-130 | 20 | 80 |
| 2-130 | 20 | 80 |
| 6-117 | 20 | 80 |
| 1-81 | 20 | 80 |
| 2-81 | 20 | 90 |
| 2-82 | 20 | 80 |
| 6-58 | 20 | 90 |
| 1-147 | 20 | 90 |
| 2-147 | 20 | 90 |
| 1-148 | 20 | 80 |

TABLE 22b-continued

| Post-emergence action at 20 G/ha against ECHCG in % | | |
|---|---|---|
| Example number | Dosage [g/ha] | ECHCG |
| 2-148 | 20 | 80 |
| 1-131 | 20 | 90 |
| 2-131 | 20 | 80 |
| 6-118 | 20 | 90 |
| 1-149 | 20 | 80 |
| 2-149 | 20 | 80 |
| 6-124 | 20 | 80 |
| 5-59 | 20 | 90 |
| 5-58 | 20 | 90 |
| 5-117 | 20 | 80 |
| 5-253 | 20 | 80 |
| 5-75 | 20 | 80 |
| 5-74 | 20 | 80 |
| 5-123 | 20 | 90 |
| 5-122 | 20 | 90 |
| 1-82 | 20 | 90 |
| 1-87 | 20 | 80 |
| 2-87 | 20 | 80 |
| 1-88 | 20 | 90 |
| 2-88 | 20 | 80 |
| 1-209 | 20 | 90 |
| 1-4 | 20 | 100 |
| 1-25 | 20 | 100 |
| 2-25 | 20 | 80 |
| 1-27 | 20 | 80 |
| 2-27 | 20 | 100 |
| 1-173 | 20 | 80 |
| 2-173 | 20 | 90 |
| 1-273 | 20 | 90 |
| 2-273 | 20 | 90 |
| 3-273 | 20 | 80 |
| 6-212 | 20 | 90 |
| 1-44 | 20 | 80 |
| 2-44 | 20 | 80 |
| 1-45 | 20 | 80 |
| 2-45 | 20 | 80 |
| 1-46 | 20 | 80 |
| 2-46 | 20 | 80 |
| 6-33 | 20 | 80 |
| 1-30 | 20 | 80 |
| 2-30 | 20 | 80 |
| 1-31 | 20 | 80 |
| 2-31 | 20 | 90 |
| 1-28 | 20 | 90 |
| 2-28 | 20 | 80 |
| 1-29 | 20 | 80 |
| 2-29 | 20 | 80 |
| 1-304 | 20 | 90 |
| 2-304 | 20 | 80 |
| 1-305 | 20 | 90 |
| 2-305 | 20 | 90 |
| 1-306 | 20 | 90 |
| 2-306 | 20 | 90 |
| 6-233 | 20 | 80 |
| 1-177 | 20 | 90 |
| 1-178 | 20 | 90 |
| 2-178 | 20 | 90 |
| 6-141 | 20 | 80 |
| 1-179 | 20 | 90 |
| 2-179 | 20 | 80 |
| 1-132 | 20 | 90 |
| 2-132 | 20 | 90 |
| 1-135 | 20 | 100 |
| 2-135 | 20 | 90 |
| 6-254 | 20 | 90 |
| 1-134 | 20 | 90 |
| 2-134 | 20 | 90 |
| 2-133 | 20 | 80 |
| 6-120 | 20 | 90 |
| 1-277 | 20 | 90 |
| 2-277 | 20 | 100 |
| 1-278 | 20 | 90 |
| 2-278 | 20 | 90 |
| 1-279 | 20 | 90 |

TABLE 22b-continued

| Post-emergence action at 20 G/ha against ECHCG in % | | |
|---|---|---|
| Example number | Dosage [g/ha] | ECHCG |
| 2-279 | 20 | 90 |
| 2-225 | 20 | 100 |
| 1-197 | 20 | 90 |
| 2-227 | 20 | 80 |
| 2-197 | 20 | 90 |
| 1-225 | 20 | 100 |
| 1-226 | 20 | 100 |
| 2-226 | 20 | 90 |
| 6-165 | 20 | 100 |
| 6-166 | 20 | 90 |
| 2-196 | 20 | 80 |
| 1-56 | 20 | 90 |
| 6-45 | 20 | 90 |
| 6-44 | 20 | 90 |
| 2-57 | 20 | 100 |
| 1-58 | 20 | 90 |
| 2-58 | 20 | 100 |
| 2-56 | 20 | 100 |
| 1-57 | 20 | 100 |
| 1-207 | 20 | 80 |
| 6-210 | 20 | 80 |
| 2-32 | 20 | 90 |
| 1-34 | 20 | 90 |
| 2-34 | 20 | 100 |
| 6-255 | 20 | 100 |
| 2-33 | 20 | 100 |
| 2-42 | 20 | 100 |
| 6-256 | 20 | 90 |
| 1-146 | 20 | 80 |
| 1-37 | 20 | 80 |
| 2-37 | 20 | 80 |
| 1-72 | 20 | 80 |
| 2-72 | 20 | 80 |
| 1-73 | 20 | 80 |
| 2-73 | 20 | 80 |
| 6-50 | 20 | 80 |
| 1-74 | 20 | 80 |
| 2-74 | 20 | 80 |
| 6-51 | 20 | 80 |
| 1-138 | 20 | 90 |
| 2-138 | 20 | 90 |
| 2-141 | 20 | 80 |
| 1-137 | 20 | 90 |
| 1-136 | 20 | 90 |
| 2-180 | 20 | 90 |
| 1-183 | 20 | 100 |
| 2-183 | 20 | 90 |
| 6-257 | 20 | 90 |
| 1-182 | 20 | 80 |
| 2-182 | 20 | 90 |
| 1-181 | 20 | 80 |
| 2-181 | 20 | 90 |
| 6-144 | 20 | 80 |
| 1-228 | 20 | 80 |
| 2-228 | 20 | 90 |
| 6-167 | 20 | 80 |
| 1-230 | 20 | 80 |
| 6-169 | 20 | 90 |
| 2-286 | 20 | 100 |
| 1-287 | 20 | 100 |
| 2-287 | 20 | 80 |
| 2-288 | 20 | 80 |
| 1-210 | 20 | 80 |
| 2-210 | 20 | 90 |
| 1-212 | 20 | 80 |
| 2-212 | 20 | 80 |
| 2-213 | 20 | 80 |
| 1-288 | 20 | 80 |
| 1-289 | 20 | 80 |
| 2-289 | 20 | 90 |
| 1-291 | 20 | 80 |
| 2-291 | 20 | 80 |
| 2-292 | 20 | 80 |
| 1-271 | 20 | 80 |

TABLE 22b-continued

| Post-emergence action at 20 G/ha against ECHCG in % | | |
|---|---|---|
| Example number | Dosage [g/ha] | ECHCG |
| 2-47 | 20 | 90 |
| 2-47 | 20 | 80 |
| 6-34 | 20 | 90 |
| 1-339 | 20 | 90 |
| 2-339 | 20 | 90 |
| 6-258 | 20 | 90 |
| 1-49 | 20 | 90 |
| 2-49 | 20 | 90 |
| 1-41 | 20 | 90 |
| 1-229 | 20 | 90 |
| 2-229 | 20 | 90 |
| 1-340 | 20 | 90 |
| 6-267 | 20 | 90 |
| 2-340 | 20 | 90 |
| 1-47 | 20 | 90 |
| 1-33 | 20 | 90 |
| 1-32 | 20 | 90 |
| 2-154 | 20 | 90 |
| 6-259 | 20 | 90 |
| 1-155 | 20 | 90 |
| 6-260 | 20 | 90 |
| 1-164 | 20 | 90 |
| 2-164 | 20 | 80 |
| 6-261 | 20 | 90 |
| 1-165 | 20 | 90 |
| 1-166 | 20 | 90 |
| 1-156 | 20 | 90 |
| 2-156 | 20 | 90 |
| 6-262 | 20 | 80 |
| 1-159 | 20 | 90 |
| 1-162 | 20 | 80 |
| 2-211 | 20 | 80 |
| 2-272 | 20 | 90 |
| 2-276 | 20 | 90 |
| 1-276 | 20 | 80 |
| 1-211 | 20 | 90 |
| 1-274 | 20 | 90 |
| 6-168 | 20 | 80 |
| 1-272 | 20 | 90 |
| 6-211 | 20 | 90 |
| 1-341 | 20 | 90 |
| 1-292 | 20 | 80 |
| 2-341 | 20 | 90 |
| 1-83 | 20 | 90 |
| 2-83 | 20 | 90 |
| 6-60 | 20 | 90 |
| 2-89 | 20 | 90 |
| 6-76 | 20 | 80 |
| 6-161 | 20 | 90 |
| 1-342 | 20 | 80 |
| 1-343 | 20 | 90 |
| 1-345 | 20 | 90 |
| 2-344 | 20 | 90 |
| 1-346 | 20 | 90 |
| 2-345 | 20 | 80 |
| 1-347 | 20 | 90 |
| 2-346 | 20 | 90 |
| 1-195 | 20 | 80 |
| 1-184 | 20 | 100 |
| 2-184 | 20 | 100 |
| 1-185 | 20 | 100 |
| 2-185 | 20 | 100 |
| 1-186 | 20 | 90 |
| 1-350 | 20 | 80 |
| 2-348 | 20 | 80 |
| 1-351 | 20 | 100 |
| 1-84 | 20 | 100 |
| 2-84 | 20 | 100 |
| 1-352 | 20 | 100 |
| 2-350 | 20 | 100 |
| 1-86 | 20 | 100 |
| 2-86 | 20 | 100 |
| 1-92 | 20 | 100 |
| 2-92 | 20 | 100 |

TABLE 22b-continued

| Post-emergence action at 20 G/ha against ECHCG in % | | |
|---|---|---|
| Example number | Dosage [g/ha] | ECHCG |
| 1-90 | 20 | 100 |
| 2-90 | 20 | 100 |
| 1-353 | 20 | 100 |
| 2-351 | 20 | 100 |
| 2-352 | 20 | 90 |
| 1-355 | 20 | 90 |

TABLE 22c

| Post-emergence action at 80 g/ha against ECHCG in % | | |
|---|---|---|
| Example number | Dosage [g/ha] | ECHCG |
| 3-129 | 80 | 100 |
| 2-129 | 80 | 100 |
| 1-129 | 80 | 100 |
| 6-116 | 80 | 100 |
| 1-338 | 80 | 90 |
| 2-338 | 80 | 100 |
| 3-338 | 80 | 80 |
| 6-253 | 80 | 90 |
| 2-337 | 80 | 90 |
| 6-117 | 80 | 80 |
| 1-81 | 80 | 90 |
| 2-81 | 80 | 90 |
| 2-82 | 80 | 80 |
| 6-58 | 80 | 90 |
| 1-147 | 80 | 90 |
| 2-147 | 80 | 90 |
| 1-148 | 80 | 80 |
| 2-148 | 80 | 90 |

TABLE 23a

| Post-emergence action at 5 g/ha against HORMU in % | | |
|---|---|---|
| Example number | Dosage [g/ha] | HORMU |
| 2-129 | 5 | 80 |
| 1-129 | 5 | 90 |
| 1-273 | 5 | 80 |

TABLE 23b

| Post-emergence action at 20 g/ha against HORMU in % | | |
|---|---|---|
| Example number | Dosage [g/ha] | HORMU |
| 3-129 | 20 | 90 |
| 2-129 | 20 | 90 |
| 1-129 | 20 | 100 |
| 6-116 | 20 | 90 |
| 1-338 | 20 | 80 |
| 2-26 | 20 | 80 |
| 6-117 | 20 | 80 |
| 2-82 | 20 | 80 |
| 1-147 | 20 | 80 |
| 2-147 | 20 | 80 |
| 2-148 | 20 | 80 |
| 1-131 | 20 | 80 |
| 2-131 | 20 | 100 |

TABLE 23b-continued

| Post-emergence action at 20 g/ha against HORMU in % | | |
|---|---|---|
| Example number | Dosage [g/ha] | HORMU |
| 5-59 | 20 | 80 |
| 5-117 | 20 | 80 |
| 5-122 | 20 | 80 |
| 1-82 | 20 | 90 |
| 1-87 | 20 | 80 |
| 2-87 | 20 | 80 |
| 2-88 | 20 | 80 |
| 1-25 | 20 | 100 |
| 2-25 | 20 | 80 |
| 1-27 | 20 | 80 |
| 2-27 | 20 | 90 |
| 1-173 | 20 | 90 |
| 2-173 | 20 | 100 |
| 1-273 | 20 | 90 |
| 2-46 | 20 | 80 |

TABLE 23c

| Post-emergence action at 80 g/ha against HORMU in % | | |
|---|---|---|
| Example number | Dosage [g/ha] | HORMU |
| 3-129 | 80 | 100 |
| 2-129 | 80 | 100 |
| 1-129 | 80 | 100 |
| 6-116 | 80 | 100 |
| 1-338 | 80 | 90 |
| 2-338 | 80 | 100 |
| 3-338 | 80 | 100 |
| 6-253 | 80 | 90 |
| 6-117 | 80 | 90 |
| 1-81 | 80 | 80 |
| 2-81 | 80 | 80 |
| 2-82 | 80 | 90 |
| 1-147 | 80 | 90 |
| 2-147 | 80 | 90 |
| 1-148 | 80 | 90 |
| 2-148 | 80 | 90 |

TABLE 24a

| Post-emergence action at 5 g/ha against LOLRI in % | | |
|---|---|---|
| Example number | Dosage [g/ha] | LOLRI |
| 1-129 | 5 | 80 |

TABLE 24b

| Post-emergence action at 20 g/ha against LOLRI in % | | |
|---|---|---|
| Example number | Dosage [g/ha] | LOLRI |
| 2-129 | 20 | 100 |
| 1-129 | 20 | 100 |
| 1-26 | 20 | 80 |
| 2-81 | 20 | 80 |
| 1-148 | 20 | 80 |

TABLE 24b-continued

| Post-emergence action at 20 g/ha against LOLRI in % | | |
|---|---|---|
| Example number | Dosage [g/ha] | LOLRI |
| 5-123 | 20 | 80 |
| 5-122 | 20 | 80 |
| 1-82 | 20 | 80 |
| 1-209 | 20 | 80 |
| 2-27 | 20 | 80 |
| 1-173 | 20 | 90 |
| 1-273 | 20 | 80 |
| 1-178 | 20 | 80 |
| 1-179 | 20 | 80 |
| 2-32 | 20 | 80 |
| 1-181 | 20 | 80 |
| 1-165 | 20 | 80 |
| 1-351 | 20 | 80 |

TABLE 24c

| Post-emergence action at 80 g/ha against LOLRI in % | | |
|---|---|---|
| Example number | Dosage [g/ha] | LOLRI |
| 3-129 | 80 | 80 |
| 2-129 | 80 | 100 |
| 1-129 | 80 | 100 |
| 6-116 | 80 | 90 |
| 1-338 | 80 | 80 |
| 2-338 | 80 | 90 |
| 2-81 | 80 | 90 |
| 2-82 | 80 | 90 |
| 1-147 | 80 | 90 |
| 2-147 | 80 | 90 |
| 1-148 | 80 | 90 |
| 2-148 | 80 | 80 |

TABLE 25a

| Post-emergence action at 5 g/ha against MATIN in % | | |
|---|---|---|
| Example number | Dosage [g/ha] | MATIN |
| 3-129 | 5 | 100 |
| 2-129 | 5 | 80 |
| 6-116 | 5 | 80 |
| 1-26 | 5 | 90 |
| 2-26 | 5 | 80 |
| 3-26 | 5 | 90 |
| 3-208 | 5 | 90 |
| 1-131 | 5 | 90 |
| 2-131 | 5 | 90 |
| 2-149 | 5 | 90 |
| 5-117 | 5 | 80 |
| 5-122 | 5 | 80 |
| 2-87 | 5 | 80 |
| 1-88 | 5 | 80 |
| 2-25 | 5 | 90 |
| 3-27 | 5 | 90 |
| 1-27 | 5 | 80 |
| 2-27 | 5 | 100 |
| 1-273 | 5 | 100 |
| 2-273 | 5 | 80 |
| 3-273 | 5 | 80 |
| 1-44 | 5 | 80 |
| 2-44 | 5 | 80 |
| 1-45 | 5 | 80 |
| 2-31 | 5 | 80 |
| 1-304 | 5 | 90 |

TABLE 25a-continued

| Post-emergence action at 5 g/ha against MATIN in % | | |
|---|---|---|
| Example number | Dosage [g/ha] | MATIN |
| 2-304 | 5 | 90 |
| 1-305 | 5 | 90 |
| 2-305 | 5 | 80 |
| 1-306 | 5 | 90 |
| 2-306 | 5 | 80 |
| 2-177 | 5 | 90 |
| 2-178 | 5 | 90 |
| 2-179 | 5 | 80 |
| 2-132 | 5 | 80 |
| 1-135 | 5 | 80 |
| 2-135 | 5 | 90 |
| 1-277 | 5 | 90 |
| 2-277 | 5 | 90 |
| 1-278 | 5 | 80 |
| 2-278 | 5 | 90 |
| 1-279 | 5 | 90 |
| 2-195 | 5 | 80 |
| 2-196 | 5 | 80 |
| 2-57 | 5 | 80 |
| 1-58 | 5 | 80 |
| 2-58 | 5 | 80 |
| 2-56 | 5 | 80 |
| 1-57 | 5 | 80 |
| 2-207 | 5 | 80 |
| 2-271 | 5 | 100 |
| 2-32 | 5 | 90 |
| 2-33 | 5 | 90 |
| 2-146 | 5 | 80 |
| 2-73 | 5 | 80 |
| 1-74 | 5 | 80 |
| 1-137 | 5 | 80 |
| 1-183 | 5 | 90 |
| 2-183 | 5 | 80 |
| 2-182 | 5 | 90 |
| 2-181 | 5 | 80 |
| 2-286 | 5 | 90 |
| 1-287 | 5 | 80 |
| 2-287 | 5 | 90 |
| 2-288 | 5 | 80 |
| 1-210 | 5 | 80 |
| 2-213 | 5 | 90 |
| 1-288 | 5 | 90 |
| 2-289 | 5 | 80 |
| 1-291 | 5 | 80 |
| 2-291 | 5 | 80 |
| 2-292 | 5 | 80 |
| 1-271 | 5 | 90 |
| 2-49 | 5 | 80 |
| 1-33 | 5 | 80 |
| 1-32 | 5 | 80 |
| 1-164 | 5 | 80 |
| 1-166 | 5 | 80 |
| 2-272 | 5 | 80 |
| 1-292 | 5 | 80 |
| 1-83 | 5 | 80 |
| 2-83 | 5 | 80 |
| 2-89 | 5 | 90 |
| 1-346 | 5 | 80 |
| 2-345 | 5 | 90 |
| 2-185 | 5 | 80 |
| 1-352 | 5 | 80 |
| 2-350 | 5 | 80 |
| 2-86 | 5 | 80 |
| 1-353 | 5 | 80 |

TABLE 25b

| Post-emergence action at 20 g/ha against MATIN in % | | |
|---|---|---|
| Example number | Dosage [g/ha] | MATIN |
| 3-129 | 20 | 100 |
| 2-129 | 20 | 100 |
| 1-129 | 20 | 90 |
| 6-116 | 20 | 90 |
| 3-337 | 20 | 80 |
| 1-26 | 20 | 90 |
| 2-26 | 20 | 90 |
| 3-26 | 20 | 90 |
| 1-208 | 20 | 80 |
| 2-208 | 20 | 80 |
| 3-208 | 20 | 90 |
| 6-159 | 20 | 90 |
| 1-130 | 20 | 80 |
| 2-130 | 20 | 80 |
| 6-117 | 20 | 90 |
| 1-81 | 20 | 80 |
| 2-81 | 20 | 100 |
| 2-82 | 20 | 90 |
| 1-147 | 20 | 100 |
| 2-147 | 20 | 100 |
| 1-148 | 20 | 100 |
| 2-148 | 20 | 90 |
| 1-131 | 20 | 90 |
| 2-131 | 20 | 100 |
| 6-118 | 20 | 80 |
| 1-149 | 20 | 100 |
| 2-149 | 20 | 100 |
| 6-124 | 20 | 80 |
| 5-58 | 20 | 80 |
| 5-117 | 20 | 90 |
| 5-75 | 20 | 80 |
| 5-123 | 20 | 80 |
| 5-122 | 20 | 80 |
| 1-82 | 20 | 80 |
| 1-87 | 20 | 80 |
| 2-87 | 20 | 90 |
| 1-88 | 20 | 80 |
| 2-88 | 20 | 80 |
| 1-25 | 20 | 100 |
| 2-25 | 20 | 100 |
| 3-27 | 20 | 100 |
| 1-27 | 20 | 100 |
| 2-27 | 20 | 100 |
| 2-173 | 20 | 100 |
| 1-273 | 20 | 100 |
| 2-273 | 20 | 90 |
| 3-273 | 20 | 90 |
| 1-44 | 20 | 90 |
| 2-44 | 20 | 80 |
| 1-45 | 20 | 80 |
| 2-45 | 20 | 80 |
| 1-46 | 20 | 80 |
| 2-46 | 20 | 80 |
| 2-31 | 20 | 80 |
| 1-28 | 20 | 80 |
| 2-28 | 20 | 80 |
| 2-29 | 20 | 80 |
| 1-304 | 20 | 90 |
| 2-304 | 20 | 90 |
| 1-305 | 20 | 90 |
| 2-305 | 20 | 90 |
| 1-306 | 20 | 90 |
| 2-306 | 20 | 90 |
| 1-177 | 20 | 90 |
| 2-177 | 20 | 90 |
| 1-178 | 20 | 90 |
| 2-178 | 20 | 90 |
| 1-179 | 20 | 80 |
| 2-179 | 20 | 90 |
| 1-132 | 20 | 80 |
| 2-132 | 20 | 80 |
| 1-135 | 20 | 90 |
| 2-135 | 20 | 90 |
| 6-254 | 20 | 80 |

TABLE 25b-continued

| Post-emergence action at 20 g/ha against MATIN in % | | |
|---|---|---|
| Example number | Dosage [g/ha] | MATIN |
| 2-134 | 20 | 80 |
| 2-133 | 20 | 90 |
| 1-277 | 20 | 90 |
| 2-277 | 20 | 90 |
| 1-278 | 20 | 90 |
| 2-278 | 20 | 90 |
| 1-279 | 20 | 90 |
| 2-279 | 20 | 80 |
| 2-195 | 20 | 90 |
| 2-225 | 20 | 80 |
| 2-197 | 20 | 80 |
| 1-226 | 20 | 80 |
| 2-226 | 20 | 80 |
| 2-196 | 20 | 90 |
| 1-56 | 20 | 90 |
| 2-57 | 20 | 90 |
| 1-58 | 20 | 90 |
| 2-58 | 20 | 90 |
| 2-56 | 20 | 90 |
| 1-57 | 20 | 90 |
| 1-207 | 20 | 90 |
| 2-207 | 20 | 90 |
| 2-271 | 20 | 100 |
| 2-32 | 20 | 90 |
| 2-33 | 20 | 90 |
| 2-42 | 20 | 80 |
| 2-146 | 20 | 90 |
| 5-255 | 20 | 80 |
| 1-72 | 20 | 80 |
| 2-72 | 20 | 80 |
| 1-73 | 20 | 80 |
| 2-73 | 20 | 80 |
| 1-74 | 20 | 90 |
| 2-74 | 20 | 80 |
| 1-137 | 20 | 80 |
| 1-136 | 20 | 80 |
| 2-180 | 20 | 80 |
| 1-183 | 20 | 90 |
| 2-183 | 20 | 90 |
| 2-182 | 20 | 90 |
| 2-181 | 20 | 90 |
| 2-228 | 20 | 80 |
| 2-286 | 20 | 90 |
| 1-287 | 20 | 90 |
| 2-287 | 20 | 90 |
| 2-288 | 20 | 90 |
| 1-210 | 20 | 90 |
| 2-210 | 20 | 90 |
| 2-213 | 20 | 100 |
| 1-288 | 20 | 100 |
| 1-289 | 20 | 80 |
| 2-289 | 20 | 90 |
| 1-291 | 20 | 90 |
| 2-291 | 20 | 90 |
| 2-292 | 20 | 90 |
| 1-271 | 20 | 90 |
| 2-47 | 20 | 80 |
| 1-339 | 20 | 80 |
| 2-339 | 20 | 80 |
| 1-49 | 20 | 80 |
| 2-49 | 20 | 80 |
| 1-229 | 20 | 80 |
| 2-229 | 20 | 80 |
| 1-340 | 20 | 80 |
| 2-340 | 20 | 80 |
| 1-33 | 20 | 80 |
| 1-32 | 20 | 90 |
| 2-154 | 20 | 80 |
| 1-155 | 20 | 80 |
| 2-155 | 20 | 90 |
| 6-260 | 20 | 80 |
| 1-164 | 20 | 80 |
| 2-164 | 20 | 80 |
| 1-165 | 20 | 80 |

TABLE 25b-continued

| Post-emergence action at 20 g/ha against MATIN in % | | |
|---|---|---|
| Example number | Dosage [g/ha] | MATIN |
| 1-166 | 20 | 80 |
| 2-161 | 20 | 80 |
| 2-211 | 20 | 80 |
| 2-272 | 20 | 80 |
| 2-276 | 20 | 90 |
| 1-276 | 20 | 80 |
| 1-274 | 20 | 80 |
| 1-272 | 20 | 90 |
| 1-341 | 20 | 80 |
| 1-292 | 20 | 80 |
| 2-341 | 20 | 80 |
| 1-83 | 20 | 90 |
| 2-83 | 20 | 100 |
| 1-89 | 20 | 80 |
| 2-89 | 20 | 90 |
| 1-345 | 20 | 80 |
| 2-344 | 20 | 80 |
| 1-346 | 20 | 90 |
| 2-345 | 20 | 100 |
| 1-195 | 20 | 80 |
| 2-185 | 20 | 90 |
| 1-84 | 20 | 90 |
| 2-84 | 20 | 80 |
| 1-352 | 20 | 90 |
| 2-350 | 20 | 90 |
| 1-86 | 20 | 80 |
| 2-86 | 20 | 90 |
| 1-92 | 20 | 80 |
| 2-92 | 20 | 80 |
| 1-90 | 20 | 80 |
| 2-90 | 20 | 90 |
| 1-353 | 20 | 90 |
| 2-351 | 20 | 80 |
| 2-352 | 20 | 80 |
| 2-353 | 20 | 80 |

TABLE 25c

| Post-emergence action at 80 g/ha against MATIN in % | | |
|---|---|---|
| Example number | Dosage [g/ha] | MATIN |
| 3-129 | 80 | 100 |
| 2-129 | 80 | 100 |
| 1-129 | 80 | 100 |
| 6-116 | 80 | 100 |
| 3-338 | 80 | 80 |
| 6-117 | 80 | 90 |
| 1-81 | 80 | 100 |
| 2-81 | 80 | 100 |
| 2-82 | 80 | 90 |
| 1-147 | 80 | 100 |
| 2-147 | 80 | 100 |
| 1-148 | 80 | 100 |
| 2-148 | 80 | 90 |

TABLE 26a

| Post-emergence action at 5 g/ha against PHBPU in % | | |
|---|---|---|
| Example number | Dosage [g/ha] | PHBPU |
| 1-129 | 5 | 80 |
| 6-116 | 5 | 80 |
| 2-26 | 5 | 80 |

TABLE 26a-continued

| Post-emergence action at 5 g/ha against PHBPU in % | | |
|---|---|---|
| Example number | Dosage [g/ha] | PHBPU |
| 3-26 | 5 | 80 |
| 1-208 | 5 | 80 |
| 2-208 | 5 | 80 |
| 3-208 | 5 | 80 |
| 1-130 | 5 | 80 |
| 5-59 | 5 | 80 |
| 5-58 | 5 | 80 |
| 5-117 | 5 | 80 |
| 5-75 | 5 | 80 |
| 1-82 | 5 | 80 |
| 1-87 | 5 | 80 |
| 2-87 | 5 | 80 |
| 1-88 | 5 | 80 |
| 2-88 | 5 | 80 |
| 2-25 | 5 | 80 |
| 3-27 | 5 | 90 |
| 2-173 | 5 | 80 |
| 2-44 | 5 | 80 |
| 1-45 | 5 | 80 |
| 1-46 | 5 | 80 |
| 2-31 | 5 | 80 |
| 2-135 | 5 | 80 |
| 1-134 | 5 | 80 |
| 1-277 | 5 | 90 |
| 2-278 | 5 | 80 |
| 1-279 | 5 | 90 |
| 1-227 | 5 | 80 |
| 2-57 | 5 | 80 |
| 2-56 | 5 | 80 |
| 2-32 | 5 | 80 |
| 1-34 | 5 | 90 |
| 2-34 | 5 | 90 |
| 6-255 | 5 | 90 |
| 2-42 | 5 | 90 |
| 2-146 | 5 | 80 |
| 1-138 | 5 | 80 |
| 1-137 | 5 | 80 |
| 1-180 | 5 | 90 |
| 2-182 | 5 | 80 |
| 1-228 | 5 | 80 |
| 2-286 | 5 | 90 |
| 1-287 | 5 | 90 |
| 2-288 | 5 | 80 |
| 1-212 | 5 | 80 |
| 2-213 | 5 | 80 |
| 1-289 | 5 | 80 |
| 1-291 | 5 | 80 |
| 2-291 | 5 | 80 |
| 2-47 | 5 | 80 |
| 1-339 | 5 | 80 |
| 2-339 | 5 | 90 |
| 1-49 | 5 | 80 |
| 2-49 | 5 | 80 |
| 1-47 | 5 | 80 |
| 2-154 | 5 | 90 |
| 1-155 | 5 | 90 |
| 1-164 | 5 | 90 |
| 1-165 | 5 | 90 |
| 1-166 | 5 | 80 |
| 1-159 | 5 | 80 |
| 2-159 | 5 | 80 |
| 2-211 | 5 | 80 |
| 2-272 | 5 | 90 |
| 2-276 | 5 | 80 |
| 1-274 | 5 | 80 |
| 1-292 | 5 | 80 |
| 1-342 | 5 | 80 |
| 2-342 | 5 | 80 |
| 1-345 | 5 | 80 |
| 1-346 | 5 | 80 |
| 1-347 | 5 | 90 |
| 1-195 | 5 | 80 |
| 1-84 | 5 | 90 |
| 2-350 | 5 | 80 |

TABLE 26a-continued

| Post-emergence action at 5 g/ha against PHBPU in % | | |
|---|---|---|
| Example number | Dosage [g/ha] | PHBPU |
| 1-86 | 5 | 80 |
| 2-86 | 5 | 80 |
| 2-353 | 5 | 80 |

TABLE 26b

| Post-emergence action at 20 g/ha against PHBPU in % | | |
|---|---|---|
| Example number | Dosage [g/ha] | PHBPU |
| 3-129 | 20 | 90 |
| 2-129 | 20 | 100 |
| 1-129 | 20 | 100 |
| 6-116 | 20 | 80 |
| 3-338 | 20 | 80 |
| 1-26 | 20 | 80 |
| 2-26 | 20 | 80 |
| 3-26 | 20 | 90 |
| 6-26 | 20 | 80 |
| 1-208 | 20 | 90 |
| 2-208 | 20 | 80 |
| 3-208 | 20 | 90 |
| 6-159 | 20 | 80 |
| 1-130 | 20 | 90 |
| 1-147 | 20 | 80 |
| 1-131 | 20 | 90 |
| 2-131 | 20 | 80 |
| 1-149 | 20 | 90 |
| 2-149 | 20 | 90 |
| 5-59 | 20 | 90 |
| 5-58 | 20 | 90 |
| 5-117 | 20 | 90 |
| 5-75 | 20 | 80 |
| 5-74 | 20 | 100 |
| 5-123 | 20 | 80 |
| 5-122 | 20 | 90 |
| 1-82 | 20 | 90 |
| 1-87 | 20 | 90 |
| 2-87 | 20 | 80 |
| 1-88 | 20 | 90 |
| 2-88 | 20 | 90 |
| 1-209 | 20 | 90 |
| 1-25 | 20 | 80 |
| 2-25 | 20 | 90 |
| 3-27 | 20 | 100 |
| 1-27 | 20 | 90 |
| 2-27 | 20 | 90 |
| 2-173 | 20 | 90 |
| 1-273 | 20 | 80 |
| 3-273 | 20 | 80 |
| 1-44 | 20 | 80 |
| 2-44 | 20 | 80 |
| 1-45 | 20 | 80 |
| 2-45 | 20 | 80 |
| 1-46 | 20 | 80 |
| 2-46 | 20 | 80 |
| 1-30 | 20 | 80 |
| 2-30 | 20 | 90 |
| 1-31 | 20 | 80 |
| 2-31 | 20 | 90 |
| 1-28 | 20 | 90 |
| 2-28 | 20 | 80 |
| 2-29 | 20 | 80 |
| 2-304 | 20 | 90 |
| 1-305 | 20 | 90 |
| 2-305 | 20 | 90 |
| 2-306 | 20 | 80 |
| 1-177 | 20 | 80 |
| 1-178 | 20 | 80 |
| 2-178 | 20 | 90 |
| 2-179 | 20 | 80 |

TABLE 26b-continued

| Post-emergence action at 20 g/ha against PHBPU in % | | |
|---|---|---|
| Example number | Dosage [g/ha] | PHBPU |
| 1-132 | 20 | 90 |
| 1-135 | 20 | 90 |
| 2-135 | 20 | 80 |
| 6-254 | 20 | 80 |
| 1-134 | 20 | 90 |
| 2-134 | 20 | 90 |
| 1-133 | 20 | 80 |
| 2-133 | 20 | 80 |
| 6-120 | 20 | 90 |
| 1-277 | 20 | 90 |
| 2-277 | 20 | 90 |
| 1-278 | 20 | 90 |
| 2-278 | 20 | 90 |
| 1-279 | 20 | 90 |
| 1-197 | 20 | 90 |
| 1-227 | 20 | 90 |
| 1-225 | 20 | 80 |
| 1-226 | 20 | 80 |
| 2-226 | 20 | 80 |
| 1-56 | 20 | 80 |
| 2-57 | 20 | 90 |
| 1-58 | 20 | 90 |
| 2-58 | 20 | 90 |
| 2-56 | 20 | 90 |
| 1-57 | 20 | 90 |
| 1-207 | 20 | 80 |
| 2-207 | 20 | 80 |
| 2-32 | 20 | 90 |
| 1-34 | 20 | 90 |
| 2-34 | 20 | 100 |
| 6-255 | 20 | 90 |
| 2-33 | 20 | 90 |
| 2-42 | 20 | 90 |
| 6-256 | 20 | 90 |
| 2-146 | 20 | 90 |
| 1-37 | 20 | 80 |
| 2-143 | 20 | 80 |
| 1-72 | 20 | 80 |
| 2-72 | 20 | 80 |
| 2-73 | 20 | 80 |
| 1-74 | 20 | 90 |
| 2-74 | 20 | 80 |
| 2-144 | 20 | 80 |
| 1-138 | 20 | 90 |
| 2-138 | 20 | 80 |
| 2-141 | 20 | 80 |
| 1-137 | 20 | 80 |
| 1-180 | 20 | 90 |
| 2-180 | 20 | 90 |
| 1-183 | 20 | 80 |
| 2-183 | 20 | 80 |
| 2-182 | 20 | 90 |
| 6-145 | 20 | 80 |
| 1-181 | 20 | 90 |
| 2-181 | 20 | 90 |
| 1-228 | 20 | 80 |
| 2-228 | 20 | 80 |
| 2-286 | 20 | 90 |
| 1-287 | 20 | 100 |
| 2-288 | 20 | 90 |
| 1-210 | 20 | 100 |
| 2-210 | 20 | 90 |
| 1-212 | 20 | 90 |
| 2-213 | 20 | 80 |
| 1-288 | 20 | 80 |
| 1-289 | 20 | 90 |
| 2-289 | 20 | 90 |
| 6-228 | 20 | 80 |
| 1-291 | 20 | 90 |
| 2-291 | 20 | 90 |
| 6-230 | 20 | 80 |
| 1-271 | 20 | 90 |
| 2-47 | 20 | 90 |

TABLE 26b-continued

| Post-emergence action at 20 g/ha against PHBPU in % | | |
|---|---|---|
| Example number | Dosage [g/ha] | PHBPU |
| 2-47 | 20 | 90 |
| 6-34 | 20 | 80 |
| 1-339 | 20 | 90 |
| 2-339 | 20 | 90 |
| 1-49 | 20 | 90 |
| 2-49 | 20 | 90 |
| 1-229 | 20 | 80 |
| 2-229 | 20 | 90 |
| 1-340 | 20 | 90 |
| 6-267 | 20 | 80 |
| 2-340 | 20 | 80 |
| 1-47 | 20 | 90 |
| 1-33 | 20 | 80 |
| 2-154 | 20 | 90 |
| 1-155 | 20 | 90 |
| 2-155 | 20 | 80 |
| 6-260 | 20 | 90 |
| 1-164 | 20 | 90 |
| 1-165 | 20 | 90 |
| 1-166 | 20 | 90 |
| 1-156 | 20 | 90 |
| 2-156 | 20 | 90 |
| 1-159 | 20 | 80 |
| 2-159 | 20 | 90 |
| 1-162 | 20 | 80 |
| 2-161 | 20 | 80 |
| 6-266 | 20 | 80 |
| 2-211 | 20 | 80 |
| 2-272 | 20 | 100 |
| 2-276 | 20 | 90 |
| 1-276 | 20 | 90 |
| 1-274 | 20 | 90 |
| 1-272 | 20 | 90 |
| 1-341 | 20 | 80 |
| 1-292 | 20 | 80 |
| 2-341 | 20 | 80 |
| 1-83 | 20 | 90 |
| 2-83 | 20 | 80 |
| 2-89 | 20 | 80 |
| 6-161 | 20 | 80 |
| 1-342 | 20 | 90 |
| 1-343 | 20 | 80 |
| 2-342 | 20 | 90 |
| 1-345 | 20 | 80 |
| 2-344 | 20 | 80 |
| 1-346 | 20 | 90 |
| 2-345 | 20 | 100 |
| 1-347 | 20 | 90 |
| 2-346 | 20 | 80 |
| 1-195 | 20 | 80 |
| 1-184 | 20 | 80 |
| 2-348 | 20 | 80 |
| 1-84 | 20 | 90 |
| 2-84 | 20 | 80 |
| 1-352 | 20 | 90 |
| 2-350 | 20 | 80 |
| 1-86 | 20 | 90 |
| 2-86 | 20 | 90 |
| 1-92 | 20 | 90 |
| 2-92 | 20 | 90 |
| 1-90 | 20 | 90 |
| 1-353 | 20 | 90 |
| 2-351 | 20 | 90 |
| 2-352 | 20 | 80 |
| 1-355 | 20 | 80 |
| 2-353 | 20 | 80 |
| 1-356 | 20 | 80 |
| 2-354 | 20 | 80 |

TABLE 26c

| Post-emergence action at 80 g/ha against PHBPU in % | | |
|---|---|---|
| Example number | Dosage [g/ha] | PHBPU |
| 3-129 | 80 | 100 |
| 2-129 | 80 | 100 |
| 1-129 | 80 | 100 |
| 6-116 | 80 | 90 |
| 1-338 | 80 | 90 |
| 2-338 | 80 | 90 |
| 3-338 | 80 | 90 |
| 2-337 | 80 | 80 |
| 6-117 | 80 | 80 |
| 1-81 | 80 | 80 |
| 2-81 | 80 | 90 |
| 1-147 | 80 | 90 |
| 2-147 | 80 | 80 |

TABLE 27a

| Post-emergence action at 5 g/ha against POLCO in % | | |
|---|---|---|
| Example number | Dosage [g/ha] | POLCO |
| 1-72 | 5 | 100 |

TABLE 27b

| Post-emergence action at 20 g/ha against POLCO in % | | |
|---|---|---|
| Example number | Dosage [g/ha] | POLCO |
| 1-26 | 20 | 90 |
| 2-26 | 20 | 80 |
| 6-26 | 20 | 80 |
| 3-125 | 20 | 80 |
| 2-130 | 20 | 80 |
| 1-147 | 20 | 90 |
| 2-148 | 20 | 90 |
| 1-149 | 20 | 100 |
| 2-149 | 20 | 80 |
| 5-122 | 20 | 80 |
| 1-88 | 20 | 80 |
| 1-27 | 20 | 90 |
| 2-173 | 20 | 90 |
| 2-30 | 20 | 80 |
| 1-28 | 20 | 80 |
| 2-304 | 20 | 80 |
| 2-305 | 20 | 100 |
| 1-306 | 20 | 80 |
| 1-178 | 20 | 80 |
| 6-141 | 20 | 80 |
| 1-179 | 20 | 80 |
| 2-179 | 20 | 90 |
| 1-207 | 20 | 100 |
| 1-72 | 20 | 100 |
| 1-73 | 20 | 80 |
| 1-74 | 20 | 80 |
| 2-180 | 20 | 100 |
| 1-183 | 20 | 100 |
| 2-287 | 20 | 100 |
| 1-212 | 20 | 100 |
| 1-271 | 20 | 80 |

TABLE 27c

| Post-emergence action at 80 g/ha against POLCO in % | | |
|---|---|---|
| Example number | Dosage [g/ha] | POLCO |
| 3-129 | 80 | 90 |
| 2-129 | 80 | 100 |
| 1-129 | 80 | 100 |

TABLE 27c-continued

| Post-emergence action at 80 g/ha against POLCO in % | | |
|---|---|---|
| Example number | Dosage [g/ha] | POLCO |
| 6-116 | 80 | 80 |
| 1-81 | 80 | 90 |
| 2-81 | 80 | 80 |
| 2-82 | 80 | 80 |
| 6-58 | 80 | 100 |
| 1-147 | 80 | 90 |
| 2-147 | 80 | 80 |
| 1-148 | 80 | 80 |
| 2-148 | 80 | 90 |

TABLE 28a

| Post-emergence action at 5 g/ha against SETVI in % | | |
|---|---|---|
| Example number | Dosage [g/ha] | SETVI |
| 2-129 | 5 | 100 |
| 1-129 | 5 | 100 |
| 6-116 | 5 | 100 |
| 1-26 | 5 | 100 |
| 2-26 | 5 | 80 |
| 1-208 | 5 | 80 |
| 2-208 | 5 | 80 |
| 2-131 | 5 | 90 |
| 1-149 | 5 | 100 |
| 2-149 | 5 | 90 |
| 6-124 | 5 | 80 |
| 5-58 | 5 | 80 |
| 5-117 | 5 | 100 |
| 5-253 | 5 | 80 |
| 5-75 | 5 | 80 |
| 5-74 | 5 | 80 |
| 5-123 | 5 | 80 |
| 5-122 | 5 | 80 |
| 1-82 | 5 | 80 |
| 1-87 | 5 | 80 |
| 2-87 | 5 | 80 |
| 1-88 | 5 | 80 |
| 2-88 | 5 | 90 |
| 1-209 | 5 | 100 |
| 1-27 | 5 | 100 |
| 2-27 | 5 | 80 |
| 1-173 | 5 | 90 |
| 2-173 | 5 | 100 |
| 1-273 | 5 | 80 |
| 2-273 | 5 | 80 |
| 6-33 | 5 | 80 |
| 1-28 | 5 | 80 |
| 1-304 | 5 | 90 |
| 2-304 | 5 | 80 |
| 2-305 | 5 | 90 |
| 1-306 | 5 | 90 |
| 2-306 | 5 | 80 |
| 1-177 | 5 | 90 |
| 2-177 | 5 | 90 |
| 1-179 | 5 | 90 |
| 2-179 | 5 | 90 |
| 1-134 | 5 | 90 |
| 1-133 | 5 | 90 |
| 2-133 | 5 | 80 |
| 1-277 | 5 | 90 |
| 2-277 | 5 | 90 |
| 2-278 | 5 | 80 |
| 1-279 | 5 | 90 |
| 2-195 | 5 | 90 |
| 2-197 | 5 | 80 |
| 1-225 | 5 | 90 |
| 1-226 | 5 | 100 |
| 2-226 | 5 | 100 |
| 1-56 | 5 | 100 |
| 2-57 | 5 | 100 |
| 1-58 | 5 | 100 |
| 2-58 | 5 | 90 |

TABLE 28a-continued

| Post-emergence action at 5 g/ha against SETVI in % | | |
|---|---|---|
| Example number | Dosage [g/ha] | SETVI |
| 2-56 | 5 | 80 |
| 1-57 | 5 | 100 |
| 1-207 | 5 | 100 |
| 2-207 | 5 | 90 |
| 2-271 | 5 | 100 |
| 6-210 | 5 | 90 |
| 2-32 | 5 | 80 |
| 1-34 | 5 | 80 |
| 2-34 | 5 | 80 |
| 6-255 | 5 | 80 |
| 2-33 | 5 | 80 |
| 1-182 | 5 | 90 |
| 2-182 | 5 | 90 |
| 6-145 | 5 | 80 |
| 2-287 | 5 | 80 |
| 2-288 | 5 | 80 |
| 1-210 | 5 | 80 |
| 1-212 | 5 | 80 |
| 1-288 | 5 | 80 |
| 1-289 | 5 | 80 |
| 1-339 | 5 | 80 |
| 1-49 | 5 | 90 |
| 1-229 | 5 | 80 |
| 1-33 | 5 | 80 |
| 1-166 | 5 | 90 |
| 2-272 | 5 | 90 |
| 1-276 | 5 | 80 |
| 1-272 | 5 | 90 |
| 2-158 | 5 | 90 |
| 1-83 | 5 | 80 |
| 1-89 | 5 | 90 |
| 2-89 | 5 | 90 |
| 1-342 | 5 | 90 |
| 2-342 | 5 | 90 |
| 1-344 | 5 | 80 |
| 2-343 | 5 | 90 |
| 1-346 | 5 | 100 |
| 2-345 | 5 | 80 |
| 1-195 | 5 | 100 |
| 1-185 | 5 | 80 |
| 1-349 | 5 | 90 |
| 2-348 | 5 | 80 |
| 2-349 | 5 | 90 |
| 1-84 | 5 | 100 |
| 2-84 | 5 | 80 |
| 1-352 | 5 | 80 |
| 2-86 | 5 | 100 |
| 1-92 | 5 | 90 |
| 2-92 | 5 | 80 |
| 2-352 | 5 | 80 |

TABLE 28b

| Post-emergence action at 20 g/ha against SETVI in % | | |
|---|---|---|
| Example number | Dosage [g/ha] | SETVI |
| 3-129 | 20 | 100 |
| 2-129 | 20 | 100 |
| 1-129 | 20 | 100 |
| 6-116 | 20 | 100 |
| 1-338 | 20 | 80 |
| 2-338 | 20 | 80 |
| 6-253 | 20 | 90 |
| 1-26 | 20 | 100 |
| 2-26 | 20 | 100 |
| 6-26 | 20 | 80 |
| 1-208 | 20 | 80 |
| 2-208 | 20 | 80 |
| 1-130 | 20 | 80 |
| 2-81 | 20 | 90 |
| 1-131 | 20 | 100 |
| 2-131 | 20 | 100 |

TABLE 28b-continued

| Post-emergence action at 20 g/ha against SETVI in % | | |
|---|---|---|
| Example number | Dosage [g/ha] | SETVI |
| 1-149 | 20 | 100 |
| 2-149 | 20 | 100 |
| 6-124 | 20 | 90 |
| 5-59 | 20 | 90 |
| 5-58 | 20 | 100 |
| 5-117 | 20 | 100 |
| 5-253 | 20 | 80 |
| 5-75 | 20 | 80 |
| 5-74 | 20 | 90 |
| 5-123 | 20 | 80 |
| 5-122 | 20 | 90 |
| 1-82 | 20 | 90 |
| 1-87 | 20 | 90 |
| 2-87 | 20 | 80 |
| 1-88 | 20 | 90 |
| 2-88 | 20 | 100 |
| 1-209 | 20 | 100 |
| 1-4 | 20 | 80 |
| 1-25 | 20 | 80 |
| 2-25 | 20 | 80 |
| 3-27 | 20 | 90 |
| 1-27 | 20 | 100 |
| 2-27 | 20 | 100 |
| 1-173 | 20 | 90 |
| 2-173 | 20 | 100 |
| 1-273 | 20 | 100 |
| 2-273 | 20 | 90 |
| 3-273 | 20 | 80 |
| 6-212 | 20 | 80 |
| 4-212 | 20 | 80 |
| 1-44 | 20 | 90 |
| 1-45 | 20 | 80 |
| 2-45 | 20 | 80 |
| 6-32 | 20 | 80 |
| 1-46 | 20 | 80 |
| 6-33 | 20 | 80 |
| 2-30 | 20 | 80 |
| 1-28 | 20 | 80 |
| 1-29 | 20 | 80 |
| 2-29 | 20 | 80 |
| 1-304 | 20 | 90 |
| 2-304 | 20 | 80 |
| 1-305 | 20 | 90 |
| 2-305 | 20 | 90 |
| 1-306 | 20 | 90 |
| 2-306 | 20 | 80 |
| 1-177 | 20 | 90 |
| 2-177 | 20 | 90 |
| 1-178 | 20 | 90 |
| 2-178 | 20 | 90 |
| 1-179 | 20 | 90 |
| 2-179 | 20 | 90 |
| 1-132 | 20 | 90 |
| 2-132 | 20 | 80 |
| 1-135 | 20 | 80 |
| 6-254 | 20 | 80 |
| 1-134 | 20 | 90 |
| 1-133 | 20 | 100 |
| 2-133 | 20 | 90 |
| 1-277 | 20 | 90 |
| 2-277 | 20 | 90 |
| 1-278 | 20 | 90 |
| 2-278 | 20 | 90 |
| 1-279 | 20 | 90 |
| 2-195 | 20 | 100 |
| 2-197 | 20 | 100 |
| 1-225 | 20 | 100 |
| 1-226 | 20 | 100 |
| 2-226 | 20 | 100 |
| 6-165 | 20 | 80 |
| 6-166 | 20 | 100 |
| 2-196 | 20 | 100 |
| 1-56 | 20 | 100 |
| 6-45 | 20 | 100 |
| 6-44 | 20 | 80 |
| 2-57 | 20 | 100 |

TABLE 28b-continued

| Post-emergence action at 20 g/ha against SETVI in % | | |
|---|---|---|
| Example number | Dosage [g/ha] | SETVI |
| 6-43 | 20 | 90 |
| 1-58 | 20 | 100 |
| 2-58 | 20 | 100 |
| 2-56 | 20 | 100 |
| 1-57 | 20 | 100 |
| 1-207 | 20 | 100 |
| 2-207 | 20 | 100 |
| 2-271 | 20 | 100 |
| 6-210 | 20 | 100 |
| 2-32 | 20 | 100 |
| 1-34 | 20 | 90 |
| 2-34 | 20 | 90 |
| 6-255 | 20 | 90 |
| 2-33 | 20 | 100 |
| 1-72 | 20 | 80 |
| 2-72 | 20 | 80 |
| 2-73 | 20 | 100 |
| 1-74 | 20 | 100 |
| 2-74 | 20 | 90 |
| 1-138 | 20 | 80 |
| 1-137 | 20 | 80 |
| 1-136 | 20 | 80 |
| 2-180 | 20 | 90 |
| 1-182 | 20 | 100 |
| 2-182 | 20 | 100 |
| 6-145 | 20 | 90 |
| 1-181 | 20 | 90 |
| 2-181 | 20 | 90 |
| 2-230 | 20 | 100 |
| 6-169 | 20 | 90 |
| 2-286 | 20 | 80 |
| 2-287 | 20 | 90 |
| 2-288 | 20 | 90 |
| 1-210 | 20 | 90 |
| 2-210 | 20 | 80 |
| 1-212 | 20 | 90 |
| 1-288 | 20 | 100 |
| 1-289 | 20 | 90 |
| 2-289 | 20 | 80 |
| 1-291 | 20 | 80 |
| 2-291 | 20 | 90 |
| 2-292 | 20 | 80 |
| 1-271 | 20 | 80 |
| 2-47 | 20 | 90 |
| 6-34 | 20 | 90 |
| 1-339 | 20 | 90 |
| 2-339 | 20 | 100 |
| 1-49 | 20 | 100 |
| 2-49 | 20 | 90 |
| 1-41 | 20 | 80 |
| 1-229 | 20 | 90 |
| 2-229 | 20 | 80 |
| 1-47 | 20 | 80 |
| 1-33 | 20 | 90 |
| 6-259 | 20 | 90 |
| 1-155 | 20 | 80 |
| 1-165 | 20 | 90 |
| 1-166 | 20 | 90 |
| 1-156 | 20 | 80 |
| 2-156 | 20 | 80 |
| 6-262 | 20 | 80 |
| 2-211 | 20 | 90 |
| 2-272 | 20 | 100 |
| 2-276 | 20 | 80 |
| 1-276 | 20 | 80 |
| 1-274 | 20 | 90 |
| 1-272 | 20 | 90 |
| 1-341 | 20 | 80 |
| 1-292 | 20 | 90 |
| 2-158 | 20 | 90 |
| 1-83 | 20 | 100 |
| 2-83 | 20 | 100 |
| 1-89 | 20 | 90 |
| 2-89 | 20 | 100 |
| 6-76 | 20 | 80 |
| 6-161 | 20 | 90 |

TABLE 28b-continued

| Post-emergence action at 20 g/ha against SETVI in % | | |
|---|---|---|
| Example number | Dosage [g/ha] | SETVI |
| 1-342 | 20 | 90 |
| 1-343 | 20 | 100 |
| 2-342 | 20 | 90 |
| 1-344 | 20 | 90 |
| 2-343 | 20 | 90 |
| 1-345 | 20 | 90 |
| 2-344 | 20 | 80 |
| 1-346 | 20 | 100 |
| 2-345 | 20 | 100 |
| 1-195 | 20 | 100 |
| 1-185 | 20 | 100 |
| 2-185 | 20 | 80 |
| 1-186 | 20 | 80 |
| 1-349 | 20 | 90 |
| 1-350 | 20 | 80 |
| 2-348 | 20 | 100 |
| 1-351 | 20 | 100 |
| 2-349 | 20 | 100 |
| 1-84 | 20 | 100 |
| 2-84 | 20 | 100 |
| 1-352 | 20 | 100 |
| 2-350 | 20 | 100 |
| 1-86 | 20 | 80 |
| 2-86 | 20 | 100 |
| 1-92 | 20 | 100 |
| 2-92 | 20 | 100 |
| 1-90 | 20 | 90 |
| 1-353 | 20 | 100 |
| 1-354 | 20 | 100 |
| 2-352 | 20 | 80 |
| 2-354 | 20 | 90 |

TABLE 28c

| Post-emergence action at 80 g/ha against SETVI in % | | |
|---|---|---|
| Example number | Dosage [g/ha] | SETVI |
| 3-129 | 80 | 100 |
| 2-129 | 80 | 100 |
| 1-129 | 80 | 100 |
| 6-116 | 80 | 100 |
| 1-338 | 80 | 100 |
| 2-338 | 80 | 100 |
| 3-338 | 80 | 90 |
| 6-253 | 80 | 100 |
| 1-81 | 80 | 90 |
| 2-81 | 80 | 90 |
| 2-148 | 80 | 80 |

TABLE 29a

| Post-emergence action at 5 g/ha against STEME in % | | |
|---|---|---|
| Example number | Dosage [g/ha] | STEME |
| 3-129 | 5 | 100 |
| 2-129 | 5 | 100 |
| 1-129 | 5 | 100 |
| 6-116 | 5 | 90 |
| 3-338 | 5 | 80 |
| 1-26 | 5 | 90 |
| 2-26 | 5 | 80 |
| 1-208 | 5 | 90 |
| 2-208 | 5 | 80 |
| 3-208 | 5 | 80 |
| 1-130 | 5 | 80 |
| 2-130 | 5 | 80 |
| 1-131 | 5 | 80 |
| 2-131 | 5 | 90 |
| 1-149 | 5 | 90 |

TABLE 29a-continued

| Post-emergence action at 5 g/ha against STEME in % | | |
|---|---|---|
| Example number | Dosage [g/ha] | STEME |
| 2-149 | 5 | 90 |
| 6-124 | 5 | 90 |
| 5-59 | 5 | 90 |
| 5-58 | 5 | 90 |
| 5-117 | 5 | 100 |
| 5-75 | 5 | 90 |
| 5-74 | 5 | 80 |
| 5-123 | 5 | 90 |
| 5-122 | 5 | 90 |
| 1-82 | 5 | 90 |
| 1-87 | 5 | 80 |
| 2-87 | 5 | 80 |
| 1-88 | 5 | 90 |
| 2-88 | 5 | 90 |
| 1-4 | 5 | 80 |
| 1-25 | 5 | 80 |
| 2-25 | 5 | 90 |
| 1-27 | 5 | 100 |
| 2-27 | 5 | 100 |
| 1-173 | 5 | 80 |
| 2-173 | 5 | 100 |
| 1-273 | 5 | 90 |
| 2-273 | 5 | 80 |
| 3-273 | 5 | 80 |
| 6-212 | 5 | 80 |
| 1-44 | 5 | 80 |
| 2-46 | 5 | 80 |

TABLE 29b

| Post-emergence action at 20 g/ha against STEME in % | | |
|---|---|---|
| Example number | Dosage [g/ha] | STEME |
| 3-129 | 20 | 100 |
| 2-129 | 20 | 100 |
| 1-129 | 20 | 100 |
| 6-116 | 20 | 100 |
| 2-338 | 20 | 90 |
| 3-338 | 20 | 100 |
| 2-337 | 20 | 90 |
| 3-337 | 20 | 100 |
| 1-26 | 20 | 90 |
| 2-26 | 20 | 90 |
| 3-26 | 20 | 90 |
| 6-26 | 20 | 80 |
| 1-208 | 20 | 90 |
| 2-208 | 20 | 100 |
| 3-208 | 20 | 90 |
| 6-159 | 20 | 90 |
| 2-125 | 20 | 80 |
| 3-125 | 20 | 80 |
| 1-130 | 20 | 80 |
| 2-130 | 20 | 80 |
| 6-117 | 20 | 90 |
| 1-81 | 20 | 90 |
| 2-81 | 20 | 90 |
| 2-82 | 20 | 80 |
| 6-58 | 20 | 80 |
| 1-147 | 20 | 80 |
| 2-147 | 20 | 80 |
| 1-148 | 20 | 90 |
| 2-148 | 20 | 80 |
| 1-131 | 20 | 100 |
| 2-131 | 20 | 90 |
| 6-118 | 20 | 100 |
| 1-149 | 20 | 90 |
| 2-149 | 20 | 90 |
| 6-124 | 20 | 90 |
| 5-59 | 20 | 100 |
| 5-58 | 20 | 90 |
| 5-117 | 20 | 100 |
| 5-253 | 20 | 80 |

TABLE 29b-continued

| Post-emergence action at 20 g/ha against STEME in % | | |
|---|---|---|
| Example number | Dosage [g/ha] | STEME |
| 5-75 | 20 | 100 |
| 5-74 | 20 | 90 |
| 5-123 | 20 | 90 |
| 5-122 | 20 | 100 |
| 1-82 | 20 | 90 |
| 1-87 | 20 | 100 |
| 2-87 | 20 | 90 |
| 1-88 | 20 | 90 |
| 2-88 | 20 | 100 |
| 1-209 | 20 | 90 |
| 1-4 | 20 | 90 |
| 1-25 | 20 | 100 |
| 2-25 | 20 | 100 |
| 3-27 | 20 | 80 |
| 1-27 | 20 | 100 |
| 2-27 | 20 | 100 |
| 1-173 | 20 | 100 |
| 2-173 | 20 | 100 |
| 1-273 | 20 | 100 |
| 2-273 | 20 | 90 |
| 3-273 | 20 | 90 |
| 6-212 | 20 | 90 |
| 1-44 | 20 | 80 |
| 2-44 | 20 | 80 |
| 1-45 | 20 | 80 |
| 6-32 | 20 | 80 |
| 1-46 | 20 | 80 |
| 2-46 | 20 | 80 |
| 6-33 | 20 | 80 |

TABLE 29c

| Post-emergence action at 80 g/ha against STEME in % | | |
|---|---|---|
| Example number | Dosage [g/ha] | STEME |
| 3-129 | 80 | 100 |
| 2-129 | 80 | 100 |
| 1-129 | 80 | 100 |
| 6-116 | 80 | 100 |
| 1-338 | 80 | 90 |
| 2-338 | 80 | 100 |
| 3-338 | 80 | 100 |
| 6-253 | 80 | 90 |
| 2-337 | 80 | 90 |
| 6-117 | 80 | 90 |
| 1-81 | 80 | 90 |
| 2-81 | 80 | 100 |
| 2-82 | 80 | 90 |
| 6-58 | 80 | 80 |
| 1-147 | 80 | 90 |
| 2-147 | 80 | 90 |
| 1-148 | 80 | 90 |
| 2-148 | 80 | 80 |

TABLE 30a

| Post-emergence action at 5 g/ha against VERPE in % | | |
|---|---|---|
| Example number | Dosage [g/ha] | VERPE |
| 1-129 | 5 | 80 |
| 2-337 | 5 | 80 |
| 1-149 | 5 | 80 |
| 1-87 | 5 | 80 |
| 1-88 | 5 | 80 |
| 1-44 | 5 | 80 |
| 2-46 | 5 | 80 |
| 1-304 | 5 | 80 |
| 1-132 | 5 | 90 |
| 1-135 | 5 | 80 |

TABLE 30a-continued

| Post-emergence action at 5 g/ha against VERPE in % | | |
|---|---|---|
| Example number | Dosage [g/ha] | VERPE |
| 2-133 | 5 | 80 |
| 1-277 | 5 | 80 |
| 2-277 | 5 | 80 |
| 1-278 | 5 | 80 |
| 1-279 | 5 | 80 |
| 1-57 | 5 | 80 |
| 2-207 | 5 | 80 |
| 2-271 | 5 | 80 |
| 2-32 | 5 | 90 |
| 1-72 | 5 | 80 |
| 1-73 | 5 | 80 |
| 2-73 | 5 | 80 |
| 1-74 | 5 | 80 |
| 1-183 | 5 | 80 |
| 2-286 | 5 | 80 |
| 2-287 | 5 | 80 |
| 1-289 | 5 | 80 |
| 2-289 | 5 | 80 |
| 1-271 | 5 | 80 |
| 1-165 | 5 | 80 |
| 1-166 | 5 | 80 |
| 1-341 | 5 | 80 |
| 1-292 | 5 | 80 |
| 1-89 | 5 | 90 |
| 2-89 | 5 | 80 |
| 1-346 | 5 | 80 |
| 1-353 | 5 | 80 |

TABLE 30b

| Post-emergence action at 20 g/ha against VERPE in % | | |
|---|---|---|
| Example number | Dosage [g/ha] | VERPE |
| 2-129 | 20 | 80 |
| 1-129 | 20 | 80 |
| 2-338 | 20 | 90 |
| 3-338 | 20 | 90 |
| 6-253 | 20 | 80 |
| 2-337 | 20 | 100 |
| 3-337 | 20 | 90 |
| 2-123 | 20 | 80 |
| 1-26 | 20 | 80 |
| 1-208 | 20 | 80 |
| 2-208 | 20 | 80 |
| 1-81 | 20 | 80 |
| 2-81 | 20 | 80 |
| 2-82 | 20 | 80 |
| 1-147 | 20 | 90 |
| 2-147 | 20 | 80 |
| 1-148 | 20 | 80 |
| 2-148 | 20 | 80 |
| 1-131 | 20 | 90 |
| 1-149 | 20 | 100 |
| 5-59 | 20 | 80 |
| 5-58 | 20 | 80 |
| 5-117 | 20 | 80 |
| 5-122 | 20 | 80 |
| 1-82 | 20 | 80 |
| 1-87 | 20 | 90 |
| 2-87 | 20 | 80 |
| 1-88 | 20 | 90 |
| 2-88 | 20 | 80 |
| 1-209 | 20 | 80 |
| 1-25 | 20 | 80 |
| 2-25 | 20 | 90 |
| 1-27 | 20 | 100 |
| 2-27 | 20 | 80 |
| 2-173 | 20 | 80 |
| 1-273 | 20 | 90 |
| 3-273 | 20 | 80 |
| 1-44 | 20 | 100 |
| 2-44 | 20 | 80 |

TABLE 30b-continued

| Post-emergence action at 20 g/ha against VERPE in % | | |
|---|---|---|
| Example number | Dosage [g/ha] | VERPE |
| 1-45 | 20 | 80 |
| 1-46 | 20 | 90 |
| 2-46 | 20 | 80 |
| 1-31 | 20 | 80 |
| 2-31 | 20 | 80 |
| 1-304 | 20 | 80 |
| 2-304 | 20 | 90 |
| 1-305 | 20 | 80 |
| 2-305 | 20 | 90 |
| 1-306 | 20 | 90 |
| 2-306 | 20 | 90 |
| 1-177 | 20 | 80 |
| 2-177 | 20 | 80 |
| 1-178 | 20 | 80 |
| 1-179 | 20 | 80 |
| 1-132 | 20 | 90 |
| 1-135 | 20 | 90 |
| 2-135 | 20 | 90 |
| 6-254 | 20 | 80 |
| 1-134 | 20 | 80 |
| 2-134 | 20 | 80 |
| 1-133 | 20 | 90 |
| 2-133 | 20 | 80 |
| 6-120 | 20 | 80 |
| 1-277 | 20 | 90 |
| 2-277 | 20 | 90 |
| 1-278 | 20 | 90 |
| 2-278 | 20 | 100 |
| 1-279 | 20 | 100 |
| 2-279 | 20 | 90 |
| 1-197 | 20 | 80 |
| 2-227 | 20 | 80 |
| 1-227 | 20 | 80 |
| 1-225 | 20 | 90 |
| 1-226 | 20 | 90 |
| 2-226 | 20 | 90 |
| 2-196 | 20 | 80 |
| 1-56 | 20 | 90 |
| 2-57 | 20 | 90 |
| 1-58 | 20 | 80 |
| 2-56 | 20 | 80 |
| 1-57 | 20 | 90 |
| 1-207 | 20 | 90 |
| 2-207 | 20 | 90 |
| 2-271 | 20 | 90 |
| 2-32 | 20 | 90 |
| 1-34 | 20 | 90 |
| 2-34 | 20 | 80 |
| 6-255 | 20 | 80 |
| 2-42 | 20 | 90 |
| 2-146 | 20 | 80 |
| 1-37 | 20 | 80 |
| 2-37 | 20 | 80 |
| 1-72 | 20 | 90 |
| 2-72 | 20 | 80 |
| 1-73 | 20 | 80 |
| 2-73 | 20 | 90 |
| 1-74 | 20 | 90 |
| 2-74 | 20 | 80 |
| 1-183 | 20 | 90 |
| 2-183 | 20 | 90 |
| 1-181 | 20 | 90 |
| 1-228 | 20 | 90 |
| 1-230 | 20 | 80 |
| 2-230 | 20 | 90 |
| 2-286 | 20 | 80 |
| 1-287 | 20 | 80 |
| 2-287 | 20 | 100 |
| 2-288 | 20 | 80 |
| 1-212 | 20 | 80 |
| 1-289 | 20 | 90 |
| 2-289 | 20 | 100 |
| 1-291 | 20 | 80 |
| 2-291 | 20 | 80 |
| 2-292 | 20 | 80 |
| 1-271 | 20 | 90 |

TABLE 30b-continued

| Post-emergence action at 20 g/ha against VERPE in % | | |
|---|---|---|
| Example number | Dosage [g/ha] | VERPE |
| 2-47 | 20 | 80 |
| 1-339 | 20 | 90 |
| 2-339 | 20 | 80 |
| 6-258 | 20 | 80 |
| 1-49 | 20 | 90 |
| 1-340 | 20 | 80 |
| 2-340 | 20 | 90 |
| 1-47 | 20 | 80 |
| 1-33 | 20 | 80 |
| 1-32 | 20 | 90 |
| 1-155 | 20 | 80 |
| 1-165 | 20 | 80 |
| 1-166 | 20 | 90 |
| 1-156 | 20 | 80 |
| 2-156 | 20 | 90 |
| 1-276 | 20 | 80 |
| 1-274 | 20 | 80 |
| 1-272 | 20 | 80 |
| 1-341 | 20 | 90 |
| 1-292 | 20 | 90 |
| 1-83 | 20 | 90 |
| 2-83 | 20 | 80 |
| 1-89 | 20 | 90 |
| 2-89 | 20 | 90 |
| 1-342 | 20 | 80 |
| 1-343 | 20 | 80 |
| 1-344 | 20 | 90 |
| 1-345 | 20 | 90 |
| 2-344 | 20 | 80 |
| 1-346 | 20 | 80 |
| 2-345 | 20 | 80 |
| 1-347 | 20 | 90 |
| 2-346 | 20 | 80 |
| 1-195 | 20 | 80 |
| 1-185 | 20 | 80 |
| 2-186 | 20 | 80 |
| 1-349 | 20 | 80 |
| 1-84 | 20 | 90 |
| 2-84 | 20 | 80 |
| 1-352 | 20 | 90 |
| 2-350 | 20 | 80 |
| 1-86 | 20 | 90 |
| 1-92 | 20 | 90 |
| 2-92 | 20 | 90 |
| 1-90 | 20 | 90 |
| 1-353 | 20 | 90 |
| 2-351 | 20 | 90 |
| 1-354 | 20 | 90 |
| 2-352 | 20 | 90 |
| 1-355 | 20 | 90 |
| 2-353 | 20 | 100 |
| 1-356 | 20 | 90 |
| 2-354 | 20 | 90 |

TABLE 30c

| Post-emergence action at 80 g/ha against VERPE in % | | |
|---|---|---|
| Example number | Dosage [g/ha] | VERPE |
| 3-129 | 80 | 80 |
| 2-129 | 80 | 90 |
| 1-129 | 80 | 100 |
| 6-116 | 80 | 90 |
| 1-338 | 80 | 100 |
| 2-338 | 80 | 100 |
| 3-338 | 80 | 90 |
| 6-253 | 80 | 90 |
| 2-337 | 80 | 100 |
| 6-117 | 80 | 80 |
| 1-81 | 80 | 90 |
| 2-81 | 80 | 90 |
| 2-82 | 80 | 90 |

TABLE 30c-continued

| Post-emergence action at 80 g/ha against VERPE in % | | |
|---|---|---|
| Example number | Dosage [g/ha] | VERPE |
| 1-147 | 80 | 90 |
| 2-147 | 80 | 90 |
| 1-148 | 80 | 80 |
| 2-148 | 80 | 90 |

TABLE 31a

| Post-emergence action at 5 g/ha against VIOTR in % | | |
|---|---|---|
| Example number | Dosage [g/ha] | VIOTR |
| 3-129 | 5 | 80 |
| 2-129 | 5 | 80 |
| 1-129 | 5 | 80 |
| 1-26 | 5 | 100 |
| 1-208 | 5 | 80 |
| 2-208 | 5 | 100 |
| 3-208 | 5 | 100 |
| 1-125 | 5 | 100 |
| 2-125 | 5 | 100 |
| 1-130 | 5 | 90 |
| 2-130 | 5 | 90 |
| 1-131 | 5 | 100 |
| 2-131 | 5 | 100 |
| 1-149 | 5 | 100 |
| 2-149 | 5 | 100 |
| 5-58 | 5 | 80 |
| 5-117 | 5 | 90 |
| 5-123 | 5 | 80 |
| 5-122 | 5 | 90 |
| 2-88 | 5 | 80 |
| 1-209 | 5 | 100 |
| 1-25 | 5 | 100 |
| 2-25 | 5 | 80 |
| 3-27 | 5 | 80 |
| 1-27 | 5 | 100 |
| 2-27 | 5 | 100 |
| 1-173 | 5 | 90 |
| 1-273 | 5 | 100 |
| 1-45 | 5 | 80 |
| 2-45 | 5 | 80 |
| 1-46 | 5 | 80 |
| 2-46 | 5 | 80 |
| 1-304 | 5 | 80 |
| 2-304 | 5 | 80 |
| 6-231 | 5 | 90 |
| 1-305 | 5 | 90 |
| 2-305 | 5 | 80 |
| 2-306 | 5 | 90 |
| 1-177 | 5 | 90 |
| 2-177 | 5 | 80 |
| 1-178 | 5 | 80 |
| 1-179 | 5 | 80 |
| 2-179 | 5 | 90 |
| 1-132 | 5 | 80 |
| 1-135 | 5 | 80 |
| 1-134 | 5 | 90 |
| 2-134 | 5 | 80 |
| 1-277 | 5 | 80 |
| 2-277 | 5 | 90 |
| 1-278 | 5 | 90 |
| 2-278 | 5 | 90 |
| 1-279 | 5 | 90 |
| 2-279 | 5 | 80 |
| 2-195 | 5 | 100 |
| 2-225 | 5 | 100 |
| 2-227 | 5 | 90 |
| 1-227 | 5 | 100 |
| 2-197 | 5 | 80 |
| 1-226 | 5 | 100 |
| 2-226 | 5 | 90 |
| 1-56 | 5 | 100 |
| 2-57 | 5 | 90 |

TABLE 31a-continued

| Post-emergence action at 5 g/ha against VIOTR in % | | |
|---|---|---|
| Example number | Dosage [g/ha] | VIOTR |
| 1-58 | 5 | 90 |
| 2-58 | 5 | 100 |
| 2-56 | 5 | 80 |
| 1-57 | 5 | 100 |
| 1-207 | 5 | 100 |
| 2-207 | 5 | 100 |
| 2-271 | 5 | 80 |
| 1-146 | 5 | 80 |
| 1-73 | 5 | 80 |
| 1-74 | 5 | 80 |
| 1-183 | 5 | 90 |
| 2-183 | 5 | 100 |
| 1-182 | 5 | 100 |
| 2-287 | 5 | 80 |
| 2-288 | 5 | 90 |
| 1-212 | 5 | 80 |
| 1-288 | 5 | 90 |
| 1-289 | 5 | 80 |
| 1-291 | 5 | 90 |
| 2-291 | 5 | 80 |
| 2-47 | 5 | 80 |
| 1-83 | 5 | 90 |
| 2-83 | 5 | 80 |
| 1-89 | 5 | 90 |
| 2-89 | 5 | 90 |
| 1-345 | 5 | 90 |
| 2-344 | 5 | 90 |
| 1-346 | 5 | 90 |
| 2-345 | 5 | 90 |
| 1-347 | 5 | 80 |
| 2-346 | 5 | 80 |
| 1-195 | 5 | 90 |
| 2-185 | 5 | 100 |
| 1-84 | 5 | 100 |
| 2-84 | 5 | 100 |
| 1-352 | 5 | 100 |
| 2-350 | 5 | 100 |
| 1-86 | 5 | 90 |
| 2-86 | 5 | 100 |
| 2-92 | 5 | 100 |
| 1-90 | 5 | 80 |
| 2-90 | 5 | 100 |
| 1-353 | 5 | 100 |
| 2-351 | 5 | 100 |

TABLE 31b

| Post-emergence action at 20 g/ha against VIOTR in % | | |
|---|---|---|
| Example number | Dosage [g/ha] | VIOTR |
| 3-129 | 20 | 90 |
| 2-129 | 20 | 100 |
| 1-129 | 20 | 100 |
| 6-116 | 20 | 80 |
| 2-338 | 20 | 100 |
| 3-338 | 20 | 90 |
| 6-253 | 20 | 80 |
| 1-337 | 20 | 80 |
| 3-337 | 20 | 100 |
| 1-123 | 20 | 100 |
| 1-26 | 20 | 100 |
| 2-26 | 20 | 80 |
| 3-26 | 20 | 90 |
| 6-26 | 20 | 100 |
| 1-208 | 20 | 100 |
| 2-208 | 20 | 100 |
| 3-208 | 20 | 100 |
| 1-125 | 20 | 100 |
| 2-125 | 20 | 100 |
| 3-125 | 20 | 80 |
| 1-130 | 20 | 90 |
| 2-130 | 20 | 100 |

TABLE 31b-continued

| Post-emergence action at 20 g/ha against VIOTR in % | | |
|---|---|---|
| Example number | Dosage [g/ha] | VIOTR |
| 2-82 | 20 | 80 |
| 1-148 | 20 | 80 |
| 1-131 | 20 | 100 |
| 2-131 | 20 | 100 |
| 6-118 | 20 | 80 |
| 1-149 | 20 | 100 |
| 2-149 | 20 | 100 |
| 6-124 | 20 | 100 |
| 5-59 | 20 | 80 |
| 5-58 | 20 | 80 |
| 5-117 | 20 | 100 |
| 5-75 | 20 | 80 |
| 5-123 | 20 | 90 |
| 5-122 | 20 | 90 |
| 1-82 | 20 | 90 |
| 1-87 | 20 | 80 |
| 2-87 | 20 | 100 |
| 1-88 | 20 | 80 |
| 2-88 | 20 | 90 |
| 1-209 | 20 | 100 |
| 1-25 | 20 | 100 |
| 2-25 | 20 | 90 |
| 3-27 | 20 | 100 |
| 1-27 | 20 | 100 |
| 2-27 | 20 | 100 |
| 1-173 | 20 | 90 |
| 2-173 | 20 | 100 |
| 1-273 | 20 | 100 |
| 1-44 | 20 | 80 |
| 2-44 | 20 | 80 |
| 1-45 | 20 | 90 |
| 2-45 | 20 | 100 |
| 1-46 | 20 | 80 |
| 2-46 | 20 | 80 |
| 1-304 | 20 | 90 |
| 2-304 | 20 | 90 |
| 6-231 | 20 | 90 |
| 1-305 | 20 | 90 |
| 2-305 | 20 | 90 |
| 1-306 | 20 | 90 |
| 2-306 | 20 | 90 |
| 1-177 | 20 | 90 |
| 2-177 | 20 | 100 |
| 1-178 | 20 | 80 |
| 2-178 | 20 | 90 |
| 6-141 | 20 | 80 |
| 1-179 | 20 | 90 |
| 2-179 | 20 | 100 |
| 1-132 | 20 | 90 |
| 2-132 | 20 | 90 |
| 1-135 | 20 | 90 |
| 2-135 | 20 | 90 |
| 1-134 | 20 | 90 |
| 2-134 | 20 | 90 |
| 1-133 | 20 | 80 |
| 2-133 | 20 | 80 |
| 1-277 | 20 | 90 |
| 2-277 | 20 | 90 |
| 1-278 | 20 | 90 |
| 2-278 | 20 | 90 |
| 1-279 | 20 | 90 |
| 2-279 | 20 | 90 |
| 2-195 | 20 | 100 |
| 2-225 | 20 | 100 |
| 1-197 | 20 | 100 |
| 2-227 | 20 | 100 |
| 1-227 | 20 | 100 |
| 2-197 | 20 | 100 |
| 1-225 | 20 | 80 |
| 1-226 | 20 | 100 |
| 2-226 | 20 | 100 |
| 6-165 | 20 | 80 |
| 1-56 | 20 | 100 |
| 2-57 | 20 | 100 |
| 1-58 | 20 | 100 |
| 2-58 | 20 | 100 |

TABLE 31b-continued

| Post-emergence action at 20 g/ha against VIOTR in % | | |
|---|---|---|
| Example number | Dosage [g/ha] | VIOTR |
| 2-56 | 20 | 100 |
| 1-57 | 20 | 100 |
| 1-207 | 20 | 100 |
| 2-207 | 20 | 100 |
| 2-271 | 20 | 80 |
| 6-210 | 20 | 80 |
| 1-140 | 20 | 80 |
| 1-146 | 20 | 100 |
| 1-37 | 20 | 80 |
| 1-72 | 20 | 90 |
| 2-72 | 20 | 80 |
| 6-49 | 20 | 80 |
| 1-73 | 20 | 80 |
| 2-73 | 20 | 100 |
| 6-50 | 20 | 80 |
| 1-74 | 20 | 90 |
| 2-74 | 20 | 80 |
| 1-180 | 20 | 90 |
| 2-180 | 20 | 100 |
| 1-183 | 20 | 90 |
| 2-183 | 20 | 100 |
| 1-182 | 20 | 100 |
| 2-182 | 20 | 100 |
| 1-228 | 20 | 80 |
| 2-228 | 20 | 80 |
| 2-286 | 20 | 80 |
| 1-287 | 20 | 80 |
| 2-287 | 20 | 90 |
| 2-288 | 20 | 100 |
| 1-210 | 20 | 90 |
| 2-210 | 20 | 90 |
| 1-212 | 20 | 90 |
| 2-213 | 20 | 90 |
| 1-288 | 20 | 90 |
| 1-289 | 20 | 90 |
| 2-289 | 20 | 90 |
| 1-291 | 20 | 100 |
| 2-291 | 20 | 90 |
| 2-292 | 20 | 80 |
| 1-271 | 20 | 90 |
| 2-47 | 20 | 90 |
| 2-47 | 20 | 80 |
| 2-340 | 20 | 80 |
| 1-47 | 20 | 80 |
| 1-33 | 20 | 80 |
| 1-32 | 20 | 80 |
| 2-155 | 20 | 80 |
| 1-165 | 20 | 80 |
| 1-166 | 20 | 80 |
| 2-156 | 20 | 80 |
| 2-272 | 20 | 80 |
| 2-276 | 20 | 80 |
| 1-276 | 20 | 80 |
| 1-274 | 20 | 80 |
| 1-272 | 20 | 90 |
| 1-341 | 20 | 80 |
| 1-292 | 20 | 80 |
| 1-83 | 20 | 90 |
| 2-83 | 20 | 80 |
| 1-89 | 20 | 90 |
| 2-89 | 20 | 90 |
| 1-342 | 20 | 80 |
| 1-343 | 20 | 80 |
| 2-342 | 20 | 80 |
| 2-343 | 20 | 90 |
| 1-345 | 20 | 100 |
| 2-344 | 20 | 100 |
| 1-346 | 20 | 100 |
| 2-345 | 20 | 90 |
| 1-347 | 20 | 100 |
| 2-346 | 20 | 100 |
| 1-195 | 20 | 100 |
| 1-184 | 20 | 90 |
| 1-185 | 20 | 80 |
| 2-185 | 20 | 100 |
| 2-186 | 20 | 80 |

TABLE 31b-continued

| Post-emergence action at 20 g/ha against VIOTR in % | | |
|---|---|---|
| Example number | Dosage [g/ha] | VIOTR |
| 2-348 | 20 | 80 |
| 1-351 | 20 | 80 |
| 2-349 | 20 | 80 |
| 1-84 | 20 | 100 |
| 2-84 | 20 | 100 |
| 1-352 | 20 | 100 |
| 2-350 | 20 | 100 |
| 1-86 | 20 | 100 |
| 2-86 | 20 | 100 |
| 1-92 | 20 | 100 |
| 2-92 | 20 | 100 |
| 1-90 | 20 | 100 |
| 2-90 | 20 | 100 |
| 1-353 | 20 | 100 |
| 2-351 | 20 | 100 |
| 1-354 | 20 | 90 |
| 2-352 | 20 | 90 |
| 1-355 | 20 | 100 |
| 2-353 | 20 | 80 |
| 1-356 | 20 | 90 |
| 2-354 | 20 | 100 |

TABLE 31c

| Post-emergence action at 80 g/ha against VIOTR in % | | |
|---|---|---|
| Example number | Dosage [g/ha] | VIOTR |
| 3-129 | 80 | 100 |
| 2-129 | 80 | 100 |
| 1-129 | 80 | 100 |
| 6-116 | 80 | 100 |
| 1-338 | 80 | 90 |
| 2-338 | 80 | 100 |
| 3-338 | 80 | 100 |
| 6-253 | 80 | 80 |
| 2-337 | 80 | 90 |
| 6-117 | 80 | 80 |
| 1-81 | 80 | 80 |
| 2-81 | 80 | 90 |
| 2-82 | 80 | 80 |
| 1-147 | 80 | 80 |
| 2-147 | 80 | 80 |
| 1-148 | 80 | 90 |
| 2-148 | 80 | 80 |

TABLE 32a

| Post-emergence action at 5 g/ha against DIGSA in % | | |
|---|---|---|
| Example number | Dosage [g/ha] | DIGSA |
| 1-26 | 5 | 90 |
| 2-26 | 5 | 90 |
| 6-26 | 5 | 90 |
| 1-208 | 5 | 80 |
| 2-208 | 5 | 80 |
| 6-159 | 5 | 80 |
| 1-130 | 5 | 90 |
| 2-130 | 5 | 80 |
| 1-131 | 5 | 100 |
| 2-131 | 5 | 90 |
| 6-118 | 5 | 100 |
| 1-149 | 5 | 100 |
| 2-149 | 5 | 100 |
| 5-59 | 5 | 90 |
| 5-58 | 5 | 90 |
| 5-117 | 5 | 90 |
| 5-75 | 5 | 90 |
| 5-74 | 5 | 90 |
| 5-123 | 5 | 90 |

TABLE 32a-continued

| Post-emergence action at 5 g/ha against DIGSA in % | | |
|---|---|---|
| Example number | Dosage [g/ha] | DIGSA |
| 5-122 | 5 | 90 |
| 1-82 | 5 | 90 |
| 1-87 | 5 | 100 |
| 2-87 | 5 | 90 |
| 1-88 | 5 | 90 |
| 2-88 | 5 | 90 |
| 1-4 | 5 | 80 |
| 1-25 | 5 | 90 |
| 2-25 | 5 | 80 |
| 1-27 | 5 | 90 |
| 2-27 | 5 | 100 |
| 1-173 | 5 | 90 |
| 1-273 | 5 | 90 |
| 2-273 | 5 | 80 |
| 3-273 | 5 | 80 |
| 6-212 | 5 | 80 |
| 1-44 | 5 | 80 |
| 1-45 | 5 | 80 |
| 6-32 | 5 | 80 |
| 1-46 | 5 | 80 |
| 2-305 | 5 | 80 |
| 1-306 | 5 | 90 |
| 2-306 | 5 | 80 |
| 1-177 | 5 | 90 |
| 1-179 | 5 | 90 |
| 6-254 | 5 | 80 |
| 1-133 | 5 | 90 |
| 1-277 | 5 | 90 |
| 2-277 | 5 | 90 |
| 1-278 | 5 | 90 |
| 2-278 | 5 | 90 |
| 1-279 | 5 | 90 |
| 2-279 | 5 | 90 |
| 2-195 | 5 | 80 |
| 1-197 | 5 | 100 |
| 1-227 | 5 | 100 |
| 1-225 | 5 | 90 |
| 1-226 | 5 | 90 |
| 1-56 | 5 | 90 |
| 6-45 | 5 | 90 |
| 6-44 | 5 | 80 |
| 2-57 | 5 | 90 |
| 6-43 | 5 | 90 |
| 1-58 | 5 | 100 |
| 2-58 | 5 | 100 |
| 2-56 | 5 | 90 |
| 1-57 | 5 | 100 |
| 1-207 | 5 | 90 |
| 2-207 | 5 | 80 |
| 6-210 | 5 | 90 |
| 1-34 | 5 | 80 |
| 2-34 | 5 | 80 |
| 6-255 | 5 | 90 |
| 6-256 | 5 | 80 |
| 1-181 | 5 | 90 |
| 1-228 | 5 | 90 |
| 2-228 | 5 | 80 |
| 2-286 | 5 | 90 |
| 1-287 | 5 | 100 |
| 2-287 | 5 | 90 |
| 2-288 | 5 | 90 |
| 1-210 | 5 | 80 |
| 2-210 | 5 | 80 |
| 1-212 | 5 | 90 |
| 1-288 | 5 | 90 |
| 1-289 | 5 | 90 |
| 2-289 | 5 | 90 |
| 1-291 | 5 | 90 |
| 2-291 | 5 | 90 |
| 2-292 | 5 | 90 |
| 1-271 | 5 | 90 |
| 2-47 | 5 | 90 |
| 1-339 | 5 | 90 |
| 2-339 | 5 | 80 |
| 1-49 | 5 | 80 |
| 2-49 | 5 | 90 |

TABLE 32a-continued

| Post-emergence action at 5 g/ha against DIGSA in % | | |
|---|---|---|
| Example number | Dosage [g/ha] | DIGSA |
| 1-41 | 5 | 80 |
| 1-229 | 5 | 90 |
| 2-340 | 5 | 80 |
| 1-155 | 5 | 90 |
| 6-260 | 5 | 90 |
| 1-165 | 5 | 90 |
| 1-166 | 5 | 90 |
| 2-272 | 5 | 90 |

TABLE 32b

| Post-emergence action at 20 g/ha against DIGSA in % | | |
|---|---|---|
| Example number | Dosage [g/ha] | DIGSA |
| 1-26 | 20 | 100 |
| 2-26 | 20 | 90 |
| 6-26 | 20 | 90 |
| 1-208 | 20 | 90 |
| 2-208 | 20 | 90 |
| 6-159 | 20 | 90 |
| 1-130 | 20 | 90 |
| 2-130 | 20 | 80 |
| 6-117 | 20 | 80 |
| 1-81 | 20 | 80 |
| 2-81 | 20 | 90 |
| 2-82 | 20 | 90 |
| 6-58 | 20 | 80 |
| 1-147 | 20 | 90 |
| 2-147 | 20 | 90 |
| 1-148 | 20 | 90 |
| 2-148 | 20 | 90 |
| 1-131 | 20 | 100 |
| 2-131 | 20 | 90 |
| 6-118 | 20 | 100 |
| 1-149 | 20 | 100 |
| 2-149 | 20 | 100 |
| 6-124 | 20 | 90 |
| 5-59 | 20 | 90 |
| 5-58 | 20 | 100 |
| 5-117 | 20 | 90 |
| 5-253 | 20 | 80 |
| 5-75 | 20 | 90 |
| 5-74 | 20 | 90 |
| 5-123 | 20 | 90 |
| 5-122 | 20 | 90 |
| 1-82 | 20 | 90 |
| 1-87 | 20 | 100 |
| 2-87 | 20 | 90 |
| 1-88 | 20 | 90 |
| 2-88 | 20 | 90 |
| 6-75 | 20 | 90 |
| 1-209 | 20 | 90 |
| 1-4 | 20 | 90 |
| 1-25 | 20 | 100 |
| 2-25 | 20 | 90 |
| 3-27 | 20 | 100 |
| 1-27 | 20 | 100 |
| 2-27 | 20 | 100 |
| 1-173 | 20 | 100 |
| 2-173 | 20 | 80 |
| 1-273 | 20 | 90 |
| 2-273 | 20 | 90 |
| 3-273 | 20 | 90 |
| 6-212 | 20 | 90 |
| 1-44 | 20 | 90 |
| 1-45 | 20 | 80 |
| 2-45 | 20 | 80 |
| 6-32 | 20 | 80 |
| 1-46 | 20 | 80 |
| 2-31 | 20 | 80 |
| 2-28 | 20 | 80 |
| 1-304 | 20 | 90 |

TABLE 32b-continued

| Post-emergence action at 20 g/ha against DIGSA in % | | |
|---|---|---|
| Example number | Dosage [g/ha] | DIGSA |
| 1-305 | 20 | 80 |
| 2-305 | 20 | 90 |
| 1-306 | 20 | 90 |
| 2-306 | 20 | 90 |
| 1-177 | 20 | 90 |
| 6-141 | 20 | 80 |
| 1-179 | 20 | 90 |
| 1-132 | 20 | 90 |
| 2-132 | 20 | 80 |
| 1-135 | 20 | 90 |
| 2-135 | 20 | 80 |
| 6-254 | 20 | 90 |
| 1-134 | 20 | 90 |
| 2-134 | 20 | 80 |
| 1-133 | 20 | 90 |
| 1-277 | 20 | 90 |
| 2-277 | 20 | 90 |
| 1-278 | 20 | 90 |
| 2-278 | 20 | 90 |
| 1-279 | 20 | 90 |
| 2-279 | 20 | 90 |
| 2-195 | 20 | 90 |
| 2-225 | 20 | 100 |
| 1-197 | 20 | 100 |
| 2-227 | 20 | 100 |
| 1-227 | 20 | 100 |
| 2-197 | 20 | 90 |
| 1-225 | 20 | 90 |
| 1-226 | 20 | 100 |
| 2-226 | 20 | 80 |
| 6-165 | 20 | 90 |
| 2-196 | 20 | 90 |
| 1-56 | 20 | 100 |
| 6-45 | 20 | 90 |
| 6-44 | 20 | 90 |
| 2-57 | 20 | 100 |
| 6-43 | 20 | 100 |
| 1-58 | 20 | 100 |
| 2-58 | 20 | 100 |
| 2-56 | 20 | 100 |
| 1-57 | 20 | 100 |
| 1-207 | 20 | 100 |
| 2-207 | 20 | 100 |
| 6-210 | 20 | 90 |
| 2-32 | 20 | 90 |
| 1-34 | 20 | 90 |
| 2-34 | 20 | 100 |
| 6-255 | 20 | 100 |
| 6-256 | 20 | 90 |
| 1-181 | 20 | 90 |
| 1-228 | 20 | 90 |
| 2-228 | 20 | 80 |
| 1-230 | 20 | 90 |
| 2-230 | 20 | 90 |
| 2-286 | 20 | 90 |
| 1-287 | 20 | 100 |
| 2-287 | 20 | 90 |
| 2-288 | 20 | 90 |
| 1-210 | 20 | 90 |
| 2-210 | 20 | 90 |
| 1-212 | 20 | 100 |
| 2-212 | 20 | 100 |
| 2-213 | 20 | 90 |
| 1-288 | 20 | 100 |
| 1-289 | 20 | 90 |
| 2-289 | 20 | 100 |
| 6-228 | 20 | 80 |
| 1-291 | 20 | 100 |
| 2-291 | 20 | 100 |
| 2-292 | 20 | 90 |
| 1-271 | 20 | 100 |
| 2-47 | 20 | 90 |

TABLE 32b-continued

| Post-emergence action at 20 g/ha against DIGSA in % | | |
|---|---|---|
| Example number | Dosage [g/ha] | DIGSA |
| 6-34 | 20 | 80 |
| 1-339 | 20 | 90 |
| 2-339 | 20 | 90 |
| 6-258 | 20 | 90 |
| 1-49 | 20 | 90 |
| 2-49 | 20 | 90 |
| 1-41 | 20 | 90 |
| 1-229 | 20 | 90 |
| 1-340 | 20 | 90 |
| 2-340 | 20 | 90 |
| 1-47 | 20 | 90 |
| 1-33 | 20 | 90 |
| 2-154 | 20 | 90 |
| 6-259 | 20 | 90 |
| 1-155 | 20 | 90 |
| 6-260 | 20 | 90 |
| 1-164 | 20 | 80 |
| 6-261 | 20 | 90 |
| 1-165 | 20 | 90 |
| 1-166 | 20 | 90 |
| 1-156 | 20 | 90 |
| 2-156 | 20 | 80 |
| 6-262 | 20 | 90 |
| 6-264 | 20 | 80 |
| 2-211 | 20 | 80 |
| 2-272 | 20 | 90 |

TABLE 32c

| Post-emergence action at 80 g/ha against DIGSA in % | | |
|---|---|---|
| Example number | Dosage [g/ha] | DIGSA |
| 2-337 | 80 | 90 |
| 6-117 | 80 | 90 |
| 1-81 | 80 | 90 |
| 2-81 | 80 | 90 |
| 2-82 | 80 | 90 |
| 6-58 | 80 | 90 |
| 1-147 | 80 | 90 |
| 2-147 | 80 | 90 |
| 1-148 | 80 | 90 |
| 2-148 | 80 | 90 |

COMPARATIVE EXPERIMENTS

In the experiments that follow, herbicidal action of numerous inventive compounds and the structurally closest compounds known from D1 (WO 2012/028579 A1) were compared under the above-specified conditions by the pre-emergence and post-emergence method. The example numbers given in the tables relate to the compounds disclosed in the respective documents.

TABLE 5

| Herbicidal pre-emergence action | | | | | | | |
|---|---|---|---|---|---|---|---|
| | Dosage | Herbicidal action against | | | | | |
| Example No.: | (g a.i./ha) | ALOMY | AVEFA | ABUTH | MATIN | STEME | VIOTR |
| 1-129, inventive | 80 | 100 | 100 | 100 | 100 | 100 | 100 |
| 4-251, from Di | 80 | 0 | 0 | 50 | 70 | 70 | 0 |
| | Dosage | Herbicidal action against | | | | | |
| Example No.: | (g a.i./ha) | ALOMY | AVEFA | SETVI | AMARE | STEME | VIOTR |
| 1-147, inventive | 80 | 90 | 100 | 100 | 100 | 100 | 100 |
| 4-251, from DI | 80 | 0 | 0 | 20 | 70 | 70 | 0 |
| | Dosage | Herbicidal action against | | | | | |
| Example No.: | (g a.i./ha) | ALOMY | AVEFA | SETVI | STEME | HORMU | |
| 2-147, inventive | 80 | 90 | 100 | 100 | 70 | 90 | |
| 5-251, from DI | 80 | 0 | 0 | 80 | 40 | 10 | |
| | Dosage | Herbicidal action against | | | | | |
| Example No.: | (g a.i./ha) | AVEFA | MATIN | ABUTH | AMARE | STEME | VIOTR |
| 1-129, inventive | 20 | 100 | 100 | 100 | 100 | 100 | 100 |
| 4-251, from DI | 20 | 0 | 0 | 40 | 0 | 30 | 80 |
| | Dosage | Herbicidal action against | | | | | |
| Example No.: | (g a.i./ha) | AVEFA | SETVI | ABUTH | MATIN | POLCO | VIOTR |
| 2-129, inventive | 20 | 100 | 100 | 100 | 100 | 100 | 100 |
| 5-251, from Di | 20 | 0 | 30 | 70 | 70 | 40 | 80 |

TABLE 6

| Herbicidal post-emergence action | | | | | | | |
|---|---|---|---|---|---|---|---|
| Example | Dosage | Herbicidal action against | | | | | |
| No.: | (g a.i./ha) | ALOMY | AVEFA | MATIN | PHBPU | POLCO | VIOTR |
| 1-147, inventive | 20 | 80 | 90 | 100 | 80 | 90 | 70 |
| 4-251, from Di | 20 | 20 | 0 | 30 | 60 | 30 | 50 |
| Example | Dosage | Herbicidal action against | | | | | |
| No.: | (g a.i./ha) | ALOMY | AVEFA | LOLRI | MATIN | PHBPU | HORMU |
| 2-147, inventive | 20 | 80 | 90 | 70 | 100 | 70 | 80 |
| 5-251, from DI | 20 | 60 | 30 | 30 | 50 | 50 | 30 |
| Example | Dosage | Herbicidal action against | | | | | |
| No.: | (g a.i./ha) | ALOMY | ECHCG | SETVI | ABUTH | STEME | VIOTR |
| 1-129, inventive | 5 | 90 | 100 | 100 | 100 | 100 | 80 |
| 4-251, from DI | 5 | 0 | 50 | 0 | 70 | 60 | 20 |
| Example | Dosage | Herbicidal action against | | | | | |
| No.: | (g a.i./ha) | ALOMY | AVEFA | SETVI | AMARE | MATIN | HORMU |
| 2-129, inventive | 5 | 100 | 100 | 100 | 100 | 80 | 80 |
| 5-251, from DI | 5 | 30 | 20 | 30 | 80 | 30 | 20 |

The invention claimed is:

1. An isophthalamide of formula (I) or salt thereof

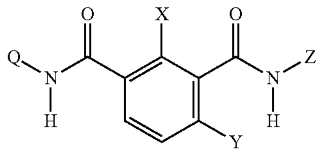

(I)

in which the symbols and indices are defined as follows:

Q is $Q^1$,

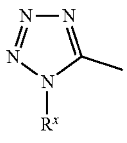

($Q^1$)

X is halogen, ($C_1$-$C_6$)-alkyl, halo-($C_1$-$C_6$)-alkyl, ($C_3$-$C_6$)-cycloalkyl, $R^1O$, $R^2(O)_nS$ or $R^1O$—($C_1$-$C_6$)-alkyl or $R^2S(O)$ n-($C_1$-$C_6$)-alkyl, Y is halogen, ($C_1$-$C_6$)-alkyl, halo-($C_1$-$C_6$)-alkyl, $R^1O$ or $R^2(O)_nS$, $R^1$ is ($C_1$-$C_6$)-alkyl, halo-($C_1$-$C_6$)-alkyl or ($C_3$-$C_6$)-cycloalkyl, $R^2$ is ($C_1$-$C_6$)-alkyl, $R^x$ is ($C_1$-$C_6$)-alkyl, ($C_1$-$C_6$)-alkyl-O—($C_1$-$C_6$)-alkyl or phenyl, Z is hydrogen, one of the following groups, each of which is substituted by s radicals from the group consisting of halogen, cyano, $R^1C(O)$, $R^1OC(O)$, $R^1O$ and $R^2(O)_n$ S: ($C_1$-$C_6$)-alkyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, ($C_2$-$C_6$)-alkenyl, ($C_2$-$C_6$)-alkenyl-($C_1$-$C_6$)-alkyl, ($C_2$-$C_6$)-alkynyl, ($C_2$-$C_6$)-alkynyl-($C_1$-$C_6$)-alkyl, ($C_1$-$C_6$)-alkoxy, $R^2S(O)n$-($C_1$-$C_6$)-alkyl, $R^1C(O)$, $R^1OC(O)$, $R^1C(O)$—($C_1$-$C_6$)-alkyl, $R^1OC(O)$—($C_1$-$C_6$)-alkyl, $R^1NH$—($C_1$-$C_6$)-alkyl, $R^1_2N$—($C_1$-$C_6$)-alkyl, $R^1NHC(O)$—($C_1$-$C_6$)-alkyl or $R^1_2NC(O)$—($C_1$-$C_6$)-alkyl, or one of the following groups, each substituted by s radicals from the group consisting of halogen, ($C_1$-$C_6$)-alkyl, halo-($C_1$-$C_6$)-alkyl, ($C_1$-$C_6$)-alkoxy, halo-($C_1$-$C_6$)-alkoxy, $R^1C(O)$ and $R^1OC(O)$: phenyl or benzyl, n is 0, 1 or 2, and s is 0, 1, 2 or 3.

2. The isophthalamide or salts thereof as claimed in claim 1, wherein

Q is $Q^1$

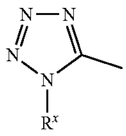

($Q^1$)

$R^x$ is ($C_1$-$C_6$)-alkyl, ($C_1$-$C_6$)-alkyl-O—($C_1$-$C_6$)-alkyl or phenyl X is halogen, ($C_1$-$C_6$)-alkyl, halo-($C_1$-$C_6$)-alkyl, c-Pr, OMe, OEt, SMe, SEt, $SO_2Me$, $SO_2Et$, $CH_2OMe$, $CH_2SMe$, $CH_2SO_2Me$, $(CH_2)_2SMe$ or $(CH_2)_2SO_2Me$, Y is halogen, halo-($C_1$-$C_6$)-alkyl, OMe, SMe, S(O)Me, $SO_2Me$, SEt, S(O)Et or $SO_2Et$, and Z is hydrogen, ($C_1$-$C_6$)-alkyl, ($C_3$-$C_6$)-cycloalkyl, $CH_2$c-Pr, halo-($C_1$-$C_6$)-alkyl, $(CH_2)_2OMe$, $(CH_2)_2OEt$, allyl, propynyl, $(CH_2)_2SMe$, $(CH_2)_2SO_2Me$, C(O)Me, C(O) cPr, C(O) OMe, C(O)OEt, $CH_2C(O)Me$, $CH_2C(O)c$-Pr, $CH_2C(O)NMe_2$, $CH_2CN$, Ph, OMe, OEt, OPr, or Oi-Pr.

3. The isophthalamide or salts thereof as claimed in claim 1, wherein

Q is $Q^1$, $R^x$ is Me, Et or Pr,

X is F, Cl, Br, I, Me, Et, c-Pr, OMe, SMe, SEt, $CH_2OMe$ or $CF_3$,

Y is F, Cl, Br, I, SMe, S(O)Me, $SO_2Me$, $CF_3$, $CHF_2$ or $C_2F_5$, and

Z is hydrogen, Me, Et, c-Pr, Pr, i-Pr, c-Bu, $CH_2$-c-Pr, $CH_2CHF_2$, $CH_2CF_3$, CH (Me)-c-Pr, $(CH_2)_2OMe$, $(CH_2)_2SMe$, $CH_2CN$, $CH_2C(O)NMe_2$, OMe, OEt, OPr, or Oi-Pr.

4. An herbicidal composition or plant growth-regulating composition, comprising one or more isophthalamides of formula (I) or salts thereof as claimed in claim 1.

5. The herbicidal composition as claimed in claim 4, further comprising a formulation auxiliary.

6. The herbicidal composition as claimed in claim 4, comprising at least one further active ingredient from the group of insecticides, acaricides, herbicides, fungicides, safeners and/or growth regulators.

7. The herbicidal composition as claimed in claim 4, comprising a safener.

8. The herbicidal composition as claimed in claim 7, in which the safener is selected from the group consisting of mefenpyr-diethyl, cyprosulfamide, isoxadifen-ethyl, cloquintocet-mexyl, benoxacor and dichlormid.

9. A method of controlling one or more unwanted plants, comprising applying an effective amount of at least one isophthalamide of formula (I) and/or salt thereof as claimed in claim 1 or an herbicidal composition thereof to the plants and/or to a site of unwanted vegetation.

10. A product comprising one or more compounds of formula (I) and/or salts as claimed in claim 1 or a herbicidal composition thereof for controlling one or more unwanted plants.

11. An isophthalamide of the formula (I-a) or salts thereof (I-a)

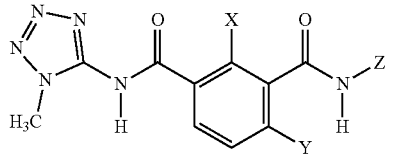

wherein the symbols and indices are defined as follows:

| No. | X | Y | Z |
|---|---|---|---|
| 1-4 | Me | Cl | Me |
| 1-25 | Me | $CF_3$ | Me |

-continued

| No. | X | Y | Z |
|---|---|---|---|
| 1-26 | Me | $CF_3$ | Et |
| 1-27 | Me | $CF_3$ | c-Pr |
| 1-28 | Me | $CF_3$ | $CH_2$-c-Pr |
| 1-29 | Me | $CF_3$ | $CH_2CF_3$ |
| 1-30 | Me | $CF_3$ | $CH_2CHF_2$ |
| 1-31 | Me | $CF_3$ | CH(Me)-c-Pr |
| 1-32 | Me | $CF_3$ | Pr |
| 1-33 | Me | $CF_3$ | i-Pr |
| 1-34 | Me | $CF_3$ | $CH_2CH_2OMe$ |
| 1-36 | Me | $CF_3$ | $CH_2CN$ |
| 1-44 | Me | $CHF_2$ | Me |
| 1-45 | Me | $CHF_2$ | Et |
| 1-46 | Me | $CHF_2$ | c-Pr |
| 1-47 | Me | $CHF_2$ | $CH_2$-c-Pr |
| 1-49 | Me | $CHF_2$ | $CH_2CHF_2$ |
| 1-56 | OMe | $CF_3$ | Me |
| 1-57 | OMe | $CF_3$ | Et |
| 1-58 | OMe | $CF_3$ | c-Pr |
| 1-72 | OMe | $CHF_2$ | Me |
| 1-73 | OMe | $CHF_2$ | Et |
| 1-74 | OMe | $CHF_2$ | c-Pr |
| 1-81 | SMe | $CF_3$ | Me |
| 1-82 | SMe | $CF_3$ | Et |
| 1-83 | SMe | $CF_3$ | c-Pr |
| 1-84 | SMe | $CF_3$ | $CH_2$-c-Pr |
| 1-85 | SMe | $CF_3$ | $CH_2CF_3$ |
| 1-86 | SMe | $CF_3$ | $CH_2CHF_2$ |
| 1-87 | SMe | $CHF_2$ | Me |
| 1-88 | SMe | $CHF_2$ | Et |
| 1-89 | SMe | $CHF_2$ | c-Pr |
| 1-90 | SMe | $CHF_2$ | $CH_2$-c-Pr |
| 1-92 | SMe | $CHF_2$ | $CH_2CHF_2$ |
| 1-123 | Cl | $SO_2Me$ | Me |
| 1-125 | Cl | $SO_2Me$ | c-Pr |
| 1-129 | Cl | $CF_3$ | Me |
| 1-130 | Cl | $CF_3$ | Et |
| 1-131 | Cl | $CF_3$ | c-Pr |
| 1-132 | Cl | $CF_3$ | $CH_2$-c-Pr |
| 1-133 | Cl | $CF_3$ | $CH_2CF_3$ |
| 1-134 | Cl | $CF_3$ | $CH_2CHF_2$ |
| 1-135 | Cl | $CF_3$ | CH(Me)-c-Pr |
| 1-136 | Cl | $CF_3$ | Pr |
| 1-137 | Cl | $CF_3$ | iPr |
| 1-138 | Cl | $CF_3$ | $CH_2CH_2OMe$ |
| 1-140 | Cl | $CF_3$ | $CH_2CN$ |
| 1-142 | Cl | $CF_3$ | $CH_2C(O)NMe_2$ |
| 1-143 | Cl | $CF_3$ | Ph |
| 1-146 | Cl | $CF_3$ | cBu |
| 1-147 | Cl | $CHF_2$ | Me |
| 1-148 | Cl | $CHF_2$ | Et |
| 1-149 | Cl | $CHF_2$ | c-Pr |
| 1-155 | Cl | $CHF_2$ | iPr |
| 1-156 | Cl | $CHF_2$ | $CH_2CH_2OMe$ |
| 1-157 | Cl | $CHF_2$ | $CH_2CH_2SMe$ |
| 1-158 | Cl | $CHF_2$ | $CH_2CN$ |
| 1-160 | Cl | $CHF_2$ | $CH_2C(O)NMe_2$ |
| 1-161 | Cl | $CHF_2$ | Ph |
| 1-164 | Cl | $CHF_2$ | cBu |
| 1-165 | Cl | $C_2F_5$ | Me |
| 1-166 | Cl | $C_2F_5$ | Et |
| 1-173 | Cl | Cl | c-Pr |
| 1-177 | Cl | Br | Me |
| 1-178 | Cl | Br | Et |
| 1-179 | Cl | Br | c-Pr |
| 1-180 | Cl | Br | $CH_2$-c-Pr |
| 1-181 | Cl | Br | $CH_2CF_3$ |
| 1-182 | Cl | Br | $CH_2CHF_2$ |
| 1-183 | Cl | Br | CH(Me)-c-Pr |
| 1-184 | Cl | Br | Pr |
| 1-185 | Cl | Br | i-Pr |
| 1-186 | Cl | Br | $CH_2CH_2OMe$ |
| 1-195 | Cl | I | Me |
| 1-197 | Cl | I | c-Pr |
| 1-207 | Br | $CF_3$ | Me |
| 1-208 | Br | $CF_3$ | Et |
| 1-209 | Br | $CF_3$ | c-Pr |
| 1-210 | Br | $CF_3$ | $CH_2$-c-Pr |

-continued

| No. | X | Y | Z |
|---|---|---|---|
| 1-211 | Br | $CF_3$ | $CH_2CF_3$ |
| 1-212 | Br | $CF_3$ | $CH_2CHF_2$ |
| 1-225 | Br | $CHF_2$ | Me |
| 1-226 | Br | $CHF_2$ | Et |
| 1-227 | Br | $CHF_2$ | c-Pr |
| 1-228 | Br | $CHF_2$ | $CH_2$-c-Pr |
| 1-229 | Br | $CHF_2$ | $CH_2CF_3$ |
| 1-230 | Br | $CHF_2$ | $CH_2CHF_2$ |
| 1-271 | Et | $CF_3$ | Me |
| 1-272 | Et | $CF_3$ | Et |
| 1-273 | Et | $CF_3$ | c-Pr |
| 1-274 | Et | $CF_3$ | $CH_2$-c-Pr |
| 1-276 | Et | $CF_3$ | $CH_2CHF_2$ |
| 1-277 | Et | $CHF_2$ | Me |
| 1-278 | Et | $CHF_2$ | Et |
| 1-279 | Et | $CHF_2$ | c-Pr |
| 1-287 | c-Pr | $CF_3$ | Et |
| 1-288 | c-Pr | $CF_3$ | c-Pr |
| 1-289 | c-Pr | $CF_3$ | $CH_2$-c-Pr |
| 1-291 | c-Pr | $CF_3$ | $CH_2CHF_2$ |
| 1-292 | c-Pr | $CF_3$ | CH(Me)-c-Pr |
| 1-304 | c-Pr | $CHF_2$ | Me |
| 1-305 | c-Pr | $CHF_2$ | Et |
| 1-306 | c-Pr | $CHF_2$ | c-Pr |
| 1-337 | Cl | $CF_3$ | acetyl |
| 1-338 | Cl | $CF_3$ | H |
| 1-339 | Me | $CHF_2$ | CH(Me)-c-Pr |
| 1-340 | Br | $CHF_2$ | CH(Me)-c-Pr |
| 1-341 | Et | $CF_3$ | CH(Me)-c-Pr |
| 1-342 | Br | Br | Me |
| 1-343 | Br | Br | Et |
| 1-344 | Br | Br | c-Pr |
| 1-345 | Me | $CHF_2$ | Pr |
| 1-346 | Me | $CHF_2$ | i-Pr |
| 1-347 | Me | $CHF_2$ | $CH_2CH_2OMe$ |
| 1-349 | Br | Cl | Me |
| 1-350 | Br | Cl | Et |
| 1-351 | Br | Cl | c-Pr |
| 1-352 | SMe | $CF_3$ | CH(Me)-c-Pr |
| 1-353 | SMe | $CHF_2$ | CH(Me)-c-Pr |
| 1-354 | Cl | OMe | Me |
| 1-355 | Cl | OMe | Et |
| 1-356 | Cl | OMe | c-Pr. |

12. The isophthalamide of the formula (I-a) or salts thereof of claim 11

(I-a)

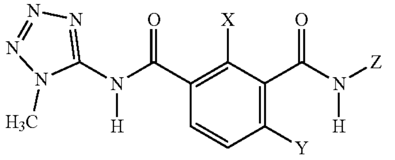

wherein the symbols and indices are defined as follows:

| No. | X | Y | Z |
|---|---|---|---|
| 1-123 | Cl | $SO_2Me$ | Me |
| 1-125 | Cl | $SO_2Me$ | c-Pr |
| 1-129 | Cl | $CF_3$ | Me |
| 1-130 | Cl | $CF_3$ | Et |
| 1-131 | Cl | $CF_3$ | c-Pr |
| 1-132 | Cl | $CF_3$ | $CH_2$-c-Pr |
| 1-133 | Cl | $CF_3$ | $CH_2CF_3$ |
| 1-134 | Cl | $CF_3$ | $CH_2CHF_2$ |
| 1-135 | Cl | $CF_3$ | CH(Me)-c-Pr |
| 1-136 | Cl | $CF_3$ | Pr |
| 1-137 | Cl | $CF_3$ | iPr |
| 1-138 | Cl | $CF_3$ | $CH_2CH_2OMe$ |

-continued

| No. | X | Y | Z |
|---|---|---|---|
| 1-140 | Cl | $CF_3$ | $CH_2CN$ |
| 1-146 | Cl | $CF_3$ | cBu |
| 1-147 | Cl | $CHF_2$ | Me |
| 1-148 | Cl | $CHF_2$ | Et |
| 1-149 | Cl | $CHF_2$ | c-Pr |
| 1-155 | Cl | $CHF_2$ | iPr |
| 1-156 | Cl | $CHF_2$ | $CH_2CH_2OMe$ |
| 1-157 | Cl | $CHF_2$ | $CH_2CH_2SMe$ |
| 1-158 | Cl | $CHF_2$ | $CH_2CN$ |
| 1-164 | Cl | $CHF_2$ | cBu |
| 1-165 | Cl | $C_2F_5$ | Me |
| 1-166 | Cl | $C_2F_5$ | Et |
| 1-173 | Cl | Cl | c-Pr |
| 1-177 | Cl | Br | Me |
| 1-178 | Cl | Br | Et |
| 1-179 | Cl | Br | c-Pr |
| 1-180 | Cl | Br | $CH_2$-c-Pr |
| 1-181 | Cl | Br | $CH_2CF_3$ |
| 1-182 | Cl | Br | $CH_2CHF_2$ |
| 1-183 | Cl | Br | CH(Me)-c-Pr |
| 1-184 | Cl | Br | Pr |
| 1-185 | Cl | Br | i-Pr |
| 1-186 | Cl | Br | $CH_2CH_2OMe$ |
| 1-195 | Cl | I | Me |
| 1-197 | Cl | I | c-Pr |
| 1-207 | Br | $CF_3$ | Me |
| 1-208 | Br | $CF_3$ | Et |
| 1-209 | Br | $CF_3$ | c-Pr |
| 1-210 | Br | $CF_3$ | $CH_2$-c-Pr |
| 1-211 | Br | $CF_3$ | $CH_2CF_3$ |
| 1-212 | Br | $CF_3$ | $CH_2CHF_2$ |
| 1-225 | Br | $CHF_2$ | Me |
| 1-226 | Br | $CHF_2$ | Et |
| 1-227 | Br | $CHF_2$ | c-Pr |
| 1-228 | Br | $CHF_2$ | $CH_2$-c-Pr |
| 1-229 | Br | $CHF_2$ | $CH_2CF_3$ |
| 1-230 | Br | $CHF_2$ | $CH_2CHF_2$ |
| 1-340 | Br | $CHF_2$ | CH(Me)-c-Pr |
| 1-342 | Br | Br | Me |
| 1-343 | Br | Br | Et |
| 1-344 | Br | Br | c-Pr |
| 1-349 | Br | Cl | Me |
| 1-350 | Br | Cl | Et |
| 1-351 | Br | Cl | c-Pr. |

13. An isophthalamide of the formula (I-b) or salts thereof (I-b)

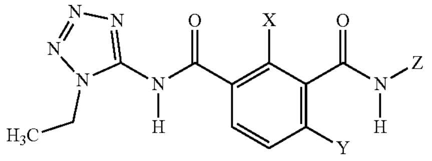

wherein the symbols and indices are defined as follows:

| No. | X | Y | Z |
|---|---|---|---|
| 2-25 | Me | $CF_3$ | Me |
| 2-26 | Me | $CF_3$ | Et |
| 2-27 | Me | $CF_3$ | c-Pr |
| 2-28 | Me | $CF_3$ | $CH_2$-c-Pr |
| 2-29 | Me | $CF_3$ | $CH_2CF_3$ |
| 2-30 | Me | $CF_3$ | $CH_2CHF_2$ |
| 2-31 | Me | $CF_3$ | CH(Me)-c-Pr |
| 2-32 | Me | $CF_3$ | Pr |
| 2-33 | Me | $CF_3$ | i-Pr |
| 2-34 | Me | $CF_3$ | $CH_2CH_2OMe$ |
| 2-35 | Me | $CF_3$ | $CH_2CH_2SMe$ |
| 2-36 | Me | $CF_3$ | $CH_2CN$ |

-continued

| No. | X | Y | Z |
|---|---|---|---|
| 2-42 | Me | $CF_3$ | c-Bu |
| 2-44 | Me | $CHF_2$ | Me |
| 2-45 | Me | $CHF_2$ | Et |
| 2-46 | Me | $CHF_2$ | c-Pr |
| 2-47 | Me | $CHF_2$ | $CH_2$-c-Pr |
| 2-49 | Me | $CHF_2$ | $CH_2CHF_2$ |
| 2-56 | OMe | $CF_3$ | Me |
| 2-57 | OMe | $CF_3$ | Et |
| 2-58 | OMe | $CF_3$ | c-Pr |
| 2-72 | OMe | $CHF_2$ | Me |
| 2-73 | OMe | $CHF_2$ | Et |
| 2-74 | OMe | $CHF_2$ | c-Pr |
| 2-81 | SMe | $CF_3$ | Me |
| 2-82 | SMe | $CF_3$ | Et |
| 2-83 | SMe | $CF_3$ | c-Pr |
| 2-84 | SMe | $CF_3$ | $CH_2$-c-Pr |
| 2-86 | SMe | $CF_3$ | $CH_2CHF_2$ |
| 2-87 | SMe | $CHF_2$ | Me |
| 2-88 | SMe | $CHF_2$ | Et |
| 2-89 | SMe | $CHF_2$ | c-Pr |
| 2-90 | SMe | $CHF_2$ | $CH_2$-c-Pr |
| 2-92 | SMe | $CHF_2$ | $CH_2CHF_2$ |
| 2-123 | Cl | $SO_2Me$ | Me |
| 2-125 | Cl | $SO_2Me$ | c-Pr |
| 2-129 | Cl | $CF_3$ | Me |
| 2-130 | Cl | $CF_3$ | Et |
| 2-131 | Cl | $CF_3$ | c-Pr |
| 2-132 | Cl | $CF_3$ | $CH_2$-c-Pr |
| 2-133 | Cl | $CF_3$ | $CH_2CF_3$ |
| 2-134 | Cl | $CF_3$ | $CH_2CHF_2$ |
| 2-135 | Cl | $CF_3$ | CH(Me)-c-Pr |
| 2-138 | Cl | $CF_3$ | $CH_2CH_2OMe$ |
| 2-142 | Cl | $CF_3$ | $CH_2C(O)NMe_2$ |
| 2-143 | Cl | $CF_3$ | Ph |
| 2-146 | Cl | $CF_3$ | c-Bu |
| 2-147 | Cl | $CHF_2$ | Me |
| 2-148 | Cl | $CHF_2$ | Et |
| 2-149 | Cl | $CHF_2$ | c-Pr |
| 2-154 | Cl | $CHF_2$ | Pr |
| 2-155 | Cl | $CHF_2$ | i-Pr |
| 2-156 | Cl | $CHF_2$ | $CH_2CH_2OMe$ |
| 2-157 | Cl | $CHF_2$ | $CH_2CH_2SMe$ |
| 2-158 | Cl | $CHF_2$ | $CH_2CN$ |
| 2-160 | Cl | $CHF_2$ | $CH_2C(O)NMe_2$ |
| 2-161 | Cl | $CHF_2$ | Ph |
| 2-164 | Cl | $CHF_2$ | c-Bu |
| 2-173 | Cl | Cl | c-Pr |
| 2-177 | Cl | Br | Me |
| 2-178 | Cl | Br | Et |
| 2-179 | Cl | Br | c-Pr |
| 2-180 | Cl | Br | $CH_2$-c-Pr |
| 2-181 | Cl | Br | $CH_2CF_3$ |
| 2-182 | Cl | Br | $CH_2CHF_2$ |
| 2-183 | Cl | Br | CH(Me)-c-Pr |
| 2-184 | Cl | Br | Pr |
| 2-185 | Cl | Br | i-Pr |
| 2-186 | Cl | Br | $CH_2CH_2OMe$ |
| 2-195 | Cl | I | Me |
| 2-196 | Cl | I | Et |
| 2-197 | Cl | I | c-Pr |
| 2-207 | Br | $CF_3$ | Me |
| 2-208 | Br | $CF_3$ | Et |
| 2-210 | Br | $CF_3$ | $CH_2$-c-Pr |
| 2-211 | Br | $CF_3$ | $CH_2CF_3$ |
| 2-212 | Br | $CF_3$ | $CH_2CHF_2$ |
| 2-213 | Br | $CF_3$ | CH(Me)-c-Pr |
| 2-225 | Br | $CHF_2$ | Me |
| 2-226 | Br | $CHF_2$ | Et |
| 2-227 | Br | $CHF_2$ | c-Pr |
| 2-228 | Br | $CHF_2$ | $CH_2$-c-Pr |
| 2-229 | Br | $CHF_2$ | $CH_2CF_3$ |
| 2-230 | Br | $CHF_2$ | $CH_2CHF_2$ |
| 2-271 | Et | $CF_3$ | Me |
| 2-272 | Et | $CF_3$ | Et |
| 2-273 | Et | $CF_3$ | c-Pr |
| 2-276 | Et | $CF_3$ | $CH_2CHF_2$ |
| 2-277 | Et | $CHF_2$ | Me |

-continued

| No. | X | Y | Z |
|---|---|---|---|
| 2-278 | Et | $CHF_2$ | Et |
| 2-279 | Et | $CHF_2$ | c-Pr |
| 2-286 | c-Pr | $CF_3$ | Me |
| 2-287 | c-Pr | $CF_3$ | Et |
| 2-288 | c-Pr | $CF_3$ | c-Pr |
| 2-289 | c-Pr | $CF_3$ | $CH_2$-c-Pr |
| 2-291 | c-Pr | $CF_3$ | $CH_2CHF_2$ |
| 2-292 | c-Pr | $CF_3$ | CH(Me)-c-Pr |
| 2-304 | c-Pr | $CHF_2$ | Me |
| 2-305 | c-Pr | $CHF_2$ | Et |
| 2-306 | c-Pr | $CHF_2$ | c-Pr |
| 2-337 | Cl | $CF_3$ | acetyl |
| 2-338 | Cl | $CF_3$ | H |
| 2-339 | Me | $CHF_2$ | CH(Me)-c-Pr |
| 2-340 | Br | $CHF_2$ | CH(Me)-c-Pr |
| 2-341 | Et | $CF_3$ | CH(Me)-c-Pr |
| 2-342 | Br | Br | Et |
| 2-343 | Br | Br | c-Pr |
| 2-344 | Me | $CHF_2$ | Pr |
| 2-345 | Me | $CHF_2$ | i-Pr |
| 2-346 | Me | $CHF_2$ | $CH_2CH_2OMe$ |
| 2-347 | Me | $CHF_2$ | $CH_2CH_2SMe$ |
| 2-348 | Br | Cl | Et |
| 2-349 | Br | Cl | c-Pr |
| 2-350 | SMe | $CF_3$ | CH(Me)-c-Pr |
| 2-351 | SMe | $CHF_2$ | CH(Me)-c-Pr |
| 2-352 | Cl | OMe | Me |
| 2-353 | Cl | OMe | Et |
| 2-354 | Cl | OMe | c-Pr. |

14. The isophthalamide of the formula (I-b) or salts thereof of claim 13

(I-b)

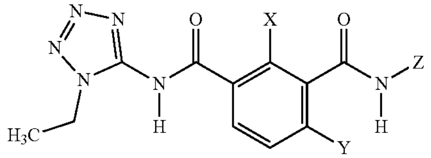

wherein the symbols and indices are defined as follows:

| No. | X | Y | Z |
|---|---|---|---|
| 2-123 | Cl | $SO_2Me$ | Me |
| 2-125 | Cl | $SO_2Me$ | c-Pr |
| 2-129 | Cl | $CF_3$ | Me |
| 2-130 | Cl | $CF_3$ | Et |
| 2-131 | Cl | $CF_3$ | c-Pr |
| 2-132 | Cl | $CF_3$ | $CH_2$-c-Pr |
| 2-133 | Cl | $CF_3$ | $CH_2CF_3$ |
| 2-134 | Cl | $CF_3$ | $CH_2CHF_2$ |
| 2-135 | Cl | $CF_3$ | CH(Me)-c-Pr |
| 2-138 | Cl | $CF_3$ | $CH_2CH_2OMe$ |
| 2-146 | Cl | $CF_3$ | c-Bu |
| 2-147 | Cl | $CHF_2$ | Me |
| 2-148 | Cl | $CHF_2$ | Et |
| 2-149 | Cl | $CHF_2$ | c-Pr |
| 2-154 | Cl | $CHF_2$ | Pr |
| 2-155 | Cl | $CHF_2$ | i-Pr |
| 2-156 | Cl | $CHF_2$ | $CH_2CH_2OMe$ |
| 2-157 | Cl | $CHF_2$ | $CH_2CH_2SMe$ |
| 2-158 | Cl | $CHF_2$ | $CH_2CN$ |
| 2-164 | Cl | $CHF_2$ | c-Bu |
| 2-173 | Cl | Cl | c-Pr |
| 2-177 | Cl | Br | Me |
| 2-178 | Cl | Br | Et |
| 2-179 | Cl | Br | c-Pr |
| 2-180 | Cl | Br | $CH_2$-c-Pr |
| 2-181 | Cl | Br | $CH_2CF_3$ |

-continued

| No. | X | Y | Z |
|---|---|---|---|
| 2-182 | Cl | Br | $CH_2CHF_2$ |
| 2-183 | Cl | Br | CH(Me)-c-Pr |
| 2-184 | Cl | Br | Pr |
| 2-185 | Cl | Br | i-Pr |
| 2-186 | Cl | Br | $CH_2CH_2OMe$ |
| 2-195 | Cl | I | Me |
| 2-196 | Cl | I | Et |
| 2-197 | Cl | I | c-Pr |
| 2-207 | Br | $CF_3$ | Me |
| 2-208 | Br | $CF_3$ | Et |
| 2-210 | Br | $CF_3$ | $CH_2$-c-Pr |
| 2-211 | Br | $CF_3$ | $CH_2CF_3$ |
| 2-212 | Br | $CF_3$ | $CH_2CHF_2$ |
| 2-213 | Br | $CF_3$ | CH(Me)-c-Pr |
| 2-225 | Br | $CHF_2$ | Me |
| 2-226 | Br | $CHF_2$ | Et |
| 2-227 | Br | $CHF_2$ | c-Pr |
| 2-228 | Br | $CHF_2$ | $CH_2$-c-Pr |
| 2-229 | Br | $CHF_2$ | $CH_2CF_3$ |
| 2-230 | Br | $CHF_2$ | $CH_2CHF_2$ |
| 2-338 | Cl | $CF_3$ | H |
| 2-340 | Br | $CHF_2$ | CH(Me)-c-Pr |
| 2-342 | Br | Br | Et |
| 2-343 | Br | Br | c-Pr |
| 2-348 | Br | Cl | Et |
| 2-349 | Br | Cl | c-Pr. |

15. The isophthalamide of the formula (I-b) or salts thereof of claim 14

(I-b)

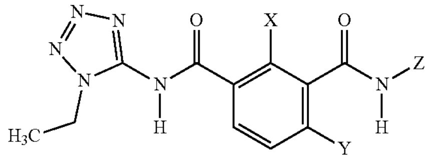

wherein the symbols and indices are defined as follows:

| No. | X | Y | Z |
|---|---|---|---|
| 2-129 | Cl | $CF_3$ | Me |
| 2-147 | Cl | $CHF_2$ | Me. |

16. An isophthalamide of the formula (I-c) or salts thereof (I-c)

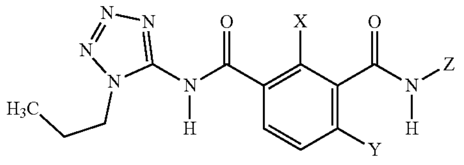

wherein the symbols and indices are defined as follows:

| No. | X | Y | Z |
|---|---|---|---|
| 3-26 | Me | $CF_3$ | Et |
| 3-27 | Me | $CF_3$ | c-Pr |
| 3-125 | Cl | $SO_2Me$ | c-Pr |
| 3-129 | Cl | $CF_3$ | Me |
| 3-208 | Br | $CF_3$ | Et |
| 3-273 | Et | $CF_3$ | c-Pr |
| 3-337 | Cl | $CF_3$ | acetyl |
| 3-338 | Cl | $CF_3$ | H. |

17. The isophthalamide of the formula (I-c) or salts thereof of claim 16

(I-c)

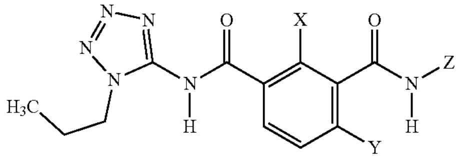

wherein the symbols and indices are defined as follows:

| No. | X | Y | Z |
|---|---|---|---|
| 3-125 | Cl | $SO_2Me$ | c-Pr |
| 3-129 | Cl | $CF_3$ | Me |
| 3-208 | Br | $CF_3$ | Et |
| 3-338 | Cl | $CF_3$ | H. |

* * * * *